(12) United States Patent
Johannes et al.

(10) Patent No.: US 12,421,208 B2
(45) Date of Patent: *Sep. 23, 2025

(54) CHEMICAL COMPOUNDS

(71) Applicant: ASTRAZENECA AB, Sodertalje (SE)

(72) Inventors: Jeffrey Wallace Johannes, Wilmington, DE (US); Sudhir Mahadeo Hande, Wilmington, DE (US); Avipsa Ghosh, Wilmington, DE (US); Xiaolan Zheng, Wilmington, DE (US); Martin Packer, Cambridge (GB); Sebastien Louis Degorce, Cambridge (GB)

(73) Assignee: ASTRAZENECA AB, Södertälje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/467,185

(22) Filed: Sep. 14, 2023

(65) Prior Publication Data
US 2024/0010631 A1    Jan. 11, 2024

Related U.S. Application Data

(63) Continuation of application No. 17/354,322, filed on Jun. 22, 2021, now Pat. No. 11,795,158.

(60) Provisional application No. 63/120,351, filed on Dec. 2, 2020, provisional application No. 63/044,095, filed on Jun. 25, 2020.

(51) Int. Cl.
    *C07D 401/12*         (2006.01)
(52) U.S. Cl.
    CPC ................. *C07D 401/12* (2013.01)
(58) Field of Classification Search
    CPC .................................. C07D 401/12
    See application file for complete search history.

(56) References Cited

U.S. PATENT DOCUMENTS

| 11,795,158 B2 * | 10/2023 | Johannes ............... A61P 35/00 |
| 2010/0190763 A1 | 7/2010 | Gangloff et al. |
| 2016/0003808 A1 | 1/2016 | Janssen et al. |

FOREIGN PATENT DOCUMENTS

| EP | 3312177 A2 | 4/2018 |
| WO | 2008050329 A2 | 5/2008 |
| WO | 2008076425 A1 | 6/2008 |
| WO | 2009053373 A1 | 4/2009 |
| WO | 2010085570 A1 | 7/2010 |
| WO | 2015010135 A2 | 1/2015 |
| WO | 2021013735 A1 | 1/2021 |

OTHER PUBLICATIONS

McMahon et al. (2000).*
Pinedo et al. (2000).*
International Search Report and Written Opinion for International Application No. PCT/EP2021/067304, dated Oct. 16, 2019, 13 pages.

* cited by examiner

*Primary Examiner* — Paul V Ward

(57) ABSTRACT

The present invention relates to azaquinolone compounds of Formula (I), and their use in medicine.

Formula (I)

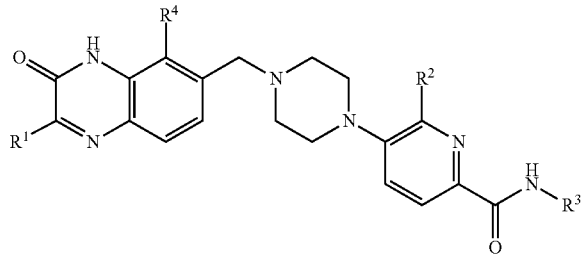

9 Claims, 6 Drawing Sheets

CHEMICAL COMPOUNDS

CROSS-REFERENCE TO RELATED APPLICATIONS

This application is a continuation of U.S. application Ser. No. 17/354,322, filed on Jun. 22, 2021, which claims the benefit of priority to U.S. Provisional Application No. 63/044,095, filed on Jun. 25, 2020, and U.S. Provisional Application No. 63/120,351, filed on Dec. 2, 2020. Each of the above listed applications is incorporated by reference herein in its entirety for all purposes.

The present disclosure relates to substituted azaquinolone compounds and pharmaceutically acceptable salts thereof that inhibit the Poly (ADP-ribose) polymerase (PARP) family of enzymes. The present disclosure also relates to the use of these compounds, and pharmaceutically acceptable salts thereof, in medicine, for example in the treatment of diseases in which inhibition of PARP1 or PARP1 function is of therapeutic significance. The present disclosure also relates to methods of treatment and methods of manufacture of medicaments using compounds according to the disclosure.

PARP family of enzymes play an important role in a number of cellular processes, such as replication, recombination, chromatin remodeling, and DNA damage repair (O'Connor M J, *Mol Cell* (2015) 60(4):547-60).

Examples of PARP inhibitors and their mechanism of action are taught in e.g. WO2004/080976.

PARP1 and PARP2 are the most extensively studied PARPs for their role in DNA damage repair. PARP1 is activated by DNA damage breaks and functions to catalyse the addition of poly (ADP-ribose) (PAR) chains to target proteins. This post-translational modification, known as PARylation, mediates the recruitment of additional DNA repair factors to DNA lesions.

Following completion of this recruitment role, PARP auto-PARylation triggers the release of bound PARP from DNA to allow access to other DNA repair proteins to complete repair. Thus, the binding of PARP to damaged sites, its catalytic activity, and its eventual release from DNA are all important steps for a cancer cell to respond to DNA damage caused by chemotherapeutic agents and radiation therapy (Bai P. Biology of poly(ADP-ribose) polymerases: the factotums of cell maintenance. *Mol Cell* 2015; 58:947-58.).

Inhibition of PARP family enzymes has been exploited as a strategy to selectively kill cancer cells by inactivating complementary DNA repair pathways. A number of pre-clinical and clinical studies have demonstrated that tumour cells bearing deleterious alterations of BRCA1 or BRCA2, key tumour suppressor proteins involved in double-strand DNA break (DSB) repair by homologous recombination (HR), are selectively sensitive to small molecule inhibitors of the PARP family of DNA repair enzymes. Such tumours have deficient homologous recombination repair (HRR) pathways and are dependent on PARP enzymes function for survival. Although PARP inhibitor therapy has predominantly targeted BRCA-mutated cancers, PARP inhibitors have been tested clinically in non-BRCA-mutant tumors, those which exhibit homologous recombination deficiency (HRD) (Turner N, Tutt A, Ashworth A. Hallmarks of 'BRCAness' in sporadic cancers. *Nat Rev Cancer* 2004; 4: 814-9.).

It is believed that PARP inhibitors having improved selectivity for PARP1 may result in improved efficacy and reduced toxicity compared to other clinical PARP1/2 inhibitors. It is believed also that selective strong inhibition of PARP1 would lead to trapping of PARP1 on DNA, resulting in DNA double-strand breaks (DSBs) through collapse of replication forks in S-phase. It is believed also that PARP1-DNA trapping is an effective mechanism for selectively killing tumour cells having HRD.

An unmet medical need therefore exists for effective and safe PARP inhibitors. Especially PARP inhibitors having selectivity for PARP1.

The applicant has discovered that the azaquinolones described herein surprisingly have PARP inhibitory activity, and therefore may be useful for the treatment of diseases and conditions in which PARP function has pharmacological significance. Furthermore, azaquinolones described herein have surprisingly high selectivity for PARP1 over other PARP family members such as PARP2, PARP3, PARP5a, and PARP6.

The applicant has further discovered that the azaquinolones described herein surprisingly are capable of penetrating the blood brain barrier (BBB). Therefore, the azaquinolones described herein may be useful for the treatment of diseases and conditions occurring in tissues in the central nervous system, such as the brain and spinal cord.

In an aspect, the applicant makes available a class of compounds of Formula (I):

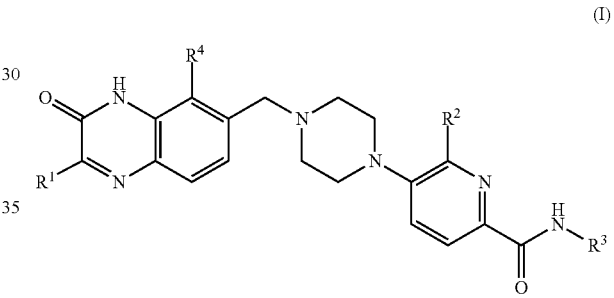

wherein:
$R^1$ is independently selected from H, $C_{1-4}$ alkyl, $C_{3-6}$ cycloalkyl, $C_{1-4}$ fluoroalkyl, and $C_{1-4}$ alkyloxy;
$R^2$ is independently selected from H, halo, $C_{1-4}$ alkyl, and $C_{1-4}$ fluoroalkyl; and
$R^3$ is H or $C_{1-4}$ alkyl;
$R^4$ is halo or $C_{1-4}$ alkyl,
or a pharmaceutically acceptable salt thereof.

In another aspect, the applicant makes available a class of compounds of Formula (I):

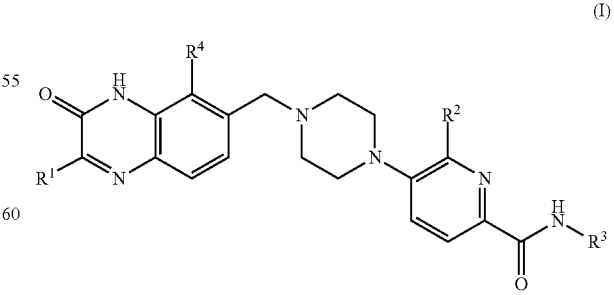

wherein:
$R^1$ is independently selected from H, $C_{1-4}$ alkyl, $C_{1-4}$ fluoroalkyl, and $C_{1-4}$ alkyloxy;

$R^2$ is independently selected from H, halo, $C_{1-4}$ alkyl, and $C_{1-4}$ fluoroalkyl; and $R^3$ is H or $C_{1-4}$ alkyl;

$R^4$ is halo or $C_{1-4}$ alkyl, or a pharmaceutically acceptable salt thereof.

In an aspect, $R^1$ is selected from any one of methyl, ethyl, isopropyl, cyclopropyl, 1,1-difluoroethyl, 1-fluoroethyl, trifluoromethyl, difluoromethyl, and methoxy. In an particular aspect, $R^1$ is methyl or ethyl.

In an aspect, $R^2$ is selected from any one of H, chloro, fluoro, methyl, and difluoromethyl. In an aspect, $R^2$ is fluoro or methyl.

In an aspect, $R^3$ is methyl or ethyl.

In an aspect, $R^4$ is selected from any one of chloro, fluoro and methyl. In a particular aspect, $R^4$ is fluoro.

In an aspect, there is provided a compound of formula I, wherein $R^1$ is $C_{1-4}$ alkyl, $R^2$ is halo, $R^3$ is $C_{1-4}$ alkyl, $R^4$ is halo or $C_{1-4}$ alkyl, or a pharmaceutically acceptable salt thereof.

In a further aspect, there is provided a pharmaceutical composition comprising a therapeutically effective amount of a compound of Formula I, or a pharmaceutically acceptable salt thereof, and at least one pharmaceutically acceptable diluent, excipient or inert carrier.

In a further aspect, there is provided a compound of Formula I or a pharmaceutically acceptable salt thereof, for use in treatment or prophylaxis of diseases and conditions in which inhibition of PARP1 is beneficial. In an aspect, the specification provides a compound of Formula I or a pharmaceutically acceptable salt thereof for use in the treatment of cancer. In an aspect, the cancer is breast, ovary, pancreas, prostate, hematological, gastrointestinal such as gastric and colorectal, or lung cancer such as small cell or non-small cell lung cancer. In an aspect, the cancer is breast, ovary, pancreas or prostate cancer. In an aspect, the cancer is of the brain, such as glioma or glioblastoma. In an aspect, the cancer of the brain is a metastatic cancer arising from a tumour elsewhere in the body such as breast, ovary, pancreas, prostate, hematological, gastrointestinal such as gastric and colorectal, or lung cancer such as small cell or non-small cell lung cancer.

In a further aspect, there is provided a method of treating diseases or conditions in which inhibition PARP1 is beneficial, comprising administering to a patient in need thereof an effective amount of a compound of Formula I or a pharmaceutically acceptable salt thereof. In an aspect, said disease or condition is cancer. In an aspect, the cancer is breast, ovary, pancreas, prostate, hematological, gastrointestinal such as gastric and colorectal, or lung cancer such as small cell or non-small cell lung cancer. In an aspect, the cancer is breast, ovary, pancreas or prostate cancer. In an aspect, the cancer is of the brain, such as glioma or glioblastoma. In an aspect, the cancer of the brain is a metastatic cancer arising from a tumour elsewhere in the body such as breast, ovary, pancreas, prostate, hematological, gastrointestinal such as gastric and colorectal, or lung cancer such as small cell or non-small cell lung cancer.

In a further aspect, there is provided the compound of Formula I or a pharmaceutically acceptable salt thereof, for use in the preparation of a medicament for the treatment of diseases or conditions in which inhibition of PARP1 is beneficial. In an aspect, the cancer is breast, ovary, pancreas, prostate, hematological, gastrointestinal such as gastric and colorectal, or lung cancer such as small cell or non-small cell lung cancer. In an aspect, the cancer is breast, ovary, pancreas or prostate cancer. In an aspect, the cancer is of the brain, such as glioma or glioblastoma. In an aspect, the cancer of the brain is a metastatic cancer arising from a tumour elsewhere in the body such as breast, ovary, pancreas, prostate, hematological, gastrointestinal such as gastric and colorectal, or lung cancer such as small cell or non-small cell lung cancer.

In a further aspect, there is provided the use of a compound of Formula I or a pharmaceutically acceptable salt thereof, in the manufacture of a medicament for use in the treatment of diseases or conditions in which inhibition of PARP1 is beneficial. In an aspect, the cancer is breast, ovary, pancreas, prostate, hematological, gastrointestinal such as gastric and colorectal, or lung cancer such as small cell or non-small cell lung cancer. In an aspect, the cancer is breast, ovary, pancreas or prostate cancer. In an aspect, the cancer is of the brain, such as glioma or glioblastoma. In an aspect, the cancer of the brain is a metastatic cancer arising from a tumour elsewhere in the body such as breast, ovary, pancreas, prostate, hematological, gastrointestinal such as gastric and colorectal, or lung cancer such as small cell or non-small cell lung cancer.

In a further aspect, there is provided a compound of Formula I capable of penetrating the blood brain barrier (BBB). In an an aspect, the ratio of compound that penetrates the BBB is >0.1, wherein 1 is complete BBB penetration, and 0 is no penetration. In an aspect, the ratio of compound that penetrates the BBB is >0.2. In an aspect, the ratio of compound that penetrates the BBB is >0.3. In an aspect the ratio of compound that penetrates the BBB is measured using the rat kpuu assay. In an aspect, the compound of Formula I has a ratio of >0.3 (i.e. from 0.3 to 1) as determined in the rat kpuu assay.

In a further aspect, there is provided a compound of Formula I, or a pharmaceutically acceptable salt thereof, for use in medicine.

In a further aspect, the compound of Formula I in the free base form.

In a further aspect, there is provided a compound of Formula I or a pharmaceutically acceptable salt thereof, for use as medicament.

In a further aspect, there is provided the Examples disclosed herein.

In an aspect, there is provided a compound of Formula I which is 5-[4-[(2-ethyl-5-fluoro-3-oxo-4H-quinoxalin-6-yl)methyl]piperazin-1-yl]-N,6-dimethyl-pyridine-2-carboxamide or a pharmaceutically acceptable salt thereof.

In an aspect, there is provided a compound of Formula I which is 6-fluoro-5-[4-[(5-fluoro-2-methyl-3-oxo-4H-quinoxalin-6-yl)methyl]piperazin-1-yl]-N-methyl-pyridine-2-carboxamide or a pharmaceutically acceptable salt thereof.

In an aspect, there is provided a compound of Formula I which is 6-fluoro-5-[4-[(5-fluoro-2-methyl-3-oxo-4H-quinoxalin-6-yl)methyl]piperazin-1-yl]-N-methyl-pyridine-2-carboxamide crystalline form B or a pharmaceutically acceptable salt thereof.

In an aspect, there is provided a compound of Formula I which is 6-fluoro-5-[4-[(5-fluoro-2-methyl-3-oxo-4H-quinoxalin-6-yl)methyl]piperazin-1-yl]-N-methyl-pyridine-2-carboxamide crystalline form D or a pharmaceutically acceptable salt thereof.

In an aspect, there is provided a compound of Formula I which is 6-fluoro-5-[4-[(5-fluoro-2-methyl-3-oxo-4H-quinoxalin-6-yl)methyl]piperazin-1-yl]-N-methyl-pyridine-2-carboxamide mesylate, optionally as crystalline form C.

Further aspects will be apparent to one skilled in the art from reading this specification.

It is well known that blockade of the cardiac ion channel coded by human ether-n-gogo-related gene (hERG) is a risk factor in drug discovery and development. Blockage of hERG can cause safety problems such as cardiac arrhythmia. Advantageously, the compounds of Formula I have low hERG activity. In an aspect, there is provided a compound of Formula I having an IC50>10 µM. In an aspect, there is provided a compound of Formula I having an IC50>20 µM.

To minimize the risks of off-target effects, it is desirable for drug molecules to possess selectivity for a specific target. The compounds of Formula I advantageously possess selectivity for PARP1 over other members of the PARP family including PARP2, PARP3, PARP5a, and PARP6. Advantageously, the compounds of Formula I possess selectivity for PARP1 over PARP2. In an aspect, there is provided a compound of Formula I having 10-fold selectivity for PARP1 over PARP2. In an aspect, there is provided a compound of Formula I having 100-fold selectivity for PARP1 over PARP2.

Another further aspect provides for the use of a compound of Formula I in the preparation of a medicament for use as an adjunct in cancer therapy or for potentiating tumour cells for treatment with ionizing radiation or chemotherapeutic agents, or antibody-based therapies such as immunooncology or antibody-drug conjugates.

Other further aspects provide for the treatment of disease ameliorated by the inhibition of PARP1, comprising administering to a subject in need of treatment a therapeutically effective amount of a compound of Formula I, preferably in the form of a pharmaceutical composition and the treatment of cancer, comprising administering to a subject in need of treatment a therapeutically-effective amount of a compound of Formula I in combination, preferably in the form of a pharmaceutical composition, simultaneously or sequentially with ionizing radiation or chemotherapeutic agents.

In further aspects, a compound of Formula I may be used in the preparation of a medicament for the treatment of cancer which is deficient in Homologous Recombination (HR) dependent DNA DSB repair activity, or in the treatment of a patient of a cancer which is deficient in HR dependent DNA DSB repair activity, comprising administering to said patient a therapeutically-effective amount of the compound.

The HR dependent DNA DSB repair pathway repairs double-strand breaks (DSBs) in DNA via homologous mechanisms to reform a continuous DNA helix (K. K. Khanna and S. P. Jackson, Nat. Genet. 27(3): 247-254 (2001)). The components of the HR dependent DNA DSB repair pathway include, but are not limited to, ATM (NM_000051), RAD51 (NM_002875), RAD51L1 (NM_002877), RAD51C (NM_002876), RAD51L3 (NM_002878), DMC1 (NM_007068), XRCC2 (NM_005431), XRCC3 (NM_005432), RAD52 (NM_002879), RAD54L (NM_003579), RAD54B (NM_012415), BRCA1 (NM_007295), BRCA2 (NM_000059), RAD50 (NM_005732), MRE11A (NM_005590) and NBS1 (NM_002485). Other proteins involved in the HR dependent DNA DSB repair pathway include regulatory factors such as EMSY (Hughes-Davies, et al., *Cell,* 115, pp 523-535). HR components are also described in Wood, et al., *Science,* 291, 1284-1289 (2001).

A cancer which is deficient in HR dependent DNA DSB repair may comprise or consist of one or more cancer cells which have a reduced or abrogated ability to repair DNA DSBs through that pathway, relative to normal cells i.e. the activity of the HR dependent DNA DSB repair pathway may be reduced or abolished in the one or more cancer cells.

The activity of one or more components of the HR dependent DNA DSB repair pathway may be abolished in the one or more cancer cells of an individual having a cancer which is deficient in HR dependent DNA DSB repair. Components of the HR dependent DNA DSB repair pathway are well characterised in the art (see for example, Wood, et al., *Science,* 291, 1284-1289 (2001)) and include the components listed above.

In an aspect, the cancer cells may have a BRCA1 and/or a BRCA2 deficient phenotype i.e. BRCA1 and/or BRCA2 activity is reduced or abolished in the cancer cells. Cancer cells with this phenotype may be deficient in BRCA1 and/or BRCA2, i.e. expression and/or activity of BRCA1 and/or BRCA2 may be reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor (Hughes-Davies, et al., *Cell,* 115, 523-535).

BRCA1 and BRCA2 are known tumour suppressors whose wild-type alleles are frequently lost in tumours of heterozygous carriers (Jasin M., Oncogene, 21(58), 8981-93 (2002); Tutt, et al., *Trends Mol Med.,* 8 (12), 571-6, (2002)). The association of BRCA1 and/or BRCA2 mutations with breast cancer is well-characterised in the art (Radice, P. J., *Exp Clin Cancer Res.,* 21(3 Suppl), 9-12 (2002)). Amplification of the EMSY gene, which encodes a BRCA2 binding factor, is also known to be associated with breast and ovarian cancer. Carriers of mutations in BRCA1 and/or BRCA2 are also at elevated risk of certain cancers, including breast, ovary, pancreas, prostate, hematological, gastrointestinal and lung cancer.

In an aspect, the individual is heterozygous for one or more variations, such as mutations and polymorphisms, in BRCA1 and/or BRCA2 or a regulator thereof. The detection of variation in BRCA1 and BRCA2 is well-known in the art and is described, for example in EP 699 754, EP 705 903, Neuhausen, S. L. and Ostrander, E. A., Genet. Test, 1, 75-83 (1992); Chappnis, P. O. and Foulkes, W. O., *Cancer Treat Res,* 107, 29-59 (2002); Janatova M., et al., *Neoplasma,* 50(4), 246-505 (2003); Jancarkova, N., Ceska Gynekol., 68{1), 11-6 (2003)). Determination of amplification of the BRCA2 binding factor EMSY is described in Hughes-Davies, et al., *Cell,* 115, 523-535).

Mutations and polymorphisms associated with cancer may be detected at the nucleic acid level by detecting the presence of a variant nucleic acid sequence or at the protein level by detecting the presence of a variant (i.e. a mutant or allelic variant) polypeptide.

Definitions

Alkyl groups and moieties are straight or branched chain, e.g. $C_{1-8}$ alkyl, $C_{1-6}$ alkyl, $C_{1-4}$ alkyl or $C_{5-6}$ alkyl.

Examples of alkyl groups are methyl, ethyl, n-propyl, i-propyl, n-butyl, t-butyl, n-pentyl, n-hexyl, n-heptyl and n-octyl, such as methyl or n-hexyl.

Cycloalky groups are saturated cyclic alkyl groups. $C_{3-6}$ cycloalkyl is a saturated cyclic alkyl group having from 3 to 6 carbon atoms. Examples of $C_{3-6}$ cycloalkyl include cyclopropyl, cyclobutyl, cyclopentyl, and cyclohexyl. $C_{3-6}$ cycloalkyl includes $C_{3-5}$ cycloalkyl and $C_{3-4}$ cycloalkyl.

Fluoroalkyl groups are alkyl groups in which one or more H atoms is replaced with one or more fluoro atoms, e.g. $C_{1-6}$ fluoroalkyl, $C_{1-6}$ fluoroalkyl, $C_{1-4}$ fluoroalkyl or $C_{1-6}$ fluoroalkyl. Examples include fluoromethyl ($CH_2F$—), difluromethyl ($CHF_2$—), trifluoromethyl ($CF_3$—), 2,2,2-trifluoroethyl ($CF_3CH_2$—), 1,1-difluoroethyl ($CH_3CHF_2$—), 2,2-difluoroethyl ($CHF_2CH_2$—), 1-fluoroethyl ($CH_3CHF$—), and 2-fluoroethyl ($CH_2FCH_2$—).

Halo means fluoro, chloro, bromo, and iodo. In an aspect, halo is fluoro or chloro.

Alkyloxy groups are alkyl groups which are connected to the rest of the molecule via an oxygen atom. Examples of suitable $C_{1-4}$ alkyloxy groups include methoxy, ethoxy, n-propoxy, i-propoxy, n-butoxy, sec-butoxy and t-butoxy.

In this specification, unless otherwise stated, the term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In this specification, unless otherwise stated, the phrase "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject. For the avoidance of doubt, reference herein to "treatment" includes reference to curative, palliative and prophylactic treatment, and to the administration of a medicament for use in such treatment.

The compounds of Formula I may form stable pharmaceutically acceptable acid or base salts, and in such cases administration of a compound as a salt may be appropriate. Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate (mesylate), meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Non-toxic physiologically-acceptable salts are preferred, although other salts may be useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

The compounds of Formula I may have more than one chiral center, and it is to be understood that the application encompasses all individual stereoisomers, enantiomers and diastereoisomers and mixtures thereof. Thus, it is to be understood that, insofar as the compounds of Formula I can exist in optically active or racemic forms by virtue of one or more asymmetric carbon atoms, the application includes in its definition any such optically active or racemic form which possesses the above-mentioned activity. The present application encompasses all such stereoisomers having activity as herein defined.

Thus, throughout the specification, where reference is made to the compound of Formula I it is to be understood that the term compound includes diastereoisomers, mixtures of diastereoisomers, and enantiomers that are PARP1 inhibitors.

It is also to be understood that certain compounds of Formula I, and pharmaceutically salts thereof, can exist in solvated as well as unsolvated forms such as, for example, hydrated and anhydrous forms. It is to be understood that the compounds herein encompass all such solvated forms. For the sake of clarity, this includes both solvated (e.g., hydrated) forms of the free form of the compound, as well as solvated (e.g., hydrated) forms of the salt of the compound.

Formula I as described herein is intended to encompass all isotopes of its constituent atoms. For example, H (or hydrogen) includes any isotopic form of hydrogen including $^1H$, $^2H$ (D), and $^3H$ (T); C includes any isotopic form of carbon including $^{12}C$, $^{13}C$, and $^{14}C$; O includes any isotopic form of oxygen including $^{16}O$, $^{17}O$ and $^{18}O$; N includes any isotopic form of nitrogen including $^{13}N$, $^{14}N$ and $^{15}N$; F includes any isotopic form of fluorine including $^{19}F$ and $^{18}F$; and the like. In one aspect, the compounds of Formula I include isotopes of the atoms covered therein in amounts corresponding to their naturally occurring abundance. However, in certain instances, it may be desirable to enrich one or more atom in a particular isotope which would normally be present in a lower abundance. For example, $^1H$ would normally be present in greater than 99.98% abundance; however, in one aspect, a compound of any formula presented herein may be enriched in $^2H$ or $^3H$ at one or more positions where H is present. In another aspect, when a compound of any formula presented herein is enriched in a radioactive isotope, for example $^3H$ and $^{14}C$, the compound may be useful in drug and/or substrate tissue distribution assays. It is to be understood that the present application encompasses all such isotopic forms.

The compounds of Formula I, or pharmaceutically acceptable salts thereof, will normally be administered via the oral route in the form of pharmaceutical preparations comprising the active ingredient or a pharmaceutically acceptable salt or solvate thereof, or a solvate of such a salt, in a pharmaceutically acceptable dosage form. Depending upon the disorder and patient to be treated, the compositions may be administered at varying doses.

The pharmaceutical formulations of the compound of Formula I described above may be prepared for oral administration, particularly in the form of tablets or capsules, and especially involving technologies aimed at furnishing colon-targeted drug release (Patel, M. M. Expert Opin. Drug Deliv. 2011, 8 (10), 1247-1258).

The pharmaceutical formulations of the compound of Formula I described above may conveniently be administered in unit dosage form and may be prepared by any of the methods well-known in the pharmaceutical art, for example as described in Remington's Pharmaceutical Sciences, 17th ed., Mack Publishing Company, Easton, PA., (1985).

Pharmaceutical formulations suitable for oral administration may comprise one or more physiologically compatible carriers and/or excipients and may be in solid or liquid form. Tablets and capsules may be prepared with binding agents, fillers, lubricants and/or surfactants, such as sodium lauryl sulfate. Liquid compositions may contain conventional additives such as suspending agents, emulsifying agents and/or preservatives. Liquid compositions may be encapsulated in, for example, gelatin to provide a unit dosage form. Solid oral dosage forms include tablets, two-piece hard shell capsules and soft elastic gelatin (SEG) capsules. Such two-piece hard shell capsules may be made for example by filling a compound of Formula (I) into a gelatin or hydroxypropyl methylcellulose (HPMC) shell.

A dry shell formulation typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitable daily doses of the compounds of Formula I, or a pharmaceutically acceptable salt thereof, in therapeutic treatment of humans are about 0.0001-100 mg/kg body weight.

Oral formulations are preferred, particularly tablets or capsules which may be formulated by methods known to those skilled in the art to provide doses of the active compound in the range of 0.1 mg to 1000 mg.

EXAMPLES

Figure 1:
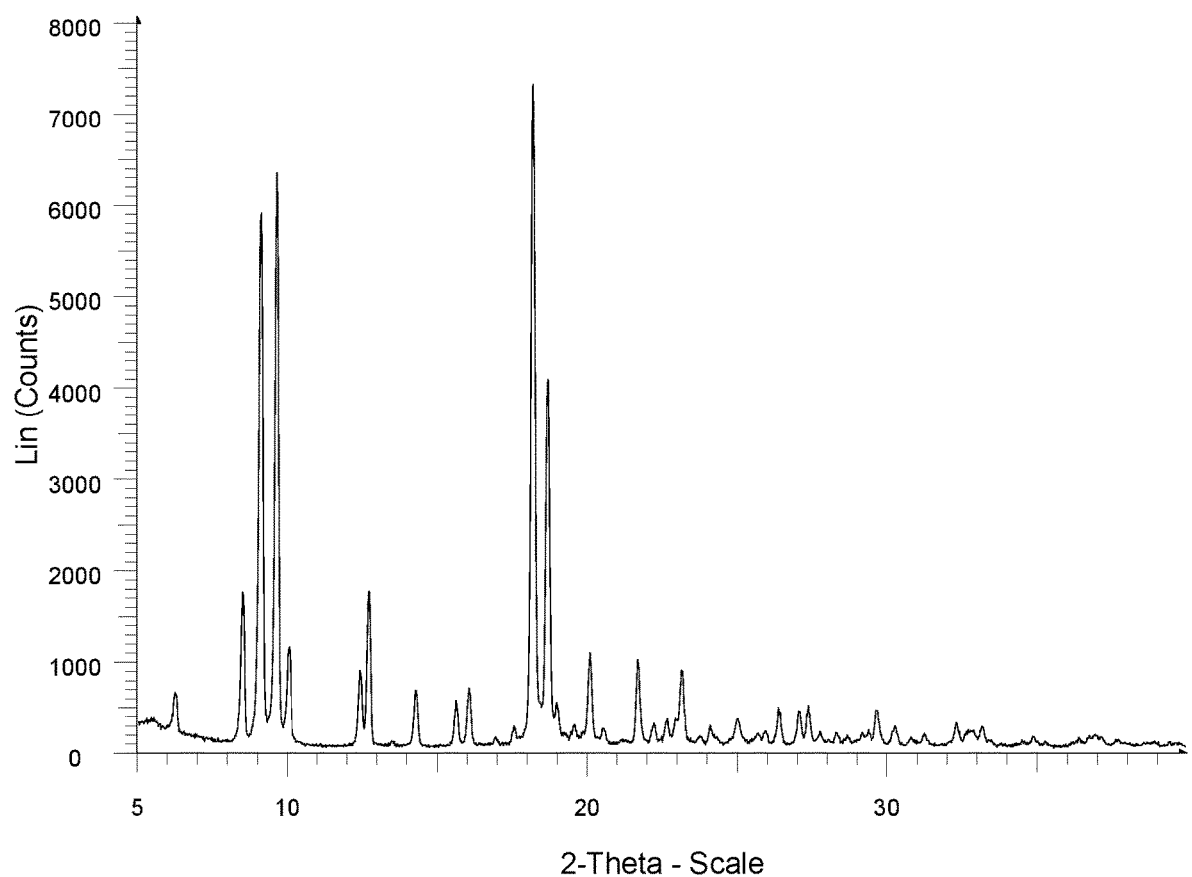
FIG. 1 shows an X-ray powder diffractogram of 6-fluoro-5-[4-[(5-fluoro-2-methyl-3-oxo-4H-quinoxalin-6-yl)methyl]piperazin-1-yl]-N-methyl-pyridine-2-carboxamide Form B

The compounds of the application will now be further explained by reference to the following non-limiting examples.

General Experimental Conditions $^1$H NMR spectra were obtained using a Bruker 300 MHz, 400 MHz or 500 MHz spectrometer at 27° C. unless otherwise noted; chemical shifts are expressed in parts per million (ppm, 6 units) and are referenced to the residual mono-$^1$H isotopologue of the solvent (CHCl$_3$: 7.24 ppm; CHDCl$_2$: 5.32 ppm; CD$_3$S(=O)CD$_2$H: 2.49 ppm). Coupling constants are given in units of hertz (Hz). Splitting patterns describe apparent multiplicities and are designated as s (singlet), d (doublet), t (triplet), q (quartet), m (multiplet) and br s (broad singlet). LC-MS was carried out using a Waters UPLC fitted with a Waters SQD mass spectrometer or Shimadzu LC-20AD LC-20XR LC-30AD with a Shimadzu 2020 mass spectrometer. Reported molecular ions correspond to [M+H]+ unless otherwise noted; for molecules with multiple isotopic patterns (Br, Cl, etc.) the reported value is the one obtained for the lowest isotope mass unless otherwise specified.

Flash chromatography was performed using straight phase flash chromatography on a SP1™ Purification system from Biotage™, CombiFlash®Rf from ISCO or on Gilson system from Thermo Fisher using normal phase silica FLASH+™ (40M, 25M or 12 M) or SNAP™ KP-Sil Cartridges (340, 100, 50 or 10), Flash Column silica-CS columns from Agela, with C18-flash columns or standard flash chromatography. In general, all solvents used were commercially available and of analytical grade. Anhydrous solvents were routinely used for reactions. Phase Separators used in the examples are ISOLUTE® Phase Separator columns. The intermediates and examples named below were named using ACD/Name 12.01 from Advanced Chemistry Development, Inc. (ACD/Labs). The starting materials were obtained from commercial sources or made via literature routes.

X-Ray Powder Diffraction (XRPD) Analysis

XRPD analysis was performed using a Bruker D8 diffractometer, which is commercially available from Bruker AXS Inc™ (Madison, Wisconsin). The XRPD spectra were obtained by mounting a sample (approximately 10 mg) of the material for analysis on a single silicon crystal wafer mount (e.g., a Bruker silicon zero background X-ray diffraction sample holder) and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 angstroms (i.e., about 1.54 angstroms). The sample was exposed for 1 second per 0.02 degree 2-theta increment (continuous scan mode) over the range 5 degrees to 40 degrees 2-theta in theta-theta mode. The running time was ~15 min for D8.

XRPD 26 values may vary with a reasonable range, e.g., in the range ±0.2° and that XRPD intensities may vary when measured for essentially the same crystalline form for a variety of reasons including, for example, preferred orientation. Principles of XRPD are described in publications, such as, for example, Giacovazzo, C. et al. (1995), Fundamentals of Crystallography, Oxford University Press; Jenkins, R. and Snyder, R. L. (1996), Introduction to X-Ray Powder Diffractometry, John Wiley & Sons, New York; and Klug, H. P. & Alexander, L. E. (1974), X-ray Diffraction Procedures, John Wiley and Sons, New York.

DSC Analysis

DSC analysis was performed on samples prepared according to standard methods using a Q SERIES™ Q1000 DSC calorimeter available from TA INSTRUMENTS® (New Castle, Delaware). A sample (approximately 2 mg) was weighed into an aluminum sample pan and transferred to the DSC. The instrument was purged with nitrogen at 50 mL/min and data collected between 22° C. and 300° C., using a dynamic heating rate of 10° C./minute. Thermal data was analyzed using standard software, e.g., Universal v.4.5A from TA INSTRUMENTS®.

The following abbreviations are used: AcOH=acetic acid; aq=aqueous; BAST=Bis(2-methoxyethyl)aminosulfur Trifluoride; Boc$_2$O=di-tert-butyl decarbonate; Boc=t-butyloxycarbonyl; CDCl$_3$=deuterated chloroform; CD$_3$OD=deuterated methanol; CH$_3$NO$_2$=nitromethane; DAST=Diethylaminosulfur trifluoride; DCE=1,2-dichloroethane; DCM=dichloromethane; DDQ=2,3-Dichloro-5,6-dicyano-1,4-benzoquinone; DEA=diethylamine; DEAD=diethyl azodicarboxylate; Dess-martin periodinane=1,1,1-Tris(acetyloxy)-1,1-dihydro-1,2-benziodoxol-3-(1H)-one; DIPEA=N,N-diisopropylethylamine; DMAP=2,6-dimethylaminopyridine; DMF=N,N-dimethylformamide; DMSO=dimethylsulfoxide; DMSO-d$_6$=deuterated dimethylsulfoxide; DPPA=diphenyl phosphorazidate; dppf=1,1'-bis(diphenylphosphino)ferrocene; DIAD=Di-isopropyl (E)-diazene-1,2-dicarboxylate; DSC=differential scanning calorimetry; DTAD=Di-tert-butyl (E)-diazene-1,2-dicarboxylate; ee=enantiomeric excess; eq.=equivalent; ESI or ES=electrospray ionization; Et$_2$O=diethyl ether; EtOAc or EA=ethylacetate; EtOH=ethanol; FA=formic acid; Grubbs catalyst (1,3-Dimesitylimidazolin-2-ylidene)(tricyclohexylphosphine)ruthenium dichloride; h=hour(s); HATU=(dimethylamino)-N,N-dimethyl(3-oxido-1H-[1,2,3]triazolo[4,5-b]pyridinyl)methaniminium hexafluorophosphate; HCl=hydrochloric acid; H$_2$O$_2$=hydrogen peroxide; HP=high pressure; IPA=isopropylalcohol; KF=potassium fluoride; LC=liquid chromatography; LiClO$_4$=lithium perchlorate; mmol=millimole; mCPBA=meta-chloroperoxybenzoic acid; MeOH=methanol; min=minute(s); MeCN or CH$_3$CN or ACN=acetonitrile; MeNO$_2$=nitromethane; MS=mass=spectrometery; NBS=N-Bromosuccinimide; NH4Cl=ammonium chloride; NMP=N-methyl-2-pyrrolidone; NMR=nuclear magnetic resonance; Pd/C=Palladium on carbon; Pd$_2$dba$_3$=Tris(dibenzylideneacetone)dipalladium (0); PdCl$_2$(dppf)=1,1'-bis(di-tert-butylphosphino)ferrocene palladium dichloride; PE=Petroleum ether; PPh$_3$=Triphenylphosphine; rt=room temperature; Rt or RT=retention time; Ruphos Pd G3=(2-Dicyclohexylphosphino-2', 6'-diisopropoxy-1,1'-biphenyl)[2-(2'-amino-1,1'-biphenyl)]palladium(II) methanesulfonate; Pd-PEPPSI™-IPent=Dichloro[1,3-bis(2,6-Di-3-pentylphenyl)imidazol-2-ylidene](3-chloropyridyl)palladium(II), [1,3-Bis(2,6-Di-3-pentylphenyl)imidazol-2-ylidene](3-chloropyridyl) dichloropalladium(II), [1,3-Bis(2,6-Di-3-pentylphenyl) imidazol-2-ylidene](3-chloropyridyl)palladium(II) dichloride; Xphos Pd G2=Chloro(2-dicyclohexylphosphino-2', 4', 6'-triisopropyl-1,1'-biphenyl)[2-(2'-amino-1,1'-biphenyl)]palladium(II), X-Phos aminobiphenyl palladium chloride; CataCXium A-Pd-G2=Chloro[(di(1-adamantyl)-N-butylphosphine)-2-(2-aminobiphenyl)]palladium(II); sat=saturated; SFC=supercritical fluid chromatography; T3P=2,4,6-tripropyl-1,3,5,2,4,6-trioxatriphosphinane 2,4,6-trioxide; PPh3O=triphenylphosphine oxide; TBTU=2-(1H-benzo[d][1,2,3]triazol-1-yl)-1,1,3,3-tetramethylisouronium tetrafluoroborate; TFA=trifluoroacetic acid; THF=tetrahydrofuran; TLC=thin layer chromatography; TMS=trimethylsilyl; Xantphos=4,5-bis(diphenylphosphino)-9,9-dimethylxanthene; CBr4=Carbon tetrabromide; HBr=hydrobromic acid; Cs2CO3=Cesium carbonate; MgSO4=Magnesium sulfate; NaHCO$_3$=Sodium bicarbonate; DDQ=2,3-Dichloro-5,6-dicyano-1,4-benzoquinone; SOCl2=Thionyl chloride; DIBAL-H=Diisobutylaluminium hydride; NH4HCO3=Ammonium bicarbonate; BINAP=2,2'-bis(diphenylphosphino)-1,1'-binaphthyl; SM=starting material; CH2Cl2=dichloromethane; Et3N=triethylamine; HCO2H=formic acid; LCMS=liquid chromatography-mass spectrometry; N2=dinitrogen; Na2SO4=sodium sulfate; NH4CO3=ammonium carbonate; UV=ultraviolet; XPhos Pd G2=Chloro(2-dicyclohexylphosphino-2', 4', 6'-triisopropyl-1,1'-biphenyl)[2-(2'-amino-1,1'-biphenyl)]palladium (II); Pd(OAc)2=palladium(II) acetate, ppt=precipitate.

Preparation of Examples

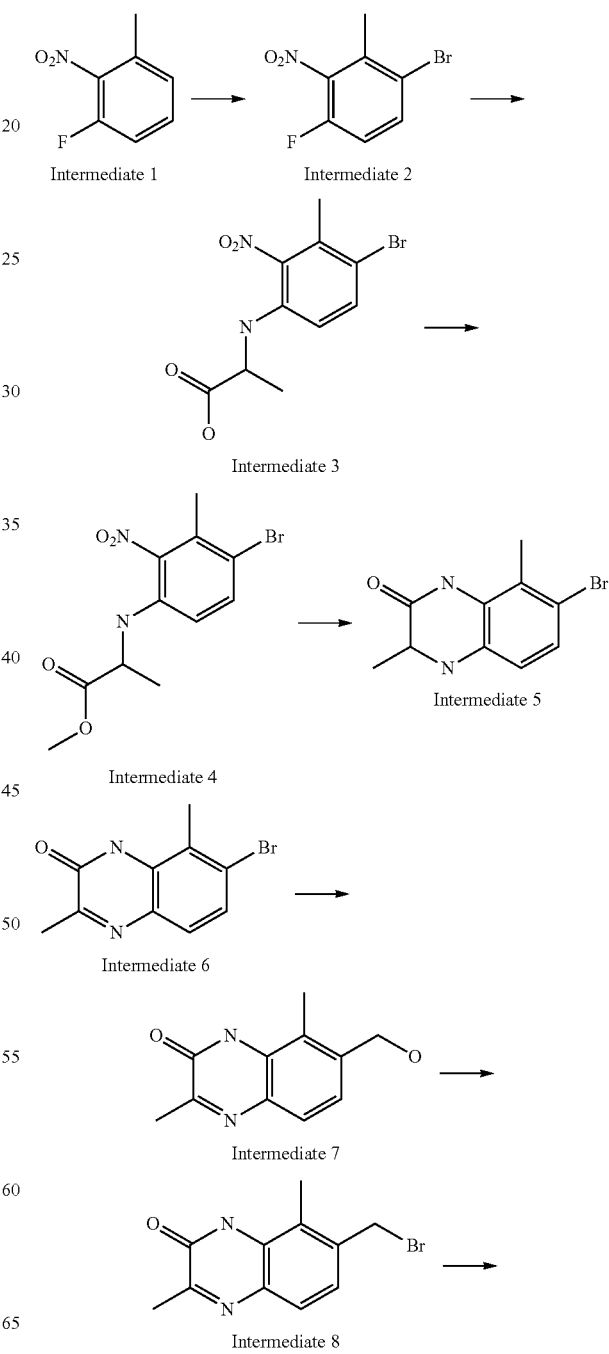

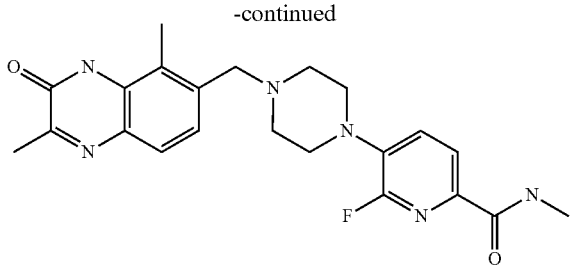

Example 1

Intermediate 2: 1-bromo-4-fluoro-2-methyl-3-nitro-benzene

To a solution of 1-fluoro-3-methyl-2-nitro-benzene (10.7 g, 68.98 mmol) (intermediate 1) in TFA (50 mL) was added conc. H$_2$SO$_4$ (20 mL) at 0° C. slowly, followed by addition of NBS (13.50 g, 75.87 mmol) in portions. After addition, the mixture was stirred at room temperature for 4 h. The resulting mixture was poured onto ice and the precipitate that formed collected by filtration, washed with water and dried under vacuum to give 1-bromo-4-fluoro-2-methyl-3-nitro-benzene (intermediate 2) as a white solid (14.80 g, 92%). 1H NMR (500 MHz, CHLOROFORM-d) 2.43 (3H, s), 7.03 (1H, t), 7.68 (1H, dd).

Intermediate 3: 2-(4-bromo-3-methyl-2-nitro-anilino)propanoic acid

A mixture of 1-bromo-4-fluoro-2-methyl-3-nitro-benzene (13.8 g, 58.97 mmol) (intermediate 2), alanine (6.30 g, 70.76 mmol) and potassium carbonate (24.45 g, 176.90 mmol) in DMF (15 mL) was stirred at 100° C. for 5 h, then the temperature was raised to 110° C. and stirred for 5 h. The mixture was poured onto ice, quenched slowly with 1M HCl aq. solution (~300 ml) at 0° C. gave a yellow suspension. The solid was collected by filtration, washed with water and dried in a vacuum oven for 2 days at 50° C. to give 2-(4-bromo-3-methyl-2-nitro-anilino)propanoic acid (14.03 g, 78%) (intermediate 3) as a yellow solid (some impurities present). 1H NMR (500 MHz, DMSO-d6) 1.39 (3H, d), 2.28 (3H, s), 4.20 (1H, quin), 6.12 (1H, br d), 6.68 (1H, d), 7.58 (1H, d), 12.98 (1H, br s); m/z (ES$^+$) [M+H]$^+$=303.

Intermediate 4: methyl 2-(4-bromo-3-methyl-2-nitro-anilino)propanoate

To a solution of 2-(4-bromo-3-methyl-2-nitro-anilino) propanoic acid (14.9 g, 49.16 mmol) (intermediate 3) in MeOH (150 mL) was added thionyl chloride (10.76 mL, 147.47 mmol) dropwise at 0° C. and the mixture was stirred at rt for overnight. LCMS indicated full conversion. The reaction mixture was quenched slowly with aq. sat. NaHCO$_3$ solution at 0° C. (~300 ml) to give an orange suspension. The solid was collected by filtration, washed with water and dried to yield the crude product (14.6 g). The solid was purified on silica gel column (eluted with 0 to 25% ethyl acetate in hexanes), to give methyl 2-(4-bromo-3-methyl-2-nitro-anilino)propanoate (intermediate 4) as a bright orange solid (12.74 g, 82%). 1H NMR (500 MHz, CHLOROFORM-d) 1.52 (3H, d), 2.43 (3H, s), 3.76 (3H, s), 4.14 (1H, quin), 5.83 (1H, br d), 6.45 (1H, d), 7.48 (1H, d); m/z (ES$^+$) [M+H]$^+$=317.

Intermediate 5: 7-bromo-3,8-dimethyl-3,4-dihydro-1H-quinoxalin-2-one

To a stirred mixture of methyl 2-(4-bromo-3-methyl-2-nitro-anilino)propanoate (11.6 g, 36.58 mmol) (intermediate 4), zinc (23.91 g, 365.77 mmol) and ammonium chloride (19.56 g, 365.77 mmol) in MeOH (100 mL) was added small ice piece at 0° C. (exothermic). The reaction mixture was then stirred for 15 min at 0° C. (ice bath). Water (2 mL) was added and the resulting mixture was stirred at r.t for 15 min. The bright orange color disappeared. The mixture was filtered through filter paper, washed with methanol and the filtrate was concentrated under vacuum. The residue was diluted with ethyl acetate and washed with water followed by brine. Organic layer was dried (anhydrous Na$_2$SO$_4$), filtered and concentrated to give a mixture of methyl 2-(2-amino-4-bromo-3-methyl-anilino)propanoate and 7-bromo-3,8-dimethyl-3,4-dihydro-1H-quinoxalin-2-one (9.8 g).

To the solution of above solid in MeOH (100 mL) was added 2 ml of 4 M HCl in dioxanes at r.t and the mixture was stirred at r.t for 10 min. Another 100 ml methanol was added (to make free suspension) and the resulting suspension was stirred at r.t for 1 hr. The mixture was diluted with ether (~200 ml), the solid was collected by filtration and washed with ether. The filtrate was concentrated until a solid precipitate and the solid was collected by filtration. This procedure was repeated couple of times to yield first portion of the product 7.2 g. The filtrate was concentrated and purified on silica gel column (eluted with 0 to 100% ethyl acetate in hexanes), and the product fraction were concentrated and resulting material was combined with above material to give 7-bromo-3,8-dimethyl-3,4-dihydro-1H-quinoxalin-2-one (9.10 g, 98%) (intermediate 5) as an off white solid. 1H NMR (500 MHz, DMSO-d6) 1.23 (3H, d), 2.24 (3H, s), 3.68 (1H, q), 3.75 (br, 1H), (6.54 (1H, d), 7.00 (1H, d), 9.77 (1H, s); m/z (ES$^+$) [M+H]$^+$=255.

Intermediate 6: 7-bromo-3,8-dimethyl-1H-quinoxalin-2-one

DDQ (8.91 g, 39.24 mmol) was added to a suspension of 7-bromo-3,8-dimethyl-3,4-dihydro-1H-quinoxalin-2-one (9.1 g, 35.67 mmol) (intermediate 5) in CH$_2$Cl$_2$ (400 mL) at room temperature and the mixture was stirred for overnight. LCMS indicated clean conversion. Solvent was removed under reduced pressure, sat. NaHCO$_3$ (~300 ml) solution was added and the yellow suspension was stirred at rt for 4 h. The solid was collected by filtration and washed with water. The solid was slurry in sat. NaHCO$_3$ (100 ml) and stirred at rt for 1 h. The solid was filtered, washed with water followed ether and dried to yield 7-bromo-3,8-dimethyl-1H-quinoxalin-2-one (7.29 g, 81%) (intermediate 6) as an off white solid. 1H NMR (500 MHz, DMSO-d6) 2.40 (3H, s), 2.50 (3H, s) (overlapped with DMSO-d6 peak), 7.32-7.65 (2H, m), 11.76 (1H, br s); m/z (ES$^+$) [M+H]$^+$=253.

Intermediate 7: 7-(hydroxymethyl)-3,8-dimethyl-1H-quinoxalin-2-one

A mixture of (tributylstannyl)methanol (1142 mg, 3.56 mmol), 7-bromo-3,8-dimethyl-1H-quinoxalin-2-one (600 mg, 2.37 mmol) (intermediate 6) and Xphos Pd G2 (280 mg, 0.36 mmol) in 1,4-dioxane (40 mL) was stirred at 80° C. for 18 h. The solvent was removed under reduced pressure and the residue was purified on silica gel column (eluted with 0 to 15% methanol in DCM) to yield 7-(hydroxymethyl)-3,8-dimethyl-1H-quinoxalin-2-one (225 mg, 46%) (intermediate 7) as an off white solid. 1H NMR (500 MHz, DMSO-d6) 2.31 (3H, s), 2.40 (3H, s), 4.58 (2H, d), 5.22 (1H, t), 7.33 (1H, d), 7.52 (1H, d), 11.53 (1H, br s); m/z (ES$^+$) [M+H]$^+$=205.

Intermediate 8: 7-(bromomethyl)-3,8-dimethyl-1H-quinoxalin-2-one 7-(hydroxymethyl)-3,8-dimethyl-1H-quinoxalin-2-one (223 mg, 1.09 mmol) (intermediate 7) in HBr (15 ml, 132.59 mmol) (48 w % in water) was stirred at 80° C. for 3.5 h. Solvent was removed under reduced pressure, diethyl ether was added to the residue, mixture was sonicated and the solid was collected to yield 7-(bromomethyl)-3,8-dimethyl-1H-quinoxalin-2-one (408 mg, 107%) (intermediate 8) as a yellow solid. 1H NMR (500 MHz, DMSO-d6) 2.36-2.45 (6H, m), 4.83 (2H, s), 7.34 (1H, d), 7.53 (1H, d), 11.63 (1H, br s); m/z (ES$^+$) [M+H]$^+$=267, 269.

Example 1: 5-[4-[(2,5-dimethyl-3-oxo-4H-quinoxalin-6-yl)methyl]piperazin-1-yl]-6-fluoro-N-methyl-pyridine-2-carboxamide To the suspension of 7-(bromomethyl)-3,8-dimethyl-1H-quinoxalin-2-one, HBr (37 mg, 0.10 mmol) (intermediate 8) was added ACN (5 ml), 6-fluoro-N-methyl-5-(piperazin-1-yl)picolinamide, 2HCl (31.5 mg, 0.10 mmol) (intermediate 32) and DIPEA (79 μl, 0.45 mmol) and the reaction mixture was stirred at 70° C. for 1 h to give a light yellow suspension. The suspension was cooled to rt, 1 drop of water was added, the solid was collected by filtration, washed with acetonitrile three time and dried to yield 5-[4-[(2,5-dimethyl-3-oxo-4H-quinoxalin-6-yl)methyl]piperazin-1-yl]-6-fluoro-N-methyl-pyridine-2-carboxamide (0.016 g, 33%) (example 1) as a yellow solid. 1H NMR (500 MHz, DMSO-d6) 2.07 (3H, br s), 2.42 (3H, br d), 2.56 (4H, br s), 2.76 (3H, br s), 3.14 (4H, br s), 3.61 (2H, br s), 7.23 (1H, br d), 7.42-7.67 (2H, m), 7.83 (1H, br d), 8.38 (1H, br s), 11.13-11.97 (1H, m); m/z (ES$^+$) [M+H]$^+$=425.

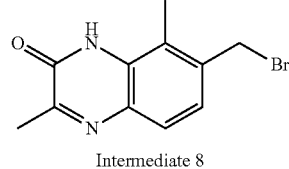

Intermediate 8

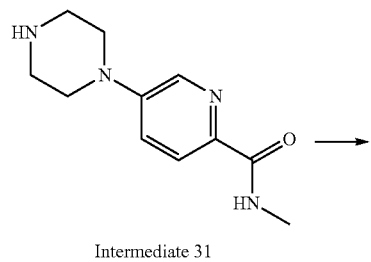

Intermediate 31

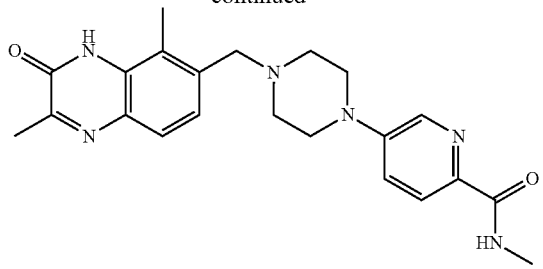

Example 2

Example 2: 5-[4-[(2,5-dimethyl-3-oxo-4H-quinoxalin-6-yl)methyl]piperazin-1-yl]-N-methyl-pyridine-2-carboxamide To a suspension of 7-(bromomethyl)-3,8-dimethylquinoxalin-2(1H)-one, HBr (240 mg, 0.69 mmol) (intermediate 8), N-methyl-5-piperazin-1-yl-pyridine-2-carboxamide, 2HCl (202 mg, 0.69 mmol) (intermediate 31) in acetonitrile (13 mL) was added DIPEA (0.723 mL, 4.14 mmol) and the resulting mixture was stirred at 70° C. for 3 h. The mixture was concentrated and purified on reverse phase (C18 column, eluted with 0 to 100% ACN/water (0.2% ammonium hydroxide)) to yield the product as a brown solid. The solid was suspended in a mixture was DCM and MeOH (2:1), concentrated to remove DCM and the solid was filtered and washed with methanol. The solid was suspended in ACN (3 ml), 0.8 ml of 1 M HCl in water was added, diluted with water (~3 ml) and lyophilized to dryness to yield the HCl salt of the product 5-[4-[(2,5-dimethyl-3-oxo-4H-quinoxalin-6-yl)methyl]piperazin-1-yl]-N-methyl-pyridine-2-carboxamide (0.033 g, 11%) (example 2). 1HNMR (500 MHz, DMSO-d6) 2.45 (3H, s), 2.54 (3H, s), 2.81 (3H, br d), 3.24-3.56 (6H, m), 3.88-4.02 (2H, m), 4.54 (2H, br s), 7.48-7.71 (3H, m), 7.97 (1H, br d), 8.33 (1H, br d), 8.59 (1H, br s), 11.28 (1H, br s), 11.48-11.95 (1H, m); m/z (ES$^+$) [M+H]$^+$=407.

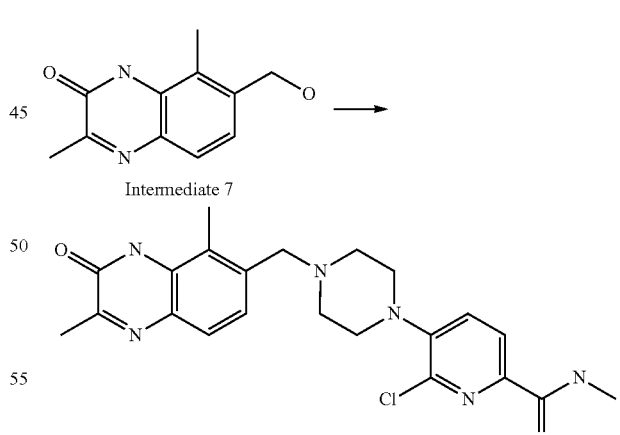

Example 3

Example 3: 6-chloro-5-[4-[(2,5-dimethyl-3-oxo-4H-quinoxalin-6-yl)methyl]piperazin-1-yl]-N-methyl-pyridine-2-carboxamide HBr in AcOH (2 mL, 0.18 mmol) (33 wt %) was added to the solution 7-(hydroxymethyl)-3,8-dimethyl-1H-quinoxalin-2-one (36 mg, 0.18 mmol) (intermediate 7) in NMP (2 mL). The resulting mixture was stirred at 100° C. for 1 hour. The solvent was removed under reduced pressure. DIPEA (0.25 mL, 1.43 mmol) was added to a solution of 6-chloro-N-methyl-5-(piperazin-1-yl)picolinamide (48 mg, 0.19 mmol) (intermediate 30) in NMP (2 mL). The resulting mixture was stirred at 100° C. for 18 hours. The crude product was purified by preparative HPLC (column: YMC-Actus Triart C18, 30*250, 5 m; Mobile Phase A: Water (0.05% NH$_3$H$_2$O), Mobile Phase B: ACN; Flow rate: 60 mL/min; Gradient: 41 B to 61 B in 7 min; 254; 220 nm. Fractions containing the desired compound were evaporated to dryness to yield 6-chloro-5-[4-[(2,5-dimethyl-3-oxo-4H-quinoxalin-6-yl)methyl]piperazin-1-yl]-N-methyl-pyridine-2-carboxamide (33.0 mg, 42%) (example 3) as a white solid. 1H NMR (400 MHz, DMSO-d6) 2.41 (3H, s), 2.43 (3H, s), 2.54-2.62 (4H, m), 2.78 (3H, d), 3.05-3.11 (4H, m), 3.62 (2H, s), 7.24 (1H, d), 7.51 (1H, d), 7.65 (1H, d), 7.92 (1H, d), 8.41-8.45 (1H, m), 11.56 (1H, s); m/z (ES$^+$) [M+H]$^+$=441.

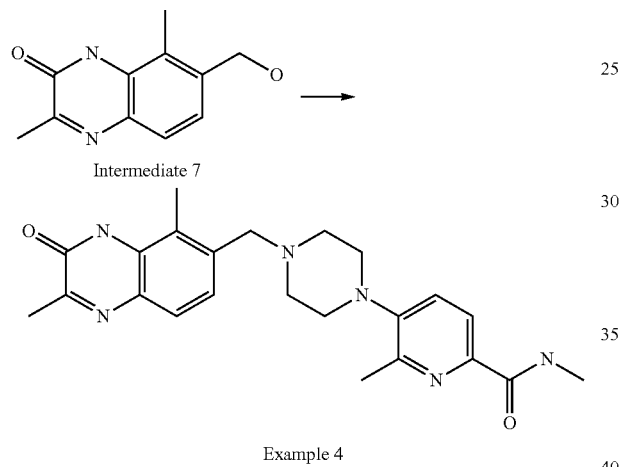

Example 4

Example 4: 5-[4-[(2,5-dimethyl-3-oxo-4H-quinoxalin-6-yl)methyl]piperazin-1-yl]-N,6-dimethyl-pyridine-2-carboxamide HBr in AcOH (2 mL, 12.15 mmol) (33 wt %) was added to the solution of 7-(hydroxymethyl)-3,8-dimethyl-1H-quinoxalin-2-one (43 mg, 0.21 mmol) (intermediate 7) in NMP (2 mL). The resulting mixture was stirred at 80° C. for 1 hour. The solvent was removed under reduced pressure. To the solution of the resulting solid in NMP (3 mL) was added DIPEA (0.25 mL, 1.43 mmol) and N,6-dimethyl-5-(piperazin-1-yl)picolinamide (42 mg, 0.18 mmol) (intermediate 33). The resulting mixture was stirred at 100° C. for 18 hours. The crude product was purified by preparative HPLC (Column: YMC-Actus Triart C18, 30*250, 5 m; using water in acetonitrile (0.05% NH$_4$OH. Fractions containing the desired compound were evaporated to dryness to afford 5-[4-[(2,5-dimethyl-3-oxo-4H-quinoxalin-6-yl)methyl]piperazin-1-yl]-N,6-dimethyl-pyridine-2-carboxamide (example 4) (18.40 mg, 24%) as a white solid. 1H NMR (400 MHz, DMSO-d6) 2.40 (3H, s), 2.43 (3H, s), 2.48 (3H, s), 2.55-2.63 (4H, m), 2.79 (3H, d), 2.87-2.94 (4H, m), 3.62 (2H, s), 7.24 (1H, d), 7.46 (1H, d), 7.51 (1H, d), 7.78 (1H, d), 8.39-8.44 (1H, m), 11.56 (1H, s); m/z (ES$^+$) [M+H]$^+$=421.

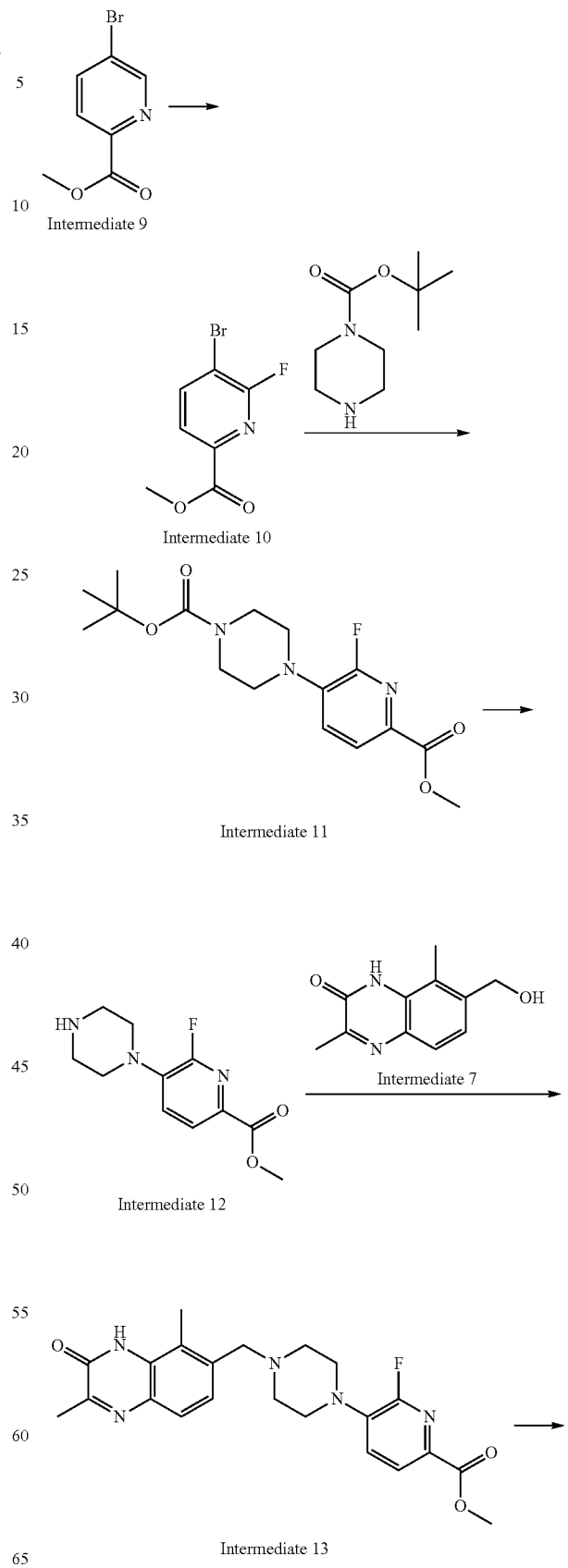

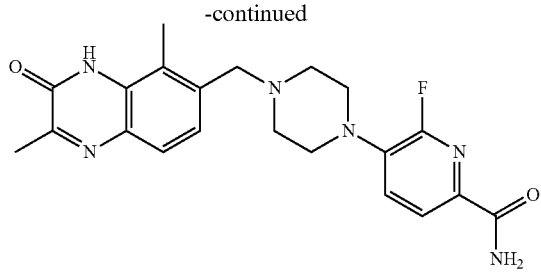

Example 5

Intermediate 10: methyl 5-bromo-6-fluoro-pyridine-2-carboxylate

A dried flask was charged with methyl 5-bromopicolinate (intermediate 9) (24 g, 111.09 mmol) in acetonitrile (300 ml), silver(II) fluoride (50 g, 342.78 mmol) was added, the mixture was stirred at r.t for 1 day under $N_2$. LCMS indicated about 70% conversion. Another batch of AgF2 (16 g) was added and the resulting mixture was continued to stir at rt for overnight. The mixture was filtered through ceilite, washed with acetonitrile followed by DCM and the filtrate was concentrated to yield a light brown solid. The residue was partitioned between DCM and sat. $NH_4Cl$ solution which gave a white suspension. The solid was filtered off and discarded. The filtrate was transferred to separating funnel, organic layer was separated, and the aqueous layer was extracted with ethyl acetate (150 ml×3). The organics were combined, dried (anhydrous $Na_2SO_4$), filtered and concentrated until solid precipitates out. The solid was collected by filtration. washed with ether, dried to yield a flaky off white solid. The combined filtrate was concentrated again and the solid was collected by filtration to give combined 19.96 g of product. The rest of the filtrate was concentrated and purified on silica gel column (eluted with 0 to 25% ethyl acetate in hexanes) to yield a second portion of the desired product as a white flaky solid 3.5 g. All the material was combined to yield methyl 5-bromo-6-fluoro-pyridine-2-carboxylate (23.46 g, 90%) (intermediate 10). 1H NMR (500 MHz, DMSO-d6) 3.89 (3H, s), 7.93 (1H, d), 8.51 (1H, t); m/z (ES$^+$) [M+H]$^+$=234.

Intermediate 11: tert-butyl 4-(2-fluoro-6-methoxycarbonyl-3-pyridyl)piperazine-1-carboxylate A mixture of tert-butyl piperazine-1-carboxylate (28.0 g, 150.37 mmol), methyl 5-bromo-6-fluoro-pyridine-2-carboxylate (intermediate 10) (23.46 g, 100.25 mmol), RuPhos Pd G3 (5.45 g, 6.52 mmol) and $Cs_2CO_3$ (82 g, 250.61 mmol) in 1,4-dioxane (400 mL) was stirred at 80° C. for overnight under $N_2$. The reaction mixture was diluted with water (250 ml) and extracted with ethyl acetate (250 ml). The organic layer was washed with brine, the water layer was extracted with ethyl acetate (100 ml×1), the organics were dried (anhydrous $Na_2SO_4$), filtered and concentrated, the residue was purified on silica gel column (eluted with 0 to 50% ethyl acetate in hexanes) to yield the product as a yellow solid, the solid was recrystallized from ethyl acetate/hexanes, filtered, washed with hexanes, dried to yield the product as a crystalline white solid (24.8 g); The filtrate was concentrated and repurified on silica gel column to yield more of the product 1.9 g. In total yield tert-butyl 4-(2-fluoro-6-methoxycarbonyl-3-pyridyl)piperazine-1-carboxylate (intermediate 11) (26.7 g, 78%). 1H NMR (500 MHz, CHLOROFORM-d) 1.51 (9H, s), 3.12-3.28 (4H, m), 3.48-3.67 (4H, m), 3.98 (3H, s), 7.27 (1H, d), 7.99 (1H, dd); m/z (ES$^+$) [M+H]$^+$=340.

Intermediate 12: methyl 6-fluoro-5-piperazin-1-yl-pyridine-2-carboxylate

To a mixture of tert-butyl 4-(2-fluoro-6-methoxycarbonyl-3-pyridyl)piperazine-1-carboxylate (1.9 g, 5.60 mmol) (intermediate 11) in MeOH (10 mL) was added HCl 4 M in dioxane (10 ml, 40.00 mmol) at rt and the resulting mixture was stirred at r.t for 1 h. The mixture was diluted with ether, the solid was collected by filtration, washed with ether and dried under vacuum to yield methyl 6-fluoro-5-piperazin-1-yl-pyridine-2-carboxylate (1.360 g, 78%) (intermediate 12) as a white solid. 1H NMR (500 MHz, DMSO-d6) 3.24 (4H, br s), 3.46 (4H, br s), 3.84 (3H, s), 7.65 (1H, br t), 7.94 (1H, br d), 9.43 (2H, br s); m/z (ES$^+$) [M+H]$^+$=240.

Intermediate 13: methyl 5-[4-[(2,5-dimethyl-3-oxo-4H-quinoxalin-6-yl)methyl]piperazin-1-yl]-6-fluoro-pyridine-2-carboxylate 7-(hydroxymethyl)-3,8-dimethylquinoxalin-2(1H)-one (223 mg, 1.09 mmol) (intermediate 7) in HBr (15 ml, 132.59 mmol) (48 w % in water) was stirred at 80° C. for 3.5 h. The solvent was removed under reduced pressure, DCM was added to the residue and concentrated to yield 7-(bromomethyl)-3,8-dimethylquinoxalin-2(1H)-one as a yellow solid.

To the solution of above solid in acetonitrile (20 ml) was added methyl 6-fluoro-5-piperazin-1-yl-pyridine-2-carboxylate, 2HCl (260 mg, 0.83 mmol) (intermediate 12), and DIPEA (1.907 ml, 10.92 mmol) at rt and the reaction mixture was stirred at 70° C. for 2 h. The mixture was cooled to rt, 0.5 ml of water was added and the solid was collected by filtration and washed with acetonitrile. The solid was dried to yield an off white solid as methyl 5-[4-[(2,5-dimethyl-3-oxo-4H-quinoxalin-6-yl)methyl]piperazin-1-yl]-6-fluoro-pyridine-2-carboxylate (0.371 g, 80%) (intermediate 13). 1H NMR (500 MHz, DMSO-d6) 2.42 (6H, m), 2.52-2.59 (4H, m), 3.20 (4H, br d), 3.61 (2H, s), 3.82 (3H, s), 7.23 (1H, d), 7.41-7.59 (2H, m), 7.91 (1H, d), 11.55 (1H, s); m/z (ES$^+$) [M+H]$^+$=426.

Example 5: 5-[4-[(2,5-dimethyl-3-oxo-4H-quinoxalin-6-yl)methyl]piperazin-1-yl]-6-fluoro-pyridine-2-carboxamide A sealed 40 ml vial was charged with methyl 5-[4-[(2,5-dimethyl-3-oxo-4H-quinoxalin-6-yl)methyl]piperazin-1-yl]-6-fluoro-pyridine-2-carboxylate (360 mg, 0.85 mmol) (intermediate 13) and ammonia (15 ml, 105.00 mmol, 7 N in methanol) and the mixture was stirred at 50° C. for overnight. LCMS indicated there was still some starting material left. The mixture was concentrated, 10 ml of 7 N ammonia in methanol was added to the solid and the mixture was stirred at 50° C. for 4 h gave a white suspension. The solid was collected by filtration, washed with hexanes and dried to yield 5-[4-[(2,5-dimethyl-3-oxo-4H-quinoxalin-6-yl)methyl]piperazin-1-yl]-6-fluoro-pyridine-2-carboxamide (example 5)(340 mg, 98%) as a white solid. 1H NMR (500 MHz, DMSO-d6) 2.40 (3H, s), 2.43 (3H, s), 2.56 (4H, br s), 3.14 (4H, br s), 3.61 (2H, s), 7.23 (1H, d), 7.46 (1H, br s), 7.48-7.58 (2H, m), 7.76 (1H, br s), 7.84 (1H, br d), 11.11-11.70 (1H, m); m/z (ES$^+$) [M+H]$^+$=411.

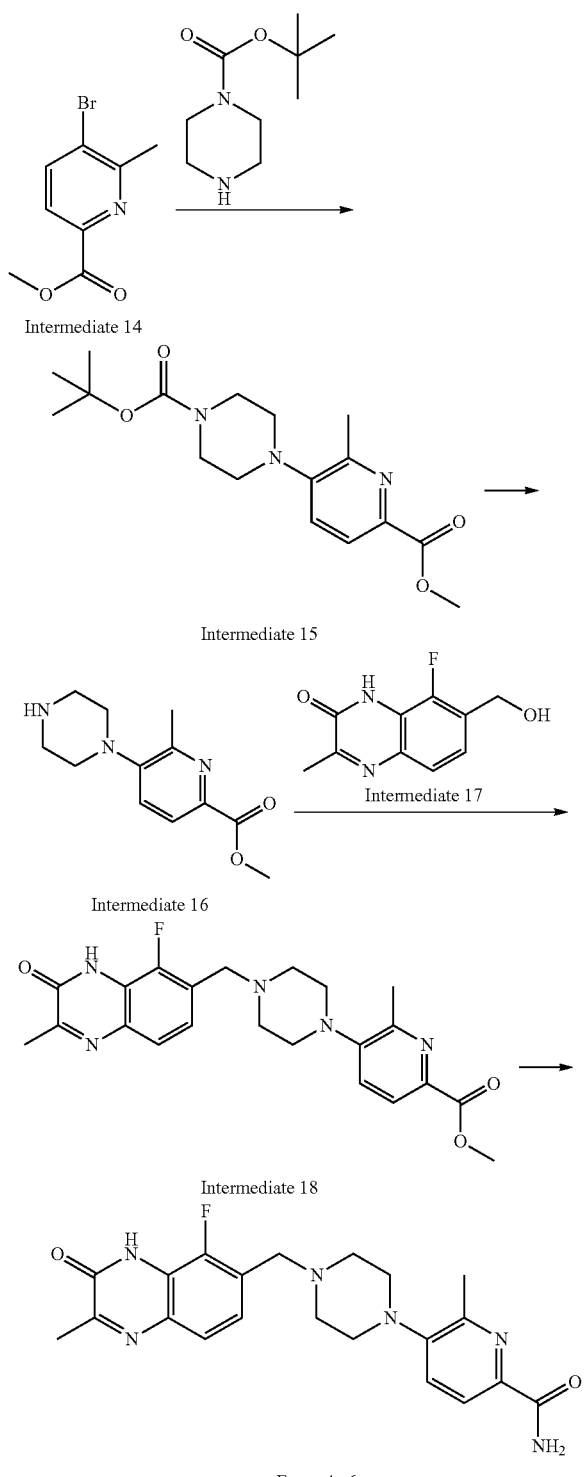

Intermediate 14

Intermediate 15

Intermediate 16

Intermediate 17

Intermediate 18

Example 6

Intermediate 15: tert-butyl 4-(6-methoxycarbonyl-2-methyl-3-pyridyl)piperazine-1-carboxylate A 40 mL vial fitted with septa cap was charged with methyl 5-bromo-6-methylpicolinate (intermediate 14) (2 g, 8.69 mmol), tert-butyl piperazine-1-carboxylate (3.24 g, 17.39 mmol), Cs$_2$CO$_3$ (5.66 g, 17.39 mmol) and Ruphos Pd G3 (0.727 g, 0.87 mmol). The reaction vial was evacuated under vacuum and filled with nitrogen. 1,4-dioxane (20 mL) was added and the reaction vial was placed in a heating block pre-heated to 80° C. and stirred for 16 h. The reaction mixture was cooled, diluted with water and extracted with ethyl acetate, the organic layer was washed with brine, dried over anhydrous Na$_2$SO$_4$ and concentrated. The residue was purified on silica gel column (eluted with 0 to 50% ethyl acetate in hexanes) to yield tert-butyl 4-(6-methoxycarbonyl-2-methyl-3-pyridyl)piperazine-1-carboxylate (intermediate 15)(2.090 g, 72%) as a light-yellow solid. 1H NMR (500 MHz, DICHLOROMETHANE-d2) 1.49 (9H, s), 2.59 (3H, s), 2.88-3.00 (4H, m), 3.55-3.65 (4H, m), 3.92 (3H, s), 7.32 (1H, d), 7.92 (1H, d); m/z (ES$^+$) [M+H]$^+$=336.

Intermediate 16: methyl 6-methyl-5-piperazin-1-yl-pyridine-2-carboxylate

4 M solution of hydrogen chloride in 1,4-dioxane (31.2 ml, 124.63 mmol) was added to a stirred solution of tert-butyl 4-(6-(methoxycarbonyl)-2-methylpyridin-3-yl)piperazine-1-carboxylate (intermediate 15) (4.18 g, 12.46 mmol) in DCM (30 mL) and the resulting solution was stirred at rt for 18 h. Solvent was removed under vacuum, the resulting solid was slurried in diethyl ether and solid was collected by filtration to give methyl 6-methyl-5-piperazin-1-yl-pyridine-2-carboxylate (intermediate 16) (3.80 g, 99%) as a light-yellow solid; m/z (ES$^+$) [M+H]$^+$=236.

Intermediate 18: methyl 5-[4-[(5-fluoro-2-methyl-3-oxo-4H-quinoxalin-6-yl)methyl]piperazin-1-yl]-6-methyl-pyridine-2-carboxylate Triphenylphosphine (1.584 g, 6.04 mmol) (4.4 g added, calculated based on PPh3 loading of 1.6 mmol/g) was added to a stirred slurry of 8-fluoro-7-(hydroxymethyl)-3-methylquinoxalin-2(1H)-one (419 mg, 2.01 mmol) (intermediate 17) and perbromomethane (1.335 g, 4.03 mmol) in DCM (40 mL) at rt. The resulting mixture was stirred for 1 h. Reaction mixture was filtered, washed with DCM and THF and the filtrate was concentrated under vacuum to yield 7-(bromomethyl)-8-fluoro-3-methylquinoxalin-2(1H)-one as a light yellow solid.

To the slurry of above freshly prepared 7-(bromomethyl)-8-fluoro-3-methylquinoxalin-2(1H)-one in acetonitrile (25 mL) was added methyl 6-methyl-5-piperazin-1-yl-pyridine-2-carboxylate, 2HCl (590 mg, 1.91 mmol) (intermediate 16), and N-ethyl-N-isopropylpropan-2-amine (1754 µl, 10.07 mmol) and the reaction was heated to 70° C. for 1 h. The reaction mixture was cooled to rt, concentrated, and quenched with sat. aqueous NaHCO$_3$ solution and stirred for 1 h. Solid was isolated by filtration and washed with water. The crude solid was purified on silica column chromatography using 0-10% MeOH in DCM to yield methyl 5-[4-[(5-fluoro-2-methyl-3-oxo-4H-quinoxalin-6-yl)methyl]piperazin-1-yl]-6-methyl-pyridine-2-carboxylate (intermediate 18) (0.263 g, 31%). 1H NMR (500 MHz, DMSO-d6) 2.40-2.49 (6H, m), 2.62 (4H, br s), 2.97 (4H, br s), 3.72 (2H, s), 3.83 (3H, s), 7.30 (1H, t), 7.44 (1H, d), 7.52 (1H, d), 7.85 (1H, d), 12.45 (1H, br s); 19F NMR (471 MHz, DMSO-d6) -135.54 (1F, s); m/z (ES$^+$) [M+H]$^+$=426.

Example 6: 5-[4-[(5-fluoro-2-methyl-3-oxo-4H-quinoxalin-6-yl)methyl]piperazin-1-yl]-6-methyl-pyridine-2-carboxamide 7 N ammonia in methanol (16.47 ml, 115.26 mmol) was added to methyl 5-[4-[(5-fluoro-2-methyl-3-oxo-4H-quinoxalin-6-yl)methyl]piperazin-1-yl]-6-methyl-pyridine-2-carboxylate (intermediate 18) (0.2452 g, 0.58 mmol) in a 40 mL scintillation vial, sealed and stirred at rt for 18 h. Additional 7 N NH$_3$ solution (15 mL) was added to the reaction mixture and stirred at 50° C. for overnight. The reaction was concentrated under vacuum, slurry in 5 mL MeOH. Solid was filtered off, washed with methanol and dried to yield 5-[4-[(5-fluoro-2-methyl-3-oxo-4H-quinoxalin-6-yl)methyl]piperazin-1-yl]-6-methyl-pyridine-2-carboxamide (Example 6)(0.151 g, 64%) as an off-white solid. 1H NMR (500 MHz, DMSO-d6) 2.42 (3H, s), 2.45-2.49 (3H, m), 2.52-2.69 (4H, m), 2.94 (4H, br s), 3.71 (2H, s), 7.29 (1H, t), 7.40-7.54 (3H, m), 7.77-7.84 (2H, m), 12.43 (1H, br s); 19F NMR (471 MHz, DMSO-d6) −135.53 (1F, s); m/z (ES$^+$) [M+H]$^+$=411.

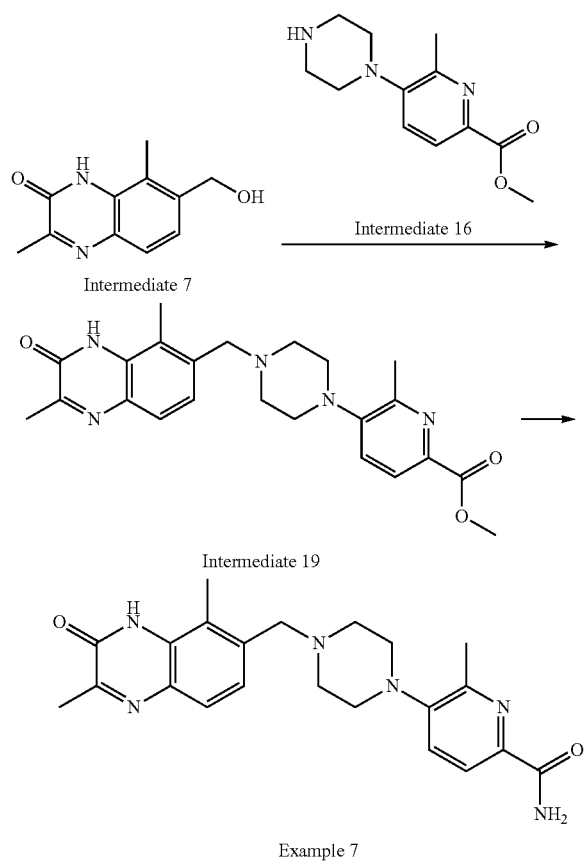 [SMILES: Cc1nc2ccc(CO)c(C)c2[nH]c1=O ; COC(=O)c1ccc(N2CCNCC2)c(C)n1 ; COC(=O)c1ccc(N2CCN(Cc3ccc4nc(C)c(=O)[nH]c4c3C)CC2)c(C)n1 ; Cc1nc(C(N)=O)ccc1N1CCN(Cc2ccc3nc(C)c(=O)[nH]c3c2C)CC1]

Intermediate 7

Intermediate 16

Intermediate 19

Example 7

Intermediate 19: methyl 5-[4-[(2,5-dimethyl-3-oxo-4H-quinoxalin-6-yl)methyl]piperazin-1-yl]-6-methyl-pyridine-2-carboxylate 7-(hydroxymethyl)-3,8-dimethylquinoxalin-2(1H)-one (intermediate 7) (223 mg, 1.09 mmol) in HBr (15 ml, 132.59 mmol) (48 w % in water) was stirred at 80° C. for 4 h. Solvent was removed under reduced pressure, DCM was added to the residue, mix was sonicated and concentrated to yield 7-(bromomethyl)-3,8-dimethylquinoxalin-2(1H)-one as a yellow solid.

To the slurry of above in acetonitrile (20 ml) was added methyl 6-methyl-5-piperazin-1-yl-pyridine-2-carboxylate, 2HCl (intermediate 16) (337 mg, 1.09 mmol), and DIPEA (1.907 ml, 10.92 mmol). The reaction mixture was stirred at 70° C. for 2 h gave clear solution. The resulting mixture was cooled to r.t, half of the solvent was removed, 0.5 ml of water was added. The solid was collected by filtration, washed with acetonitrile and dried to yield a yellow solid. This solid was purified on silica gel column (eluted with 0 to 20% methanol in DCM) to Yield methyl 5-[4-[(2,5-dimethyl-3-oxo-4H-quinoxalin-6-yl)methyl]piperazin-1-yl]-6-methyl-pyridine-2-carboxylate (intermediate 19) (213 mg, 46%) as an off white solid. 1H NMR (500 MHz, DMSO-d6) 2.41 (3H, s), 2.43 (3H, s), 2.47 (3H, s), 2.58 (4H, br s), 2.95 (4H, br s), 3.63 (2H, s), 3.82 (3H, s), 7.24 (1H, d), 7.43 (1H, d), 7.51 (1H, d), 7.84 (1H, d), 11.55 (1H, s). m/z (ES$^+$) [M+H]$^+$=422.

Example 7: 5-[4-[(2,5-dimethyl-3-oxo-4H-quinoxalin-6-yl)methyl]piperazin-1-yl]-6-methyl-pyridine-2-carboxamide A sealed 40 ml vial was charged with methyl 5-[4-[(2,5-dimethyl-3-oxo-4H-quinoxalin-6-yl)methyl]piperazin-1-yl]-6-methyl-pyridine-2-carboxylate (intermediate 19) (210 mg, 0.50 mmol) and ammonia (15 ml, 105.00 mmol, 7 N in methanol) and the reaction was stirred at 50° C. for overnight. Reaction was not complete. The mixture was concentrated, 10 ml of 7 N ammonia in methanol was added to this solid. Vial was capped and stirred at 50° C. for 4 h to give a white suspension. The mixture was cooled to rt, the solid was collected by filtration, washed with hexanes and dried to yield 5-[4-[(2,5-dimethyl-3-oxo-4H-quinoxalin-6-yl)methyl]piperazin-1-yl]-6-methyl-pyridine-2-carboxamide (example 7)(191 mg, 94%) as a white solid. 1H NMR (500 MHz, DMSO-d6) 2.41 (3H, s), 2.44 (3H, s), 2.49 (3H, s), 2.58 (4H, br s), 2.92 (4H, br s), 3.63 (2H, br s), 7.24 (1H, br d), 7.42 (1H, br s), 7.46 (1H, br d), 7.51 (1H, br d), 7.79 (2H, br d), 10.53-11.23 (1H, m); m/z (ES$^+$) [M+H]$^+$=407.

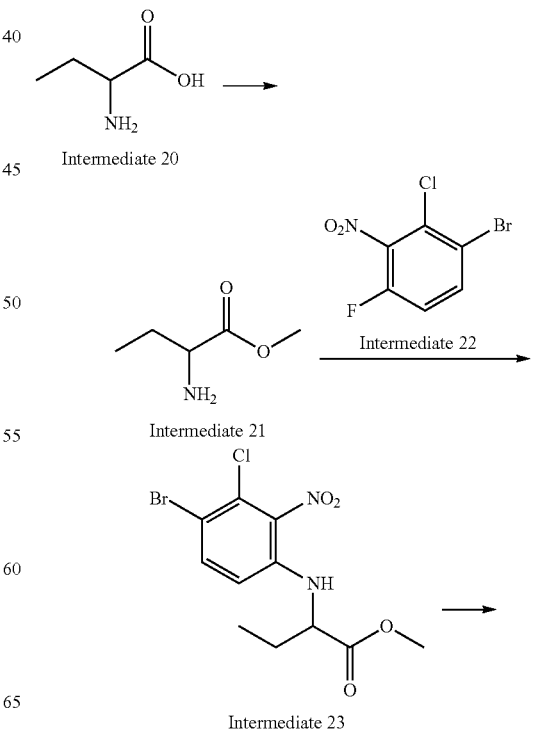

Intermediate 20

Intermediate 22

Intermediate 21

Intermediate 23

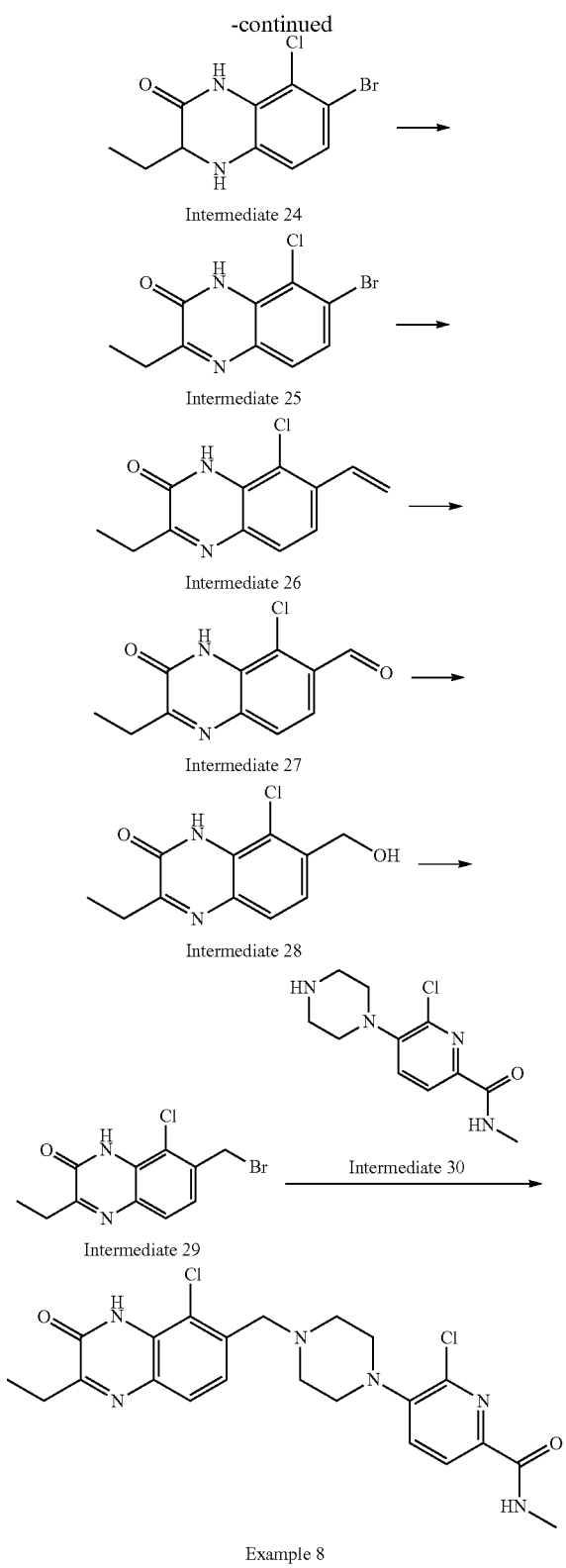

Intermediate 21: methyl 2-aminobutanoate

A slurry of 2-aminobutanoic acid (intermediate 20) (5 g, 48.49 mmol) in methanol (35 mL) was cooled in an ice bath. Thionyl chloride (11 mL, 150.72 mmol) was added dropwise to the above mixture at 0° C. The reaction was allowed to warm to rt and stirred overnight. The clear solution was concentrated to dryness to obtain a residue. The resulting solid was suspended into ether, filtered, washed with ether and dried to yield methyl 2-aminobutanoate·HCl (intermediate 21) (7.35 g, 99%) as a white solid as HCl salt. 1H NMR (500 MHz, DMSO-d6) 0.92 (3H, t), 1.76-1.93 (2H, m), 3.75 (3H, s), 3.95-4.05 (1H, m), 8.53 (3H, br s).

Intermediate 23: methyl 2-(4-bromo-3-chloro-2-nitro-anilino)butanoate

A flask was charged with methyl 2-aminobutanoate, HCl (intermediate 21)(1.811 g, 11.79 mmol), 1-bromo-2-chloro-4-fluoro-3-nitrobenzene (intermediate 22) (2.0 g, 7.86 mmol) in 1,4-dioxane (30 mL), DIPEA (8.24 mL, 47.16 mmol) was added and the mixture was stirred at 105° C. for 24 h. The mixture was concentrated, and the residue was purified on silica gel column (eluted with 0 to 50% ethyl acetate in hexanes) to yield methyl 2-(4-bromo-3-chloro-2-nitro-anilino)butanoate (intermediate 23) (2.100 g, 76%) as a bright yellow oil, turned into yellow solid after standing. 1H NMR (500 MHz, CHLOROFORM-d) 0.99 (3H, t), 1.78-1.89 (1H, m), 1.91-2.02 (1H, m), 3.77 (3H, s), 4.04 (1H, q), 5.63 (1H, br d), 6.55 (1H, d), 7.52 (1H, d); m/z (ES$^+$) [M+H]$^+$=351.

Intermediate 24: 7-bromo-8-chloro-3-ethyl-3,4-dihydro-1H-quinoxalin-2-one

Sodium dithionite (3.05 g, 17.49 mmol) was added to a stirred mixture of methyl 2-(4-bromo-3-chloro-2-nitro-anilino)butanoate (intermediate 23) (2.05 g, 5.83 mmol) in DMSO (50 mL) and the mixture was stirred at 120° C. for 3 h. The mixture was quenched with water and extracted with ethyl acetate (50 ml×2). The organic layer was dried (anhydrous Na$_2$SO$_4$), filtered, concentrated and the residue was purified on silica gel column (0 to 55% ethyl acetate in hexanes) to yield peak 1 as 7-bromo-8-chloro-3-ethyl-1H-quinoxalin-2-one (intermediate 25) (0.319 g, 19%) as a light yellow solid. 1H NMR (500 MHz, METHANOL-d4) 1.31 (3H, t), 2.89 (2H, q), 7.56-7.67 (2H, m); m/z (ES$^+$) [M+H]$^+$=287, 289 and peak 2 as 7-bromo-8-chloro-3-ethyl-3,4-dihydro-1H-quinoxalin-2-one (intermediate 24) (0.895 g, 53%) as a yellow oil which turned into a yellow solid upon standing. 1H NMR (500 MHz, CHLOROFORM-d) 1.04 (3H, t), 1.75-1.84 (1H, m), 1.85-1.93 (1H, m), 3.89 (1H, dd), 6.51 (1H, d), 7.12 (1H, d), 7.82 (1H, br s). m/z (ES$^+$) [M+H]$^+$=289, 291.

Intermediate 25: 7-bromo-8-chloro-3-ethyl-1H-quinoxalin-2-one

DDQ (772 mg, 3.40 mmol) was added to a mixture of 7-bromo-8-chloro-3-ethyl-3,4-dihydro-1H-quinoxalin-2-one (intermediate 24)(895 mg, 3.09 mmol) in 1,4-dioxane (20 mL) at rt and the resulting suspension was stirred at rt for 3 h. LCMS indicated full conversion. The solvent was removed under reduced pressure and the residue was treated with sat. NaHCO$_3$ solution, stirred at rt for 2 h. Solid was collected by filtration, washed with sat. NaHCO$_3$ solution, water and dried to yield 7-bromo-8-chloro-3-ethyl-1H-quinoxalin-2-one (intermediate 25) (780 mg, 88%) as an off white solid. 1H NMR (500 MHz, METHANOL-d4) 1.31 (3H, t), 2.89 (2H, q), 7.56-7.67 (2H, m); m/z (ES$^+$) [M+H]$^+$=287, 289.

Intermediate 26: 8-chloro-3-ethyl-7-vinyl-1H-quinoxalin-2-one

A mixture of 7-bromo-8-chloro-3-ethyl-1H-quinoxalin-2-one (intermediate 25) (1.05 g, 3.65 mmol), tributyl(vinyl) stannane (1.737 g, 5.48 mmol) and Pd(PPh$_3$)$_4$ (0.422 g, 0.37 mmol) in toluene (50 mL) was stirred at 110° C. under N$_2$ for 2 h. LCMS indicated about 44% starting material left. The mixture was continued to stir at this temperature for 4.5 h and then at 80° C. for overnight. The mixture was concentrated, purified on silica gel column (eluted with 0 to 100% ethyl acetate in hexanes) to yield low soluble desired product 8-chloro-3-ethyl-7-vinyl-1H-quinoxalin-2-one (intermediate 26) (0.850 g, 99%) as a light yellow solid. m/z (ES$^+$) [M+H]$^+$=235 (the product was contaminated by PPh$_3$O).

Intermediate 27: 5-chloro-2-ethyl-3-oxo-4H-quinoxaline-6-carbaldehyde

Osmium tetroxide in H$_2$O (0.568 mL, 0.07 mmol) was added to a solution of 8-chloro-3-ethyl-7-vinyl-1H-quinoxalin-2-one (intermediate 26) (850 mg, 3.62 mmol), 2,6-lutidine (0.844 mL, 7.24 mmol) and sodium periodate (3099 mg, 14.49 mmol) in THF (50 mL)/water (10 mL)/tert-butanol (3.46 mL, 36.22 mmol) and stirred at rt for overnight gave a yellow suspension. Reaction was concentrated, partitioned between water, sat. NH4Cl solution and DCM and the layers were separated. The aqueous layer was extracted with DCM and the combined organic layer was dried (anhydrous Na$_2$SO$_4$), filtered and concentrated. The residue was purified on silica gel column (eluted with 0 to 50% ethyl acetate in hexanes) to yield 5-chloro-2-ethyl-3-oxo-4H-quinoxaline-6-carbaldehyde (intermediate 27) (808 mg, 94%) as a light yellow solid. 1H NMR (500 MHz, CHLOROFORM-d) 1.34-1.42 (3H, m), 3.03 (2H, q), 7.88 (2H, d), 8.99-9.38 (1H, m), 10.54 (1H, s); m/z (ES$^+$) [M+H]$^+$=237.

Intermediate 28: 8-chloro-3-ethyl-7-(hydroxymethyl)-1H-quinoxalin-2-one 5-chloro-2-ethyl-3-oxo-4H-quinoxaline-6-carbaldehyde (intermediate 27) (808 mg, 3.41 mmol) in MeOH (30 mL) was cooled to 0° C. and sodium borohydride (1292 mg, 3.41 mmol) (10 wt % on basic alumina) was added in one portion. The reaction mixture was continued to stir at 0° C. for 40 min. LCMS indicated some starting material remaining. Another 213 mgs of the NaBH$_4$ (10 wt %) was added to this mixture and stirring was continued at 0° C. for 10 min. To the mixture was added 1 ml of water, concentrated and the residue was purified on silica gel column (eluted with 0 to 25% methanol in DCM) to yield 8-chloro-3-ethyl-7-(hydroxymethyl)-1H-quinoxalin-2-one (intermediate 28) (625 mg, 77%) (contaminated by 26% of over reduced side product). 1H NMR (500 MHz, METHANOL-d4) 1.27-1.34 (3H, m), 2.91 (2H, q), 4.79-4.82 (2H, m), 7.54 (1H, d), 7.75 (1H, d); m/z (ES$^+$) [M+H]$^+$=239.

Intermediate 29: 7-(bromomethyl)-8-chloro-3-ethyl-1H-quinoxalin-2-one carbon tetrabromide (1612 mg, 4.86 mmol) was added in one portion to a solution of 8-chloro-3-ethyl-7-(hydroxymethyl)-1H-quinoxalin-2-one (intermediate 28) (580 mg, 2.43 mmol) and triphenylphosphine (1275 mg, 4.86 mmol) in CH$_2$Cl$_2$ (40 mL) at 0° C. and the mixture was stirred at 0° C. for 1 h. LCMS indicated full conversion. The solvent was removed under reduced pressure and the residue was purified on silica gel column (eluted with 0 to 50% ethyl acetate in hexanes) to yield pure 7-(bromomethyl)-8-chloro-3-ethyl-1H-quinoxalin-2-one (intermediate 29)(200 mgs, 27%) as a white solid. 1H NMR (500 MHz, DMSO-d6) 1.22 (3H, t), 2.83 (2H, q), 4.85 (2H, s), 7.51 (1H, d), 7.71 (1H, d), 11.89 (1H, br s); m/z (ES$^+$) [M+H]$^+$=301, 303.

Example 8: 6-chloro-5-[4-[(5-chloro-2-ethyl-3-oxo-4H-quinoxalin-6-yl)methyl]piperazin-1-yl]-N-methyl-pyridine-2-carboxamide DIPEA (0.058 mL, 0.33 mmol) was added to a stirred suspension of 7-(bromomethyl)-8-chloro-3-ethyl-1H-quinoxalin-2-one (intermediate 29) (25 mg, 0.08 mmol) and 6-chloro-N-methyl-5-piperazin-1-yl-pyridine-2-carboxamide, 2HCl (intermediate 30) (27.2 mg, 0.08 mmol) in acetonitrile (4 mL) and the resulting mixture was stirred at 70° C. for 1.5 h gave a suspension, LCMS indicated full conversion. The solvent was removed under reduced pressure and submitted to analytical purification group which after purification gave 6-chloro-5-[4-[(5-chloro-2-ethyl-3-oxo-4H-quinoxalin-6-yl)methyl]piperazin-1-yl]-N-methyl-pyridine-2-carboxamide (example 8) (24.00 mg, 61%) as a yellow solid. Purification conditions (achiral): column (Xbridge C18 19 mm×100 mm 5 μm, mobile phase A: H$_2$O with 0.2% NH$_4$OH PH 10, mobile phase B: Acetonitrile; Gradient B %: 13-95% B over 8 min; Flow rate: 20 ml/min; Concentration: 35 mg/ml in DMSO; Loading (mg/injection): 15; Column temperature: room temperature. 1H NMR (500 MHz, DMSO-d6) 1.23 (3H, t), 2.66 (4H, br s), 2.76-2.92 (5H, m), 3.13 (4H, br s), 3.77 (2H, s), 7.44 (1H, d), 7.69 (2H, dd), 7.94 (1H, d), 8.43 (1H, q), 10.75-11.45 (1H, m); m/z (ES$^+$) [M+H]$^+$=475.

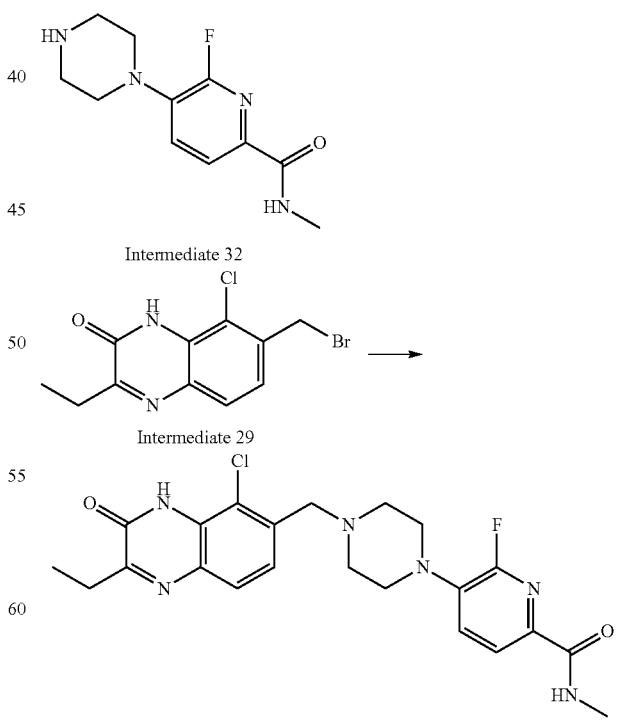

Intermediate 32

Intermediate 29

Example 9

Example 9: 5-[4-[(5-chloro-2-ethyl-3-oxo-4H-quinoxalin-6-yl)methyl]piperazin-1-yl]-6-fluoro-N-methyl-pyridine-2-carboxamide DIPEA (0.116 mL, 0.66 mmol) was added to a stirred suspension of 6-fluoro-N-methyl-5-piperazin-1-yl-pyridine-2-carboxamide, 2HCl (intermediate 32) (51.6 mg, 0.17 mmol) and 7-(bromomethyl)-8-chloro-3-ethylquinoxalin-2 (1H)-one (intermediate 29) (50 mg, 0.17 mmol) in acetonitrile (4 mL) and the resulting mixture was stirred at 70° C. for 1.5 h. LCMS indicated full conversion. The solvent was removed under reduced pressure and the residue was purified on silica gel column (eluted with 0 to 20% methanol in DCM) to give mixture of product and PPh30. Material was submitted for analytical group for purification which after purification yield 5-[4-[(5-chloro-2-ethyl-3-oxo-4H-quinoxalin-6-yl)methyl]piperazin-1-yl]-6-fluoro-N-methyl-pyridine-2-carboxamide (example 9) (47.0 mg, 62%) as a yellow solid. Purification conditions (achiral): column (Xbridge C18 19 mm×100 mm 5 µm, mobile phase A: H$_2$O with 0.2% NH$_4$OH PH 10, mobile phase B: Acetonitrile; Gradient B %: 13-95% B over 8 min; Flow rate: 20 ml/min; Concentration: 35 mg/ml in DMSO; Loading (mg/injection): 15; Column temperature: room temperature.

1H NMR (500 MHz, DMSO-d6) 1.22 (3H, t), 2.63 (4H, br s), 2.76 (3H, d), 2.82 (2H, q), 3.19 (4H, br s), 3.75 (2H, s), 7.43 (1H, d), 7.52-7.64 (1H, m), 7.70 (1H, d), 7.84 (1H, d), 8.39 (1H, q), 11.17-11.55 (1H, m); m/z (ES$^+$) [M+H]$^+$=459.

2HCl (intermediate 31) (34.0 mg, 0.12 mmol) and 7-(bromomethyl)-8-chloro-3-ethylquinoxalin-2(1H)-one (intermediate 29) (35 mg, 0.12 mmol) in acetonitrile (4 mL) and the resulting mixture was stirred at 70° C. for 1.5 h. LCMS indicated full conversion. The solvent was removed under reduced pressure and the resulting residue was submitted to analytical group for purification which after purification gave 5-[4-[(5-chloro-2-ethyl-3-oxo-4H-quinoxalin-6-yl)methyl]piperazin-1-yl]-N-methyl-pyridine-2-carboxamide (example 10) (13.00 mg, 20%) as a white solid. Purification conditions (achiral) column (Xbridge C18 19 mm×100 mm 5 µm, mobile phase A: H$_2$O with 0.2% NH4OH PH 10, mobile phase B: Acetonitrile; Gradient B % 13-95% B over 8 min; Flow rate: 20 ml/min; Concentration: 35 mg/ml in DMSO; Loading (mg/injection): 15; Column temperature: room temperature. 1H NMR (500 MHz, DMSO-d6) 1.24 (3H, t), 2.79 (3H, d), 2.86 (2H, q), 3.22-3.37 (8H, m, merged into water peak), 4.39-4.65 (2H, m), 7.46 (1H, dd), 7.57 (1H, br d), 7.79-7.90 (2H, m), 8.32 (1H, d), 8.43 (1H, br d), 11.87-12.21 (1H, m). m/z (ES$^+$) [M+H]$^+$=441.

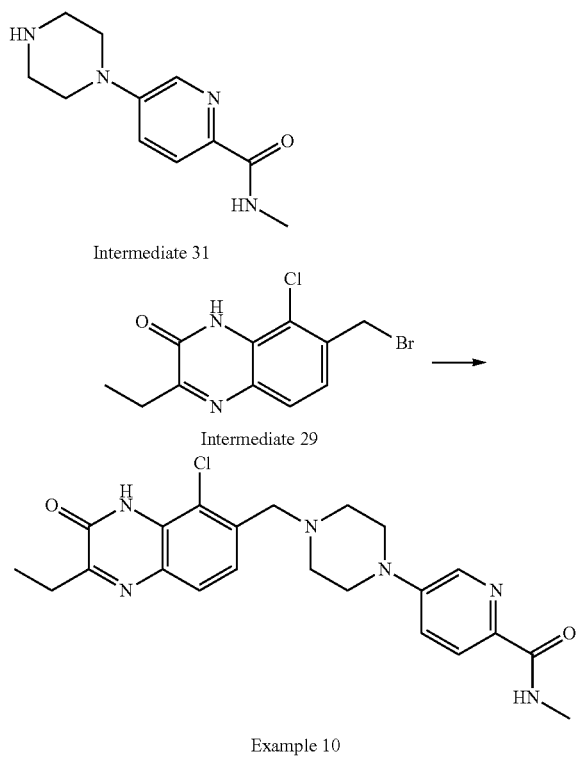

Intermediate 31

Intermediate 29

Example 10

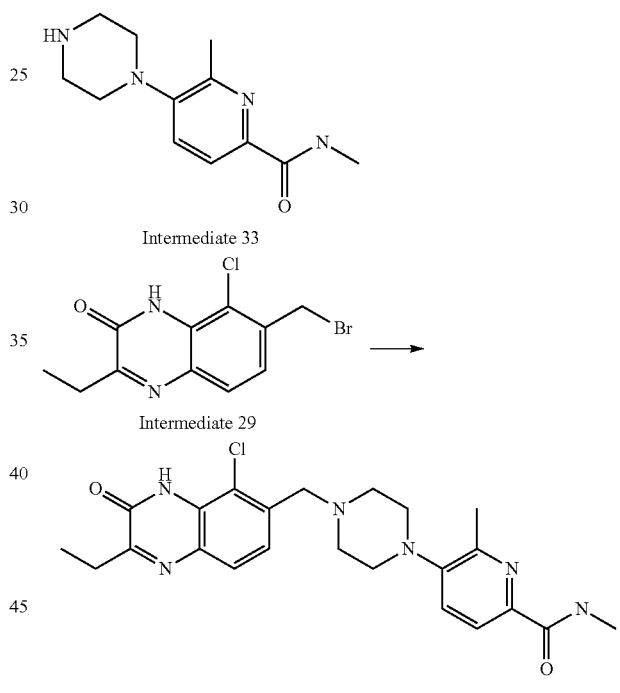

Intermediate 33

Intermediate 29

Example 11

Example 10: 5-[4-[(5-chloro-2-ethyl-3-oxo-4H-quinoxalin-6-yl)methyl]piperazin-1-yl]-N-methyl-pyridine-2-carboxamide DIPEA (0.081 mL, 0.46 mmol) was added to a stirred suspension of N-methyl-5-(piperazin-1-yl)picolinamide,

Example 11: 5-[4-[(5-chloro-2-ethyl-3-oxo-4H-quinoxalin-6-yl)methyl]piperazin-1-yl]-N,6-dimethyl-pyridine-2-carboxamide DIPEA (0.111 mL, 0.64 mmol) was added to a stirred suspension of N,6-dimethyl-5-piperazin-1-yl-pyridine-2-carboxamide, 2HCl (intermediate 33) (48.9 mg, 0.16 mmol) and 7-(bromomethyl)-8-chloro-3-ethyl-1H-quinoxalin-2-one (intermediate 29)(48 mg, 0.16 mmol) in acetonitrile (10 mL) and the resulting mixture was stirred at 70° C. for 2 h gave a suspension. LCMS indicated full conversion. The mixture was cooled to rt, solid was collected by filtration, washed with water and dried to yield 5-[4-[(5-chloro-2-ethyl-3-oxo-4H-quinoxalin-6-yl)methyl]piperazin-1-yl]-N,6-dimethyl-pyridine-2-carboxamide (example 11)(42.0 mg, 58%) as a white solid. 1H NMR (500 MHz, DMSO-d6) 1.22

(3H, t), 2.65 (4H, br s), 2.78-2.88 (5H, m), 2.95 (4H, br s), 3.38 (3H, s, overlapped water peak), 3.76 (2H, s), 7.47 (2H, dd), 7.71 (1H, d), 7.79 (1H, d), 8.42 (1H, br d), 11.59-11.99 (1H, m); m/z (ES+) [M+H]+=455.

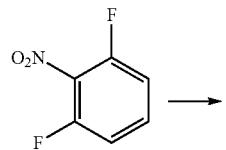

Intermediate 34

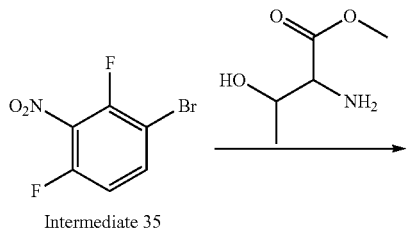

Intermediate 35

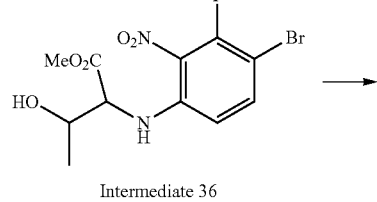

Intermediate 36

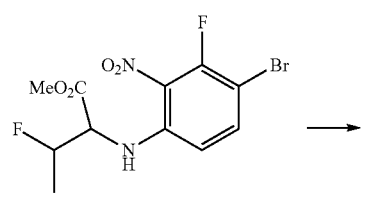

Intermediate 37

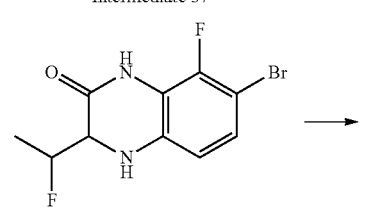

Intermediate 38

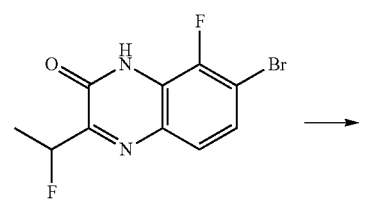

Intermediate 39

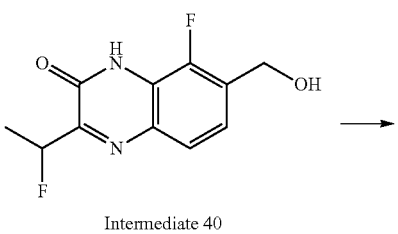

Intermediate 40

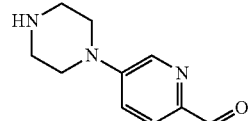

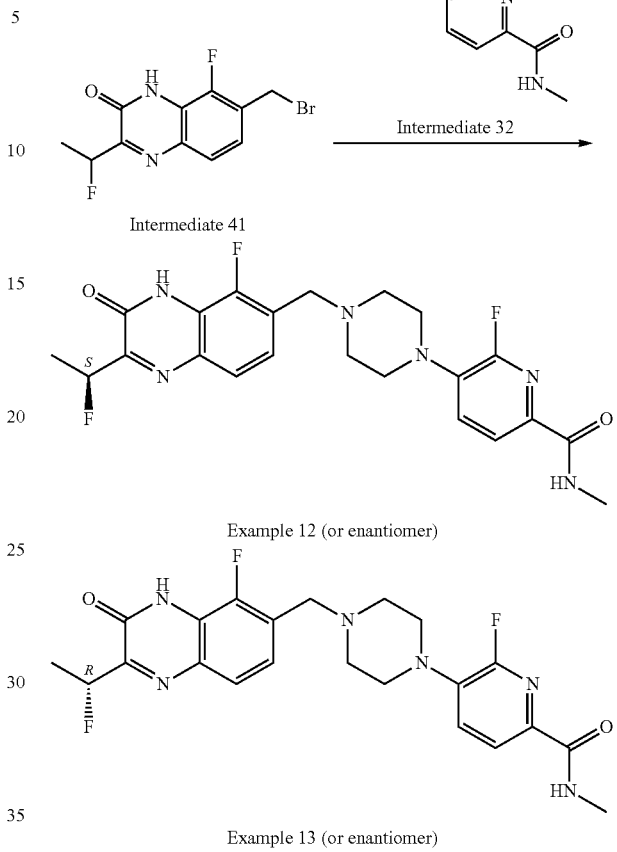

Intermediate 41

Example 12 (or enantiomer)

Example 13 (or enantiomer)

Intermediate 35: 1-bromo-2,4-difluoro-3-nitro-benzene

A mixture of 1,3-difluoro-2-nitrobenzene (intermediate 34) (19.5 g, 122.57 mmol) and NBS (26.2 g, 147.08 mmol) in sulfuric acid (150 mL) was stirred at 80° C. for overnight. LCMS indicated full conversion. The mixture was cooled to rt and slowly poured onto ice. This mixture was extracted with ethyl acetate (200 ml), the organic layer was washed with water (50 ml×2), sat. NaHCO₃ solution (50 ml×2), brine, dried (anhydrous Na₂SO₄), filtered and concentrated. The residue was purified on silica gel column (eluted with 0 to 20% ethyl acetate in hexanes) to yield 1-bromo-2,4-difluoro-3-nitro-benzene (intermediate 35) (26.8 g, 92%) as a light-yellow oil. 1H NMR (500 MHz, DMSO-d6) 7.42-7.73 (1H, in), 8.06-8.26 (1H, in); m/z (ES+) [M+H]+=238.

Intermediate 36: methyl 2-(4-bromo-3-fluoro-2-nitro-anilino)-3-hydroxy-butanoate DIPEA (8.56 mL, 48.99 mmol) was added slowly to a stirred solution of 1-bromo-2,4-difluoro-3-nitro-benzene (intermediate 35) (5.3 g, 22.27 mmol) and methyl 2-amino-3-hydroxybutanoate, HCl (4.53 g, 26.72 mmol) in 1,4-dioxane (50 mL) at r.t and the resulting mixture was stirred at 40° C. for 3 h. LCMS indicated some starting material remaining. To the mixture was added 800 mgs of the DL-threonine methyl ester Hi salt and the mixture was then continued to stir at 40° C. for overnight. The solvent was removed under reduced pressure and the residue was purified on silica gel column (eluted with 0 to 30% ethyl acetate in hexanes) to yield methyl 2-(4-bromo-3-fluoro-2-nitro-anilino)-3-hydroxy-butanoate (intermediate 36) (4.69 g, 60%) as a bright orange solid. (HNMR indicated it was a mixture of diastereomers). 1H NMR (500 MHz, CHLOROFORM-d) 1.30-1.44 (3H, m), 3.81 (3H, s), 4.00-4.22 (1H, m), 4.22-4.48 (1H, m), 6.32-6.68 (1H, m), 7.40-7.66 (2H, m); m/z (ES$^+$) [M+H]$^+$=351, 353.

Intermediate 37: methyl 2-(4-bromo-3-fluoro-2-nitro-anilino)-3-fluoro-butanoate

DAST (0.919 mL, 6.95 mmol) was added slowly over 10 min to a mixture of methyl 2-(4-bromo-3-fluoro-2-nitro-anilino)-3-hydroxy-butanoate (intermediate 36) (2.22 g, 6.32 mmol) in CH$_2$Cl$_2$ (40 mL) at 0° C., the mixture was stirred at 0° C. for 20 min. LCMS and TLC showed starting material remaining. To the mixture was added 0.4 ml of DAST and reaction was stirred another 10 min. The mixture was quenched with sat. NaHCO$_3$ solution and extracted with DCM. The organic layer was dried (anhydrous Na$_2$SO$_4$), filtered and concentrated to yield a yellow oil. Resulting residue was purified on silica gel column (eluted with 0 to 30% ethyl acetate in hexanes) to yield peak 2 as methyl 2-(4-bromo-3-fluoro-2-nitro-anilino)-3-fluoro-butanoate (1.110 g, 50%) (intermediate 37) as a yellow oil and peak 4 as starting material methyl 2-((4-bromo-3-fluoro-2-nitrophenyl)amino)-3-hydroxybutanoate (0.300 g, 13%) along with other byproduct. 1H NMR (500 MHz, CHLOROFORM-d) 1.37-1.51 (3H, m), 2.80-2.93 (0.5H, m), 3.00 (0.5H, br d), 3.75 (1.5H, s), 3.85 (1.5H, s), 4.40-4.56 (0.5H, m), 5.01-5.23 (0.5H, m), 6.43-6.58 (0.5H, m), 6.71-6.74 (0.5H, m), 7.38-7.69 (2H, m). m/z (ES$^+$) [M+H]$^+$=353.

Intermediate 38: 7-bromo-8-fluoro-3-(1-fluoroethyl)-3,4-dihydro-1H-quinoxalin-2-one To a mixture of methyl 2-(4-bromo-3-fluoro-2-nitro-anilino)-3-fluoro-butanoate (intermediate 37)(1.11 g, 3.14 mmol), Zinc (2.466 g, 37.72 mmol) and ammonium chloride (3.36 g, 62.87 mmol) in MeOH (20 mL) was added water (2 mL) and the mixture was stirred at rt for 10 min. The orange color disappeared (exothermic) and LCMS showed full conversion. The mixture was filtered, the solid washed with methanol and the filtrate was concentrated. The resulting residue was dissolved DCM and the organic was washed with water, dried (anhydrous Na$_2$SO$_4$), filtered and concentrated to yield crude product. The residue was purified on silica gel column (0 to 30% ethyl acetate in hexanes) to yield methyl 2-((2-amino-4-bromo-3-fluorophenyl)amino)-3-fluorobutanoate (0.533 g, 52%) a light yellow solid.

Above yellow solid was dissolved in 15 ml of methanol, 0.5 1 M HCl in methanol was added and the reaction was stirred at rt for 4 h. LCMS indicated full conversion. The solvent was removed, and the residue was diluted with DCM/methanol (5:1). The organic layer was washed once with 50% NaHCO$_3$ solution, dried (anhydrous Na$_2$SO$_4$) and concentrated. The residue was purified on silica gel column (eluted with 0 to 31% ethyl acetate in hexanes) to yield 7-bromo-8-fluoro-3-(1-fluoroethyl)-3,4-dihydro-1H-quinoxalin-2-one (intermediate 38) (0.337 g, 37%) as a white solid. 1H NMR (500 MHz, METHANOL-d4) 1.27-1.46 (3H, m), 4.26 (1H, dd), 4.90-5.12 (1H, m), 6.50 (1H, dd), 6.97 (1H, dd). m/z (ES$^+$) [M+H]$^+$=291, 293.

Intermediate 39: 7-bromo-8-fluoro-3-(1-fluoroethyl)-1H-quinoxalin-2-one

DDQ (289 mg, 1.27 mmol) was added to a slurry of 7-bromo-8-fluoro-3-(1-fluoroethyl)-3,4-dihydro-1H-quinoxalin-2-one (intermediate 38) (337 mg, 1.16 mmol) in CH$_2$Cl$_2$ (10 mL) and the mixture was stirred at rt for 2 h. The solvent was removed under reduced pressure, the residue was diluted with sat. NaHCO$_3$ solution (~20 ml) and the suspension was stirred at r.t for 3 h. The solid was collected by filtration, washed with water and dried to yield 7-bromo-8-fluoro-3-(1-fluoroethyl)-1H-quinoxalin-2-one (intermediate 39) (333 mg, 100%) as a white solid. 1H NMR (500 MHz, METHANOL-d4) 1.65-1.84 (3H, m), 5.87-6.18 (1H, m), 7.50-7.60 (1H, m), 7.61-7.78 (1H, m). m/z (ES$^+$) [M+H]$^+$=289, 291.

Intermediate 40: 8-fluoro-3-(1-fluoroethyl)-7-(hydroxymethyl)-1H-quinoxalin-2-one A mixture of Pd-PEPPSI™-IPent catalyst (26 mg, 0.03 mmol), (tributylstannyl)methanol (1638 mg, 5.10 mmol) and 7-bromo-8-fluoro-3-(1-fluoroethyl)-1H-quinoxalin-2-one (intermediate 39) (590 mg, 2.04 mmol) in 1,4-dioxane (25 mL) was degassed, back filled with N$_2$ and the mixture was stirred at 80° C. for 17 h. The mixture was concentrated, and the residue was purified on silica gel column (eluted with 0 to 50% ethyl acetate in hexanes (to recover the remaining SM) followed by 0 to 20% methanol in DCM) to yield 8-fluoro-3-(1-fluoroethyl)-7-(hydroxymethyl)-1H-quinoxalin-2-one (intermediate 40) (282 mg, 57%). 1H NMR (500 MHz, DMSO-d6) 1.58-1.81 (3H, m), 4.67 (2H, br d), 5.46 (1H, br t), 5.87-6.24 (1H, m), 7.33-7.48 (1H, m), 7.65 (1H, br d), 12.65-12.83 (1H, m); m/z (ES$^+$) [M+H]$^+$=241.

Intermediate 41: 7-(bromomethyl)-8-fluoro-3-(1-fluoroethyl)-1H-quinoxalin-2-one

A suspension of triphenylphosphine (1223 mg, 4.66 mmol) and 8-fluoro-3-(1-fluoroethyl)-7-(hydroxymethyl)-1H-quinoxalin-2-one (280 mg, 1.17 mmol) (intermediate 40) in CH$_2$Cl$_2$ (15 mL) was cooled to 0° C., carbon tetrabromide (1546 mg, 4.66 mmol) was added, the mixture turned clear and purple color instantly, the mixture was continued to stir at this temperature for 10 min, the mixture turned into a yellow solution, checked by LCMS which indicated full conversion (not very clean), the mixture was concentrated, purified on silica gel column (eluted with 0 to 20% methanol in DCM) to yield a major peak as 7-(bromomethyl)-8-fluoro-3-(1-fluoroethyl)-1H-quinoxalin-2-one (intermediate 41) which was contaminated by some impurities. Concentrated to yield 2.5 g of solid (theory mass was 353 mgs, assumed 100% yield to carry over to next step). m/z (ES$^+$) [M+H]$^+$=303, 305.

Example 12 and Example 13: 6-fluoro-5-[4-[[5-fluoro-2-[(1S and 1R)-1-fluoroethyl]-3-oxo-4H-quinoxalin-6-yl]methyl]piperazin-1-yl]-N-methyl-pyridine-2-carboxamide DIPEA (0.265 mL, 1.52 mmol) was added to a mixture of 7-(bromomethyl)-8-fluoro-3-(1-fluoroethyl)-1H-quinoxalin-2-one (intermediate 41) (115 mg, 0.38 mmol) and 6-fluoro-N-methyl-5-(piperazin-1-yl)picolinamide, 2HCl (94 mg, 0.30 mmol) (intermediate 32) in acetonitrile (20 mL) and the resulting mixture was stirred at 70° C. for 1 h.

LCMS indicated full conversion. The mixture was concentrated, the residue was dissolved in DMSO (~4 ml) and purified on C18 reverse phase column (eluted with 0 to 100% ACN/water/0.1% TFA). The product containing fractions were combined and lyophilized to dryness. Material was repurified on Gilson (eluted with 0 to 80% ACN/water/0.1% TFA) to yield the product 6-fluoro-5-[4-[[5-fluoro-2-[(1S and 1R)-1-fluoroethyl]-3-oxo-4H-quinoxalin-6-yl]methyl]piperazin-1-yl]-N-methyl-pyridine-2-carboxamide. The enantiomers were separated by chiral column. Chiral purification conditions: Column info: chiralpak OD 4.6 mm×100 mm 5 μm, mobile phase A: $CO_2$ (100%), mobile phase B: methanol with 0.2% $NH_4OH$, isocratic 25% B over 6 min, flow rate: 4.0 ml/min, diluent: methanol, column temperature: room temperature, Outlet pressure (SFC): N/A.

Peak 1: The white solid was diluted with water and ACN 0.1 mL of aq. 0.5M HCl was added and the mixture was lyophilized to dryness to yield isomer 1, 6-fluoro-5-[4-[[5-fluoro-2-[(1S OR 1R)-1-fluoroethyl]-3-oxo-4H-quinoxalin-6-yl]methyl]piperazin-1-yl]-N-methyl-pyridine-2-carboxamide as a HCl salt (Example 12, absolute stereochemistry not determined) (5.42 mg, 10.90 μmol, 3%) as HCl salt as a yellow solid. 1H NMR (500 MHz, DMSO-d6) 1.54-1.73 (3H, m), 2.70-2.87 (3H, m), 3.53-3.90 (8H, m), 4.57 (2H, br s), 5.79-6.21 (1H, m), 7.59-7.81 (3H, m), 7.87 (1H, d), 8.43 (1H, br d), 11.40-11.85 (1H, m), 12.78-13.14 (1H, m); m/z (ES$^+$) [M+H]$^+$=461, >95% ee.

Peak 2: The white solid was diluted with water and ACN, 0.1 mL of aq. 0.5M HCl was added and the mixture was lyophilized to dryness to yield isomer 2, 6-fluoro-5-[4-[[5-fluoro-2-[(1S OR 1R)-1-fluoroethyl]-3-oxo-4H-quinoxalin-6-yl]methyl]piperazin-1-yl]-N-methyl-pyridine-2-carboxamide as a HCl salt (Example 13, absolute stereochemistry not determined). 1H NMR (500 MHz, DMSO-d6) 1.49-1.83 (3H, m), 2.77 (3H, br d), 3.46-3.91 (8H, m), 4.56 (2H, br s), 5.80-6.26 (1H, m), 7.52-7.80 (3H, m), 7.87 (1H, br d), 8.43 (1H, br d), 11.44-11.82 (1H, m), 12.77-13.24 (1H, m); m/z (ES$^+$) [M+H]$^+$=461, >95% ee.

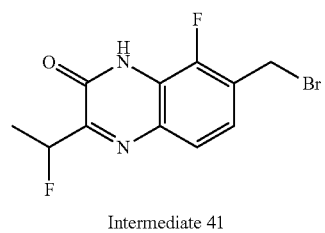

Intermediate 41

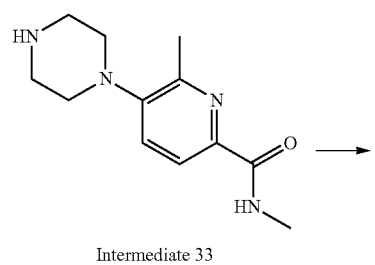

Intermediate 33

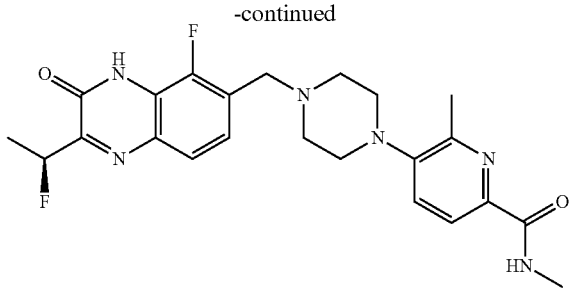

Example 14 (or enantiomer)

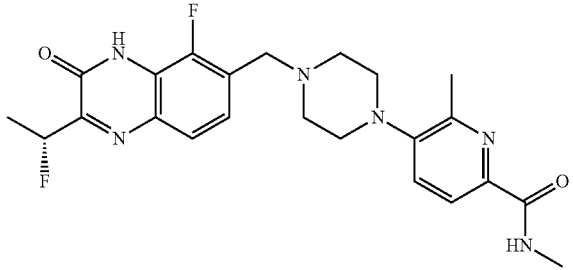

Example 15 (or enantiomer)

Example 14 and Example 15: 5-[4-[[5-fluoro-2-[(1S and 1R)-1-fluoroethyl]-3-oxo-4H-quinoxalin-6-yl]methyl]piperazin-1-yl]-N,6-dimethyl-pyridine-2-carboxamide To a suspension of 7-(bromomethyl)-8-fluoro-3-(1-fluoroethyl)quinoxalin-2(1H)-one (intermediate 41) (138 mg, 0.41 mmol) and N,6-dimethyl-5-(piperazin-1-yl)picolinamide, 2HCl (126 mg, 0.41 mmol) (intermediate 33) in acetonitrile (13 mL) was added DIPEA (429 μl, 2.46 mmol) and the resulting mixture was stirred at 70° C. for 3 h. LCMS indicated full conversion. Reaction was concentrated and the residue was purified on silica gel column (eluted with 0 to 20% methanol in DCM) to yield the racemic product 5-[4-[[5-fluoro-2-[(1S/1R)-1-fluoroethyl]-3-oxo-4H-quinoxalin-6-yl]methyl]piperazin-1-yl]-N,6-dimethyl-pyridine-2-carboxamide as a light yellow solid (169 mgs). Enantiomers were separated by chiral separation. Chiral purification conditions: Column info: chiralpak OD 21.2 mm×250 mm 5 μm, mobile phase A: $CO_2$ (100%), mobile phase B: methanol with 0.2% $NH_4OH$, isocratic 25% B over 12 min, flow rate: 70.0 ml/min, concentration: 8.45 mg/ml in methanol, loading: 4.23 mg/injection, column temperature: room temperature, Outlet pressure (SFC): N/A.

After chiral separation, each isomer was repurified on reverse phase column (eluted with 0 to 60% ACN/water/0.2% ammonium hydroxide) to yield;

Peak 1: 5-[4-[[5-fluoro-2-[(1S OR 1R)-1-fluoroethyl]-3-oxo-4H-quinoxalin-6-yl]methyl]piperazin-1-yl]-N,6-dimethyl-pyridine-2-carboxamide, isomer 1 (example 14, absolute stereochemistry not determined) (30.7 mg, 0.067 mmol, 16%) as a white solid. 1H NMR (500 MHz, DMSO-d6) 1.40-1.70 (3H, m), 2.48 (3H, s), 2.54-2.69 (4H, m), 2.79 (3H, d), 2.94 (4H, br s), 3.74 (2H, s), 5.83-6.22 (1H, m), 7.17-7.41 (1H, m), 7.47 (1H, d), 7.65 (1H, d), 7.78 (1H, d), 8.40 (1H, br d), 11.65-12.88 (1H, m); m/z (ES$^+$) [M+H]$^+$=457; >98% ee.

Peak 2: 5-[4-[[5-fluoro-2-[(1S OR 1R)-1-fluoroethyl]-3-oxo-4H-quinoxalin-6-yl]methyl]piperazin-1-yl]-N,6-dimethyl-pyridine-2-carboxamide, isomer 2 (example 15, absolute stereochemistry not determined) (37 mg, 0.081 mmol, 20%) as a white solid. 1H NMR (500 MHz, CHLOROFORM-d) 1.68-1.88 (3H, m), 2.51 (3H, s), 2.71 (4H, br s), 2.86-3.12 (7H, m), 3.81 (2H, s), 5.92-6.29 (1H, m), 7.34 (1H, d), 7.44 (1H, t), 7.76 (1H, d), 7.95 (1H, br d), 7.99 (1H, d), 10.24 (1H, br s); m/z (ES+) [M+H]+=457; 94.5% ee.

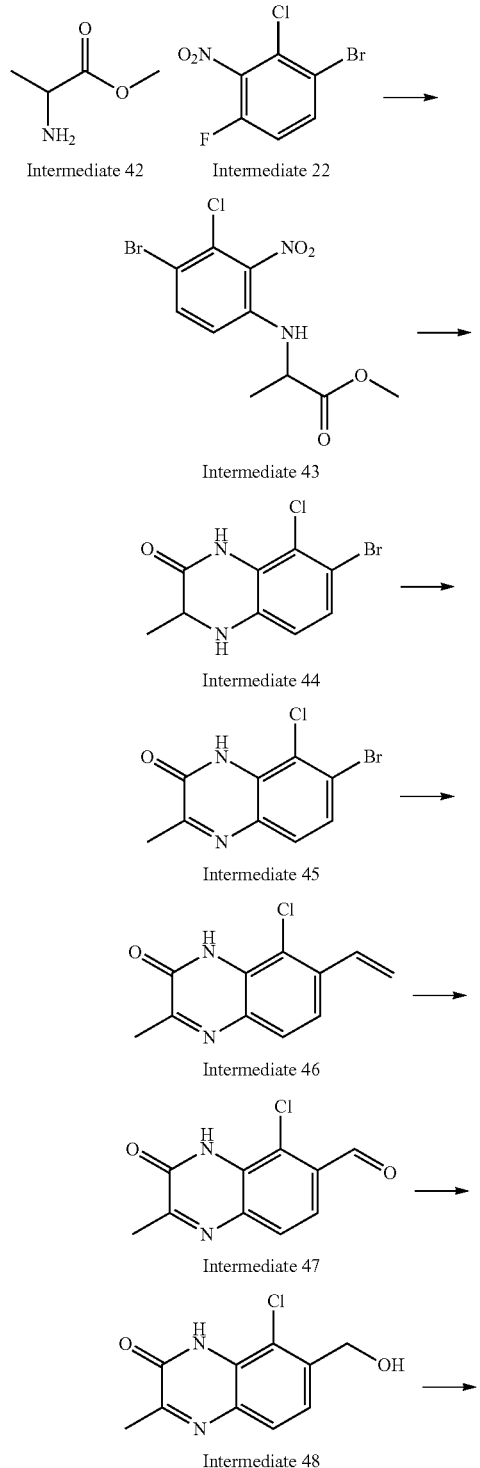

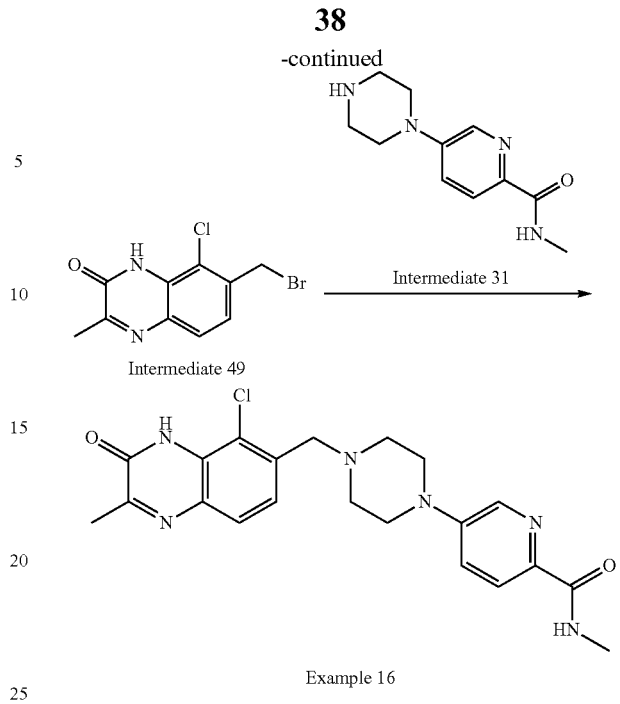

Intermediate 43: methyl 2-(4-bromo-3-chloro-2-nitro-anilino)propanoate

A flask was charged with methyl alaninate, HCl (intermediate 42) (1.851 g, 13.26 mmol) and 1-bromo-2-chloro-4-fluoro-3-nitrobenzene (intermediate 22) (2.25 g, 8.84 mmol) in 1,4-dioxane (70 mL). DIPEA (9.27 mL, 53.06 mmol) was added and the mixture was stirred at 105° C. for 24 h gave a brown solution. LCMS showed reaction was complete. The mixture was concentrated, and the residue was purified on silica gel column (eluted with 0 to 30% ethyl acetate in hexanes) to yield methyl 2-(4-bromo-3-chloro-2-nitro-anilino)propanoate (intermediate 43) (2.120 g, 71%) as a bright yellow oil, turned into yellow solid after standing. 1H NMR (500 MHz, CHLOROFORM-d) 1.52 (3H, d), 3.77 (3H, s), 6.53 (1H, d), 7.15 (1H, t), 7.53 (1H, d), 7.78 (1H, dd); m/z (ES+) [M+H]+=337.

Intermediate 44: 7-bromo-8-chloro-3-methyl-3,4-dihydro-1H-quinoxalin-2-one

Sodium dithionite (3.28 g, 18.84 mmol) was added to a stirred solution of methyl 2-(4-bromo-3-chloro-2-nitro-anilino)propanoate (intermediate 43) (2.12 g, 6.28 mmol) in DMSO (50 mL) and the mixture was stirred at 120° C. for 5 h. LCMS and TLC indicated full conversion. The mixture was quenched with water and extracted with ethyl acetate (50 mL×2). The organic layer was dried (anhydrous Na2SO4), filtered, concentrated and the residue was purified on silica gel column (0 to 55% ethyl acetate in hexanes) to yield 7-bromo-8-chloro-3-methyl-1H-quinoxalin-2-one (intermediate 45) (0.055 g, 3%). m/z (ES+) [M+H]+ 273, 275 and 7-bromo-8-chloro-3-methyl-3,4-dihydro-1H-quinoxalin-2-one (intermediate 44) (0.190 g, 11%). m/z (ES+) [M+H]+=275, 277.

Intermediate 45: 7-bromo-8-chloro-3-methyl-1H-quinoxalin-2-one

DDQ (157 mg, 0.69 mmol) was added to a mixture of 7-bromo-8-chloro-3-methyl-3,4-dihydro-1H-quinoxalin-2- one (intermediate 44) (190 mg, 0.69 mmol) in 1,4-dioxane (10 mL) and the resulting mixture was stirred at rt for overnight, LCMS indicated full conversion. The mixture was concentrated and the residue was treated with sat. NaHCO$_3$ solution. Mixture was stirred at rt for 4, solid was isolated by filtration, washed with sat. NaHCO$_3$ solution and water. The solid was then purified on silica gel column (eluted with 0 to 20% methanol in DCM) to yield 7-bromo-8-chloro-3-methyl-1H-quinoxalin-2-one (intermediate 45) (122 mg, 65%) as a yellow solid. m/z (ES$^+$) [M+H]$^+$=273, 275.

Intermediate 46: 8-chloro-3-methyl-7-vinyl-1H-quinoxalin-2-one

A mixture of 7-bromo-8-chloro-3-methyl-1H-quinoxalin-2-one (intermediate 45) (122 mg, 0.45 mmol), tetrakis(triphenylphosphine)palladium(0) (51.5 mgs, 0.04 mmol) and tributyl(vinyl)stannane (212 mg, 0.67 mmol) in toluene (15 ml) was stirred at 110° C. under N$_2$ for 16 h. LCMS indicated reaction completion. The mixture was concentrated, and residue was purified on silica gel column (eluted with 0 to 16% methanol in DCM) to yield 8-chloro-3-methyl-7-vinyl-1H-quinoxalin-2-one (intermediate 46) (98 mg, 100%) as a brown solid. (contaminated by PPh3O). m/z (ES$^+$) [M+H]$^+$=221.

Intermediate 47: 5-chloro-2-methyl-3-oxo-4H-quinoxaline-6-carbaldehyde

Osmium tetroxide in H$_2$O (0.1 mL, 0.01 mmol) was added to a solution of 8-chloro-3-methyl-7-vinyl-1H-quinoxalin-2-one (140 mg, 0.63 mmol) (intermediate 46), 2,6-lutidine (0.148 ml, 1.27 mmol) and sodium periodate (543 mg, 2.54 mmol) in THF (10 mL)/water (2 mL)/tert-butanol (0.607 mL, 6.34 mmol) and stirred at rt for overnight gave a yellow suspension. LCMS and TLC indicated there was still starting material remained. To the mixture was added THF (10 ml)/water (2.000 ml), 200 mgs of sodium periodate, 0.3 ml of osmium tetroxide and the mixture was continued to stir at rt for 5 h. LCMS indicated full conversion. Reaction was diluted with water, sat. NH4Cl solution was added and extracted with DCM. The combined organic layer was dried (anhydrous Na$_2$SO$_4$), filtered and concentrated. The residue was purified on silica gel column (eluted with 0 to 20% methanol in DCM) to yield 5-chloro-2-methyl-3-oxo-4H-quinoxaline-6-carbaldehyde (intermediate 47) (141 mg, 100%) as a yellow solid. (not very pure, carried over to the next step). m/z (ES$^+$) [M+H]$^+$=223.

Intermediate 48: 8-chloro-7-(hydroxymethyl)-3-methyl-1H-quinoxalin-2-one

Sodium borohydride (23.96 mg, 0.63 mmol) was added to a cooled solution of 5-chloro-2-methyl-3-oxo-4H-quinoxaline-6-carbaldehyde (intermediate 47) (141 mg, 0.63 mmol) in a mixture of MeOH (16 mL) and DCM (8.00 mL) was cooled to 0° C. and the mixture was continued to stir at 0° C. for 1 h. LCMS indicated full conversion. To the mixture was added 1 ml of water, concentrated and the residue was purified on silica gel column (eluted with 40 to 100% ethyl acetate in hexanes; then 0 to 20% methanol in DCM) to yield 8-chloro-7-(hydroxymethyl)-3-methyl-1H-quinoxalin-2-one (intermediate 48) (142 mg, 100%) as a yellow solid; 1H NMR (500 MHz, DMSO-d6) 2.42 (3H, s), 4.65 (2H, br d), 5.53 (1H, br t), 7.46 (1H, br d), 7.69 (1H, br d), 11.77 (1H, br s); m/z (ES$^+$) [M+H]$^+$=225.

Intermediate 49: 7-(bromomethyl)-8-chloro-3-methyl-1H-quinoxalin-2-one 8-chloro-7-(hydroxymethyl)-3-methyl-1H-quinoxalin-2-one (intermediate 48) (142 mg, 0.63 mmol) and triphenylphosphine (332 mg, 1.26 mmol) in CH$_2$Cl$_2$ (20 ml) was cooled to 0° C. Perbromomethane (419 mg, 1.26 mmol) was added in one portion and the mixture was stirred at 0° C. for 1 h and at rt for 2 h. LCMS indicated no progress. To the mixture was added a second portion of triphenylphosphine (332 mg, 1.26 mmol) and perbromomethane (419 mg, 1.26 mmol) at rt and the mixture was stirred for 1 h. LCMS indicated full conversion. The solvent was removed under reduced pressure and the residue was purified on silica gel column (eluted with 0 to 100% ethyl acetate in hexanes) to yield the product 7-(bromomethyl)-8-chloro-3-methyl-1H-quinoxalin-2-one as a yellow solid (intermediate 49) (32 mgs, 18%). Further elution with 20% methanol in DCM gave the second portion 100 mgs (55%) of the product as a brown solid (47% purity). m/z (ES$^+$) [M+H]$^+$=287, 289.

Example 16: 5-[4-[(5-chloro-2-methyl-3-oxo-4H-quinoxalin-6-yl)methyl]piperazin-1-yl]-N-methyl-pyridine-2-carboxamide DIPEA (0.053 mL, 0.31 mmol) was added to a mixture of N-methyl-5-(piperazin-1-yl)picolinamide, 2HCl (22.43 mg, 0.08 mmol) (intermediate 31) and 7-(bromomethyl)-8-chloro-3-methyl-1H-quinoxalin-2-one (intermediate 49)(22 mg, 0.08 mmol) in acetonitrile (4 mL) and the resulting suspension was stirred at 70° C. for 1 h. LCMS indicated full conversion. The mixture was concentrated, the residue was dissolved in DMSO and purified on reverse phase C18 column (eluted with 0 to 100% ACN/water/0.1% TFA). The fractions containing pure product were lyophilized to dryness to yield 5-[4-[(5-chloro-2-methyl-3-oxo-4H-quinoxalin-6-yl)methyl]piperazin-1-yl]-N-methyl-pyridine-2-carboxamide (20 mg, 56%). 1 mL of 2M HCl in ether was added and the solvent was removed under vacuum to give the corresponding HCl salt as a yellow solid (example 16). 1H NMR (500 MHz, METHANOL-d4) 2.96-3.03 (3H, m), 3.48-3.86 (6H, m), 4.04-4.41 (2H, m), 4.78 (2H, s), 4.86 (3H, d, merged into water peak), 7.74 (1H, d), 7.84 (1H, d), 8.14 (1H, dd), 8.31 (1H, d), 8.47 (1H, d); m/z (ES$^+$) [M+H]$^+$=427.

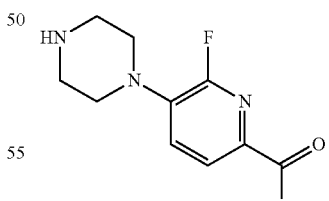

Intermediate 32

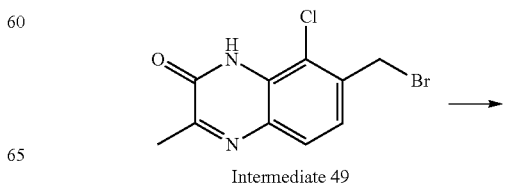

Intermediate 49

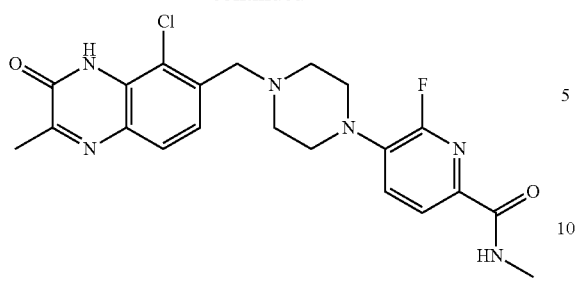

Example 17

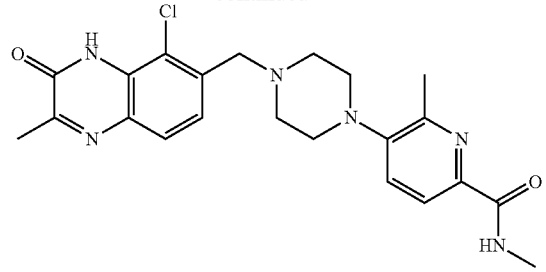

Example 18

Example 17: 5-[4-[(5-chloro-2-methyl-3-oxo-4H-quinoxalin-6-yl)methyl]piperazin-1-yl]-6-fluoro-N-methyl-pyridine-2-carboxamide DIPEA (0.061 mL, 0.35 mmol) was added to a mixture of 6-fluoro-N-methyl-5-(piperazin-1-yl)picolinamide, 2HCl (intermediate 32) (27.1 mg, 0.09 mmol) and 7-(bromomethyl)-8-chloro-3-methyl-1H-quinoxalin-2-one (intermediate 49) (50 mg, 0.09 mmol) (around 50% purity) in acetonitrile (5 mL) and the resulting solution was stirred at 70° C. for 1 h. LCMS indicated full conversion. The mixture was concentrated, and the residue was dissolved in DMSO and purified on a reverse phase C18 column (eluted with 0 to 100% ACN/water/0.1% TFA), then purified a second time on a reverse phase C18 column (eluted with 0 to 100% ACN/water/0.1% TFA). Material was finally purified a third time on reverse phase column (eluted with 0 to 100% ACN/water/ammonium hydroxide, PH~10) to yield 5-[4-[(5-chloro-2-methyl-3-oxo-4H-quinoxalin-6-yl)methyl]piperazin-1-yl]-6-fluoro-N-methyl-pyridine-2-carboxamide (example 17) (16.50 mg, 43%) as a white solid. 1H NMR (500 MHz, DMSO-d6) 2.37-2.47 (3H, m), 2.63 (4H, br s), 2.76 (3H, d), 3.13-3.23 (4H, m), 3.74 (2H, s), 7.45 (1H, d), 7.57 (1H, dd), 7.68 (1H, d), 7.84 (1H, d), 8.39 (1H, br d), 10.71-12.11 (1H, m); m/z (ES$^+$) [M+H]$^+$=445.

Example 18: 5-[4-[(5-chloro-2-methyl-3-oxo-4H-quinoxalin-6-yl)methyl]piperazin-1-yl]-N,6-dimethyl-pyridine-2-carboxamide DIPEA (0.061 mL, 0.35 mmol) was added to a mixture of N,6-dimethyl-5-(piperazin-1-yl)picolinamide, 2HCl (intermediate 33) (26.7 mg, 0.09 mmol) and 7-(bromomethyl)-8-chloro-3-methyl-1H-quinoxalin-2-one (50 mg, 0.09 mmol) (intermediate 49, ~50% purity) in acetonitrile (5 mL) and the resulting solution was stirred at 70° C. for 1 hr. LCMS indicated full conversion. The mixture was concentrated, the residue was dissolved in DMSO and the residue was purified on reverse phase C18 column (eluted with 0 to 100% ACN/water/0.1% TFA). After concentration of the fraction, the residue was repurified on reverse phase C18 column (eluted with 0 to 100% ACN/water/ammonium hydroxide, PH-10). The pure fractions were lyophilized to dryness to yield 5-[4-[(5-chloro-2-methyl-3-oxo-4H-quinoxalin-6-yl)methyl]piperazin-1-yl]-N,6-dimethyl-pyridine-2-carboxamide (example 18) (18.4 mg, 48%) as free base. 1H NMR (500 MHz, METHANOL-d4) 2.53 (6H, d), 2.76 (4H, br s), 2.94 (3H, s), 3.04 (4H, br t), 3.86 (2H, s), 7.48 (1H, d), 7.51-7.60 (1H, m), 7.69 (1H, d), 7.86 (1H, d); m/z (ES$^+$) [M+H]$^+$=441.

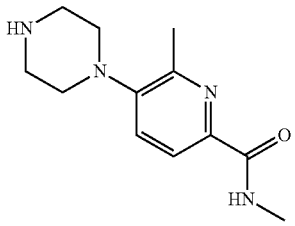

Intermediate 33

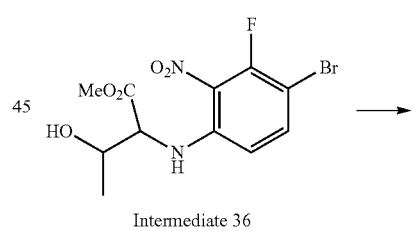

Intermediate 36

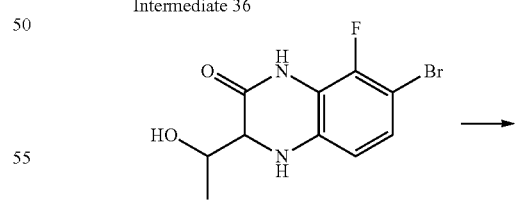

Intermediate 50

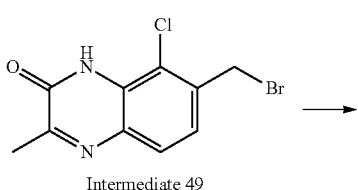

Intermediate 49

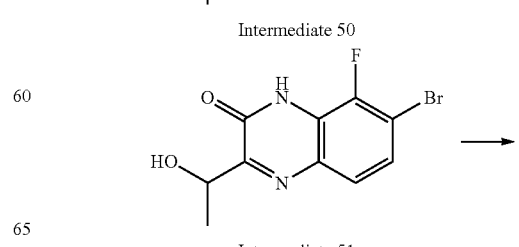

Intermediate 51

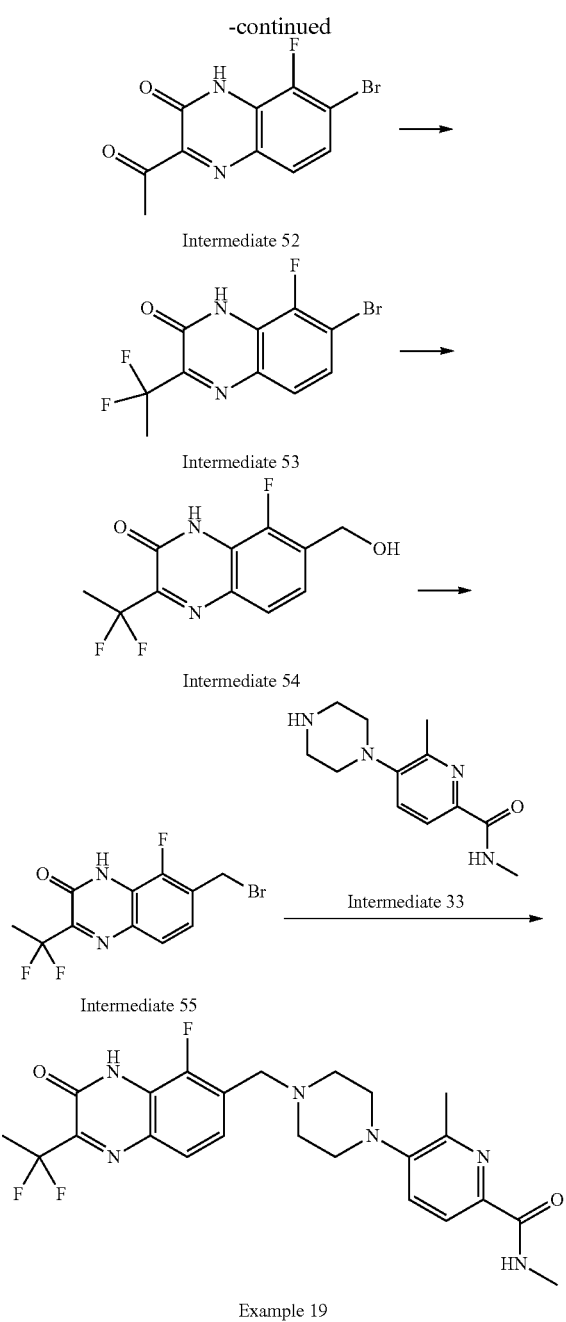

Intermediate 52

Intermediate 53

Intermediate 54

Intermediate 55

Example 19

Intermediate 50: 7-bromo-8-fluoro-3-(1-hydroxyethyl)-3,4-dihydro-1H-quinoxalin-2-one Ammonium chloride (6.70 g, 125.31 mmol) was added to a suspension of methyl 2-((4-bromo-3-fluoro-2-nitrophenyl)amino)-3-hydroxybutanoate (intermediate 36) (4.4 g, 12.53 mmol) and zinc (8.19 g, 125.31 mmol) in MeOH (65 mL) at 0° C. To this was added water (2 mL) and the mixture was stirred at 0° C. for 60 min. The orange color disappeared which indicated full conversion, LCMS indicated the reaction was complete. The mixture was filtered, washed with methanol and the filtrate was concentrated. The residue was diluted with ethyl acetate/methanol (10/1), the organic was washed e with water (~20 ml), brine, dried (anhydrous Na$_2$SO$_4$), concentrated to yield the intermediate methyl 2-((2-amino-4-bromo-3-fluorophenyl)amino)-3-hydroxybutanoate.

The above solid was slurried in methanol (~30 ml), 4 M HCl in dioxanes (~1 ml) was added and the mixture was stirred at rt for 2 h. LCMS indicated full conversion. The mixture was concentrated, and the residue was purified on silica gel column (eluted with 0 to 100% ethyl acetate in hexanes) to yield 7-bromo-8-fluoro-3-(1-hydroxyethyl)-3,4-dihydro-1H-quinoxalin-2-one (intermediate 50) (3.20 g, 88%) as a yellow solid. (a mixture of diastereomers). m/z (ES$^+$) [M+H]$^+$=289, 291.

Intermediate 51: 7-bromo-8-fluoro-3-(1-hydroxyethyl)-1H-quinoxalin-2-one

DDQ (432 mg, 1.90 mmol) was added to a suspension of 7-bromo-8-fluoro-3-(1-hydroxyethyl)-3,4-dihydro-1H-quinoxalin-2-one (intermediate 50) (500 mg, 1.73 mmol) in CH$_2$I$_2$ (30 mL) and the mixture was stirred at rt for overnight. LCMS indicated clean conversion. The solvent was removed under reduced pressure, sat. NaHCO$_3$ (~100 ml) solution was added and the mixture was stirred at rt for 3 h. The solid was collected by filtration, washed with water and dried to yield 7-bromo-8-fluoro-3-(1-hydroxyethyl)-1H-quinoxalin-2-one (intermediate 51) (439 mg, 88%). 1H NMR (500 MHz, DMSO-d6) 1.39 (3H, d), 4.78-5.31 (2H, m), 7.39-7.71 (2H, m), 12.72 (1H, br s); m/z (ES$^+$) [M+H]$^+$=287, 289.

Intermediate 52: 3-acetyl-7-bromo-8-fluoro-1H-quinoxalin-2-one

A solution of DMSO (0.651 mL, 9.17 mmol) in DCM was added dropwise to a stirred solution of oxalyl chloride (3.06 mL, 6.12 mmol) (2 M in DCM) in dichloromethane (20 ml) at −78° C. The solution of 7-bromo-8-fluoro-3-(1-hydroxyethyl)-1H-quinoxalin-2-one (intermediate 51) (439 mg, 1.53 mmol) was added slowly to the above reaction mixture and the resultant slurry was stirred for 15 min at −78° C. Triethylamine (1.279 mL, 9.17 mmol) was added dropwise and the resultant slurry was stirred an additional 30 min at 0° C. LCMS indicated the formation of desired product. Water (30 ml) was added and the mixture was extracted with dichloromethane/MeOH (5:1) (2×50 ml). The organic phases were combined and dried over magnesium sulfate. The solvent was removed under vacuum and the residue was purified by reverse phase C18 column (eluted with 0 to 100% ACN/water/0.1% TFA) to yield 3-acetyl-7-bromo-8-fluoro-1H-quinoxalin-2-one (intermediate 52) (85 mg, 19%) as a yellow solid. 1H NMR (500 MHz, DMSO-d6) 2.52-2.66 (3H, m), 7.42-7.76 (2H, m), 13.03 (1H, br s). m/z (ES$^+$) [M+H]$^+$=285, 287.

Intermediate 53: 7-bromo-3-(1,1-difluoroethyl)-8-fluoro-1H-quinoxalin-2-one

DAST (0.148 mL, 1.12 mmol) was added to a suspension of 3-acetyl-7-bromo-8-fluoro-1H-quinoxalin-2-one (intermediate 52) (80 mg, 0.28 mmol) in CH$_2$Cl$_2$ (20 mL) at rt and the resulting suspension was stirred at rt for 24 h. LCMS indicated 42% of the product formation. The mixture was continued to stir for over the weekend. To the mixture was added water and extracted with DCM. The organic layer was dried (anhydrous Na$_2$SO$_4$), filtered and concentrated. The residue was purified on silica gel column (eluted with 0 to 20% methanol in DCM) to yield 7-bromo-3-(1,1-difluoroethyl)-8-fluoro-1H-quinoxalin-2-one (intermediate 53) (65.0 mg, 75%) as a light yellow solid. m/z (ES+) [M+H]+ =307, 309. (the material was not very pure, carried onto next step).

Intermediate 54: 3-(1,1-difluoroethyl)-8-fluoro-7-(hydroxymethyl)-1H-quinoxalin-2-one A mixture of (tributylstannyl)methanol (102 mg, 0.32 mmol), Xphos Pd G2 (24.98 mg, 0.03 mmol) and 7-bromo-3-(1,1-difluoroethyl)-8-fluoro-1H-quinoxalin-2-one (intermediate 53) (65 mg, 0.21 mmol) in 1,4-dioxane (10 mL) was stirred at 80° C. for 6 h under N₂ atmosphere. LCMS indicated full conversion. Solvent was removed under vacuum and the residue was purified on silica gel column (eluted with 0 to 20% methanol in DCM) to yield 3-(1,1-difluoroethyl)-8-fluoro-7-(hydroxymethyl)-1H-quinoxalin-2-one (intermediate 54) (55.0 mg, 100%) as a brown solid. m/z (ES+) [M+H]+=259.

Intermediate 55: 7-(bromomethyl)-3-(1,1-difluoroethyl)-8-fluoro-1H-quinoxalin-2-one CBr₄ (129 mg, 0.39 mmol) was added to a mixture of 3-(1,1-difluoroethyl)-8-fluoro-7-(hydroxymethyl)-1H-quinoxalin-2-one (intermediate 54) (67 mg, 0.26 mmol) and triphenylphosphine (102 mg, 0.39 mmol) in CH₂Cl₂ (6 mL) at 0° C. and the resulting mixture was stirred at rt for overnight. LCMS indicated full conversion. The solvent was removed under vacuum and the residue was purified on silica gel column (eluted with 0 to 100% ethyl acetate in hexanes) to yield 7-(bromomethyl)-3-(1,1-difluoroethyl)-8-fluoro-1H-quinoxalin-2-one (intermediate 55) (56.0 mg, 67%) as a white solid. m/z (ES+) [M+H]+=321, 323.

Example 19: 5-[4-[[2-(1,1-difluoroethyl)-5-fluoro-3-oxo-4H-quinoxalin-6-yl]methyl]piperazin-1-yl]-N,6-dimethyl-pyridine-2-carboxamide To a suspension of 7-(bromomethyl)-3-(1,1-difluoroethyl)-8-fluoro-1H-quinoxalin-2-one (intermediate 55) (56 mg, 0.16 mmol) and N,6-dimethyl-5-(piperazin-1-yl)picolinamide, 2HCl (intermediate 33) (48.2 mg, 0.16 mmol) in acetonitrile (4 mL) was added DIPEA (0.164 mL, 0.94 mmol) and the resulting mixture was stirred at 70° C. for 1.5 h. LCMS indicated full conversion. The mixture was concentrated, and the residue was purified on reverse phase Gilson column (eluted with 0 to 70% ACN/water/0.1% TFA). The pure fractions were combined, 0.5 ml of aq. 1 M HCl was added to the combined fractions and lyophilized to dryness to yield 5-[4-[[2-(1,1-difluoroethyl)-5-fluoro-3-oxo-4H-quinoxalin-6-yl]methyl]piperazin-1-yl]-N,6-dimethyl-pyridine-2-carboxamide as HCl salt (example 19) (35.0 mg, 44%) as a yellow solid. 1H NMR (500 MHz, DMSO-d6) 2.08 (3H, br t), 2.52 (3H, s), 2.80 (3H, br d), 3.02-3.54 (8H, m), 4.61 (2H, br s), 7.57 (1H, br d), 7.67-8.04 (3H, m), 8.52 (1H, br d), 11.74 (1H, br s), 12.77-13.55 (1H, m); m/z (ES+) [M+H]+=475.

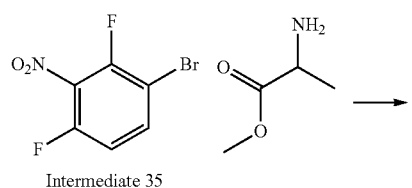

Intermediate 35

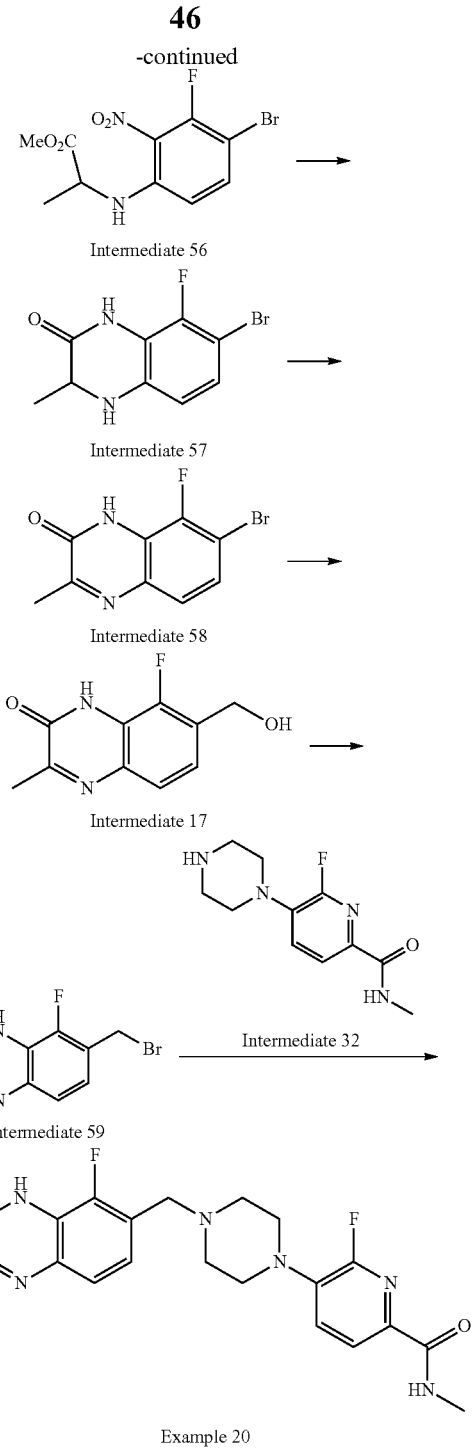

Intermediate 56

Intermediate 57

Intermediate 58

Intermediate 17

Intermediate 59

Example 20

Intermediate 56: methyl 2-(4-bromo-3-fluoro-2-nitro-anilino)propanoate

DIPEA (151 ml, 867.27 mmol) was added slowly to a stirred solution of 1-bromo-2,4-difluoro-3-nitrobenzene (intermediate 35) (68.8 g, 289.09 mmol) and methyl alaninate, HCl (40.4 g, 289.09 mmol) in DMF (300 mL). The resulting solution was stirred at rt for 18 hours (Complete conversion to desired product by LCMS). Reaction mixture was concentrated using rocket evaporation system, diluted with water and extracted with ethyl acetate. Organic layer was washed thoroughly with water, dried over sodium sulphate, filtered and concentrated under vacuum. 100 mL DCM was added to the above orange solid, the suspension was stirred at r.t for 30 min, and the solid was filtered to yield methyl 2-(4-bromo-3-fluoro-2-nitro-anilino)propanoate (24.00 g, 26%) (intermediate 56) as a bright orange solid. 1H NMR (500 MHz, DICHLOROMETHANE-d2) 1.52-1.62 (3H, m), 3.80 (3H, s), 4.28 (1H, quin), 6.49 (1H, dd), 7.19-7.39 (1H, m), 7.54 (1H, dd); 19F NMR (471 MHz, DICHLOROMETHANE-d2) −109.49 (1F, s); m/z (ES$^+$) [M+H]$^+$=321, 323.

Intermediate 57: 7-bromo-8-fluoro-3-methyl-3,4-dihydro-1H-quinoxalin-2-one

Zinc (78 g, 1195.88 mmol) was added portion wise to a mixture of methyl 2-(4-bromo-3-fluoro-2-nitro-anilino)propanoate (intermediate 56) (48 g, 149.49 mmol) and ammonium chloride (64.0 g, 1195.88 mmol) in MeOH (720 ml) and water (16 ml) at 0° C. (exothermic reaction) and the mixture was stirred at rt for 2 h (Complete disappearance of orange coloration is indicative of reaction completion). Solid was filtered off and the solid cake was washed with 20% MeOH in DCM. The filtrate was concentrated, water was added to the crude product and the product was extracted by ethyl acetate. The organic layer was dried and concentrated under vacuum to furnish an oil. m/z (ES$^+$) [M+H]$^+$=291, 293.

This material was slurry in ethyl acetate (50 mL) and methanol (50 mL), 2 mL 4N HCl in dioxane was added and the mixture was stirred for 1 h. The reaction mixture was concentrated to yield the crude product 7-bromo-8-fluoro-3-methyl-3,4-dihydro-1H-quinoxalin-2-one (intermediate 57) (38.7 g) as a grey solid. The crude product (38.7 g) was subjected to the next step without any further purification assuming the yield of this reaction to be 100%. m/z (ES$^+$) [M+H]$^+$=259.

Intermediate 58: 7-bromo-8-fluoro-3-methyl-1H-quinoxalin-2-one

DDQ (21.55 g, 94.95 mmol) was added in one portion to a stirred solution of 7-bromo-8-fluoro-3-methyl-3,4-dihydro-1H-quinoxalin-2-one (intermediate 57) (20.5 g, 79.13 mmol) in DCM (200 mL), resulted in a very thick off-white slurry, added additional dichloromethane (800 mL). The resulting slurry was stirred at rt for 2 hours (Complete conversion to desired product by LCMS). The reaction mixture was concentrated under vacuum and quenched with saturated aq. sodium bicarbonate solution (about 500 mL, quenching leads to intense frothing). The above slurry was stirred at rt for overnight and the solid was filtered off, washed thoroughly with water and solid dried on the filter for overnight. This solid was washed with diethyl ether and dried for 30 mins to give 7-bromo-8-fluoro-3-methyl-1H-quinoxalin-2-one (intermediate 58) (16.28 g, 80%) as an off-white solid. 19F NMR (471 MHz, DMSO-d6) −124.18 (1F, s); 1H NMR (500 MHz, DMSO-d6) 2.41 (3H, s), 7.45-7.54 (2H, m), 12.60 (1H, br s); m/z (ES$^+$) [M+H]$^+$=257.

Intermediate 17: 8-fluoro-7-(hydroxymethyl)-3-methyl-1H-quinoxalin-2-one

A mixture of (tributylstannyl)methanol (15.39 g, 47.93 mmol), 7-bromo-8-fluoro-3-methyl-1H-quinoxalin-2-one (intermediate 58) (11.2 g, 43.57 mmol) and Xphos Pd G2 (1.714 g, 2.18 mmol) in 1,4-dioxane (200 mL) was stirred at 80° C. for 7 h. LCMS indicated full conversion. The solvent was removed under reduced pressure, the residue was purified on silica gel column (eluted with 0 to 15% methanol in DCM). The fractions were concentrated to a slurry, diluted with ether, the solid was collected by filtration and dried to yield 8-fluoro-7-(hydroxymethyl)-3-methyl-1H-quinoxalin-2-one (intermediate 17) (8.10 g, 89%) as a white solid. 1H NMR (500 MHz, DMSO-d6) 2.41 (3H, s), 4.63 (2H, br d), 5.39 (1H, t), 7.31 (1H, br t), 7.51 (1H, d), 12.41 (1H, br s). m/z (ES$^+$) [M+H]$^+$=209.

Example 20: 6-fluoro-5-[4-[(5-fluoro-2-methyl-3-oxo-4H-quinoxalin-6-yl)methyl]piperazin-1-yl]-N-methyl-pyridine-2-carboxamide Triethylphosphane (20.90 ml, 145.06 mmol) was added dropwise with an addition funnel to a stirred suspension of 8-fluoro-7-(hydroxymethyl)-3-methyl-1H-quinoxalin-2-one (intermediate 17) (15.1 g, 72.53 mmol) and 1,2-dibromo-1,1,2,2-tetrachloroethane (52.0 g, 159.56 mmol) in DCM (400 mL) at 0° C. under nitrogen. The mixture was stirred at r.t for 3 h gave a light-yellow suspension. Crude LCMS indicated full conversion. DCM was removed under vacuum; the residue was slurry in 300 mL diethyl ether at rt and the light yellow ppt was filtered and washed with 200 ml ether. The solid was taken into 300 ml of water, stirred at rt for 10 min, the solid was collected by filtration, thorough wash (200 ml) with water to remove the salts. The solid was dried under vacuum for overnight (no heat). The solid was washed with hexanes and dried in vacuum in a bushel funnel to give 7-(bromomethyl)-8-fluoro-3-methylquinoxalin-2(1H)-one (intermediate 59) (22.76 g, 116%, likely contains some inorganic salts) as an off white solid. Used as such for next reaction. 1H NMR (500 MHz, DMSO-d6) 2.42 (3H, s), 4.65-4.93 (2H, m), 7.28-7.42 (1H, m), 7.51 (1H, d), 12.53 (1H, br s); m/z (ES$^+$) [M+H]$^+$=271, 273.

To a flask charged with 7-(bromomethyl)-8-fluoro-3-methylquinoxalin-2(1H)-one (intermediate 59) (22.76 g) and 6-fluoro-N-methyl-5-(piperazin-1-yl)picolinamide, 2HCl (intermediate 32) (24.24 g, 77.9 mmol) in acetonitrile (350 ml), was added DIPEA (38.0 ml, 217.59 mmol) at rt and the resulting mixture was stirred at 70° C. for 4 h. Reaction was not complete. To the mixture was added 5 g of KI and 2 g of NaI and the mixture was stirred at 50° C. for 20 h. More 540 mgs (~0.03 eq) of 6-fluoro-N-methyl-5-(piperazin-1-yl)picolinamide, 2HCl (intermediate 32) was added to the mixture and the stirring continued at 50° C. for 2 h. The solid from the reaction suspension was collected by filtration, washed with acetonitrile and dried. The resulting material was then suspended in water (~400 ml), slurred at rt for 20 min, filtered and dried (97% purity by LCMS). The solid was then dissolved into a mixture of DCM/MeOH (3/1) (about 1.5 L) at reflux, filtered through a pad of silica gel, removed most of the DCM until solid precipitate out and the mixture was kept at rt for 20 min. The solid was collected by filtration and repeated the procedure for the filtrate, and the solids were combined to yield the product 6-fluoro-5-[4-[(5-fluoro-2-methyl-3-oxo-4H-quinoxalin-6-yl)methyl]piperazin-1-yl]-N-methyl-pyridine-2-carboxamide (example 20) (26 g, 84%) as a light yellow solid. 1H NMR (500 MHz, DMSO-d6) 2.41 (3H, s), 2.57-2.69 (4H, m), 2.76 (3H, d), 3.16 (4H, br s), 3.70 (2H, s), 7.29 (1H, br t), 7.40-7.60 (2H, m), 7.83 (1H, d), 8.38 (1H, br d), 12.44 (1H, br s); m/z (ES$^+$) [M+H]$^+$=429.

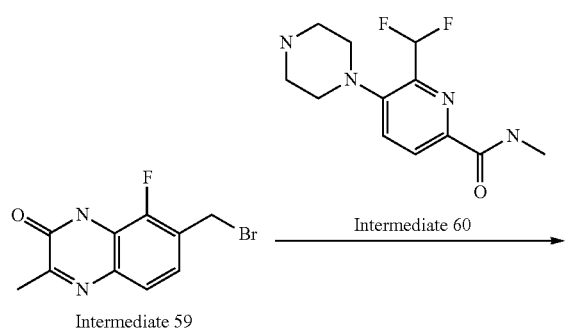

Intermediate 59 → Intermediate 60

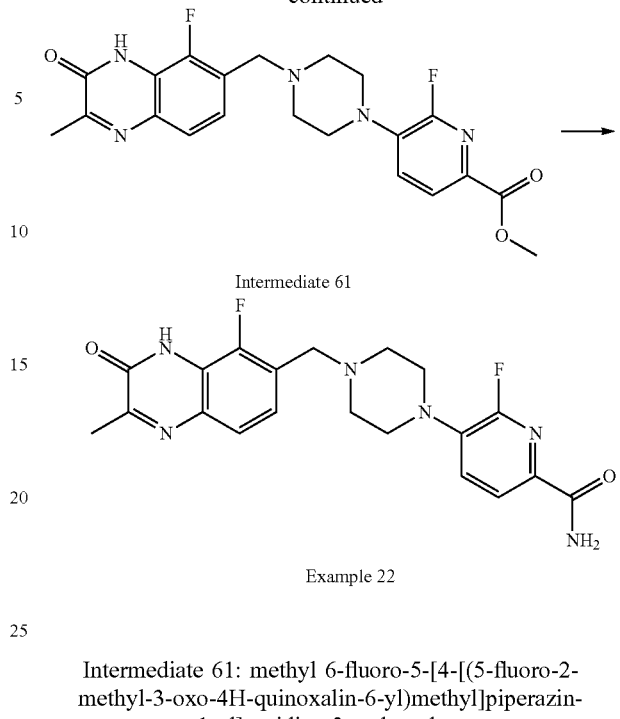

Intermediate 61

Example 22

Example 21

Example 21: 6-(difluoromethyl)-5-[4-[(5-fluoro-2-methyl-3-oxo-4H-quinoxalin-6-yl)methyl]piperazin-1-yl]-N-methyl-pyridine-2-carboxamide DIPEA (0.052 mL, 0.30 mmol) was added to a stirred mixture of 7-(bromomethyl)-8-fluoro-3-methylquinoxalin-2(1H)-one (intermediate 59)(40 mg, 0.15 mmol) and 6-(difluoromethyl)-N-methyl-5-(piperazin-1-yl)picolinamide, 2HCl (intermediate 60) (50.6 mg, 0.15 mmol) in acetonitrile (mL) and The resulting mixture was stirred at 70° C. for 2 h. Reaction was concentrated and submitted to analytical group for purification (Purification conditions: the residue was purified by reverse phase C18 column (eluted with 0 to 100% ACN/water/0.1% NH4OH) which yield 6-(difluoromethyl)-5-[4-[(5-fluoro-2-methyl-3-oxo-4H-quinoxalin-6-yl)methyl]piperazin-1-yl]-N-methyl-pyridine-2-carboxamide (example 21) (15 mg, 22%) as white solid. 1H NMR (500 MHz, DMSO-d6) 2.37 (3H, s), 2.64 (4H, br s), 2.84 (3H, d), 3.01 (4H, br d), 3.70 (2H, s), 7.00-7.28 (2H, m), 7.42 (1H, br d), 7.86 (1H, d), 8.09 (1H, d), 8.39 (1H, q), 12.24-12.63 (1H, m); m/z (ES$^+$) [M+H]$^+$=461.

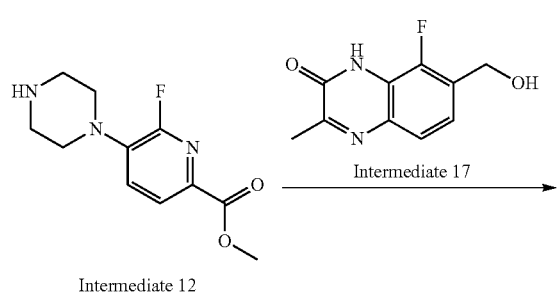

Intermediate 12 + Intermediate 17 →

Intermediate 61: methyl 6-fluoro-5-[4-[(5-fluoro-2-methyl-3-oxo-4H-quinoxalin-6-yl)methyl]piperazin-1-yl]pyridine-2-carboxylate Polymer supported triphenylphosphine (1.512 g, 5.76 mmol) (3.4 g added, calculated based on PPh3 loading of 1.6 mmol/g) was added to a stirred slurry of 8-fluoro-7-(hydroxymethyl)-3-methylquinoxalin-2(1H)-one (intermediate 17) (400 mg, 1.92 mmol) and perbromomethane (1.274 g, 3.84 mmol) in DCM (40 mL) at rt. The resulting mixture was stirred at 23° C. for 1 h. Reaction was not complete. Additional polymer bound-PPh$_3$ (1 g) was added to get the reaction to complete. Reaction mixture was filtered, washed with DCM, THF and the filtrate was concentrated under vacuum to yield 7-(bromomethyl)-8-fluoro-3-methylquinoxalin-2(1H)-one as a light-yellow solid.

To the above freshly prepared 7-(bromomethyl)-8-fluoro-3-methylquinoxalin-2(1H)-one, was added methyl 6-fluoro-5-(piperazin-1-yl)picolinate, 2HCl (intermediate 12) (600 mg, 1.92 mmol), acetonitrile (25 mL) and N-ethyl-N-isopropylpropan-2-amine (1674 μl, 9.61 mmol) and the reaction mixture was heated to 70° C. 1 h. The reaction mixture was cooled to rt, concentrated, and the crude solid was purified via normal phase chromatography using 0-10% MeOH in DCM to yield methyl 6-fluoro-5-[4-[(5-fluoro-2-methyl-3-oxo-4H-quinoxalin-6-yl)methyl]piperazin-1-yl]pyridine-2-carboxylate (intermediate 61) (0.484 g, 59%) as an off-white solid. 1H NMR (500 MHz, DMSO-d6) 2.34-2.49 (3H, m), 2.52-2.62 (4H, m), 3.08-3.28 (4H, m), 3.70 (2H, s), 3.83 (3H, s), 7.29 (1H, t), 7.44-7.54 (2H, m), 7.91 (1H, dd), 12.45 (1H, s); 19F NMR (471 MHz, DMSO-d6) −135.50 (1F, s), −70.49 (1F, s). m/z (ES$^+$) [M+H]$^+$=430.

Example 22: 6-fluoro-5-[4-[(5-fluoro-2-methyl-3-oxo-4H-quinoxalin-6-yl)methyl]piperazin-1-yl]pyridine-2-carboxamide Ammonia (7 N Ammonia in MeOH) (31.3 ml, 218.90 mmol) was added to methyl 6-fluoro-5-[4-[(5-fluoro-2-methyl-3-oxo-4H-quinoxalin-6-yl)methyl]piperazin-1-yl]pyridine-2-carboxylate (intermediate 61)(0.470 g, 1.09 mmol) in a 40 mL scintillation vial, sealed and stirred at rt for 18 h. Complete conversion to desired product by LCMS. The white solid was filtered to give 103 mg pure product. The filtrate was concentrated under vacuum, the resulting off-white solid was slurry in about 5 mL methanol and filtered to obtain additional pure product 298 mg. Both batches were combined to obtain 6-fluoro-5-[4-[(5-fluoro-2-methyl-3-oxo-4H-quinoxalin-6-yl)methyl]piperazin-1-yl]pyridine-2-carboxamide (example 22) (0.401 g, 88%). 1H NMR (500 MHz, DMSO-d6) 2.42 (3H, s), 2.59 (4H, br s), 3.09-3.27 (4H, m), 3.70 (2H, s), 7.29 (1H, br t), 7.46 (1H, br s), 7.49-7.58 (2H, m), 7.76 (1H, br s), 7.85 (1H, br d), 12.35 (1H, br s); 19F NMR (471 MHz, DMSO-d6) −135.49 (1F, s), −72.40 (1F, s); m/z (ES+) [M+H]+=415.

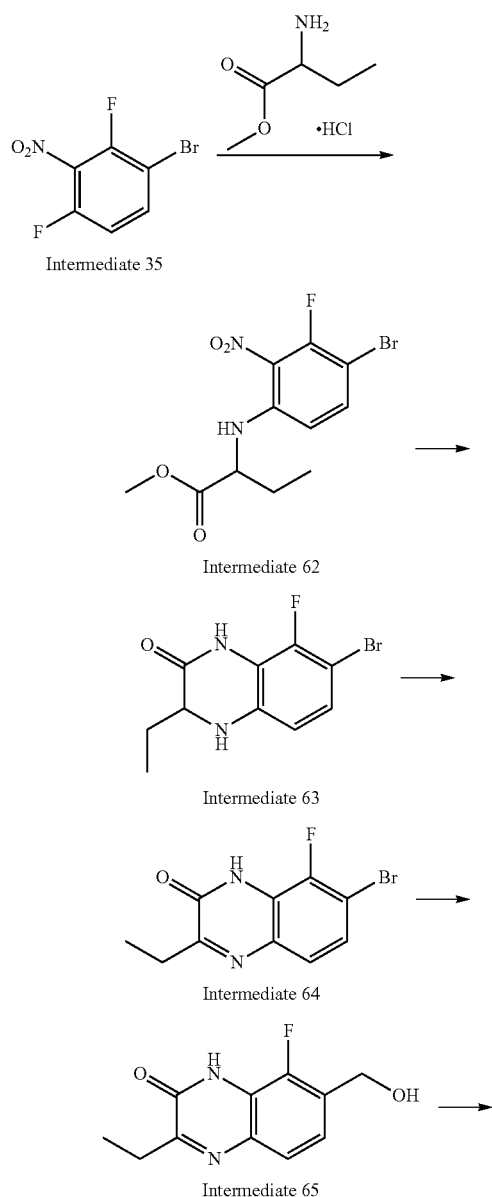

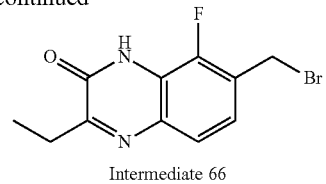

Intermediate 66

Intermediate 62: methyl 2-(4-bromo-3-fluoro-2-nitro-anilino)butanoate

DIPEA (165 ml, 942.91 mmol) was added slowly to a stirred solution of 1-bromo-2,4-difluoro-3-nitro-benzene (intermediate 35) (74.8 g, 314.30 mmol) and methyl 2-aminobutanoate, HCl (48.3 g, 314.30 mmol) in DMF (733 mL) and the resulting solution was stirred at rt for 18 hours. DMF was removed on rocket evaporator, diluted with water and extracted with ethyl acetate. After concentration the crude material was purified by flash silica chromatography, elution gradient 0 to 70% EtOAc in hexanes. Product fractions were concentrated under reduced pressure to afford methyl 2-(4-bromo-3-fluoro-2-nitro-anilino)butanoate (intermediate 62) (49.4 g, 47%) as a red solid. 1H NMR (500 MHz, DMSO-d6) 0.82-0.98 (3H, m), 1.77-1.93 (2H, m), 3.70 (3H, d), 4.38-4.54 (1H, m), 6.77 (1H, br d), 7.28 (1H, br d), 7.64-7.80 (1H, t); m/z (ES+) [M+H]+=335.

Intermediate 63: 7-bromo-3-ethyl-8-fluoro-3,4-dihydro-1H-quinoxalin-2-one

Zinc (44.1 g, 674.07 mmol) was added portion wise (exothermic reaction) to a mixture of methyl 2-(4-bromo-3-fluoro-2-nitro-anilino)butanoate (intermediate 62) (50.2 g, 149.79 mmol) and ammonium chloride (64.1 g, 1198.34 mmol) in MeOH (468 mL). The mixture was stirred at rt for 1 h. Solid was filtered off and washed with 20% MeOH in DCM. This material was dissolved in methanol (120 mL) and 4N HCl in dioxane (10 mL) was added and reaction was stirred for 30 min. Solvent was removed under vacuum, diluted with ethyl acetate and basified with sat NaHCO3 solution. Organic layer was separated, washed with water, dried over sodium sulphate and concentrated to give the crude product. The solid was triturated with 100 mL methanol, stirred for 10 min and the light brown solid was filtered off to give 7-bromo-3-ethyl-8-fluoro-3,4-dihydro-1H-quinoxalin-2-one (intermediate 63) (39.8 g, 97%) product. 1H NMR (500 MHz, DMSO-d6) 0.92 (3H, t), 1.49-1.77 (2H, m), 3.57-3.87 (1H, m), 6.24-6.62 (2H, m), 6.99 (1H, dd), 10.44 (1H, s); m/z (ES+) [M+H]+=273.

Intermediate 64: 7-bromo-3-ethyl-8-fluoro-1H-quinoxalin-2-one

DDQ (29.7 g, 130.94 mmol) was added in one portion to a stirred solution of 7-bromo-3-ethyl-8-fluoro-3,4-dihydro-1H-quinoxalin-2-one (intermediate 63) (29.8 g, 109.12 mmol) in DCM (546 mL) and the resulting solution was stirred at rt for 2 h. Solvent was removed under vacuum, and the solid was slurry with 150 mL of methanol and stirred for 30 min. Solid was filtered off and washed with 30 mL methanol. Solid was transferred to a 2 L round bottom flask; 200 mL water was added follow by slow addition of 300 mL of sodium bicarbonate. After complete addition the mixture was stirred for overnight at rt to give light yellow slurry.

Stirring was stopped and the aq layer was decanned. Solid was collected by filtration and washed thoroughly with water to give 7-bromo-3-ethyl-8-fluoro-1H-quinoxalin-2-one (intermediate 64) (24.45 g, 83%) as yellow colored solid. 1H NMR (500 MHz, DMSO-d6) 1.22 (3H, t), 2.81 (2H, q), 7.27-7.69 (2H, m), 12.59 (1H, br s); m/z (ES$^+$) [M+H]$^+$=271.

Intermediate 65: 3-ethyl-8-fluoro-7-(hydroxymethyl)-1H-quinoxalin-2-one

Xphos Pd G2 (1.121 g, 1.43 mmol) was added to a stirred degassed solution of 7-bromo-3-ethyl-8-fluoro-1H-quinoxalin-2-one (intermediate 64) (7.727 g, 28.50 mmol) and (tributylstannyl)methanol (10.98 g, 34.20 mmol) in 1,4-dioxane (143 mL). The resulting solution was stirred at 80° C. for 6 hours. Solvent was removed under vacuum, 100 mL diethyl ether was added, and the slurry was stirred for 30 min. Solid was filtered off and washed with 50 mL of diethyl ether to give 3-ethyl-8-fluoro-7-(hydroxymethyl)-1H-quinoxalin-2-one (5.88 g, 93%) (intermediate 65) as off white solid. 1H NMR (500 MHz, DMSO-d6) 1.22 (3H, t), 2.82 (2H, q), 4.64 (2H, br d), 5.40 (1H, t), 7.32 (1H, br t), 7.55 (1H, d), 12.40 (1H, br s); m/z (ES$^+$) [M+H]$^+$=223.

Intermediate 66: 7-(bromomethyl)-3-ethyl-8-fluoro-1H-quinoxalin-2-one

Triethylphosphane (19.94 ml, 135.00 mmol) was added dropwise to a stirred solution of 3-ethyl-8-fluoro-7-(hydroxymethyl)-1H-quinoxalin-2-one (intermediate 65) (10 g, 45.00 mmol) and CBr$_4$ (49.2 g, 148.50 mmol) in DCM (355 mL) at 0° C. over a period of 5 minutes under nitrogen. Reaction was stirred at rt for 1 h. DCM was removed under vacuum and residue was slurry in 150 mL diethyl ether. The white ppt was filtered off and washed with 50 mL diethyl ether. This solid was slurry with water (200 mL) and stirred for 30 min. Solid was filtered off and washed thoroughly with water. The solid was dried under vacuum for overnight to give 7-(bromomethyl)-3-ethyl-8-fluoroquinoxalin-2(1H)-one (intermediate 66) (11.38 g, 89%) as light brown solid. 1H NMR (500 MH z, DMSO-d6) 1.22 (3H, t), 2.83 (2H, q), 4.81 (2H, s), 7.37 (1H, br t), 7.55 (1H, d), 12.53 (1H, br s); m/z (ES$^+$) [M+H]$^+$=285.

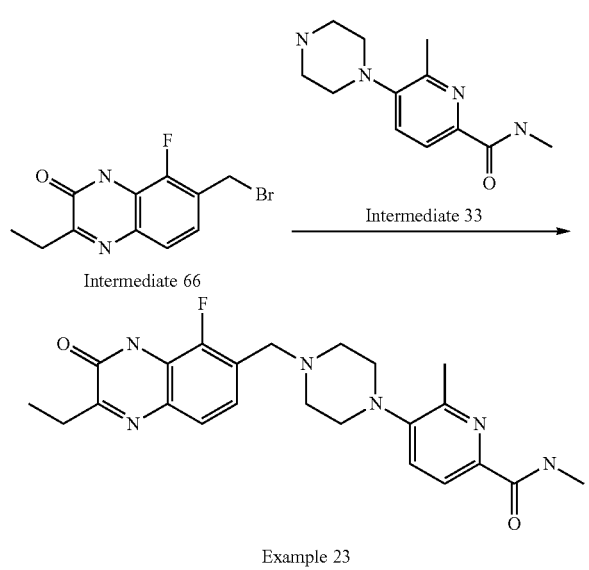

Example 23

Example 23: 5-[4-[(2-ethyl-5-fluoro-3-oxo-4H-quinoxalin-6-yl)methyl]piperazin-1-yl]-N,6-dimethyl-pyridine-2-carboxamide DIPEA (20.90 ml, 119.64 mmol) was added to a stirred slurry of 7-(bromomethyl)-3-ethyl-8-fluoroquinoxalin-2(1H)-one (intermediate 66) (11.37 g, 39.88 mmol) and N,6-dimethyl-5-piperazin-1-yl-pyridine-2-carboxamide, 2HCl (intermediate 33) (14.09 g, 45.86 mmol) in acetonitrile (178 mL). The resulting solution was stirred at 50° C. for 2 h. Reaction was complete. Half of the solvent was removed by evaporation, 10 mL sat sodium bicarbonate was added and mixture was stirred for 15 min. Solid was filtered off, washed with water followed by 50 mL acetonitrile. Solid was dissolved in DCM/Methanol (~9/1) and filtered through silica bed. Filtrate was concentrated to give the light yellow solid. This material was triturated with ~120 mL methanol, solid was filtered off and dried. LCMS still shows ~2.1% impurity (likely from the reagent). Material was again triturated with acetonitrile and then with 3% methanol in acetonitrile to give ~14 g white solid. Methanol (40 mL) was added and stirred for 3 h. Solid was filtered off to give pure product 5-[4-[(2-ethyl-5-fluoro-3-oxo-4H-quinoxalin-6-yl)methyl]piperazin-1-yl]-N,6-dimethyl-pyridine-2-carboxamide (example 23) (12.26 g, 70%). 1HNMR (500 MHz, DMSO-d6) 1.23 (3H, t), 2.48 (3H, s), 2.62 (4H, br s), 2.76-2.88 (5H, m), 2.95 (4H, br s), 3.73 (2H, s), 7.31 (1H, t), 7.47 (1H, d), 7.56 (1H, d), 7.79 (1H, d), 8.41 (1H, q), 12.44 (1H, s); m/z (ES$^+$) [M+H]$^+$=439.

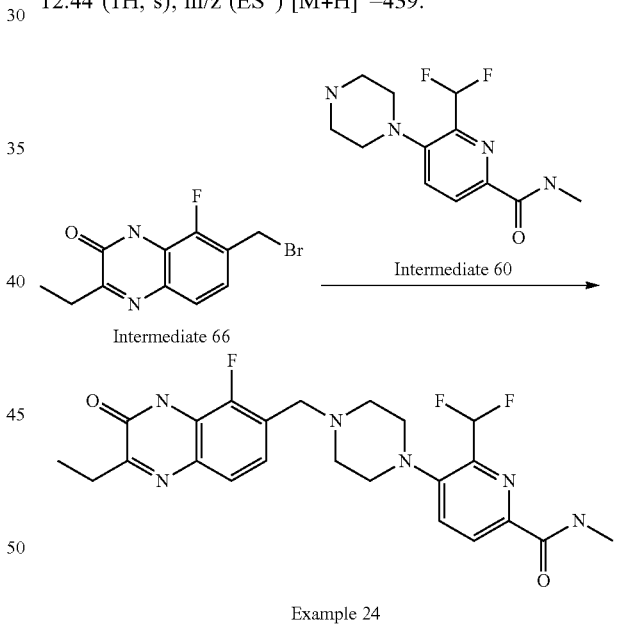

Example 24

Example 24: 6-(difluoromethyl)-5-[4-[(2-ethyl-5-fluoro-3-oxo-4H-quinoxalin-6-yl)methyl]piperazin-1-yl]-N-methyl-pyridine-2-carboxamide DIPEA (0.049 mL, 0.28 mmol) was added to a stirred mixture of 7-(bromomethyl)-3-ethyl-8-fluoroquinoxalin-2(1H)-one (intermediate 66) (40 mg, 0.14 mmol) and 6-(difluoromethyl)-N-methyl-5-(piperazin-1-yl)picolinamide, 2HCl (intermediate 60) (48.1 mg, 0.14 mmol) in acetonitrile (2 mL) and The resulting mixture was stirred at 70° C. for 2 hours. Reaction was concentrated and submitted to analytical group for purification (Purification conditions: the residue was purified by reverse phase C18 column (eluted with 0 to 100% ACN/water/0.1% NH4OH) which yield 6-(difluoromethyl)-5-[4-[(2-ethyl-5-fluoro-3-oxo-4H-quinoxalin-6-yl)methyl]piperazin-1-yl]-N-methyl-pyridine-2-carboxamide (example 24) (56.0 mg, 84%). 1H NMR (500 MHz, DMSO-d6) 1.23 (3H, t), 2.65 (4H, br d), 2.77-2.86 (5H, m), 2.97-3.06 (4H, m), 3.73 (2H, s), 7.00-7.26 (1H, t), 7.30 (1H, br d), 7.55 (1H, br d), 7.86 (1H, d), 8.09 (1H, d), 8.39 (1H, q), 12.45 (1H, br d); m/z (ES$^+$) [M+H]$^+$=475.

suspension was stirred at 50° C. for 24 hours (sealed tube). Solvent was removed and the resulting residue was purified by flash silica chromatography, elution gradient 0 to 35% MeOH in DCM. Product fractions were concentrated under reduced pressure to afford 5-[4-[(2-ethyl-5-fluoro-3-oxo-4H-quinoxalin-6-yl)methyl]piperazin-1-yl]pyridine-2-carboxamide (example 25) (0.079 g, 63%) as a pale yellow solid. 1H NMR (500 MHz, DMSO-d6) 1.23 (3H, t), 2.54-2.61 (4H, m), 2.83 (2H, q), 3.32-3.40 (4H, m), 3.70 (2H, s), 7.24-7.34 (2H, m), 7.38 (1H, dd), 7.56 (1H, d), 7.76 (1H, br d), 7.84 (1H, d), 8.27 (1H, d), 12.44 (1H, br s); m/z (ES$^+$) [M+H]$^+$=411.

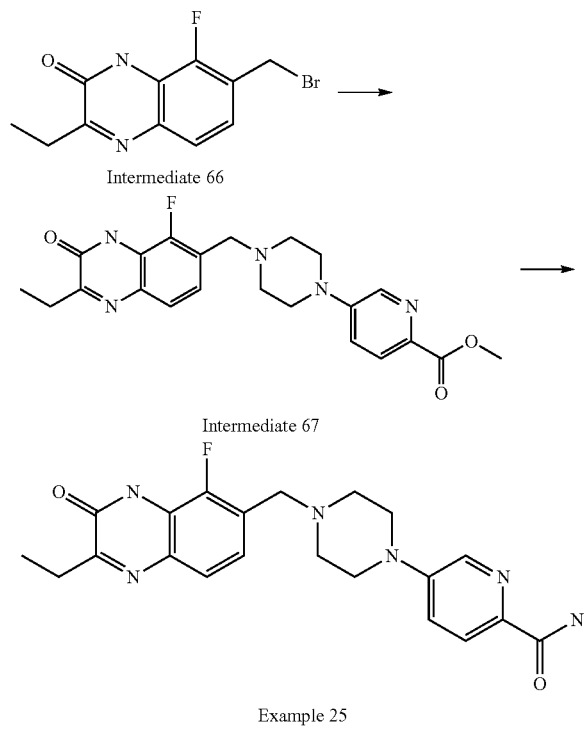

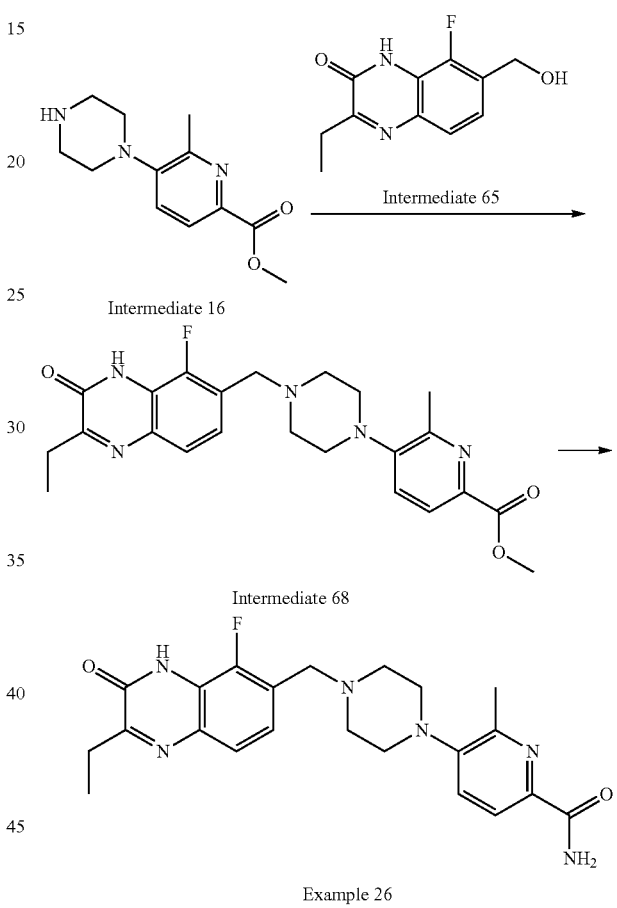

Intermediate 67: methyl 5-[4-[(2-ethyl-5-fluoro-3-oxo-4H-quinoxalin-6-yl)methyl]piperazin-1-yl]pyridine-2-carboxylate DIPEA (246 µl, 1.41 mmol) was added to a stirred slurry of 7-(bromomethyl)-3-ethyl-8-fluoro-1H-quinoxalin-2-one (intermediate 66) (134 mg, 0.47 mmol) and methyl 5-(piperazin-1-yl)picolinate, 2HCl (intermediate 119)(138 mg, 0.47 mmol) in acetonitrile (2 mL). The resulting solution was stirred at 50° C. for 2 h. Solvent was removed under vacuum and the resulting residue was purified by flash silica chromatography, elution gradient 0 to 20% MeOH in DCM. Product fractions were concentrated under reduced pressure to afford methyl 5-[4-[(2-ethyl-5-fluoro-3-oxo-4H-quinoxalin-6-yl)methyl]piperazin-1-yl]pyridine-2-carboxylate (intermediate 67) (0.142 g, 71.0%) as a white solid; m/z (ES$^+$) [M+H]$^+$=426.

Example 25: 5-[4-[(2-ethyl-5-fluoro-3-oxo-4H-quinoxalin-6-yl)methyl]piperazin-1-yl]pyridine-2-carboxamide Ammonia (7 N) in methanol (3 mL, 6.00 mmol) was added to methyl methyl 5-[4-[(2-ethyl-5-fluoro-3-oxo-4H-quinoxalin-6-yl)methyl]piperazin-1-yl]pyridine-2-carboxylate (intermediate 67) (130 mg, 0.31 mmol). The resulting

Intermediate 68: methyl 5-[4-[(2-ethyl-5-fluoro-3-oxo-4H-quinoxalin-6-yl)methyl]piperazin-1-yl]-6-methyl-pyridine-2-carboxylate Triethylphosphine (0.399 ml, 2.70 mmol) was added dropwise to a stirred solution of 3-ethyl-8-fluoro-7-(hydroxymethyl)quinoxalin-2(1H)-one (intermediate 65) (0.2 g, 0.90 mmol) and CBr$_4$ (0.985 g, 2.97 mmol) in DCM (7.10 mL) at 0° C. over a period of 5 minutes under nitrogen. Reaction was stirred at rt for 1 h. DCM was removed under vacuum and the resulting solid was slurry in diethyl ether. The white ppt was filtered under vacuum, washed with water followed by ether. The solid was dried under vacuum for overnight (no heat) to give 7-(bromomethyl)-3-ethyl-8-fluoroquinoxalin-2(1H)-one as a light brown solid.

To the above crude product was added methyl 6-methyl-5-(piperazin-1-yl)picolinate, 2HCl (intermediate 16) (278 mg, 0.90 mmol), acetonitrile (10 mL) and N-ethyl-N-isopropylpropan-2-amine (785 µl, 4.51 mmol) and heated to 70° C. for 1 h. The reaction mixture was cooled, concentrated, quenched with aq. NaHCO$_3$ solution (1 mL) and stirred for 1 h at rt. Water (3 mL) was added to the above mixture and stirred for 10 mins. The precipitate was filtered and washed with water (50 mL). The solid was purified via normal phase chromatography using 0-10% MeOH in DCM. The isolated product was 89% pure by LCMS. The above solid was further purified using mass directed Prep HPLC using 20-40% acetonitrile in water with NH4OH modifier to yield methyl 5-[4-[(2-ethyl-5-fluoro-3-oxo-4H-quinoxalin-6-yl)methyl]piperazin-1-yl]-6-methyl-pyridine-2-carboxylate (intermediate 68) (115 mg, 0.262 mmol, 29%) as white solid with 93% LCMS purity. 1H NMR (500 MHz, DMSO-d6) 1.23 (3H, t), 2.45-2.49 (3H, m), 2.53-2.69 (4H, m), 2.83 (2H, q), 2.98 (4H, br s), 3.73 (2H, s), 3.83 (3H, s), 7.31 (1H, t), 7.45 (1H, d), 7.56 (1H, d), 7.86 (1H, d), 12.44 (1H, br s); 19F NMR (471 MHz, DMSO-d6) −135.54 (1F, s). m/z (ES$^+$) [M+H]$^+$=440.

Example 26: 5-[4-[(2-ethyl-5-fluoro-3-oxo-4H-quinoxalin-6-yl)methyl]piperazin-1-yl]-6-methyl-pyridine-2-carboxamide 7 N ammonia in methanol (6.40 ml, 44.78 mmol) was added to methyl 5-[4-[(2-ethyl-5-fluoro-3-oxo-4H-quinoxalin-6-yl)methyl]piperazin-1-yl]-6-methyl-pyridine-2-carboxylate (intermediate 68) (0.0984 g, 0.22 mmol) in a 40 mL scintillation vial, sealed and stirred at rt for 18 h. The reaction was concentrated under vacuum, added additional ammonia (6.40 ml, 44.78 mmol) solution and stirred at 50° C. for 16 h. The reaction was concentrated under vacuum and additional NH3 in methanol was added and stirred at rt for the weekend. Reaction was complete by LCMS. The reaction mixture was concentrated under vacuum, the resulting solid was slurry in diethyl ether. Solid was filtered and washed with additional ether and methanol to yield 5-[4-[(2-ethyl-5-fluoro-3-oxo-4H-quinoxalin-6-yl)methyl]piperazin-1-yl]-6-methyl-pyridine-2-carboxamide (example 26) (0.095 g, 100%) as a white solid; 1H NMR (500 MHz, DMSO-d6) 1.22 (3H, br t), 2.45-2.49 (3H, m), 2.52-2.68 (4H, m), 2.82 (2H, q), 2.94 (4H, br s), 3.72 (2H, br s), 7.30 (1H, br t), 7.38-7.51 (2H, m), 7.55 (1H, br d), 7.80 (2H, br d), 12.41 (1H, br s); 19F NMR (471 MHz, DMSO-d6) −135.53 (1F, s); m/z (ES$^+$) [M+H]$^+$=425.

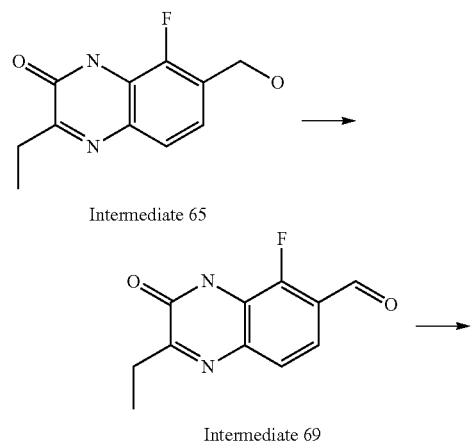

Intermediate 65

Intermediate 69

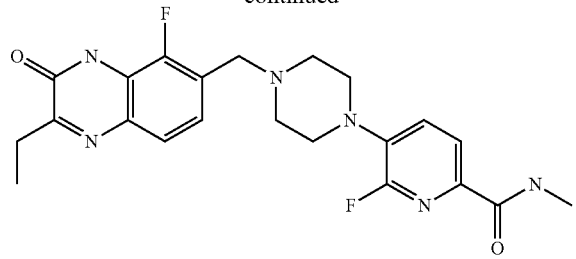

Example 27

Intermediate 69: 2-ethyl-5-fluoro-3-oxo-4H-quinoxaline-6-carbaldehyde

Dess-Martin periodinane (458 mg, 1.08 mmol) was added to 3-ethyl-8-fluoro-7-(hydroxymethyl)-1H-quinoxalin-2-one (intermediate 65) (contaminated by its regio isomer 3-ethyl-8-fluoro-5-(hydroxymethyl)-1H-quinoxalin-2-one) (160 mg, 0.72 mmol) in DCM (5 mL). The resulting mixture was stirred at room temperature for 4 h. The solvent was evaporated to afford crude product which was purified by flash C18-flash chromatography, elution gradient 5 to 30% MeCN in water (0.4% FA). Pure fractions were evaporated to dryness to afford 2-ethyl-5-fluoro-3-oxo-4H-quinoxaline-6-carbaldehyde (contaminated by its regio isomer 3-ethyl-8-fluoro-2-oxo-1H-quinoxaline-5-carbaldehyde) (intermediate 69) (110 mg, 69%) as a yellow solid. m/z (ES$^+$) [M+H]$^+$=221.

Example 27: 5-[4-[(2-ethyl-5-fluoro-3-oxo-4H-quinoxalin-6-yl)methyl]piperazin-1-yl]-6-fluoro-N-methyl-pyridine-2-carboxamide Titanium isopropoxide (64.5 mg, 0.23 mmol) was added to 2-ethyl-5-fluoro-3-oxo-4H-quinoxaline-6-carbaldehyde (intermediate 69) (contaminated by its regio isomer 3-ethyl-8-fluoro-2-oxo-1H-quinoxaline-5-carbaldehyde) (50 mg, 0.23 mmol) and 6-fluoro-N-methyl-5-(piperazin-1-yl)picolinamide (54.1 mg, 0.23 mmol) in THF (3 mL). The resulting mixture was stirred at room temperature for 2 mins. Sodium triacetoxyborohydride (intermediate 32)(192 mg, 0.91 mmol) was added. The resulting mixture was stirred at room temperature for 16 h. The reaction mixture was quenched with MeOH (0.1 mL). The solvent was evaporated to afford crude product. The crude residue was purified by preparative HPLC (Column: Xselect CSH OBD Column 30*150 mm 5 um; Mobile Phase A: Water (0.05% TFA), Mobile Phase B: ACN; Flow rate:60 mL/min; Gradient:10% B to 20% B in 10 min; 254; 220 nm) and (Column: XBridge Shield RP18 OBD Column, 19*250 mm, 10 um; Mobile Phase A:Water (10 MMOL/L NH4HCO$_3$+0.1% NH3·H$_2$O), Mobile Phase B:ACN; Flow rate:20 mL/min; Gradient:21 B to 95 B in 7 min; 254/220 nm. Fractions containing the desired compound were evaporated to dryness to afford 5-[4-[(2-ethyl-5-fluoro-3-oxo-4H-quinoxalin-6-yl)methyl]piperazin-1-yl]-6-fluoro-N-methyl-pyridine-2-carboxamide (example 27) (6 mg, 6%) as a white solid. 1H NMR (400 MHz, DMSO-d6) 1.22 (3H, t), 2.56-2.64 (4H, m), 2.76 (3H, d), 2.82 (2H, q), 3.14-3.20 (4H, m), 3.71 (2H, s), 7.27-7.33 (1H, m), 7.53-7.59 (2H, m), 7.82-7.86 (1H, m), 8.38-8.45 (1H, m), 12.46 (1H, s); 19F NMR (376 MHz, DMSO-d6) −72.58, −135.51; m/z (ES$^+$) [M+H]$^+$=443.

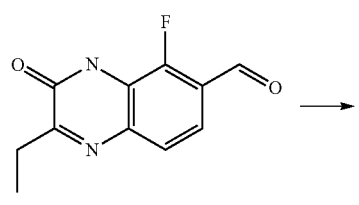

Intermediate 69

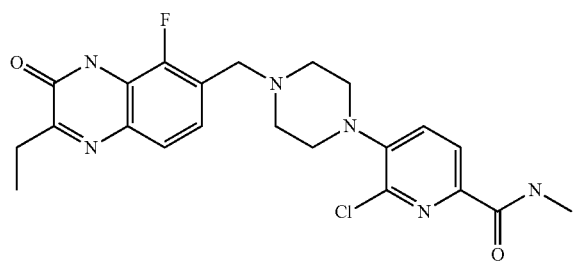

Example 28

Example 28: 6-chloro-5-[4-[(2-ethyl-5-fluoro-3-oxo-4H-quinoxalin-6-yl)methyl]piperazin-1-yl]-N-methyl-pyridine-2-carboxamide Titanium isopropoxide (51.6 mg, 0.18 mmol) was added to 2-ethyl-5-fluoro-3-oxo-4H-quinoxaline-6-carbaldehyde (intermediate 69) (contaminated by its regio isomer 3-ethyl-8-fluoro-2-oxo-1H-quinoxaline-5-carbaldehyde) (40 mg, 0.18 mmol) and 6-chloro-N-methyl-5-(piperazin-1-yl)picolinamide (intermediate 30)(50 mg, 0.20 mmol) in THF (3 mL). The resulting mixture was stirred at room temperature for 2 minutes. Sodium triacetoxyborohydride (154 mg, 0.73 mmol) was added. The resulting mixture was stirred at room temperature for 16 hours. The reaction mixture was quenched with MeOH (0.1 mL) and evaporated to afford crude product. The crude product was purified by preparative HPLC (Column: XBridge Shield RP18 OBD Column, 30*150 mm, 5 um; Mobile Phase A:Water (0.05% NH$_3$H$_2$O), Mobile Phase B:ACN; Flow rate:60 mL/min; Gradient:21 B to 41 B in 7 min; 254/220 nm. Fractions containing the desired compound were evaporated to dryness to afford 6-chloro-5-[4-[(2-ethyl-5-fluoro-3-oxo-4H-quinoxalin-6-yl)methyl]piperazin-1-yl]-N-methyl-pyridine-2-carboxamide (example 28) (37.5 mg, 45%) as a white solid. 1H NMR (400 MHz, DMSO-d6) 1.22 (3H, t), 2.57-2.65 (4H, m), 2.76-2.86 (5H, m), 3.05-3.15 (4H, m), 3.72 (2H, s), 7.29 (1H, t), 7.55 (1H, d), 7.65 (1H, d), 7.93 (1H, d), 8.40-8.45 (1H, m), 12.45 (1H, s); 19F NMR (376 MHz, DMSO-d6) −135.46; m/z (ES$^+$) [M+H]$^+$=459.

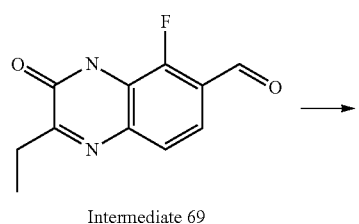

Intermediate 69

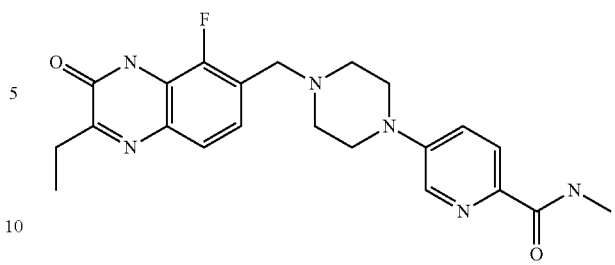

Example 29

Example 29: 5-[4-[(2-ethyl-5-fluoro-3-oxo-4H-quinoxalin-6-yl)methyl]piperazin-1-yl]-N-methyl-pyridine-2-carboxamide Titanium isopropoxide (51.6 mg, 0.18 mmol) was added to 2-ethyl-5-fluoro-3-oxo-4H-quinoxaline-6-carbaldehyde (intermediate 69) (contaminated by its regio isomer 3-ethyl-8-fluoro-2-oxo-1H-quinoxaline-5-carbaldehyde) (40 mg, 0.18 mmol) and N-methyl-5-(piperazin-1-yl)picolinamide (intermediate 31)(50 mg, 0.23 mmol) in THF (3 mL). The resulting mixture was stirred at room temperature for 2 minutes. Sodium triacetoxyborohydride (154 mg, 0.73 mmol) was added. The resulting mixture was stirred at room temperature for 16 hours. The reaction mixture was quenched with MeOH (0.1 mL) and concentrated to afford crude product. The crude product was purified by preparative HPLC (Column: Xselect CSH OBD Column 30*150 mm 5 um, n; Mobile Phase A:Water (0.1% FA), Mobile Phase B:ACN; Flow rate:60 mL/min; Gradient:6 B to 17 B in 7 min; 254; 220 nm. Fractions containing the desired compound were evaporated to dryness to afford 5-[4-[(2-ethyl-5-fluoro-3-oxo-4H-quinoxalin-6-yl)methyl]piperazin-1-yl]-N-methyl-pyridine-2-carboxamide (example 29) (17.29 mg, 22%) as a white solid. 1H NMR (400 MHz, DMSO-d6) 1.22 (3H, t), 2.53-2.63 (4H, m), 2.74-2.87 (5H, m), 3.05-3.15 (4H, m, merged into water peak), 3.69 (2H, s), 7.29 (1H, t), 7.37 (1H, dd), 7.54 (1H, d), 7.81 (1H, d), 8.25 (1H, d), 8.35-8.42 (1H, m), 12.44 (1H, s); 19F NMR (376 MHz, DMSO-d6) −135.49; m/z (ES$^+$) [M+H]$^+$=425.

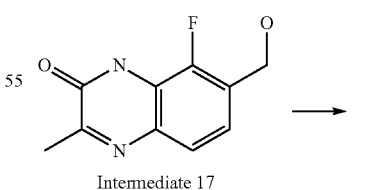

Intermediate 17

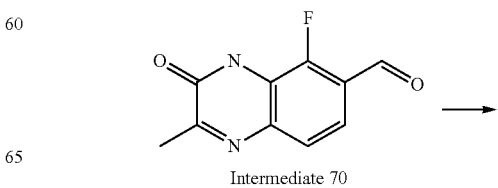

Intermediate 70

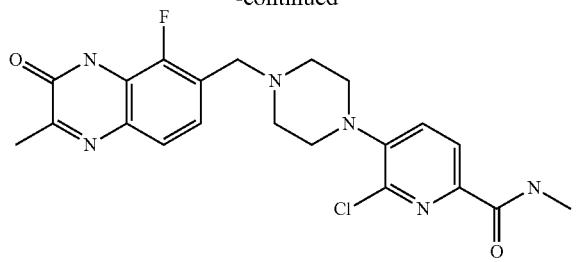

Example 30

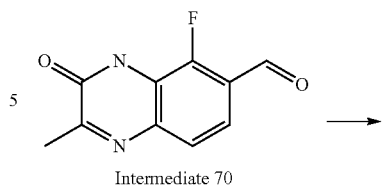

Intermediate 70

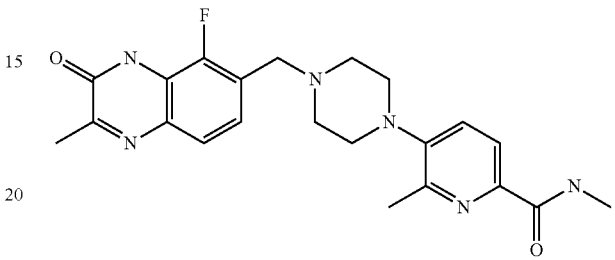

Example 31

Intermediate 70: 5-fluoro-2-methyl-3-oxo-4H-quinoxaline-6-carbaldehyde

Dess-Martin periodinane (1.34 g, 3.16 mmol) was added to 8-fluoro-7-(hydroxymethyl)-3-methyl-1H-quinoxalin-2-one (intermediate 17) (contaminated with 8-fluoro-5-(hydroxymethyl)-3-methyl-1H-quinoxalin-2-one) (0.33 g, 0.79 mmol) in DCM (20 ml). The resulting mixture was stirred at room temperature for 6 hours. The reaction mixture was evaporated to afford crude product. The crude product was purified by flash C18-flash chromatography, elution gradient 5 to 30% MeCN in water (0.4% FA). Pure fractions were evaporated to dryness to afford 5-fluoro-2-methyl-3-oxo-4H-quinoxaline-6-carbaldehyde (contaminated with 8-fluoro-3-methyl-2-oxo-1H-quinoxaline-5-carbaldehyde) (intermediate 70) (0.300 g, 92%) as an off-white solid. m/z (ES$^+$) [M+H]$^+$=207.

Example 30: 6-chloro-5-[4-[(5-fluoro-2-methyl-3-oxo-4H-quinoxalin-6-yl)methyl]piperazin-1-yl]-N-methyl-pyridine-2-carboxamide Titanium isopropoxide (89 mg, 0.31 mmol) was added to 5-fluoro-2-methyl-3-oxo-4H-quinoxaline-6-carbaldehyde (contaminated with 8-fluoro-3-methyl-2-oxo-1H-quinoxaline-5-carbaldehyde) (intermediate 70) (150 mg, 0.36 mmol) and 6-chloro-N-methyl-5-piperazin-1-yl-pyridine-2-carboxamide (intermediate 30)(80 mg, 0.31 mmol) in THF (3 mL). The resulting mixture was stirred at room temperature for 20 minutes. Sodium triacetoxyborohydride (266 mg, 1.26 mmol) was added. The resulting mixture was stirred at room temperature for 16 hours. The reaction mixture was quenched with MeOH (0.1 mL) and concentrated to afford crude product. The crude product was purified by preparative HPLC (Column: XBridge Shield RP18 OBD Column, 19*250 mm, 10 um; Mobile Phase A: Water (10 mmol/L NH$_4$HCO$_3$+0.1% NH$_3$·H$_2$O), Mobile Phase B: MeOH-Preparative; Flow rate: 20 mL/min; Gradient: 57 B to 80 B in 7 min; 254/220 nm. Fractions containing the desired compound were evaporated to dryness to afford 6-chloro-5-[4-[(5-fluoro-2-methyl-3-oxo-4H-quinoxalin-6-yl)methyl]piperazin-1-yl]-N-methyl-pyridine-2-carboxamide (example 30) (35.6 mg, 25%) as a white solid. 1H NMR (400 MHz, DMSO-d6) 2.42 (3H, s), 2.58-2.66 (4H, m), 2.79 (3H, d), 3.06-3.16 (4H, m), 3.72 (2H, s), 7.30 (1H, t), 7.53 (1H, d), 7.65 (1H, d), 7.93 (1H, d), 8.41-8.48 (1H, m), 12.47 (1H, s); 19F NMR (376 MHz, DMSO-d6) −135.45; m/z (ES$^+$) [M+H]$^+$=445.

Example 31: 5-[4-[(5-fluoro-2-methyl-3-oxo-4H-quinoxalin-6-yl)methyl]piperazin-1-yl]-N,6-dimethyl-pyridine-2-carboxamide Titanium isopropoxide (105 mg, 0.37 mmol) was added to 5-fluoro-2-methyl-3-oxo-4H-quinoxaline-6-carbaldehyde (contaminated with 8-fluoro-3-methyl-2-oxo-1H-quinoxaline-5-carbaldehyde) (intermediate 70) (150 mg, 0.36 mmol) and N,6-dimethyl-5-piperazin-1-yl-pyridine-2-carboxamide, HCl (intermediate 33)(100 mg, 0.37 mmol) in THF (3 mL). The resulting mixture was stirred at rt for 2 minutes. Sodium triacetoxyborohydride (313 mg, 1.48 mmol) was added. The resulting mixture was stirred at room temperature for 16 hours. The reaction mixture was quenched with MeOH (0.1 mL) and evaporated to afford crude product. The crude product was purified by preparative HPLC (Column: XBridge Shield RP18 OBD Column, 30*150 mm, 5 um; Mobile Phase A:Water (0.05% NH$_3$H$_2$O), Mobile Phase B:ACN; Flow rate:60 mL/min; Gradient:19 B to 39 B in 7 min; 254/220 nm. Fractions containing the desired compound were evaporated to dryness to afford 5-[4-[(5-fluoro-2-methyl-3-oxo-4H-quinoxalin-6-yl)methyl]piperazin-1-yl]-N,6-dimethyl-pyridine-2-carboxamide (example 31) (12.39 mg, 8%) as an off-white solid. 1H NMR (400 MHz, DMSO-d6) 2.42 (3H, s), 2.48 (3H, s), 2.57-2.67 (4H, m), 2.80 (3H, d), 2.90-2.98 (4H, m), 3.72 (2H, s), 7.30 (1H, t), 7.47 (1H, d), 7.52 (1H, d), 7.79 (1H, d), 8.39-8.46 (1H, m), 12.46 (1H, s); 19F NMR (376 MHz, DMSO-d6) −135.52; m/z (ES$^+$) [M+H]$^+$=425.

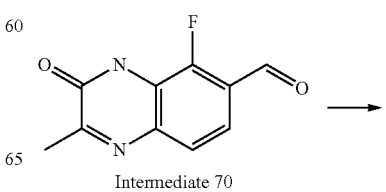

Intermediate 70

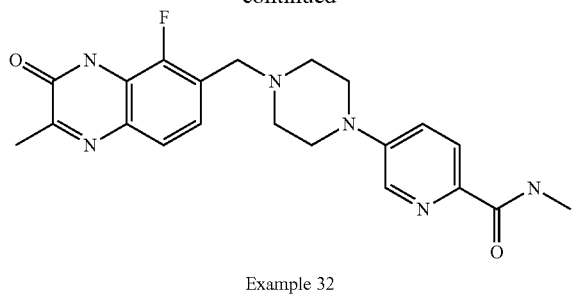

Example 32

Example 32: 5-[4-[(5-fluoro-2-methyl-3-oxo-4H-quinoxalin-6-yl)methyl]piperazin-1-yl]-N-methyl-pyridine-2-carboxamide Titanium isopropoxide (103 mg, 0.36 mmol) was added to 5-fluoro-2-methyl-3-oxo-4H-quinoxaline-6-carbaldehyde (contaminated with 8-fluoro-3-methyl-2-oxo-1H-quinoxaline-5-carbaldehyde) (150 mg, 0.36 mmol) and N-methyl-5-(piperazin-1-yl)picolinamide (intermediate 31)(80 mg, 0.36 mmol) in THF (3 mL). The resulting mixture was stirred at room temperature for 2 minutes. Sodium triacetoxyborohydride (308 mg, 1.45 mmol) was added. The resulting mixture was stirred at room temperature for 16 hours. The reaction mixture was quenched with MeOH (0.1 mL). The reaction mixture was evaporated to afford crude product. The crude product was purified by preparative HPLC (Column: Xbridge Phenyl OBD Column, um, 19*150 mm; Mobile Phase A:Water (0.05% TFA), Mobile Phase B:MeOH-Preparative; Flow rate:20 mL/min; Gradient:24 B to 32 B in 12 min; 254/220 nm and (Column: XBridge Shield RP18 OBD Column, 19*250 mm, 10 um; Mobile Phase A:Water (10 mmol/L $NH_4HCO_3$+0.1% $NH_3 \cdot H_2O$), Mobile Phase B:ACN; Flow rate:20 mL/min; Gradient:15 B to 30 B in 10 min; 254/220 nm. Fractions containing the desired compound were evaporated to dryness to afford 5-[4-[(5-fluoro-2-methyl-3-oxo-4H-quinoxalin-6-yl)methyl]piperazin-1-yl]-N-methyl-pyridine-2-carboxamide (12.4 mg, 8%) as a white solid. 1H NMR (400 MHz, DMSO-d6) 2.42 (3H, s), 2.55-2.60 (4H, m), 2.78 (3H, d), 2.90-2.98 (4H, m, merged into water peak), 3.70 (2H, s), 7.30 (1H, t), 7.38 (1H, dd), 7.52 (1H, d), 7.82 (1H, d), 8.26 (1H, d), 8.38-8.43 (1H, m), 12.47 (1H, s); 19F NMR (376 MHz, DMSO-d6) −135.48; m/z (ES$^+$) [M+H]$^+$=411.

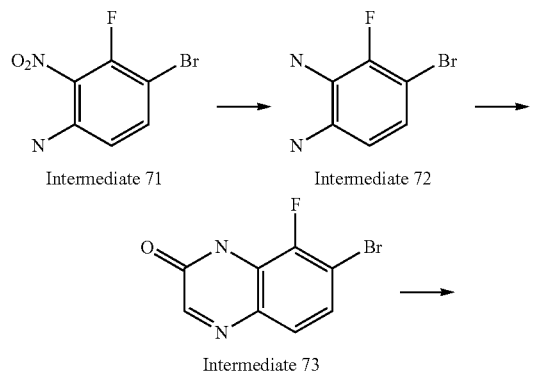

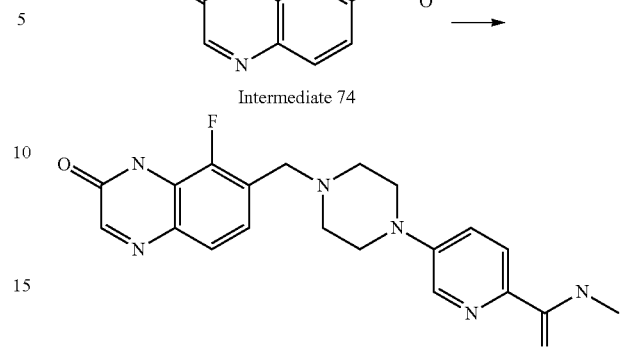

Example 33

Intermediate 72: 4-bromo-3-fluoro-benzene-1,2-diamine

Iron powder (5.2 g, 93.11 mmol) was added to 4-bromo-3-fluoro-2-nitro-aniline (intermediate 71) (7.3 g, 31.06 mmol) and HCl (10 mL, 100.00 mmol)(10 M) in MeOH (30 mL). The resulting mixture was stirred at room temperature for 18 hours. The solvent was removed under reduced pressure. The reaction mixture was basified with saturated $Na_2CO_3$ solution (100 mL). The aqueous layer was extracted with EtOAc (2×100 mL). The organic layer was dried over $Na_2SO_4$, filtered and evaporated to afford 4-bromo-3-fluoro-benzene-1,2-diamine (intermediate 72) (6.05 g, 95%) as a dark solid. 1H NMR (400 MHz, DMSO-d6) 4.66 (2H, s), 4.94 (2H, s), 6.30 (1H, dd), 6.56 (1H, dd); m/z (ES$^+$) [M+H]$^+$=205, 207.

Intermediate 73: 7-bromo-8-fluoro-1H-quinoxalin-2-one

Ethyl 2-oxoacetate in toluene (6.41 g, 31.39 mmol) was added to 4-bromo-3-fluoro-benzene-1,2-diamine (intermediate 72) (4.46 g, 21.75 mmol) in toluene (30 mL). The resulting mixture was stirred at 100° C. for 30 minutes. The solvent was removed under reduced pressure. The reaction mixture was diluted with (PE: 10 mL and EA: 2 mL). The precipitate was collected by filtration, washed with EtOAc (5 mL) and dried under vacuum to afford 7-bromo-8-fluoro-1H-quinoxalin-2-one (intermediate 73) (contaminated by 6-bromo-5-fluoro-1H-quinoxalin-2-one) (2.75 g, 52%) as an off-white solid. m/z (ES$^+$) [M+H]$^+$=243.

Intermediate 74: 8-fluoro-7-(hydroxymethyl)-1H-quinoxalin-2-one

CataCXium A-Pd-G2 (0.12 g, 0.18 mmol) was added to (tributylstannyl)methanol (1.25 g, 3.89 mmol) and 7-bromo-8-fluoro-1H-quinoxalin-2-one (intermediate 73) (1 g, 2.06 mmol) (contaminated by 6-bromo-5-fluoro-1H-quinoxalin-2-one) in 1,4-dioxane (30 mL). The resulting mixture was stirred at 100° C. for 18 hours under nitrogen. The reaction mixture was quenched with saturated KF (10 mL), filtered and evaporated to afford crude product. The crude product was purified by flash C18-flash chromatography, elution gradient 3 to 30% MeCN in water (0.1% formic acid). Pure fractions were evaporated to dryness to afford 8-fluoro-7-(hydroxymethyl)-1H-quinoxalin-2-one (intermediate 74) (260 mg, 69%) (contaminated by 5-fluoro-6-(hydroxymethyl)-1H-quinoxalin-2-one) as an off-white solid. m/z (ES⁺) [M+H]⁺=195.

Example 33: 5-[4-[(5-fluoro-3-oxo-4H-quinoxalin-6-yl)methyl]piperazin-1-yl]-N-methyl-pyridine-2-carboxamide SOCl₂ (0.3 mL, 4.11 mmol) was added to 8-fluoro-7-(hydroxymethyl)-1H-quinoxalin-2-one (intermediate 74) (158 mg, 0.41 mmol) (contaminated by 5-fluoro-6-(hydroxymethyl)-1H-quinoxalin-2-one) in DCM (3 mL). The resulting mixture was stirred at room temperature for 1 h. The solvent was removed under reduced pressure. DIPEA (0.25 mL, 1.43 mmol) and N-methyl-5-piperazin-1-yl-pyridine-2-carboxamide (intermediate 31)(141 mg, 0.64 mmol) were added to the mixture in NMP (3.00 mL). The resulting mixture was stirred at 80° C. for 1 h. The crude product was purified by preparative HPLC (Column: XBridge Prep OBD C18 Column, 19*250 mm, 5 um; Mobile Phase A:Water (10 mmol/L NH₄HCO₃+0.1% NH₃·H₂O), Mobile Phase B:ACN; Flow rate:20 mL/min; Gradient:18 B to 24 B in 9 min; 254; 220 nm). Fractions containing the desired compound were evaporated to dryness to afford 5-[4-[(5-fluoro-3-oxo-4H-quinoxalin-6-yl)methyl]piperazin-1-yl]-N-methyl-pyridine-2-carboxamide (example 33) (13.00 mg, 8%) as a white solid. 1H NMR (400 MHz, DMSO-d6) 2.55-2.60 (4H, m), 2.77 (3H, d), 3.28-3.33 (4H, m), 3.71 (2H, s), 7.30-7.42 (2H, m), 7.61 (1H, d), 7.82 (1H, d), 8.20 (1H, s), 8.25 (1H, d), 8.37-8.42 (1H, m); 19F NMR (376 MHz, DMSO-d6) –129.26; m/z (ES⁺) [M+H]⁺=397.

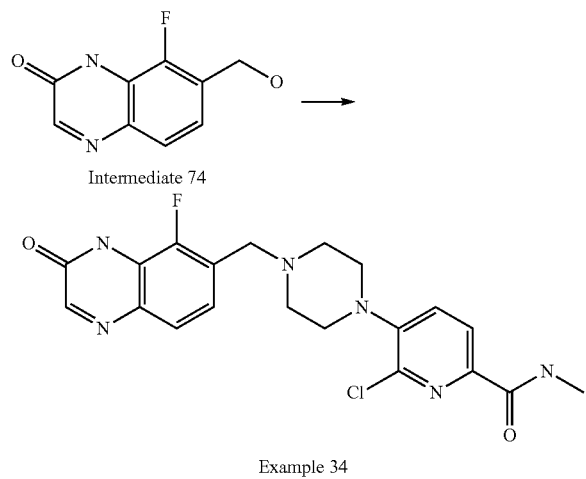

Example 34

Example 34: 6-chloro-5-[4-[(5-fluoro-3-oxo-4H-quinoxalin-6-yl)methyl]piperazin-1-yl]-N-methyl-pyridine-2-carboxamide SOCl₂ (0.3 mL, 4.11 mmol) was added to 8-fluoro-7-(hydroxymethyl)-1H-quinoxalin-2-one (intermediate 74) (contaminated by 5-fluoro-6-(hydroxymethyl)-1H-quinoxalin-2-one) (143 mg, 0.37 mmol) in DCM (3 30 mL). The resulting mixture was stirred at room temperature for 1 h. The solvent was removed under reduced pressure. DIPEA (0.25 mL, 1.43 mmol) and 6-chloro-N-methyl-5-piperazin-1-yl-pyridine-2-carboxamide (intermediate 30)(101 mg, 0.40 mmol) were added to the mixture in NMP (3.00 mL). The resulting mixture was stirred at 80° C. for 1 h. The crude product was purified by preparative HPLC (Column: XBridge Prep OBD C18 Column, 19*250 mm, 5 um; Mobile Phase A:Water (10 MMOL/L NH₄HCO₃+0.1% NH₃·H₂O), Mobile Phase B:ACN; Flow rate:20 mL/min; Gradient:25 B to 28 B in 9 min; 254/220 nm. Fractions containing the desired compound were evaporated to dryness to afford 6-chloro-5-[4-[(5-fluoro-3-oxo-4H-quinoxalin-6-yl)methyl]piperazin-1-yl]-N-methyl-pyridine-2-carboxamide (example 34) (23.0 mg, 14%) as a white solid. 1H NMR (400 MHz, DMSO-d6) 2.58-2.65 (4H, m), 2.78 (3H, d), 3.07-3.14 (4H, m), 3.73 (2H, s), 7.35 (1H, dd), 7.61 (1H, d), 7.65 (1H, d), 7.93 (1H, d), 8.20 (1H, s), 8.41-8.45 (1H, m), 12.58 (1H, s); 19F NMR (376 MHz, DMSO-d6) –135.18; m/z (ES⁺) [M+H]⁺=431.

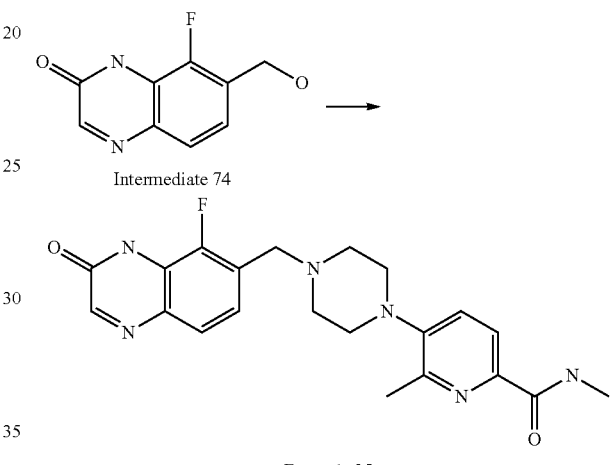

Example 35

Example 35: 5-[4-[(5-fluoro-3-oxo-4H-quinoxalin-6-yl)methyl]piperazin-1-yl]-N,6-dimethyl-pyridine-2-carboxamide SOCl₂ (0.3 mL, 4.11 mmol) was added to 8-fluoro-7-(hydroxymethyl)-1H-quinoxalin-2-one (intermediate 74) (contaminated by 5-fluoro-6-(hydroxymethyl)-1H-quinoxalin-2-one) (143 mg, 0.37 mmol) (153 mg, 0.39 mmol) in DCM (3 mL). The resulting mixture was stirred at room temperature for 1 h. The solvent was removed under reduced pressure. DIPEA (0.25 mL, 1.43 mmol) and N,6-dimethyl-5-piperazin-1-yl-pyridine-2-carboxamide (intermediate 33) (137 mg, 0.58 mmol) in NMP (3 mL) were added to the mixture. The resulting mixture was stirred at 80° C. for 1 h. The crude product was purified by preparative HPLC (Column: XBridge Prep OBD C18 Column, 19*250 mm, 5 um; Mobile Phase A:Water (10 MMOL/L NH₄HCO₃+0.1% NH₃·H₂O), Mobile Phase B:ACN; Flow rate:20 mL/min; Gradient:24 B to 28 B in 9 min; 254/220 nm. Fractions containing the desired compound were evaporated to dryness to afford 5-[4-[(5-fluoro-3-oxo-4H-quinoxalin-6-yl)methyl]piperazin-1-yl]-N,6-dimethyl-pyridine-2-carboxamide (example 35) (13.0 mg, 8%) as a white solid. 1H NMR (400 MHz, DMSO-d6) 2.48 (3H, s), 2.56-2.65 (4H, s), 2.79 (3H, d), 2.92-2.97 (4H, m), 3.73 (2H, s), 7.31-7.39 (1H, m), 7.47 (1H, d), 7.61 (1H, d), 7.78 (1H, d), 8.19 (1H, s), 8.39-8.44 (1H, m), 12.55 (1H, s); 19F NMR (376 MHz, DMSO-d6) –135.25; m/z (ES⁺) [M+H]⁺=411.

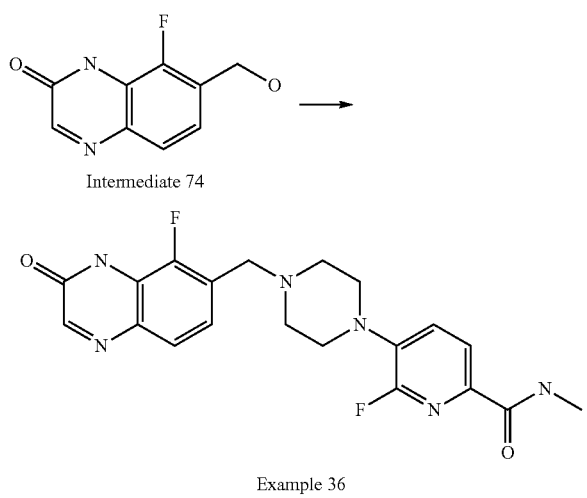 [SMILES: O=c1cnc2ccc(CO)c(F)c2[nH]1 ; CNC(=O)c1ccc(N2CCN(Cc3ccc4ncc(=O)[nH]c4c3F)CC2)c(Cl)n1]

Intermediate 74

Example 36

Example 36: 6-fluoro-5-[4-[(5-fluoro-3-oxo-4H-quinoxalin-6-yl)methyl]piperazin-1-yl]-N-methyl-pyridine-2-carboxamide SOCl₂ (0.3 mL, 4.11 mmol) was added to 8-fluoro-7-(hydroxymethyl)-1H-quinoxalin-2-one (contaminated by 5-fluoro-6-(hydroxymethyl)-1H-quinoxalin-2-one) (144 mg, 0.37 mmol) in DCM (3 mL). The resulting mixture was stirred at room temperature for 1 h. The solvent was removed under reduced pressure. DIPEA (0.25 mL, 1.43 mmol) and 6-fluoro-N-methyl-5-piperazin-1-yl-pyridine-2-carboxamide (intermediate 32)(94 mg, 0.39 mmol) were added to the mixture in NMP (3.00 mL). The resulting mixture was stirred at 80° C. for 1 h. The crude product was purified by preparative HPLC (Column: XBridge Prep OBD C18 Column, 19*250 mm, 5 um; Mobile Phase A:Water (10 MMOL/L NH₄HCO₃+0.1% NH₃·H₂O), Mobile Phase B:ACN; Flow rate:20 mL/min; Gradient:23 B to 25 B in 9 min; 254/220 nm; RT1:6.9, 8.46. Fractions containing the desired compound were evaporated to dryness to afford 6-fluoro-5-[4-[(5-fluoro-3-oxo-4H-quinoxalin-6-yl)methyl]piperazin-1-yl]-N-methyl-pyridine-2-carboxamide (example 36) (16.0 mg, 10%) as a white solid. 1H NMR (400 MHz, DMSO-d6) 2.56-2.62 (4H, m), 2.76 (3H, d), 3.13-3.20 (4H, m), 3.71 (2H, d), 7.33 (1H, dd), 7.55 (1H, t), 7.61 (1H, d), 7.83 (1H, dd), 8.19 (1H, s), 8.37-8.43 (1H, m), 12.56 (1H, brs); 19F NMR (376 MHz, DMSO-d6) −72.57, −135.21; m/z (ES⁺) [M+H]⁺=415.

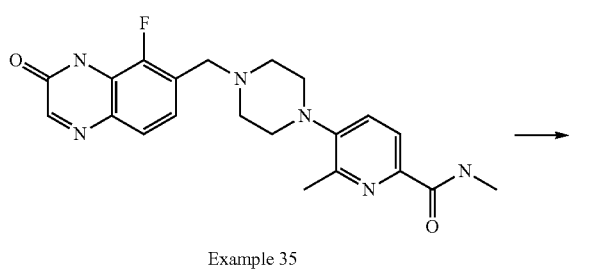

Example 35

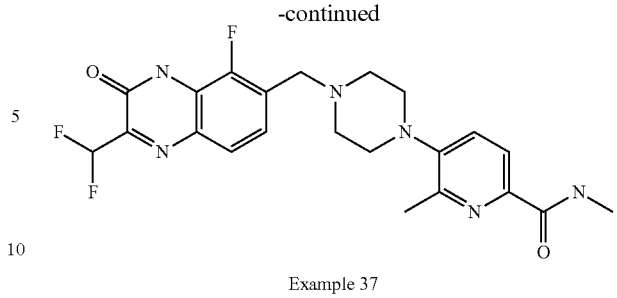

Example 37

Example 37: 5-[4-[[2-(difluoromethyl)-5-fluoro-3-oxo-4H-quinoxalin-6-yl]methyl]piperazin-1-yl]-N,6-dimethyl-pyridine-2-carboxamide A solution of iron(II) chloride (6.18 mg, 0.05 mmol) and zinc(II) difluoromethanesulfinate (86 mg, 0.29 mmol) in water (0.5 mL) was added portion wise to a stirred solution of 5-[4-[(5-fluoro-3-oxo-4H-quinoxalin-6-yl)methyl]piperazin-1-yl]-N,6-dimethyl-pyridine-2-carboxamide (example 35) (40.0 mg, 0.10 mmol) and TFA (7.51 µl, 0.10 mmol) in DMSO (3 mL) at room temperature. Followed by addition of tert-butyl hydroperoxide (9.44 µl, 0.10 mmol) and the resulting mixture was stirred at room temperature for 2 h. The crude product was purified by preparative HPLC (column, Column: XBridge Prep OBD C18 Column 30×150 mm 5 um; Mobile Phase A: Water (0.05% NH₃H₂O), Mobile Phase B: ACN; Flow rate: 60 mL/min; Gradient: 12% B to 32% B in 7 min; 254/220 nm; Rt: 6.07 min. Fractions containing the desired compound were evaporated to dryness to afford 5-[4-[[2-(difluoromethyl)-5-fluoro-3-oxo-4H-quinoxalin-6-yl]methyl]piperazin-1-yl]-N,6-dimethyl-pyridine-2-carboxamide (example 37) (2.2 mg, 5%) as a pale yellow solid. 1H NMR (400 MHz, DMSO-d6) 2.49 (3H, s), 2.60-2.65 (4H, m), 2.80 (3H, d), 2.92-2.99 (4H, m), 3.76 (2H, s), 7.08 (1H, t), 7.39 (1H, t), 7.48 (1H, d), 7.70 (1H, d), 7.79 (1H, d), 8.42 (1H, q), 13.01 (1H, s); 19F NMR (376 MHz, DMSO-d6) −124.324, −134.183; m/z (ES⁺) [M+H]⁺=461.

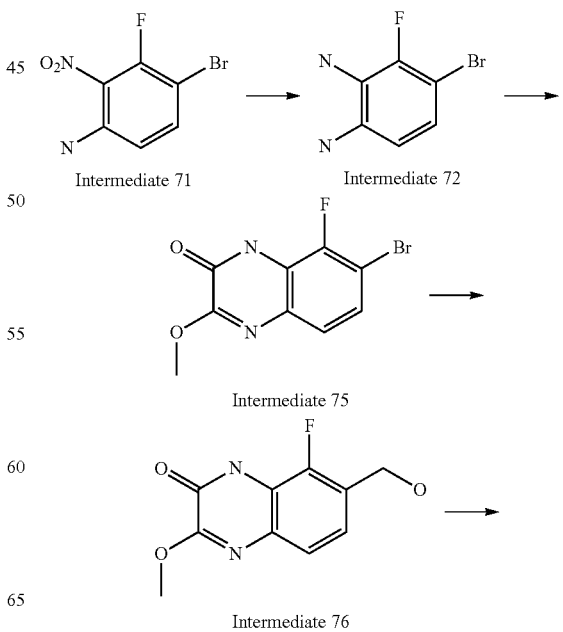

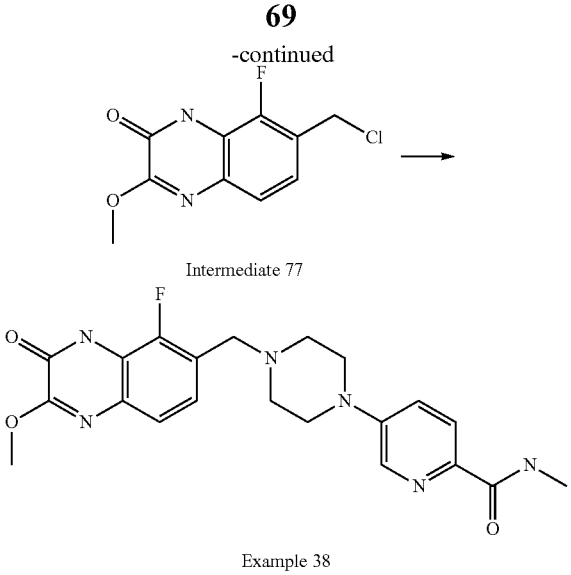

Intermediate 77

Example 38

Intermediate 72: 4-bromo-3-fluoro-benzene-1,2-diamine

Iron powder (3.56 g, 63.83 mmol) was added to 4-bromo-3-fluoro-2-nitro-aniline (intermediate 71) (3.00 g, 12.77 mmol), concentrated hydrogen chloride (10.64 ml, 127.65 mmol) in MeOH (30 mL) at rt. The resulting mixture was stirred at rt for 16 h. The reaction mixture was diluted with water (100 mL) and extracted with ethyl acetate (100 mL×3). The organic layer was dried over MgSO₄, filtered and evaporated to afford 4-bromo-3-fluoro-benzene-1,2-diamine (intermediate 72) (2.5 g, 96%). 1H NMR (400 MHz, DMSO-d6) 4.66 (2H, s), 4.94 (2H, s), 6.30 (dd, 1H), 6.56 (dd, 1H); m/z (ES⁺) [M+H]⁺=205.

Intermediate 75: 7-bromo-8-fluoro-3-methoxy-1H-quinoxalin-2-one

Methyl 2,2,2-trimethoxyacetate (2.402 g, 14.63 mmol) was added to 4-bromo-3-fluorobenzene-1,2-diamine (intermediate 72) (1.500 g, 7.32 mmol), tris(((trifluoromethyl)sulfonyl)oxy)ytterbium (0.454 g, 0.73 mmol) in toluene (20 mL) at room temperature. The resulting mixture was stirred at 100° C. for 5 h. The solvent was removed under reduced pressure. The crude product was purified by reverse phase chromatography on C18 column, elution gradient 5 to 70% MeCN in water. Pure fractions were evaporated to dryness to afford 7-bromo-8-fluoro-3-methoxy-1H-quinoxalin-2-one (intermediate 75) (0.650 g, 32%) as a white solid. 1H NMR (300 MHz, DMSO-d6) 3.97 (3H, s), 7.31 (1H, dd), 7.45 (1H, dd); m/z (ES⁺) [M+H]⁺=273.

Intermediate 76: 8-fluoro-7-(hydroxymethyl)-3-methoxy-1H-quinoxalin-2-one (tributylstannyl)methanol (882 mg, 2.75 mmol) was added to 7-bromo-8-fluoro-3-methoxyquinoxalin-2(1H)-one (intermediate 75) (300.0 mg, 1.1 mmol), cataCXium A-Pd-G2 (73 mg, 0.11 mmol) in 1,4-dioxane (20 mL) at room temperature under nitrogen. The resulting mixture was stirred at 100° C. for 16 h. The reaction mixture was quenched with sat. KF (10 mL) and then filtered. The solvent was removed under reduced pressure. The crude product was purified by reverse phase chromatography on C18 column, elution gradient 5 to 100% MeOH in water. Pure fractions were evaporated to dryness to afford 8-fluoro-7-(hydroxymethyl)-3-methoxy-1H-quinoxalin-2-one (intermediate 76) (130 mg, 53%) as a white solid. 1H NMR (300 MHz, DMSO-d6) 3.97 (3H, s), 4.88 (2H, d), 5.36 (1H, s), 7.27-7.32 (1H, m), 7.36 (1H, d), 12.45 (1H, s); m/z (ES⁺) [M+H]⁺=225.

Intermediate 77: 7-(chloromethyl)-8-fluoro-3-methoxy-1H-quinoxalin-2-one

SOCl₂ (8 ml, 109.62 mmol) was added to 8-fluoro-7-(hydroxymethyl)-3-methoxy-1H-quinoxalin-2-one (intermediate 76) (50.0 mg, 0.22 mmol) in diethyl ether (50 mL) at room temperature. The resulting mixture was stirred at room temperature for 16 h. The solvent was removed under reduced pressure to afford 7-(chloromethyl)-8-fluoro-3-methoxy-1H-quinoxalin-2-one (intermediate 77) (66.7 mg, 122%, crude) as a yellow oil. The product was used in the next step directly without further purification. 1H NMR (300 MHz, DMSO-d6) 3.97 (3H, s), 4.88 (2H, s), 7.27-7.42 (2H, m), 12.60 (1H, s) m/z (ES⁺) [M+H]⁺=243.

Example 38: 5-[4-[(5-fluoro-2-methoxy-3-oxo-4H-quinoxalin-6-yl)methyl]piperazin-1-yl]-N-methyl-pyridine-2-carboxamide N-methyl-5-piperazin-1-yl-pyridine-2-carboxamide (intermediate 31)(150 mg, 0.68 mmol) was added to 7-(chloromethyl)-8-fluoro-3-methoxy-1H-quinoxalin-2-one (intermediate 77)(198 mg, 0.82 mmol), DIPEA (0.595 mL, 3.40 mmol) in MeCN (10 mL) at room temperature. The resulting mixture was stirred at 60° C. for 16 h. The solvent was removed under reduced pressure. The crude product was purified by flash C18-flash chromatography, elution gradient 5 to 70% MeCN in water. Pure fractions were evaporated to dryness to afford the product (103.0 mg) as a yellow solid (80% purity by UV). Repurified by flash C18-flash chromatography, elution gradient 5 to 70% MeCN in water. Pure fractions were evaporated to dryness to afford 5-[4-[(5-fluoro-2-methoxy-3-oxo-4H-quinoxalin-6-yl)methyl]piperazin-1-yl]-N-methyl-pyridine-2-carboxamide (example 38) (36.0 mg, 12%) as a yellow solid. 1H NMR (300 MHz, DMSO-d6) 2.51-2.60 (4H, m), 2.77 (3H, d), 3.18-3.45 (4H, m), 3.66 (2H, s), 3.95 (3H, s), 7.10-7.27 (1H, m), 7.27-7.42 (2H, m), 7.81 (1H, d), 8.25 (1H, d), 8.39 (1H, q), 12.30 (1H, s); 19F NMR (282 MHz, DMSO-d6) −134.783; m/z (ES⁺) [M+H]⁺=427.

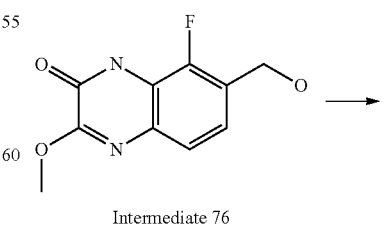

Intermediate 76

-continued

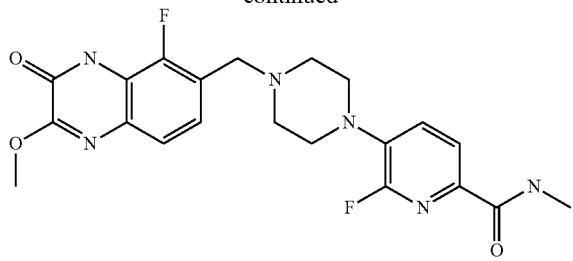

Example 39

Example 39: 6-fluoro-5-[4-[(5-fluoro-2-methoxy-3-oxo-4H-quinoxalin-6-yl)methyl]piperazin-1-yl]-N-methyl-pyridine-2-carboxamide SOCl$_2$ (0.065 mL, 0.89 mmol) was added to 8-fluoro-7-(hydroxymethyl)-3-methoxy-1H-quinoxalin-2-one (intermediate 76) (0.040 g, 0.18 mmol) in diethyl ether (10 mL) at room temperature. The resulting mixture was stirred at room temperature for 16 h. The solvent was removed under reduced pressure. 6-fluoro-N-methyl-5-piperazin-1-yl-pyridine-2-carboxamide (intermediate 32)(0.043 g, 0.18 mmol) and DIPEA (0.156 mL, 0.89 mmol) in MeCN (10.00 mL) were added to the above solid at room temperature. The resulting mixture was stirred at 60° C. for 16 h. The solvent was removed under reduced pressure. The crude product was purified by preparative HPLC column, Column: XBridge Shield RP18 OBD Column, 19*250 mm, 10 um; Mobile Phase A: Water (10 mmol/L NH$_4$HCO$_3$+0.1% NH$_3$·H$_2$O), Mobile Phase B: ACN; Flow rate: 20 mL/min; Gradient: 34 B to 48 B in 7 min; 254/220 nm; RT1:5.9. Fractions containing the desired compound were evaporated to dryness to afford 6-fluoro-5-[4-[(5-fluoro-2-methoxy-3-oxo-4H-quinoxalin-6-yl)methyl]piperazin-1-yl]-N-methyl-pyridine-2-carboxamide (example 39)(0.020 g, 25%) as a white solid. 1H NMR (300 MHz, DMSO-d6) 2.55-2.61 (4H, m), 2.75 (3H, d), 3.11-3.19 (4H, m), 3.67 (2H, s), 3.96 (3H, s), 7.18-7.29 (1H, m), 7.35 (1H, d), 7.55 (1H, dd), 7.79-7.88 (1H, m), 8.41 (1H, d), 12.50 (1H, s); 19F NMR (282 MHz, DMSO-d6) −72.581, −134.799; m/z (ES$^+$) [M+H]$^+$=445.

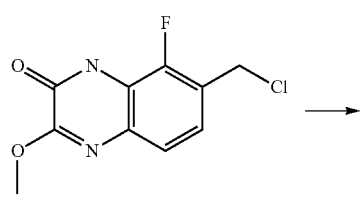

Intermediate 77

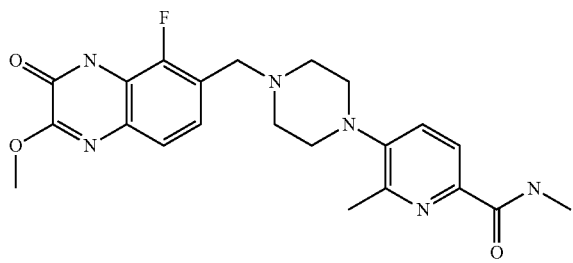

Example 40

Example 40: 5-[4-[(5-fluoro-2-methoxy-3-oxo-4H-quinoxalin-6-yl)methyl]piperazin-1-yl]-N,6-dimethyl-pyridine-2-carboxamide N,6-dimethyl-5-piperazin-1-yl-pyridine-2-carboxamide (intermediate 33)(0.097 g, 0.41 mmol) was added to 7-(chloromethyl)-8-fluoro-3-methoxyquinoxalin-2(1H)-one (intermediate 77) (0.100 g, 0.41 mmol), DIPEA (0.360 mL, 2.06 mmol) in MeCN (10 mL) at room temperature. The resulting mixture was stirred at 60° C. for 16 h. The solvent was removed under reduced pressure. The crude product was purified by preparative HPLC, Column: XBridge Prep OBD C18 Column, 30×150 mm 5 um; Mobile Phase A: Water (0.05% NH$_3$H$_2$O), Mobile Phase B: ACN; Flow rate: 60 mL/min; Gradient: 10B to 30B in 7 min; 254/220 nm. Fractions containing the desired compound were evaporated to dryness to afford 5-[4-[(5-fluoro-2-methoxy-3-oxo-4H-quinoxalin-6-yl)methyl]piperazin-1-yl]-N,6-dimethyl-pyridine-2-carboxamide (example 40) (0.063 g, 35%) as a white solid. 1H NMR (400 MHz, DMSO-d6) 2.48 (3H, s), 2.58-2.63 (4H, m), 2.80 (3H, d), 2.92-2.96 (4H, m), 3.69 (2H, s), 3.97 (3H, s), 7.25 (1H, t), 7.36 (1H, d), 7.47 (1H, d), 7.79 (1H, d), 8.43 (1H, q), 12.51 (1H, s); 19F NMR (376 MHz, DMSO-d6) −134.815; m/z (ES$^+$) [M+H]$^+$=441.

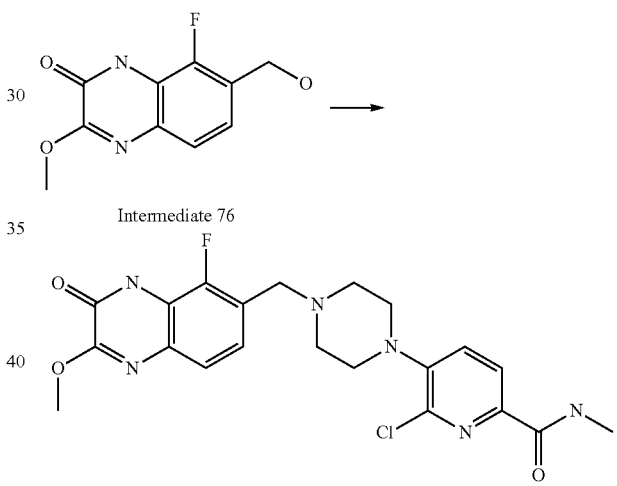

Example 41

Example 41: 6-chloro-5-[4-[(5-fluoro-2-methoxy-3-oxo-4H-quinoxalin-6-yl)methyl]piperazin-1-yl]-N-methyl-pyridine-2-carboxamide SOCl$_2$ (0.065 mL, 0.89 mmol) was added to 8-fluoro-7-(hydroxymethyl)-3-methoxy-1H-quinoxalin-2-one (intermediate 76) (0.040 g, 0.18 mmol) in diethyl ether (10 mL) at room temperature. The resulting mixture was stirred at room temperature for 16 h. The solvent was removed under reduced pressure to afford crude 7-(chloromethyl)-8-fluoro-3-methoxy-1H-quinoxalin-2-one (0.045 g, 0.18 mmol). MeCN (10.00 mL) was added to the above solid followed by addition of 6-chloro-N-methyl-5-piperazin-1-yl-pyridine-2-carboxamide (intermediate 30)(0.045 g, 0.18 mmol) and DIPEA (0.156 mL, 0.89 mmol). The resulting mixture was stirred at 80° C. for 16 hours. The solvent was removed under reduced pressure. The crude product was purified by preparative HPLC column, Column: YMC-Actus Triart C18, 30*250.5 um; Mobile Phase A: Water (0.05%

NH₃H₂O), Mobile Phase B: ACN; Flow rate: 60 mL/min; Gradient: 21 B to 41 B in 7 min; 254, 220 nm; RT1:6.18. Fractions containing the desired compound were evaporated to dryness to afford 6-chloro-5-[4-[(5-fluoro-2-methoxy-3-oxo-4H-quinoxalin-6-yl)methyl]piperazin-1-yl]-N-methyl-pyridine-2-carboxamide (example 41) (0.041 g, 50%) as a white solid. 1H NMR (300 MHz, DMSO-d6) 2.56-2.66 (4H, m), 2.79 (3H, d), 3.06-3.16 (4H, m), 3.70 (2H, s), 3.97 (3H, s), 7.19-7.30 (m, 1H), 7.36 (d, 1H), 7.66 (d, 1H), 7.93 (d, 1H), 8.44 (d, 1H), 12.47 (s, 1H); 19F NMR (282 MHz, DMSO-d6) −134.746; m/z (ES⁺) [M+H]⁺=461.

Intermediate 78: 2-(4-bromo-3-methyl-2-nitro-anlino)butanoic acid 2-aminobutanoic acid (0.793 g, 7.69 mmol) was added to 1-bromo-4-fluoro-2-methyl-3-nitrobenzene (intermediate 2)(1.500 g, 6.41 mmol), K₂CO₃ (2.66 g, 19.23 mmol) in DMF (20 mL) at room temperature. The resulting mixture was stirred at 100° C. for 6 h. The reaction mixture was poured into ice water, quenched slowly with 1 M HCl (20 mL) at 0° C. to give a yellow suspension. The solid was collected by filtration, washed with water and dried to afford 2-(4-bromo-3-methyl-2-nitro-anilino)butanoic acid (intermediate 78) (1.4 g, 74%) as a yellow solid (not very pure, carried over to next step without further purification). m/z (ES⁺) [M+H]⁺=317.

Intermediate 79: 7-bromo-3-ethyl-8-methyl-3,4-dihydro-1H-quinoxalin-2-one

Iron powder (1.585 g, 28.38 mmol) was added slowly to 2-(4-bromo-3-methyl-2-nitro-anilino)butanoic acid (intermediate 78) (1.800 g, 5.68 mmol), concentrated hydrogen chloride (4.73 ml, 56.76 mmol) in MeOH (100 mL) at room temperature. The resulting mixture was stirred at room temperature for 7 h. The reaction mixture was filtered. The solvent was removed under reduced pressure. The reaction mixture was quenched with saturated Na₂CO₃ (40 mL) and extracted with EtOAc (3×50 mL). The organic layer was dried over Na₂SO₄, filtered and evaporated to afford brown solid. The crude product was purified by flash C18-flash chromatography, elution gradient 5 to 50% MeCN in water. Pure fractions were evaporated to dryness to afford 7-bromo-3-ethyl-8-methyl-3,4-dihydro-1H-quinoxalin-2-one (intermediate 79) (650 mg, 43%) as a white solid. 1H NMR (300 MHz, DMSO-d6) 0.90 (3H, t), 1.43-1.72 (2H, m), 2.22 (3H, s), 3.56 (1H, ddd), 6.16 (1H, d), 6.56 (1H, d), 6.97 (1H, d), 9.76 (1H, s); m/z (ES⁺) [M+H]⁺=269.

Intermediate 80: 7-bromo-3-ethyl-8-methyl-1H-quinoxalin-2-one

DDQ (1.316 g, 5.80 mmol) was added to 7-bromo-3-ethyl-8-methyl-3,4-dihydro-1H-quinoxalin-2-one (intermediate 79) (1.300 g, 4.83 mmol) in 1,4-dioxane (150 mL) at room temperature. The resulting mixture was stirred at room temperature for 3 h. The solvent was removed under reduced pressure. The reaction mixture was quenched with saturated NaHCO₃ (150 mL). The precipitate was collected by filtration. The solid was washed with water (10 mL×3) and dried under vacuum to afford the desired product 7-bromo-3-ethyl-8-methyl-1H-quinoxalin-2-one (intermediate 80) (1.2 g, 93%) as yellow solid. 1H NMR (300 MHz, DMSO-d6) 1.20 (3H, t), 2.44-2.53 (3H, m), 2.78 (2H, q), 7.48 (2H, s), 11.74 (1H, s); m/z (ES⁺) [M+H]⁺=267.

Intermediate 81: 3-ethyl-7-(hydroxymethyl)-8-methyl-1H-quinoxalin-2-one (tributylstannyl)methanol (1202 mg, 3.74 mmol) was added to 7-bromo-3-ethyl-8-methylquinoxalin-2(1H)-one (intermediate 80) (400 mg, 1.50 mmol), Pd(PPh₃)₄ (173 mg, 0.15 mmol) in 1,4-dioxane (40 mL) at room temperature under nitrogen. The resulting mixture was stirred at 60° C. for 16 h. The reaction mixture was quenched with KF (10 mL) and the solid was filtered off. The solvent was removed under reduced pressure. The crude product was purified by flash C18-flash chromatography, elution gradient 5 to 100%

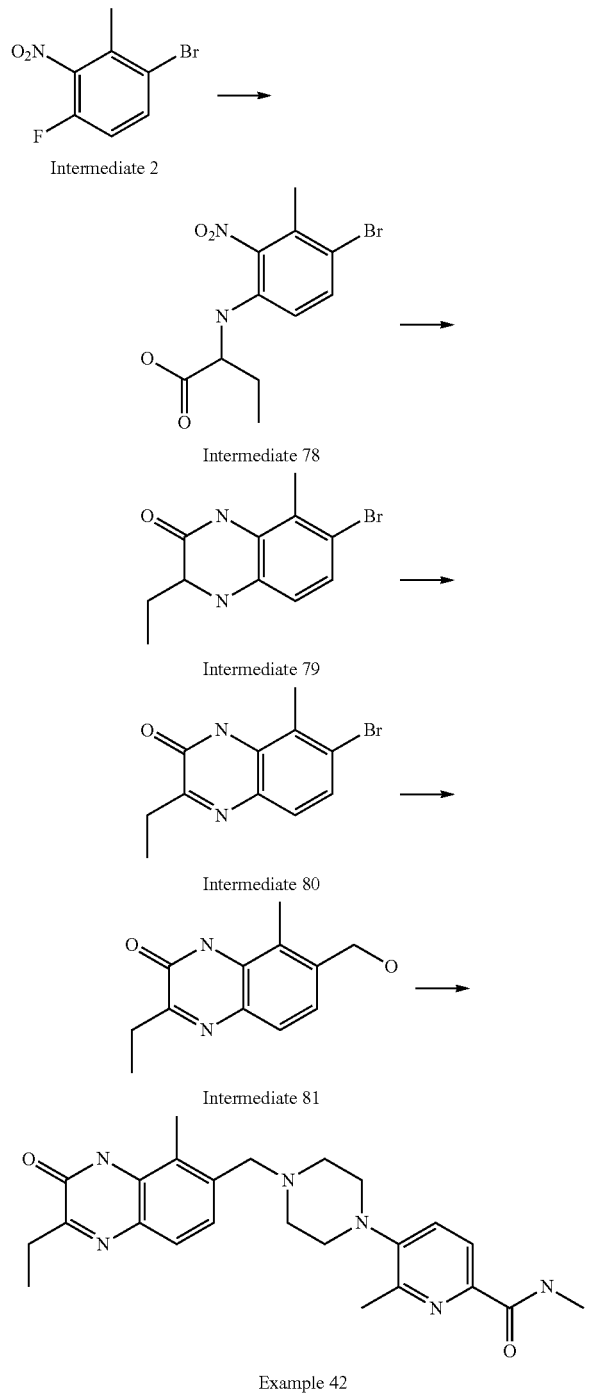

MeOH in water. Pure fractions were evaporated to dryness to afford 3-ethyl-7-(hydroxymethyl)-8-methyl-1H-quinoxalin-2-one (intermediate 81) (100 mg, 31%) as a white solid. 1H NMR (400 MHz, DMSO-d6) 1.22 (3H, t), 2.32 (3H, s), 2.81 (2H, q), 4.59 (2H, d), 5.25 (1H, s), 7.33 (1H, d), 7.55 (1H, d); m/z (ES$^+$) [M+H]$^+$=219.

Example 42: 5-[4-[(2-ethyl-5-methyl-3-oxo-4H-quinoxalin-6-yl)methyl]piperazin-1-yl]-N,6-dimethyl-pyridine-2-carboxamide HBr in AcOH (1 ml, 6.08 mmol) (33 w %) was added to 3-ethyl-7-(hydroxymethyl)-8-methylquinoxalin-2(1H)-one (intermediate 81) (65.0 mg, 0.30 mmol) at rt. The resulting mixture was stirred at 60° C. for 2 h. The solvent was removed under reduced pressure. N,6-dimethyl-5-piperazin-1-yl-pyridine-2-carboxamide (intermediate 33)(69.8 mg, 0.30 mmol) and DIPEA (0.156 ml, 0.89 mmol) in NMP (3 mL) were added to the above solid at room temperature. The resulting mixture was stirred at 60° C. for 2 h. The crude product was purified by preparative HPLC (column, Column: Sunfire prep C18 column, 30*150, 5um; Mobile Phase A:Water (0.1% FA), Mobile Phase B:ACN; Flow rate:60 mL/min; Gradient:9 B to 20 B in 7 min; 254/220 nm; RT1:5.15; Fractions containing the desired compound were evaporated to dryness to afford 5-[4-[(2-ethyl-5-methyl-3-oxo-4H-quinoxalin-6-yl)methyl]piperazin-1-yl]-N,6-dimethyl-pyridine-2-carboxamide (example 42) (0.049 g, 38%) as a pale yellow solid. 1H NMR (300 MHz, DMSO-d6) 1.20 (3H, t), 2.42 (3H, s), 2.50 (3H, s), 2.53-2.59 (4H, m), 2.73-2.86 (5H, m), 2.87-2.93 (4H, m), 3.61 (2H, s), 7.23 (1H, d), 7.45 (1H, d), 7.52 (1H, d), 7.76 (1H, d), 8.39 (1H, d), 11.52 (1H, s); m/z (ES$^+$) [M+H]$^+$=435.

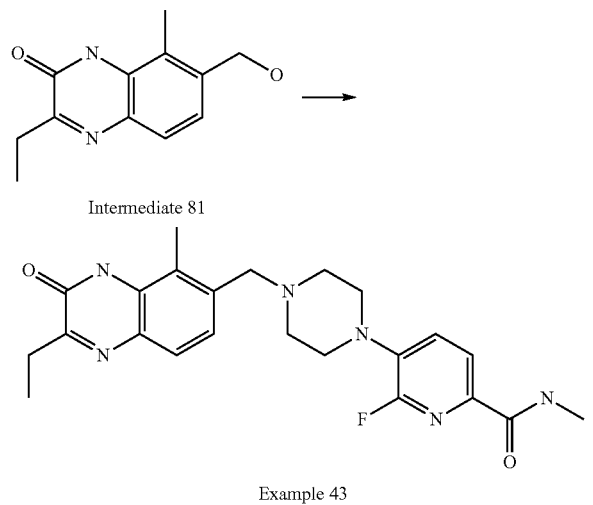

Intermediate 81

Example 43

Example 43: 5-[4-[(2-ethyl-5-methyl-3-oxo-4H-quinoxalin-6-yl)methyl]piperazin-1-yl]-6-fluoro-N-methyl-pyridine-2-carboxamide HBr in AcOH (1 ml, 6.08 mmol)(33 w %) was added to 3-ethyl-7-(hydroxymethyl)-8-methyl-1H-quinoxalin-2-one (intermediate 81) (65.0 mg, 0.30 mmol) at room temperature. The resulting mixture was stirred at 60° C. for 2 hours. The solvent was removed under reduced pressure. 6-fluoro-N-methyl-5-(piperazin-1-yl)picolinamide (intermediate 32) (71.0 mg, 0.30 mmol) was added to the above solid, followed by addition of DIPEA (0.156 ml, 0.89 mmol) in NMP (3 mL) at room temperature. The resulting mixture was stirred at 60° C. for 2 hours. The crude product was purified by preparative HPLC (column, Column: XBridge Prep OBD C18 Column, 30×150 mm 5 um; Mobile Phase A:Water (0.05% NH$_3$H$_2$O), Mobile Phase B:ACN; Flow rate:60 mL/min; Gradient:31 B to 51 B in 7 min; 254/220 nm; RT1:6.27; Fractions containing the desired compound were evaporated to dryness to afford 5-[4-[(2-ethyl-5-methyl-3-oxo-4H-quinoxalin-6-yl)methyl]piperazin-1-yl]-6-fluoro-N-methyl-pyridine-2-carboxamide (example 43) (0.043 g, 33%) as a pale yellow solid. 1H NMR (300 MHz, DMSO-d6) 1.20 (3H, t), 2.41 (3H, s), 2.49-2.59 (4H, m), 2.70-2.81 (5H, m), 3.08-3.16 (4H, m), 3.59 (2H, s), 7.22 (1H, d), 7.47-7.60 (2H, m), 7.82 (1H, dd), 8.37 (1H, d), 11.52 (1H, s); 19F NMR (282 MHz, DMSO-d6) −72.539; m/z (ES$^+$) [M+H]$^+$=439.

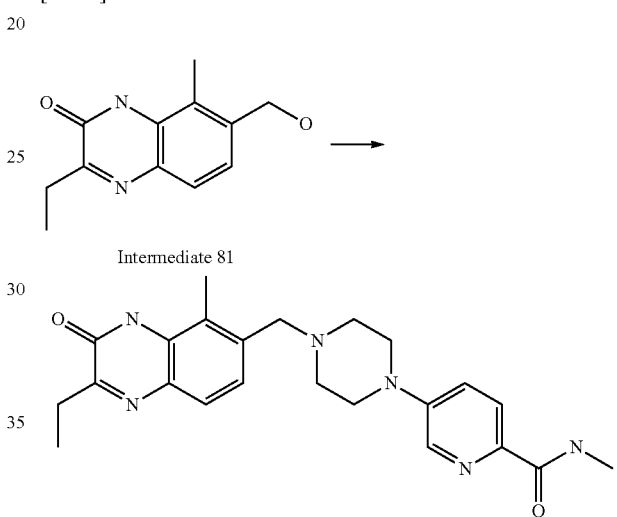

Intermediate 81

Example 44

Example 44: 5-[4-[(2-ethyl-5-methyl-3-oxo-4H-quinoxalin-6-yl)methyl]piperazin-1-yl]-N-methyl-pyridine-2-carboxamide HBr in AcOH (1 ml, 18.42 mmol) (33 wt %) was added to 3-ethyl-7-(hydroxymethyl)-8-methyl-1H-quinoxalin-2-one (intermediate 81) (65.0 mg, 0.30 mmol) at room temperature. The resulting mixture was stirred at 60° C. for 2 hours. The solvent was removed under reduced pressure. N-methyl-5-(piperazin-1-yl)picolinamide (intermediate 31) (65.6 mg, 0.30 mmol) and DIPEA (0.156 ml, 0.89 mmol) was added to the above solid in NMP (3 mL) at room temperature. The resulting mixture was stirred at 60° C. for 2 h. The crude product was purified by preparative HPLC (Column: Sunfire prep C18 column, 30*150, 5um; Mobile Phase A:Water (0.1% FA), Mobile Phase B:ACN; Flow rate:60 mL/min; Gradient:9 B to 20 B in 7 min; 254/220 nm; RT1:5.15; Fractions containing the desired compound were evaporated to dryness to afford 5-[4-[(2-ethyl-5-methyl-3-oxo-4H-quinoxalin-6-yl)methyl]piperazin-1-yl]-N-methyl-pyridine-2-carboxamide (example 44) (0.014 g, 10%) as a pale yellow solid. 1H NMR (400 MHz, DMSO-d6) 1.16-1.26 (3H, m), 2.41 (3H, s), 2.49-2.59 (4H, m), 2.70-2.81 (5H, m), 3.30-3.35 (4H, m, merged into water peak), 3.61

(2H, s), 7.25 (1H, d), 7.38 (1H, d), 7.55 (1H, d), 7.82 (1H, d), 8.26 (1H, s), 8.38 (1H, s), 11.53 (1H, s); m/z (ES$^+$) [M+H]$^+$=421.

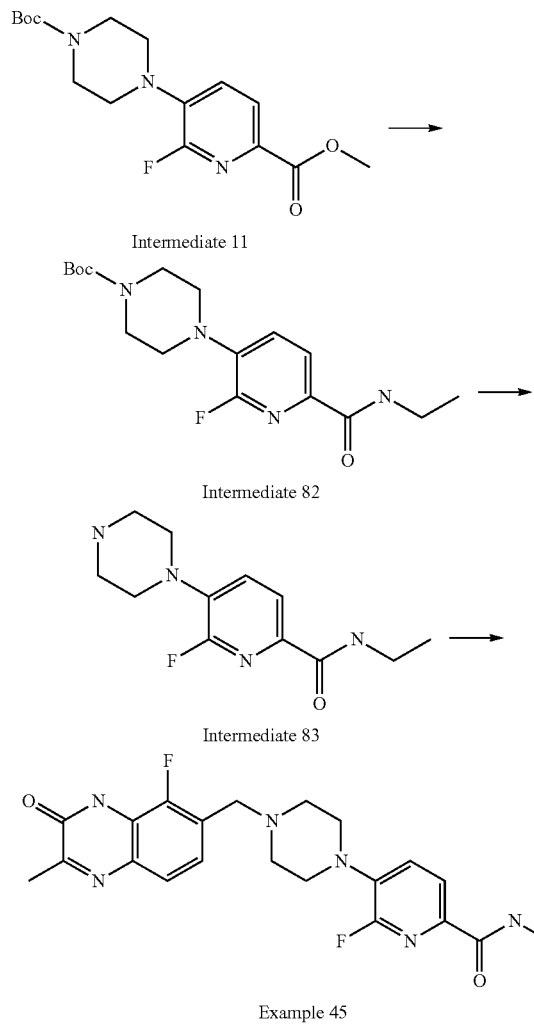

Intermediate 11

Intermediate 82

Intermediate 83

Example 45

Intermediate 82: tert-butyl 4-[6-(ethylcarbamoyl)-2-fluoro-3-pyridyl]piperazine-1-carboxylate tert-butyl 4-(2-fluoro-6-methoxycarbonyl-3-pyridyl)piperazine-1-carboxylate (intermediate 11) (500 mg, 1.47 mmol) was added to ethylamine in water (10 mL, 1.47 mmol) (65 wt %). The resulting mixture was stirred at room temperature for 2 h. The reaction went to completion. The precipitate was collected by filtration, washed with water (2 mL×3) and dried under vacuum to afford tert-butyl 4-[6-(ethylcarbamoyl)-2-fluoro-3-pyridyl]piperazine-1-carboxylate (intermediate 82) (0.515 g, 99%) as an off-white solid. 1H NMR (400 MHz, DMSO-d6) 1.09 (3H, t), 1.42 (9H, s), 3.11 (4H, t), 3.23-3.30 (2H, m), 3.49 (4H, t), 7.59 (1H, dd), 7.85 (1H, d), 8.45 (1H, t); m/z (ES$^+$) [M+H]$^+$=353.

Intermediate 83: N-ethyl-6-fluoro-5-piperazin-1-yl-pyridine-2-carboxamide tert-butyl 4-[6-(ethylcarbamoyl)-2-fluoro-3-pyridyl]piperazine-1-carboxylate (intermediate 82) (536 mg, 1.52 mmol) was added to HCl in 1,4-dioxane (5 mL, 20.00 mmol). The resulting mixture was stirred at room temperature for 1 h. DIPEA (5 mL) was added and the resulting mixture was stirred at room temperature for 15 min. The reaction mixture was evaporated to afford crude product. The crude product was purified by flash C18-flash chromatography, elution gradient 5 to 50% MeCN in water (0.1% NH$_4$HCO$_3$). Pure fractions were evaporated to dryness to afford N-ethyl-6-fluoro-5-piperazin-1-yl-pyridine-2-carboxamide (intermediate 83) (0.368 g, 96%) as a yellow solid. The sample was not pure, carried over to next step without further purification; m/z (ES$^+$) [M+H]$^+$=253.

Example 45: N-ethyl-6-fluoro-5-[4-[(5-fluoro-2-methyl-3-oxo-4H-quinoxalin-6-yl)methyl]piperazin-1-yl]pyridine-2-carboxamide Ph$_3$P (94 mg, 0.36 mmol) was added to CBr$_4$ (119 mg, 0.36 mmol), 8-fluoro-7-(hydroxymethyl)-3-methylquinoxalin-2(1H)-one (intermediate 17) (50 mg, 0.24 mmol) in CH$_2$Cl2 (3 mL). The resulting mixture was stirred at room temperature for 1 h. The solvent was removed under reduced pressure. N-ethyl-6-fluoro-5-piperazin-1-yl-pyridine-2-carboxamide (intermediate 83) (60 mg, 0.24 mmol) and DIPEA (1.5 mL, 8.59 mmol) in NMP (3 mL) were added to the mixture. The resulting mixture was stirred at 80° C. for 2 h. The solvent was removed under reduced pressure. The crude product was purified by flash C18-flash chromatography, elution gradient 0 to 25% MeCN in water (NH$_4$HCO$_3$). Pure fractions were evaporated to dryness to afford N-ethyl-6-fluoro-5-[4-[(5-fluoro-2-methyl-3-oxo-4H-quinoxalin-6-yl)methyl]piperazin-1-yl]pyridine-2-carboxamide (example 45) (2.60 mg, 3%) as a white solid. 1H NMR (300 MHz, DMSO-d6) 1.09 (3H, t), 2.40 (3H, s), 2.52-2.62 (4H, m), 3.17-3.27 (4H, m), 3.25 (2H, q), 3.68 (2H, s), 7.28 (1H, t), 7.48-7.59 (2H, m), 7.82 (1H, d), 8.41 (1H, t), 12.48 (1H, s); 19F NMR (282 MHz, DMSO-d6) -72.58, -135.52; m/z (ES$^+$) [M+H]$^+$=443.

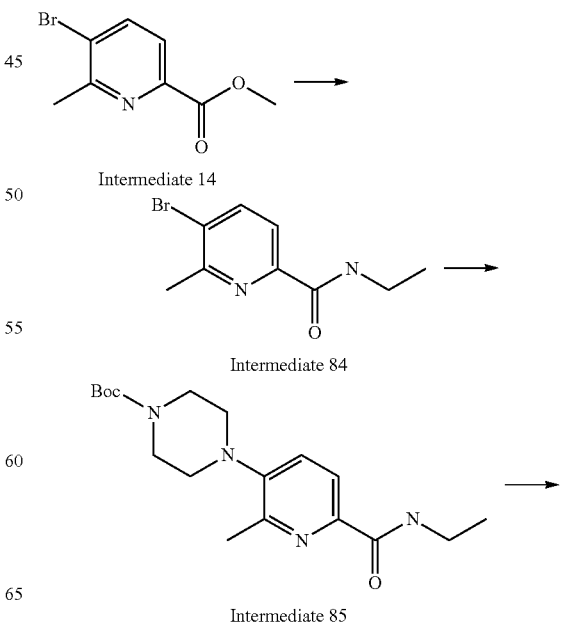

Intermediate 14

Intermediate 84

Intermediate 85

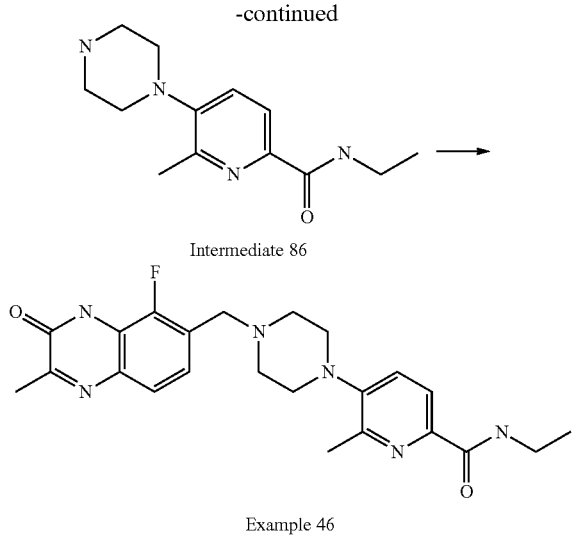

Intermediate 86

Example 46

Intermediate 84: 5-bromo-N-ethyl-6-methyl-pyridine-2-carboxamide

Ethanamine in H₂O (3 mL, 2.20 mmol) (65 wt %) was added to methyl 5-bromo-6-methyl-pyridine-2-carboxylate (intermediate 14) (505 mg, 2.20 mmol). The resulting mixture was stirred at room temperature for 18 h. The solvent was removed under reduced pressure to afford 5-bromo-N-ethyl-6-methyl-pyridine-2-carboxamide (intermediate 84) (0.500 g, 94%) as a yellow solid. 1H NMR (300 MHz, DMSO-d6) 1.13 (3H, t), 2.66 (3H, s), 3.26-3.39 (2H, in), 7.76 (1H, d), 8.18 (1H, d), 8.67-8.72 (1H, in); m/z (ES⁺) [M+H]⁺=243.

Intermediate 85: tert-butyl 4-[6-(ethylcarbamoyl)-2-methyl-3-pyridyl]piperazine-1-carboxylate Cs₂CO₃ (1.340 g, 4.11 mmol) was added to 5-bromo-N-ethyl-6-methyl-pyridine-2-carboxamide (intermediate 84) (0.5 g, 2.06 mmol), tert-butyl piperazine-1-carboxylate (0.575 g, 3.09 mmol), BINAP (0.128 g, 0.21 mmol) and Pd(OAc)₂ (0.046 g, 0.21 mmol) in 1,4-dioxane (5 mL). The resulting mixture was stirred at 100° C. for 18 h under nitrogen. The reaction mixture was diluted with EtOAc (10 mL), and washed sequentially with water (10 mL×2) followed by brine (10 mL×1). The organic layer was dried over Na₂SO₄, filtered and evaporated to afford crude product. The crude product was purified by flash silica chromatography, elution gradient 0 to 40% EtOAc in petroleum ether. Pure fractions were evaporated to dryness to afford tert-butyl 4-[6-(ethylcarbamoyl)-2-methyl-3-pyridyl]piperazine-1-carboxylate (intermediate 85) (0.481 g, 67%) as a yellow solid. 1H NMR (300 MHz, Chloroform-d) 1.26 (3H, t), 1.49 (9H, s), 2.54 (3H, s), 2.85-2.98 (4H, in), 3.49 (2H, qd), 3.56-3.65 (4H, in), 7.32 (1H, d), 7.91-8.01 (2H, in); m/z (ES⁺) [M+H]⁺=349.

Intermediate 86: N-ethyl-6-methyl-5-piperazin-1-yl-pyridine-2-carboxamide

HCl in 1,4-dioxane (4 ml, 16.00 mmol, 4M) was added to tert-butyl 4-[6-(ethylcarbamoyl)-2-methyl-3-pyridyl]piperazine-1-carboxylate (intermediate 85) (0.481 g, 1.38 mmol) in MeOH (10 mL). The resulting mixture was stirred at room temperature for 2 hours. The solvent was removed under reduced pressure. The reaction mixture was basified with DIPEA (1 mL) in MeOH (3 mL). The solvent was removed under reduced pressure. The crude product was purified by flash 018-flash chromatography, elution gradient 0 to 20% MeCN in water (NH₄HCO₃). Pure fractions were evaporated to dryness to afford N-ethyl-6-methyl-5-piperazin-1-yl-pyridine-2-carboxamide (intermediate 86) (0.189 g, 55%) as a yellow oil. 1H NMR (400 MHz, DMSO-d6) 1.12 (3H, t), 2.81-2.92 (8H, m), 3.27-3.36 (5H, m), 7.46 (1H, d), 7.81 (1H, d), 8.43 (1H, t); m/z (ES⁺) [M+H]⁺=249.

Example 46: N-ethyl-5-[4-[(5-fluoro-2-methyl-3-oxo-4H-quinoxalin-6-yl)methyl]piperazin-1-yl]-6-methyl-pyridine-2-carboxamide Ph₃P (299 mg, 1.14 mmol) was added to 8-fluoro-7-(hydroxymethyl)-3-methylquinoxalin-2(1H)-one (158 mg, 0.76 mmol) (intermediate 17), CBr₄ (378 mg, 1.14 mmol) in CH₂Cl₂ (3.00 mL). The resulting mixture was stirred at room temperature for 1 h. The solvent was removed under reduced pressure. N-ethyl-6-methyl-5-piperazin-1-yl-pyridine-2-carboxamide (intermediate 86) (188 mg, 0.76 mmol) and DIPEA (1.5 mL, 8.59 mmol) were added to the mixture in NMP (3 mL). The resulting mixture was stirred at 80° C. for 2 h. The solvent was removed under reduced pressure. The crude product was purified by flash C18-flash chromatography, elution gradient 0 to 25% MeCN in water (NH₄HCO₃). Pure fractions were evaporated to dryness to afford N-ethyl-5-[4-[(5-fluoro-2-methyl-3-oxo-4H-quinoxalin-6-yl)methyl]piperazin-1-yl]-6-methyl-pyridine-2-carboxamide (example 46) (7.40 mg, 2%) as a white solid. 1H NMR (300 MHz, DMSO-d6) 1.10 (3H, t), 2.40 (3H, s), 2.50 (3H, s), 2.54-2.64 (4H, m), 2.87-2.97 (4H, m), 3.30 (2H, q), 3.70 (2H, s), 7.28 (1H, t), 7.47 (1H, d), 7.52 (1H, d), 7.77 (1H, d), 8.42 (1H, t), 12.44 (1H, s); 19F NMR (282 MHz, DMSO-d6) −135.54; m/z (ES⁺) [M+H]⁺=439.

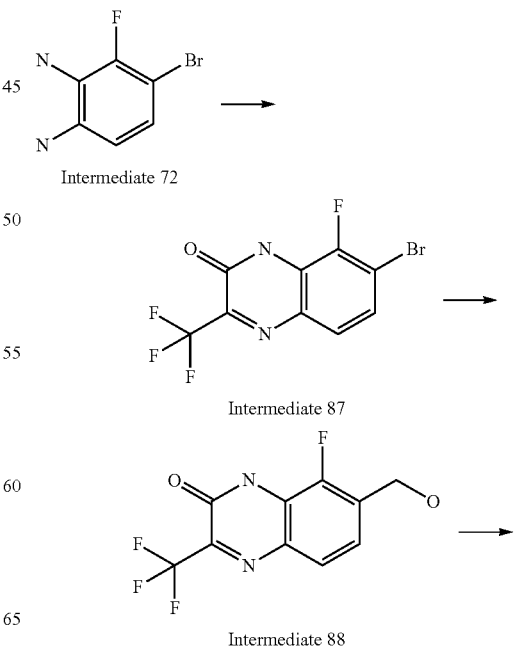

Intermediate 72

Intermediate 87

Intermediate 88

-continued

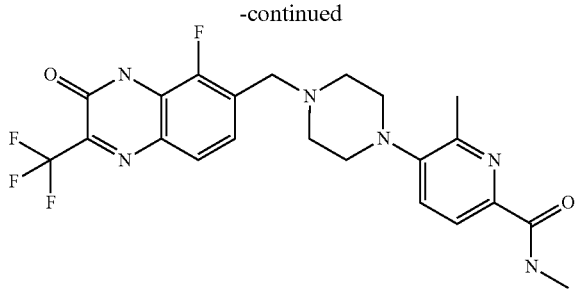

Example 47

Intermediate 87: 7-bromo-8-fluoro-3-(trifluoromethyl)-1H-quinoxalin-2-one

Ethyl 3,3,3-trifluoro-2-oxopropanoate (2.30 g, 13.52 mmol) was added to 4-bromo-3-fluoro-benzene-1,2-diamine (intermediate 72) (2.20 g, 10.73 mmol) in toluene (10 mL). The resulting mixture was stirred at 100° C. for 18 h. The solvent was removed under reduced pressure. The crude product was purified by flash C18-flash chromatography, elution gradient 3 to 70% MeCN in water (0.1% NH$_4$HCO$_3$). Pure fractions were evaporated to dryness to afford 7-bromo-8-fluoro-3-(trifluoromethyl)-1H-quinoxalin-2-one (intermediate 87) (contaminated by 6-bromo-5-fluoro-3-(trifluoromethyl)-1H-quinoxalin-2-one) (3.40 g, 501%) as an off-white solid. m/z (ES$^+$) [M+H]$^+$=311.

Intermediate 88: 8-fluoro-7-(hydroxymethyl)-3-(trifluoromethyl)-1H-quinoxalin-2-one CataCxium A Pd G2 (53 mg, 0.08 mmol) was added to 7-bromo-8-fluoro-3-(trifluoromethyl)-1H-quinoxalin-2-one (intermediate 87) (contaminated by 6-bromo-5-fluoro-3-(trifluoromethyl)-1H-quinoxalin-2-one) (0.5 g, 0.80 mmol) and (Tributylstannyl)methanol (0.5 mL, 0.80 mmol) in 1,4-dioxane (15 mL). The resulting mixture was stirred at 80° C. for 18 h under nitrogen. The reaction mixture was quenched with saturated KF (1.25 mL). The reaction solution was collected by filtration, washed with dioxane (2.5 mL). The solvent of the combined organic layers was removed under reduced pressure. The crude product was purified by flash C18-flash chromatography, elution gradient 3 to 40% MeCN in water (0.1%, TFA). Pure fractions were evaporated to dryness to afford 8-fluoro-7-(hydroxymethyl)-3-(trifluoromethyl)-1H-quinoxalin-2-one (intermediate 88) (contaminated by 5-fluoro-6-(hydroxymethyl)-3-(trifluoromethyl)-1H-quinoxalin-2-one) (0.217 g, 51%) as an off-white solid. m/z (ES$^+$) [M+H]$^+$=263.

Example 47: 5-[4-[[5-fluoro-3-oxo-2-(trifluoromethyl)-4H-quinoxalin-6-yl]methyl]piperazin-1-yl]-N,6-dimethyl-pyridine-2-carboxamide SOCl$_2$ (0.5 mL, 6.85 mmol) was added to 8-fluoro-7-(hydroxymethyl)-3-(trifluoromethyl)-1H-quinoxalin-2-one (intermediate 88) (contaminated by 5-fluoro-6-(hydroxymethyl)-3-(trifluoromethyl)-1H-quinoxalin-2-one) (160 mg, 0.31 mmol) in Et$_2$O (5 mL). The resulting mixture was stirred at room temperature for 2 h. The solvent was removed under reduced pressure. DIPEA (4 mL, 22.90 mmol) and N,6-dimethyl-5-piperazin-1-yl-pyridine-2-carboxamide (intermediate 33)(134 mg, 0.57 mmol) were added to the mixture in MeCN (10 mL). The resulting mixture was stirred at room temperature for 24 h. The crude product was purified by preparative HPLC (Column: XBridge BEH C18 OBD Prep Column, 5 μm, 19 mm 250 mm; Mobile Phase A: Water (10 mmol/L NH$_4$HCO$_3$+0.1% NH$_3$·H$_2$O), Mobile Phase B: ACN; Flow rate: 20 mL/min; Gradient: 24 B to 33 B in 10 min; 254/220 nm; RT1:8.2/9.5) Fractions containing the desired compound were evaporated to dryness to afford 5-[4-[[5-fluoro-3-oxo-2-(trifluoromethyl)-4H-quinoxalin-6-yl]methyl]piperazin-1-yl]-N,6-dimethyl-pyridine-2-carboxamide (example 47) (8.8 mg, 6%) as a white solid. 1H NMR (400 MHz, DMSO-d6) 2.50 (3H, s), 2.58-2.66 (4H, m), 2.79 (3H, d), 2.90-2.99 (4H, m), 3.77 (2H, s), 7.41 (1H, t), 7.47 (1H, d), 7.72 (1H, d), 7.78 (1H, d), 8.39-8.44 (1H, m), 13.21 (1H, brs); 19F NMR (376 MHz, DMSO-d6) −68.50, −133.81; m/z (ES$^+$) [M+H]$^+$=479.

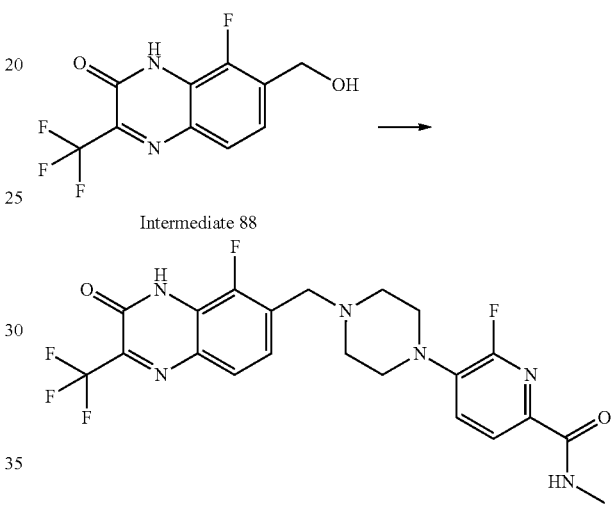

Intermediate 88

Example 48

Example 48: 6-fluoro-5-[4-[[5-fluoro-3-oxo-2-(trifluoromethyl)-4H-quinoxalin-6-yl]methyl]piperazin-1-yl]-N-methyl-pyridine-2-carboxamide SOCl$_2$ (0.4 mL, 5.48 mmol) was added to 8-fluoro-7-(hydroxymethyl)-3-(trifluoromethyl)-1H-quinoxalin-2-one (intermediate 88) (contaminated by 5-fluoro-6-(hydroxymethyl)-3-(trifluoromethyl)-1H-quinoxalin-2-one) (120 mg, 0.23 mmol) in Et$_2$O (5 mL). The resulting mixture was stirred at room temperature for 2 h. The solvent was removed under reduced pressure. DIPEA (2 mL, 11.45 mmol) and 6-fluoro-N-methyl-5-piperazin-1-yl-pyridine-2-carboxamide (intermediate 32)(156 mg, 0.65 mmol) were added to the mixture in MeCN (10 mL). The resulting mixture was stirred at room temperature for 24 h. The crude product was purified by preparative HPLC (Column: XBridge BEH C18 OBD Prep Column, 5 μm, 19 mm 250 mm; Mobile Phase A: Water (10 mmol/L NH$_4$HCO$_3$+0.1% NH$_3$·H$_2$O), Mobile Phase B: ACN; Flow rate: 20 mL/min; Gradient: 25 B to 37 B in 10 min; 254/220 nm; RT1:7.58/8.97). Fractions containing the desired compound were evaporated to dryness to afford 6-fluoro-5-[4-[[5-fluoro-3-oxo-2-(trifluoromethyl)-4H-quinoxalin-6-yl]methyl]piperazin-1-yl]-N-methyl-pyridine-2-carboxamide (example 48) (8.9 mg, 8%) as a white solid. 1H NMR (400 MHz, DMSO-d6) 2.58-2.65 (4H, m), 2.76 (3H, d), 3.14-3.21 (4H, m), 3.75 (2H, s), 7.39 (1H, t), 7.56 (1H, dd), 7.71 (1H, d), 7.84 (1H, dd), 8.37-8.43 (1H, m), 13.39 (1H, brs); 19F NMR (376 MHz, DMSO-d6) −68.48, −72.59, −133.78; m/z (ES+) [M+H]+=483.

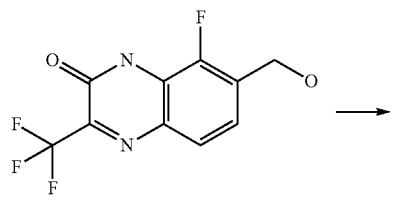

Intermediate 88

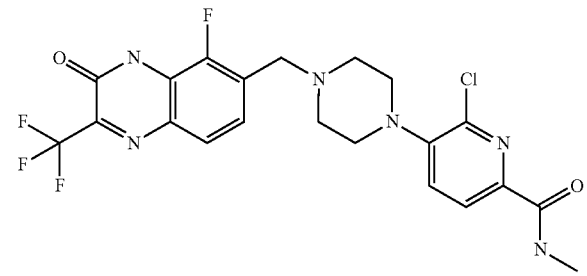

Example 49

Example 49: 6-chloro-5-[4-[[5-fluoro-3-oxo-2-(trifluoromethyl)-4H-quinoxalin-6-yl]methyl]piperazin-1-yl]-N-methyl-pyridine-2-carboxamide SOCl2 (0.4 mL, 5.48 mmol) was added to 8-fluoro-7-(hydroxymethyl)-3-(trifluoromethyl)-1H-quinoxalin-2-one (intermediate 88) (contaminated by 5-fluoro-6-(hydroxymethyl)-3-(trifluoromethyl)-1H-quinoxalin-2-one) (120 mg, 0.23 mmol) in Et2O (5 mL). The resulting mixture was stirred at room temperature for 2 h. The solvent was removed under reduced pressure. DIPEA (2 mL, 11.45 mmol) and 6-chloro-N-methyl-5-piperazin-1-yl-pyridine-2-carboxamide (intermediate 30)(157 mg, 0.62 mmol) were added to the mixture in MeCN (10 mL). The resulting mixture was stirred at room temperature for 24 h. The crude product was purified by preparative HPLC (Column: XBridge Shield RP18 OBD Column, 19*250 mm, 10 um; Mobile Phase A: Water (10 MMOL/L NH4HCO3+0.1% NH3·H2O), Mobile Phase B: ACN; Flow rate: 20 mL/min; Gradient: 45 B to 57 B in 10 min; 254/220 nm). Fractions containing the desired compound were evaporated to dryness to afford 6-chloro-5-[4-[[5-fluoro-3-oxo-2-(trifluoromethyl)-4H-quinoxalin-6-yl]methyl]piperazin-1-yl]-N-methyl-pyridine-2-carboxamide (example 49) (18 mg, 16%) as a white solid. 1H NMR (400 MHz, DMSO-d6) 2.60-2.68 (4H, m), 2.78 (3H, d), 3.07-3.16 (4H, m), 3.77 (2H, s), 7.40 (1H, t), 7.66 (1H, d), 7.72 (1H, d), 7.93 (1H, d), 8.40-8.43 (1H, m), 13.25 (1H, brs); 19F NMR (376 MHz, DMSO-d6) −68.51, −133.73; m/z (ES+) [M+H]+=499.

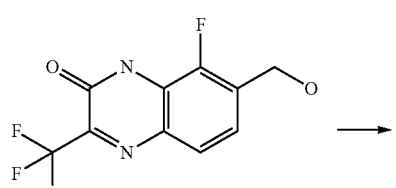

Intermediate 88

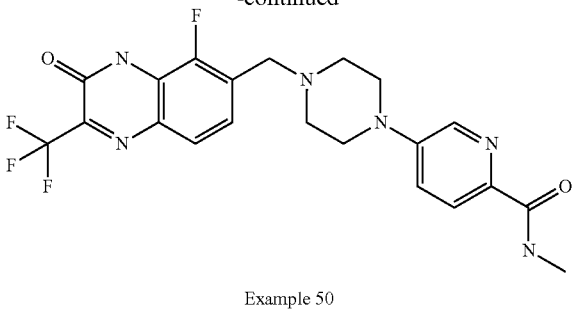

Example 50

Example 50: 5-[4-[[5-fluoro-3-oxo-2-(trifluoromethyl)-4H-quinoxalin-6-yl]methyl]piperazin-1-yl]-N-methyl-pyridine-2-carboxamide SOCl2 (0.4 mL, 5.48 mmol) was added to 8-fluoro-7-(hydroxymethyl)-3-(trifluoromethyl)-1H-quinoxalin-2-one (intermediate 88) (contaminated by 5-fluoro-6-(hydroxymethyl)-3-(trifluoromethyl)-1H-quinoxalin-2-one) (120 mg, 0.23 mmol) in Et2O (5 mL). The resulting mixture was stirred at room temperature for 2. The solvent was removed under reduced pressure. DIPEA (2 mL, 11.45 mmol) and N-methyl-5-piperazin-1-yl-pyridine-2-carboxamide (intermediate 31)(259 mg, 1.18 mmol) were added to the mixture in MeCN (10 mL). The resulting mixture was stirred at room temperature for 24 h. The crude product was purified by preparative HPLC (Column: XBridge Shield RP18 OBD Column, 19*250 mm, 10 um; Mobile Phase A: Water (10 mmol/L NH4HCO3+0.1% NH3·H2O), Mobile Phase B: ACN; Flow rate: 20 mL/min; Gradient: 15 B to 35 B in 10 min; 254/220 nm; RT1:10.18/11.2). Fractions containing the desired compound were evaporated to dryness to afford 5-[4-[[5-fluoro-3-oxo-2-(trifluoromethyl)-4H-quinoxalin-6-yl]methyl]piperazin-1-yl]-N-methyl-pyridine-2-carboxamide (example 50) (6 mg, 6%) as a white solid. 1H NMR (400 MHz, DMSO-d6) 2.51-2.57 (4H, m), 2.76 (3H, d), 3.25-3.34 (4H, m), 3.72 (2H, s), 7.30 (1H, t), 7.39 (1H, dd), 7.65 (1H, d), 7.83 (1H, d), 8.27 (1H, d), 8.36-8.41 (1H, m); 19F NMR (376 MHz, DMSO-d6) −68.34, −133.80; m/z (ES+) [M+H]+ =465.

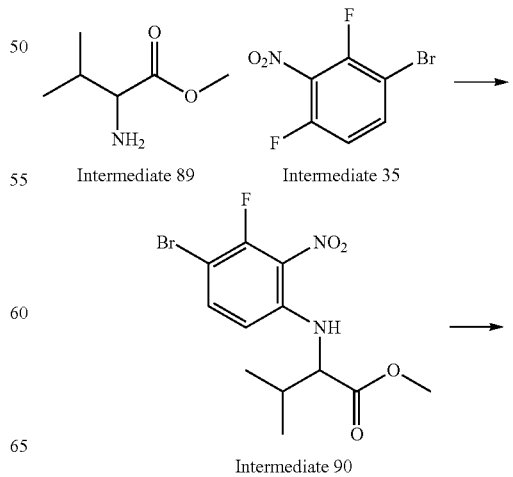

Intermediate 89  Intermediate 35

Intermediate 90

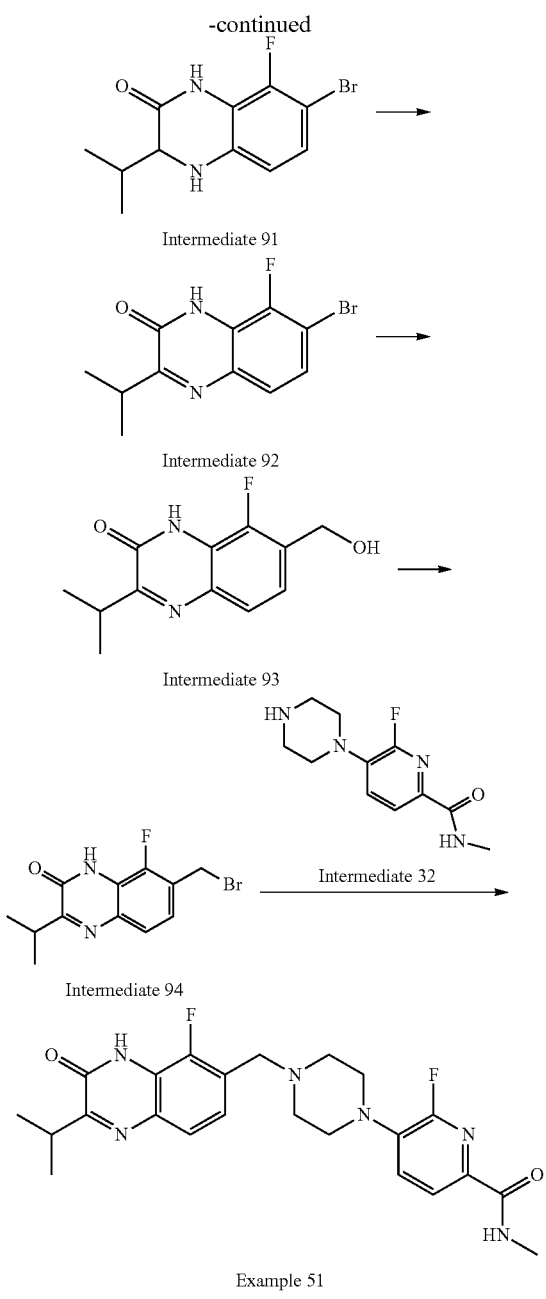

ROMETHANE-d2) 1.00-1.14 (6H, m), 2.20-2.35 (1H, m), 3.78 (3H, s), 4.06 (1H, dd), 6.52 (1H, br d), 7.39 (1H, br d), 7.52 (1H, dd); 19F NMR (471 MHz, DICHLOROMETH-ANE-d2) −109.33 (1F, s); m/z (ES$^+$) [M+H]$^+$=349.

Intermediate 91: 7-bromo-8-fluoro-3-isopropyl-3,4-dihydro-1H-quinoxalin-2-one

Zinc powder (1.143 g, 17.48 mmol) was added to a mixture of methyl 2-(4-bromo-3-fluoro-2-nitro-anilino)-3-methyl-butanoate (0.763 g, 2.19 mmol) (intermediate 90) and ammonium chloride (0.935 g, 17.48 mmol) in MeOH (12 mL) and water (0.3 mL) at 0° C. portion-wise (exothermic reaction), the mixture was stirred at rt for 2 h (No SM remaining, complete disappearance of orange coloration is indicative of reaction completion). Zn was filtered off, the solid cake was washed with 20% MeOH in DCM and the filtrate was concentrated under vacuum. Water was added to the above crude product and the product was extracted into the ethyl acetate layer. The organic layer was dried and concentrated under vacuum to furnish a colorless oil. The crude product was slurried in 1:1 ethylacetate:methanol, 0.5 mL 4N HCl in dioxane was added and the reaction was stirred for 1 h (No uncyclized product remaining). The reaction mixture was concentrated to yield 7-bromo-8-fluoro-3-isopropyl-3,4-dihydro-1H-quinoxalin-2-one (intermediate 91). The crude product was subjected to reagents for the next step without any further purification assuming the yield of this reaction to be 100%. m/z (ES$^+$) [M+H]$^+$=287.

Intermediate 92: 7-bromo-8-fluoro-3-isopropyl-1H-quinoxalin-2-one 4,5-dichloro-3,6-dioxocyclohexa-1,4-diene-1,2-dicarbonitrile (595 mg, 2.62 mmol) was added in one portion to a stirred solution of 7-bromo-8-fluoro-3-isopropyl-3,4-dihydroquinoxalin-2(1H)-one (627 mg, 2.18 mmol) (intermediate 91) in DCM (20 mL). The resulting slurry was stirred at rt for 2 hours (complete conversion to desired product by LCMS). The reaction mixture was concentrated under vacuum and quenched with saturated aq. sodium bicarbonate solution. The above slurry was stirred at rt for overnight and the solid was filtered off. The filtered solid was washed thoroughly with water followed by diethyl ether and dried to give 7-bromo-8-fluoro-3-isopropyl-1H-quinoxalin-2-one (0.425 g, 68.3%) (intermediate 92) as an off-white solid. 1H NMR (500 MHz, DMSO-d6) 1.22 (6H, d), 3.36-3.52 (1H, m), 7.45-7.58 (2H, m), 12.62 (1H, br s); 19F NMR (471 MHz, DMSO-d6) −124.16 (1F, s); m/z (ES$^+$) [M+H]$^+$=285.

Intermediate 93: 8-fluoro-7-(hydroxymethyl)-3-isopropyl-1H-quinoxalin-2-one

Xphos Pd G2 (103 mg, 0.13 mmol) was added to a stirred degassed solution of 7-bromo-8-fluoro-3-isopropylquinoxalin-2(1H)-one (375 mg, 1.32 mmol) (intermediate 92) and (tributylstannyl)methanol (507 mg, 1.58 mmol) in 1,4-dioxane (6.58 mL). The resulting solution was stirred at 80° C. for 16 hours. The reaction mixture was concentrated under vacuum, and purified via normal phase chromatography using 0-10% MeOH in DCM to yield 8-fluoro-7-(hydroxymethyl)-3-isopropyl-1H-quinoxalin-2-one (0.255 g, 82%) (intermediate 93) as a white solid. 1H NMR (500 MHz, DMSO-d6) 1.22 (6H, d), 3.39-3.52 (1H, m), 4.64 (2H, d), 5.41 (1H, t), 7.33 (1H, s), 7.55 (1H, d), 12.42 (1H, br s); 19F NMR (471 MHz, DMSO-d6) −137.71 (1F, s); m/z (ES$^+$) [M+H]$^+$=237.

Intermediate 90: Methyl 2-(4-bromo-3-fluoro-2-nitro-anilino)-3-methyl-butanoate

DIPEA (2.202 mL, 12.61 mmol) was added slowly to a stirred solution of 1-bromo-2,4-difluoro-3-nitrobenzene (intermediate 35) (1 g, 4.20 mmol) and methyl valinate, HCl (intermediate 89) (0.704 g, 4.20 mmol) in DMF (6 mL). The resulting solution was stirred at rt for 18 hours (complete conversion to desired product by LCMS). Reaction mixture was concentrated, diluted with water and extracted with ethyl acetate, organic layer was dried over sodium sulphate, filtered and concentrated under vacuum. The crude product was purified via normal phase chromatography with hexane: Ethyl acetate to yield methyl 2-(4-bromo-3-fluoro-2-nitro-anilino)-3-methyl-butanoate (0.763 g, 52.0%) (intermediate 90) as a bright orange solid. 1H NMR (500 MHz, DICHLO-

Intermediate 94: 7-(bromomethyl)-8-fluoro-3-iso-propyl-1H-quinoxalin-2-one

Triethylphosphane (0.477 ml, 3.23 mmol) was added dropwise to a stirred solution of 8-fluoro-7-(hydroxymethyl)-3-isopropylquinoxalin-2(1H)-one (0.2541 g, 1.08 mmol) (intermediate 93) and $CBr_4$ (1.177 g, 3.55 mmol) in DCM (8.49 mL) at 0° C. over a period of 5 minutes under nitrogen. The reaction mixture was stirred at rt for 1 h, DCM was removed under vacuum and the resulting solid was slurried in diethyl ether. The white ppt was filtered under vacuum, washed with water followed by ether. The solid was dried under vacuum for overnight (no heat) to give 7-(bromomethyl)-8-fluoro-3-isopropyl-1H-quinoxalin-2-one (0.313 g, 97%) (intermediate 94) as light brown solid. m/z $(ES^+)$ $[M+H]^+$=299.

Example 51: 6-fluoro-5-[4-[(5-fluoro-2-isopropyl-3-oxo-4H-quinoxalin-6-yl)methyl]piperazin-1-yl]-N-methyl-pyridine-2-carboxamide To 7-(bromomethyl)-8-fluoro-3-isopropylquinoxalin-2 (1H)-one (100 mg, 0.33 mmol) (intermediate 94) was added 6-fluoro-N-methyl-5-piperazin-1-yl-pyridine-2-carboxamide, 2HCl (104 mg, 0.33 mmol) (intermediate 32), acetonitrile (5 mL) and N-ethyl-N-isopropylpropan-2-amine (291 μL, 1.67 mmol) and heated to 70° C. LCMS indicated complete disappearance of SM and formation of desired product after 1 h. The reaction mixture was cooled, concentrated, quenched with aq $NaHCO_3$ solution (1 mL) and stirred for 1 h at rt. Water (3 mL) was added to the above mixture and stirred for 10 mins. The precipitate was filtered and washed with copious amounts of water (50 mL). The solid was purified via normal phase chromatography using 0-10% MeOH in DCM to yield 6-fluoro-5-[4-[(5-fluoro-2-isopropyl-3-oxo-4H-quinoxalin-6-yl)methyl]piperazin-1-yl]-N-methyl-pyridine-2-carboxamide (0.050 g, 32.8%) (Example 51) as a white solid. 1H NMR (500 MHz, DMSO-d6) 1.22 (6H, d), 2.53-2.65 (4H, m), 2.77 (3H, d), 3.12-3.24 (4H, m), 3.36-3.52 (1H, m), 3.71 (2H, s), 7.30 (1H, t), 7.52-7.59 (2H, m), 7.84 (1H, d), 8.36-8.41 (1H, m), 12.46 (1H, br s); 19F NMR (471 MHz, DMSO-d6) −135.53 (1F, s), −72.59 (1F, s); m/z $(ES^+)$ $[M+H]^+$=457.

Example 52: 5-[4-[(5-fluoro-2-isopropyl-3-oxo-4H-quinoxalin-6-yl)methyl]piperazin-1-yl]-N,6-dimethyl-pyridine-2-carboxamide To 7-(bromomethyl)-8-fluoro-3-isopropylquinoxalin-2 (1H)-one (109 mg, 0.36 mmol) (intermediate 94), was added N,6-dimethyl-5-(piperazin-1-yl)picolinamide, 2HCl (112 mg, 0.36 mmol) (intermediate 33), acetonitrile (5 mL) and N-ethyl-N-isopropylpropan-2-amine (317 μl, 1.82 mmol) and heated to 70 C. LCMS indicated complete disappearance of SM and formation of desired product after 1 h. The reaction mixture was cooled, concentrated, quenched with aq $NaHCO_3$ solution (1 mL) and stirred for 1 h at rt. Water (3 mL) was added to the above mixture and stirred for 10 mins. The precipitate was filtered and washed with copious amounts of water (50 mL). The solid was purified via normal phase chromatography using 0-10% MeOH in DCM to yield 5-[4-[(5-fluoro-2-isopropyl-3-oxo-4H-quinoxalin-6-yl) methyl]piperazin-1-yl]-N,6-dimethyl-pyridine-2-carboxamide (0.057 g, 34.6%) as a white solid (Example 52). 1H NMR (500 MHz, DMSO-d6) 1.22 (6H, d), 2.46-2.49 (3H, m), 2.52-2.68 (4H, m), 2.80 (3H, d), 2.94 (4H, br s), 3.36-3.52 (1H, m), 3.73 (2H, s), 7.30 (1H, t), 7.47 (1H, d), 7.56 (1H, d), 7.79 (1H, d), 8.37-8.44 (1H, m), 12.46 (1H, s); 19F NMR (471 MHz, DMSO-d6) −135.55 (1F, s); m/z $(ES^+)$ $[M+H]^+$=453.

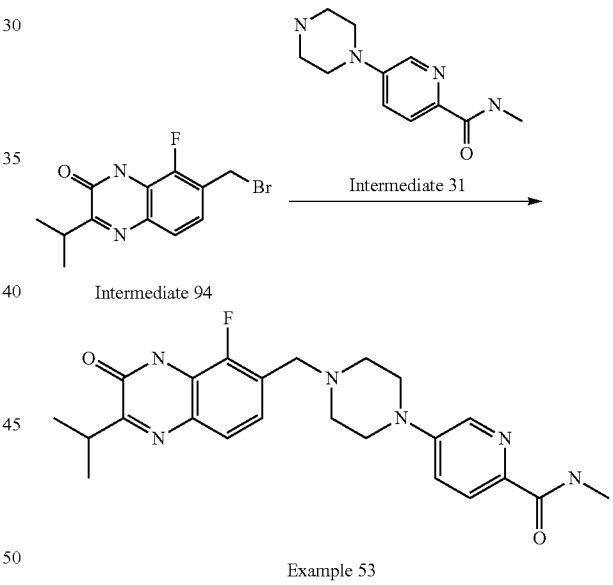

Example 53

Example 53: 5-[4-[(5-fluoro-2-isopropyl-3-oxo-4H-quinoxalin-6-yl)methyl]piperazin-1-yl]-N-methyl-pyridine-2-carboxamide To 7-(bromomethyl)-8-fluoro-3-isopropylquinoxalin-2 (1H)-one (100 mg, 0.33 mmol) (intermediate 94), was added N-methyl-5-(piperazin-1-yl)picolinamide, 2HCl (98 mg, 0.33 mmol) (intermediate 31), acetonitrile (5 mL) and N-ethyl-N-isopropylpropan-2-amine (291 μl, 1.67 mmol) and heated to 70° C. LCMS indicated complete disappearance of SM and formation of desired product after 1 h. The reaction mixture was cooled, concentrated, quenched with aq $NaHCO_3$ solution (1 mL) and stirred for 1 h at rt. Water (3 mL) was added to the above mixture and stirred for 10

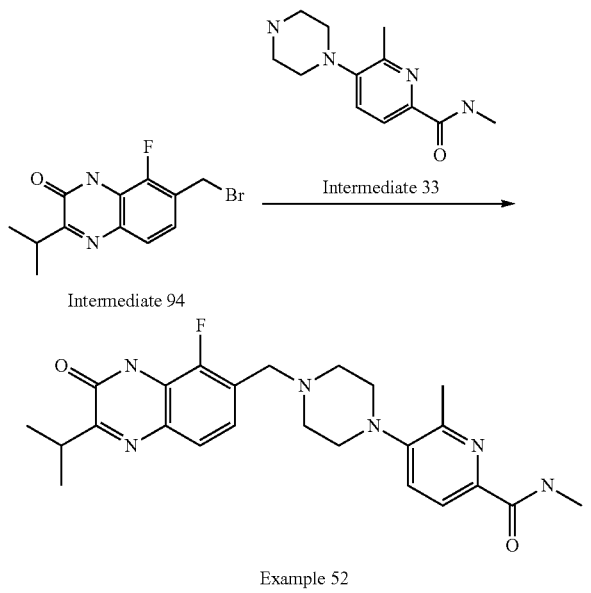

Example 52 mins. The precipitate was filtered and washed with copious amounts of water (50 mL). The solid was purified via normal phase chromatography using 0-10% MeOH in DCM to yield 5-[4-[(5-fluoro-2-isopropyl-3-oxo-4H-quinoxalin-6-yl)methyl]piperazin-1-yl]-N-methyl-pyridine-2-carboxamide (0.052 g, 35.5%) (Example 53) as a white solid. 1H NMR (500 MHz, DMSO-d6) 1.22 (6H, d), 2.52-2.61 (4H, m), 2.78 (3H, d), 3.26-3.30 (4H, m), 3.36-3.52 (1H, m), 3.70 (2H, s), 7.31 (1H, t), 7.38 (1H, dd), 7.56 (1H, d), 7.82 (1H, d), 8.26 (1H, d), 8.38 (1H, br d), 12.45 (1H, br s); 19F NMR (471 MHz, DMSO-d6) −135.54 (1F, s); m/z (ES+) [M+H]+=439.

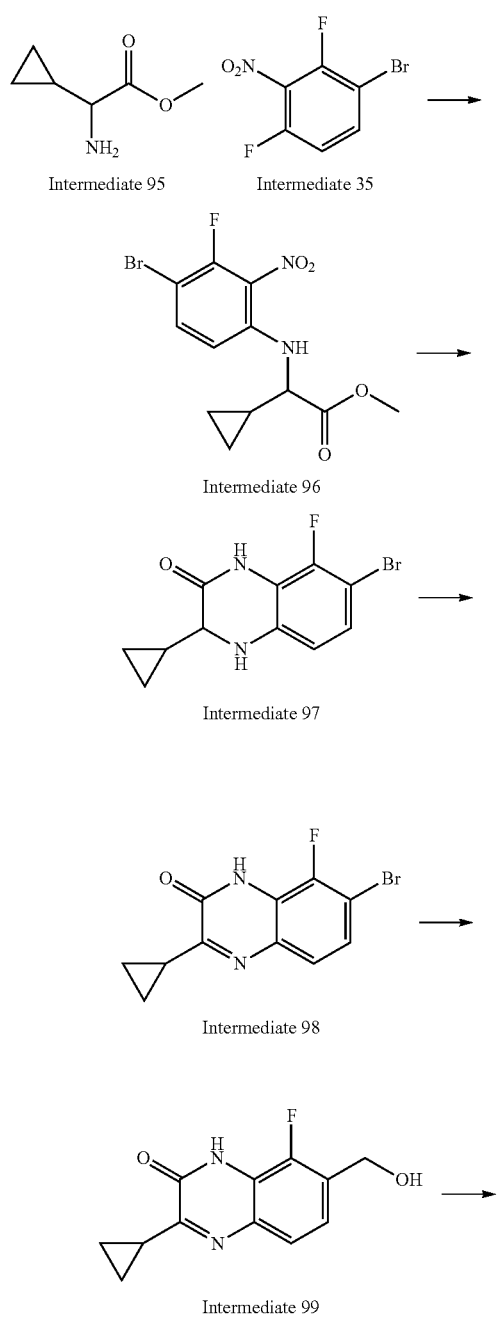

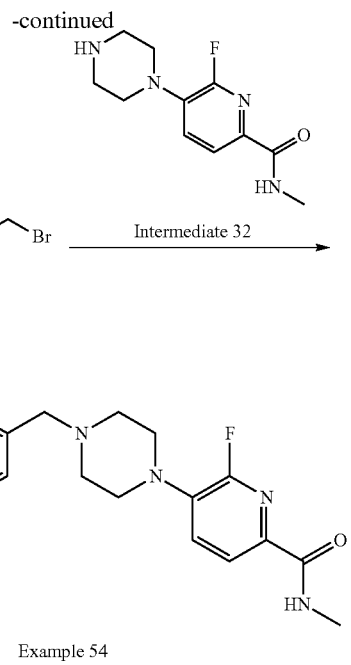

Intermediate 96: methyl 2-(4-bromo-3-fluoro-2-nitro-anilino)-2-cyclopropyl-acetate DIPEA (2.202 mL, 12.61 mmol) was added slowly to a stirred solution of 1-bromo-2,4-difluoro-3-nitrobenzene (intermediate 35) (1 g, 4.20 mmol) and methyl 2-amino-2-cyclopropylacetate, HCl (intermediate 95) (0.696 g, 4.20 mmol) in DMF (6 mL). The resulting solution was stirred at rt for 18 hours (complete conversion to desired product by LCMS). The reaction mixture was concentrated, diluted with water and extracted with ethyl acetate, organic layer was dried over sodium sulphate, filtered and concentrated under vacuum. The crude product was purified via normal phase chromatography using hexane and ethyl acetate to yield methyl 2-(4-bromo-3-fluoro-2-nitro-anilino)-2-cyclopropyl-acetate (0.635 g, 43.5%) (intermediate 96) as a bright orange solid. 1H NMR (500 MHz, DICHLOROMETHANE-d2) 0.39-0.49 (1H, m), 0.54 (1H, td), 0.64-0.75 (2H, m), 1.25-1.39 (1H, m), 3.74-3.83 (4H, m), 6.45 (1H, dd), 7.34 (1H, br d), 7.52 (1H, dd). 19F NMR (471 MHz, DICHLOROMETHANE-d2) −109.53 (1F, s); m/z (ES+) [M+H]+=347.

Intermediate 97: 7-bromo-3-cyclopropyl-8-fluoro-3,4-dihydro-1H-quinoxalin-2-one Zinc powder (957 mg, 14.63 mmol) was added to a mixture of methyl 2-((4-bromo-3-fluoro-2-nitrophenyl)amino)-2-cyclopropylacetate (635 mg, 1.83 mmol) (intermediate 96) and ammonium chloride (783 mg, 14.63 mmol) in MeOH (12 mL) and water (0.3 mL) at 0° C. portion-wise (exothermic reaction), the mixture was stirred at rt for 2 h (No SM remaining, Complete disappearance of orange coloration is indicative of reaction completion). Zn was filtered off and the solid cake was washed with 20% MeOH in DCM. The filtrate was concentrated, the crude material showed mostly uncyclized product. Water was added to the above crude product and the product was extracted into the ethyl acetate layer. The organic layer was dried and concentrated under vacuum to furnish an oil. This material was slurried in 1:1 ethylacetate:methanol, 0.5 mL 4 N HCl in dioxane was added and the reaction mixture was stirred for 1 h (No uncyclized product remaining). The reaction mixture was concentrated to yield 7-bromo-3-cyclopropyl-8-fluoro-3,4-dihydro-1H-quinoxalin-2-one (intermediate 97) as a grey solid. The crude product was subjected to reagents for the next step without any further purification assuming the yield of this reaction to be 100%. m/z (ES$^+$) [M+H]$^+$=285.

Intermediate 98: 7-bromo-3-cyclopropyl-8-fluoro-1H-quinoxalin-2-one 4,5-dichloro-3,6-dioxocyclohexa-1,4-diene-1,2-dicarbonitrile (499 mg, 2.20 mmol) was added in one portion to a stirred solution of 7-bromo-3-cyclopropyl-8-fluoro-3,4-dihydroquinoxalin-2(1H)-one (522 mg, 1.83 mmol) (intermediate 97) in DCM (20 mL). The resulting slurry was stirred at rt for 2 hours (complete conversion to desired product by LCMS). The reaction mixture was concentrated under vacuum and quenched with saturated aq. sodium bicarbonate solution. The above slurry was stirred at rt for overnight and the solid was filtered off. The solid was washed thoroughly with water followed by diethyl ether and dried to give 7-bromo-3-cyclopropyl-8-fluoro-1H-quinoxalin-2-one (0.382 g, 73.7%) (intermediate 98) as an off-white solid. m/z (ES$^+$) [M+H]$^+$=283.

Intermediate 99: 3-cyclopropyl-8-fluoro-7-(hydroxymethyl)-1H-quinoxalin-2-one

Xphos Pd G2 (92 mg, 0.12 mmol) was added to a stirred degassed solution of 7-bromo-3-cyclopropyl-8-fluoroquinoxalin-2(1H)-one (332 mg, 1.17 mmol) (intermediate 98) and (tributylstannyl)methanol (452 mg, 1.41 mmol) in 1,4-dioxane (5.86 mL) and the resulting solution was stirred at 80° C. for 16 hours. The reaction mixture was concentrated under vacuum, and purified via normal phase chromatography using 0-10% MeOH in DCM to yield 3-cyclopropyl-8-fluoro-7-(hydroxymethyl)-1H-quinoxalin-2-one (0.224 g, 82%) (intermediate 99) as a white solid. 1H NMR (500 MHz, DMSO-d6) 1.02-1.14 (4H, m), 2.52-2.73 (1H, m), 4.62 (2H, d), 5.38 (1H, t), 7.29 (1H, t), 7.43 (1H, d), 12.43 (1H, br s); 19F NMR (471 MHz, DMSO-d6) −137.67 (1F, s); m/z (ES$^+$) [M+H]$^+$=235.

Intermediate 100: 7-(bromomethyl)-3-cyclopropyl-8-fluoro-1H-quinoxalin-2-one

Triethylphosphane (0.422 ml, 2.86 mmol) was added dropwise to a mixture of 3-cyclopropyl-8-fluoro-7-(hydroxymethyl)quinoxalin-2(1H)-one (0.223 g, 0.95 mmol) (intermediate 99) and CBr$_4$ (1.043 g, 3.14 mmol) in DCM (7.52 mL) at 0° C. over a period of 5 minutes under nitrogen. Reaction was stirred at rt for 1 h. DCM was removed under vacuum and the resulting solid was slurried in diethyl ether. The light greenish white ppt was filtered under vacuum, washed with water followed by ether. The solid was dried under vacuum for overnight (no heat) to give 7-(bromomethyl)-3-cyclopropyl-8-fluoro-1H-quinoxalin-2-one (0.193 g, 68.2%) (intermediate 100) as a light green solid. 1H NMR (500 MHz, DMSO-d6) 1.03-1.17 (4H, m), 2.63-2.76 (1H, m), 4.79 (2H, s), 7.33 (1H, t), 7.43 (1H, d), 12.55 (1H, br s); 19F NMR (471 MHz, DMSO-d6) −133.65 (1F, s); m/z (ES$^+$) [M+H]$^+$=297.

Example 54: 5-[4-[(2-cyclopropvl-5-fluoro-3-oxo-4H-quinoxalin-6-yl)methyl]piperazin-1-yl]-6-fluoro-N-methyl-pyridine-2-carboxamide To 7-(bromomethyl)-3-cyclopropyl-8-fluoroquinoxalin-2 (1H)-one (75 mg, 0.25 mmol) (intermediate 100), was added 6-fluoro-N-methyl-5-(piperazin-1-yl)picolinamide, 2HCl (79 mg, 0.25 mmol) (intermediate 32), acetonitrile (5 mL) and N-ethyl-N-isopropylpropan-2-amine (220 µl, 1.26 mmol) and heated to 70 C. LCMS indicated complete disappearance of SM and formation of desired product after 1 h. The reaction mixture was cooled, concentrated, quenched with aq NaHCO$_3$ solution (1 mL) and stirred for 1 h at rt. Water (3 mL) was added to the above mixture and stirred for 10 mins. The precipitate was filtered and washed with copious amounts of water (50 mL). The solid was purified via normal phase chromatography using 0-10% MeOH in DCM to yield 5-[4-[(2-cyclopropyl-5-fluoro-3-oxo-4H-quinoxalin-6-yl)methyl]piperazin-1-yl]-6-fluoro-N-methyl-pyridine-2-carboxamide (0.048 g, 41.8%) (Example 54) as a white solid. 1H NMR (500 MHz, DMSO-d6) 1.04-1.13 (4H, m), 2.52-2.63 (4H, m), 2.71 (1H, s), 2.77 (3H, d), 3.12-3.21 (4H, m), 3.69 (2H, s), 7.26 (1H, t), 7.43 (1H, d), 7.55 (1H, dd), 7.84 (1H, d), 8.39 (1H, br d), 12.46 (1H, br s); 19F NMR (471 MHz, DMSO-d6) −135.52 (1F, s), −72.58 (1F, s); m/z (ES$^+$) [M+H]$^+$=455.

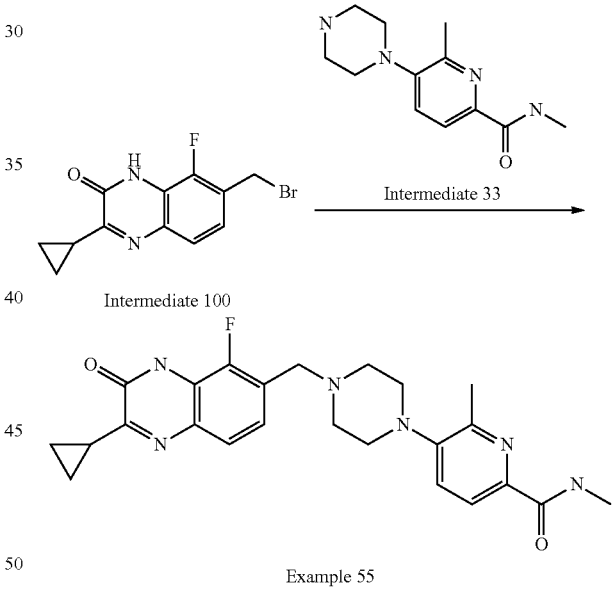

Example 55: 5-[4-[(2-cyclopropyl-5-fluoro-3-oxo-4H-quinoxalin-6-yl)methyl]piperazin-1-yl]-N,6-dimethyl-pyridine-2-carboxamide To 7-(bromomethyl)-3-cyclopropyl-8-fluoroquinoxalin-2 (1H)-one (75 mg, 0.25 mmol) (intermediate 100), was added N,6-dimethyl-5-(piperazin-1-yl)picolinamide, 2HCl (78 mg, 0.25 mmol) (intermediate 33), acetonitrile (5 mL) and N-ethyl-N-isopropylpropan-2-amine (220 µL, 1.26 mmol) and heated to 70° C. LCMS indicated complete conversion to the desired product after 1 h. The reaction mixture was cooled, concentrated, quenched with aq NaHCO$_3$ solution (1 mL) and stirred for 1 h at rt. Water (3 mL) was added to the above mixture and stirred for 10 mins. The precipitate was filtered and washed with copious amounts of water (50 mL). The solid was purified via normal phase chromatography using 0-10% MeOH in DCM to yield 5-[4-[(2-cyclopropyl-5-fluoro-3-oxo-4H-quinoxalin-6-yl)methyl]piperazin-1-yl]-N,6-dimethyl-pyridine-2-carboxamide (0.049 g, 43.1%) (Example 55) as a white solid. 1H NMR (500 MHz, DMSO-d6) 1.03-1.15 (4H, m), 2.46-2.49 (3H, m), 2.52-2.65 (4H, m), 2.65-2.75 (1H, m), 2.80 (3H, d), 2.94 (4H, br s), 3.71 (2H, s), 7.26 (1H, t), 7.40-7.50 (2H, m), 7.79 (1H, d), 8.37-8.44 (1H, m), 12.46 (1H, s); 19F NMR (471 MHz, DMSO-d6) −135.54 (1F, s); m/z (ES+) [M+H]+=451.

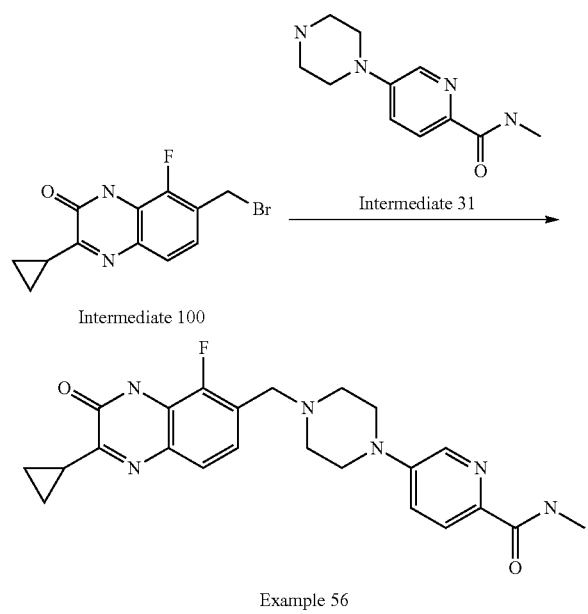

Example 56

Example 56: 5-[4-[(2-cyclopropyl-5-fluoro-3-oxo-4H-quinoxalin-6-yl)methyl]piperazin-1-yl]-N-methyl-pyridine-2-carboxamide To 7-(bromomethyl)-3-cyclopropyl-8-fluoroquinoxalin-2(1H)-one (43 mg, 0.14 mmol) (intermediate 100), was added N-methyl-5-(piperazin-1-yl)picolinamide, 2HCl (42.4 mg, 0.14 mmol) (intermediate 31), acetonitrile (5 mL) and N-ethyl-N-isopropylpropan-2-amine (126 µl, 0.72 mmol) and heated to 70° C. LCMS indicated complete disappearance of SM and formation of desired product after 1 h. The reaction mixture was cooled, concentrated, quenched with aq NaHCO3 solution (1 mL) and stirred for 1 h at rt. Water (3 mL) was added to the above mixture and stirred for 10 mins. The precipitate was filtered and washed with copious amounts of water (25 mL). The solid was purified via normal phase chromatography using 0-10% MeOH in DCM to yield 5-[4-[(2-cyclopropyl-5-fluoro-3-oxo-4H-quinoxalin-6-yl)methyl]piperazin-1-yl]-N-methyl-pyridine-2-carboxamide (0.020 g, 31.7%) (Example 56) as a white solid. 1H NMR (500 MHz, DMSO-d6) 1.03-1.16 (4H, m), 2.53-2.60 (4H, m), 2.65-2.80 (5H, m), 3.68 (2H, s), 7.25 (1H, br t), 7.38 (1H, dd), 7.42 (1H, d), 7.82 (1H, d), 8.25 (1H, d), 8.35-8.40 (1H, m), 12.38-12.51 (1H, m) (missing 3H likely overlaps with DMSO peak); 19F NMR (471 MHz, DMSO-d6) −135.52 (1F, s); m/z (ES+) [M+H]+=437

Intermediate 102: 7-bromo-3-methoxy-8-methyl-1H-quinoxalin-2-one

A mixture of 4-bromo-3-methylbenzene-1,2-diamine (1.75 g, 8.70 mmol) (Intermediate 101), methyl 2,2,2-trimethoxyacetate (2.86 g, 17.41 mmol) and ytterbium(III) trifluoromethanesulfonate (0.540 g, 0.87 mmol) in toluene (10 mL) in a sealed tube was degassed, back filled with N2, stirred at 100° C. for overnight gave a brown suspension, LCMS indicated the formation of desired product, the mixture was cooled to rt, the solid was collected by filtration, washed with methanol, dried to yield 7-bromo-3-methoxy-8-methyl-1H-quinoxalin-2-one (1.2 g, 51.2%) (Intermediate 102) as a yellow solid (contaminated by about 8% of its regio-isomer 6-bromo-3-methoxy-5-methylquinoxalin-2(1H)-one). 1H NMR (500 MHz, DMSO-d6) 2.50 (3H, br s), 3.97 (3H, s), 7.32 (1H, d), 7.45 (1H, d), 11.79 (1H, br s); (m/z) (ES+) [M+H]+=269.

Intermediate 103: 7-(hydroxymethyl)-3-methoxy-8-methyl-1H-quinoxalin-2-one

A mixture of (tributylstannyl)methanol (1.844 g, 5.74 mmol), 7-bromo-3-methoxy-8-methyl-1H-quinoxalin-2-one (1.03 g, 3.83 mmol) (Intermediate 102) and Xphos Pd G2 (0.452 g, 0.57 mmol) in 1,4-dioxane (40 mL) was stirred at 80° C. for overnight under $N_2$ gave a dark mixture, LCMS indicated near full conversion. The solvent was removed under reduced pressure, the residue was purified on silica gel column (eluted with 0 to 20% methanol in DCM), the fractions were concentrated to a yellow solid, the solid was checked by LCMS which indicated it was not very pure, the product was then slurried in 20 mL of methanol, the solid was collected by filtration, dried to yield the product with 55% purity as a yellow solid (contaminated by 30% starting material and 9.5% de-brominated side product).

The solid obtained above was charged into a dry flask with 1,4-dioxane (40 mL), to the flask was added 900 mg of (tributylstanny)methanol and 300 mg of xphos Pd G2, the mixture was degassed, then stirred at 80° C. for overnight under $N_2$. The solvent was removed under reduced pressure, the mixture was purified on silica gel column (eluted with 0 to 20% methanol in DCM) to yield 7-(hydroxymethyl)-3-methoxy-8-methyl-1H-quinoxalin-2-one (800 mg, 95%) (Intermediate 103) as a yellow solid with 80% purity by LCMS. 1H NMR (500 MHz, DMSO-d6) 2.32 (3H, s), 3.91-4.01 (3H, m), 4.56 (2H, d), 5.15 (1H, t), 7.27 (1H, d), 7.37 (1H, d), 11.57 (1H, br s); (m/z) (ES⁺) [M+H]⁺=221.

Intermediate 104: 7-(bromomethyl)-3-methoxy-8-methyl-1H-quinoxalin-2-one

Triethylphosphane (294 μl, 2.04 mmol) was added dropwise to a suspension of 7-(hydroxymethyl)-3-methoxy-8-methyl-1H-quinoxalin-2-one (300 mg, 1.36 mmol) (Intermediate 103) and 1,1,2,2-tetrabromo-1,2-dichloroethane (875 mg, 2.11 mmol) in $CH_2Cl_2$ (20 mL) at 0° C. under $N_2$, the resulting mixture was then stirred at rt for 3.5 h, the solvent was removed under reduced pressure, the residue was suspended in ether (10 mL), filtered, the solid was washed with ether (10 mL×2), the solid was then suspended in water (20 mL), filtered, washed with water (5 mL×3), dried to yield 7-(bromomethyl)-3-methoxy-8-methyl-1H-quinoxalin-2-one (0.250 g, 64.8%) (Intermediate 104) as a light yellow solid. (m/z) (ES⁺) [M+H]⁺=285.

Example 57: 5-[4-[(2-methoxy-5-methyl-3-oxo-4H-quinoxalin-6-yl)methyl]piperazin-1-yl]-N,6-dimethyl-pyridine-2-carboxamide To a suspension of N,6-dimethyl-5-(piperazin-1-yl)picolinamide, 2HCl (83 mg, 0.27 mmol) (Intermediate 33) and 7-(bromomethyl)-3-methoxy-8-methyl-1H-quinoxalin-2-one (85 mg, 0.27 mmol) (Intermediate 104) in acetonitrile (6 mL) was added DIPEA (236 μL, 1.35 mmol), the resulting mixture was stirred at 70° C. for 2 h gave a clear solution, the mixture was cooled to rt gave a suspension, the solid was collected by filtration, washed with water, acetonitrile, dried to yield 5-[4-[(2-methoxy-5-methyl-3-oxo-4H-quinoxalin-6-yl)methyl]piperazin-1-yl]-N,6-dimethyl-pyridine-2-carboxamide (0.064 g, 54.3%) (Example 57) as a white solid. 1H NMR (500 MHz, DMSO-d6) 2.43 (3H, s), 2.49 (3H, s), 2.57 (4H, br s), 2.80 (3H, d), 2.91 (4H, br s), 3.60 (2H, s), 3.95 (3H, s), 7.18 (1H, d), 7.35 (1H, d), 7.46 (1H, d), 7.78 (1H, d), 8.40 (1H, q), 11.58 (1H, br s); (m/z) (ES⁺) [M+H]⁺=437

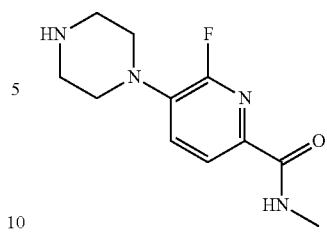

Intermediate 32

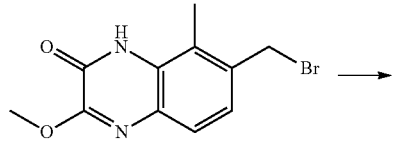

Intermediate 104

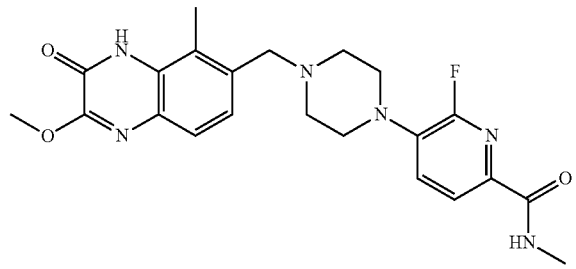

Example 58

Example 58: 6-fluoro-5-[4-[(2-methoxy-5-methyl-3-oxo-4H-quinoxalin-6-yl)methyl]piperazin-1-yl]-N-methyl-pyridine-2-carboxamide To a suspension of 6-fluoro-N-methyl-5-(piperazin-1-yl)picolinamide, 2HCl (84 mg, 0.27 mmol) (Intermediate 32) and 7-(bromomethyl)-3-methoxy-8-methyl-1H-quinoxalin-2-one (85 mg, 0.27 mmol) (Intermediate 104) in acetonitrile (6 mL) was added DIPEA (236 μL, 1.35 mmol), the resulting mixture was stirred at 70° C. for 2 h gave a suspension, the mixture was cooled to rt, the solid was collected by filtration, washed with water, acetonitrile, dried, the solid was suspended in acetonitrile, filtered and dried to yield 6-fluoro-5-[4-[(2-methoxy-5-methyl-3-oxo-4H-quinoxalin-6-yl) methyl]piperazin-1-yl]-N-methyl-pyridine-2-carboxamide (0.073 g, 61.3%) (Example 58) as a beige colored solid. 1H NMR (500 MHz, DMSO-d6) 2.42 (3H, s), 2.55 (4H, br s), 2.76 (3H, d), 3.14 (4H, br s), 3.58 (2H, s), 3.95 (3H, s), 7.17 (1H, br d), 7.35 (1H, br d), 7.50-7.63 (1H, m), 7.83 (1H, br d), 8.38 (1H, br d), 11.58 (1H, s); (m/z) (ES⁺) [M+H]⁺=442.

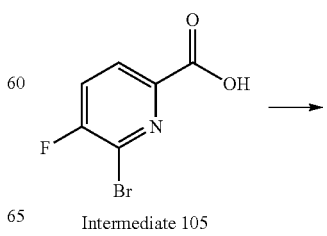

Intermediate 105

-continued

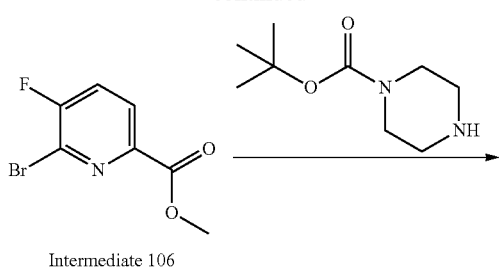

Intermediate 106

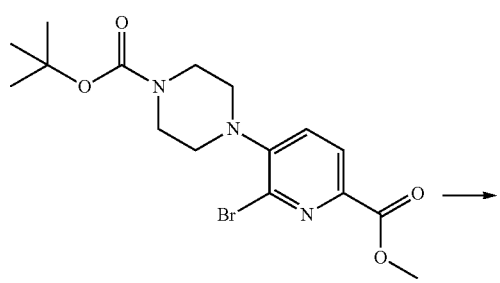

Intermediate 107

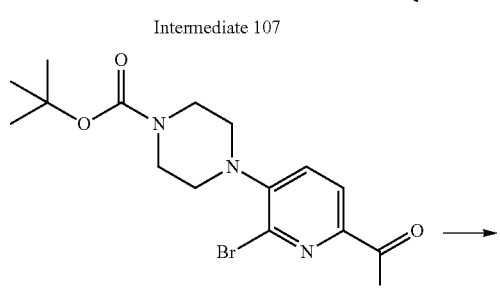

Intermediate 108

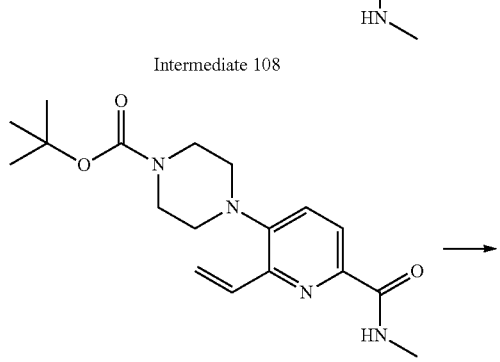

Intermediate 109

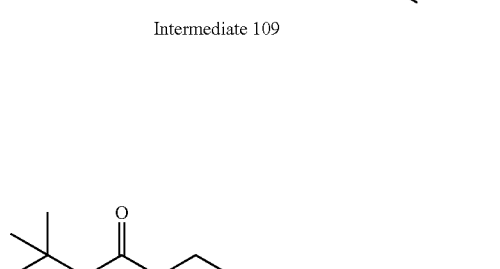

Intermediate 110

-continued

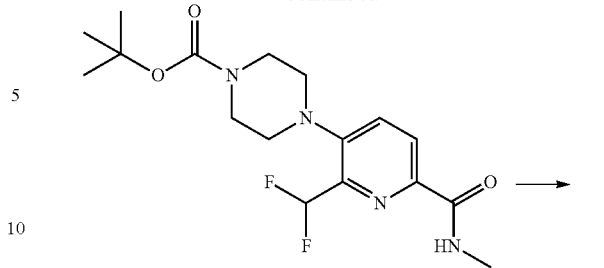

Intermediate 111

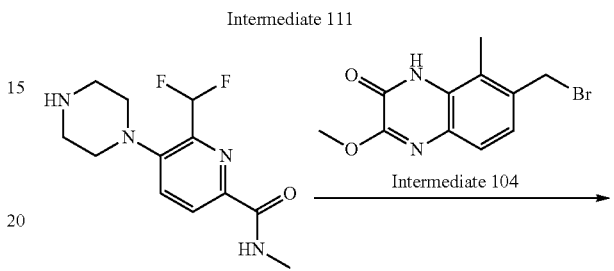

Intermediate 60

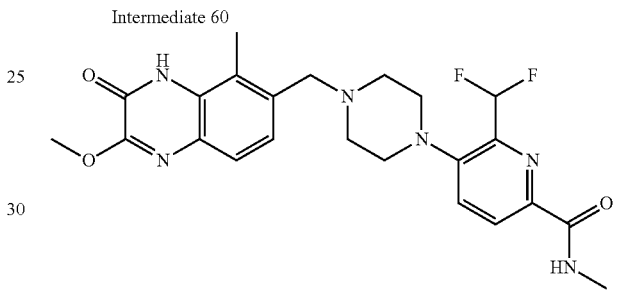

Eample 59

Intermediate 106: methyl 6-bromo-5-fluoro-pyridine-2-carboxylate

Sulfuric acid (1.5 mL, 28.14 mmol) was added to a mixture of 6-bromo-5-fluoropicolinic acid (500 mg, 2.27 mmol) (Intermediate 105) in MeOH (8 mL) slowly. The mixture was continued to stir at rt for 3 h gave a white suspension. LCMS indicated full conversion, the mixture was poured into sat. aq $NaHCO_3$ solution, extracted with DCM (40 mL×2), the organic layers were dried (anhydrous $Na_2SO_4$), filtered and concentrated to yield methyl 6-bromo-5-fluoro-pyridine-2-carboxylate (532 mg, 100%) (Intermediate 106) as a white solid which was used for next step without further purification. 1H NMR (500 MHz, CHLOROFORM-d) 4.01 (3H, s), 7.55 (1H, t), 8.15 (1H, dd); (m/z) ($ES^+$) $[M+H]^+=236$.

Intermediate 107: tert-butyl 4-(2-bromo-6-methoxycarbonyl-3-pyridyl)piperazine-1-carboxylate A mixture of tert-butyl piperazine-1-carboxylate (8.21 g, 44.06 mmol), methyl 6-bromo-5-fluoro-pyridine-2-carboxylate (6.065 g, 25.92 mmol) (Intermediate 106) and potassium carbonate (4.66 g, 33.69 mmol) in DMF (60 mL) was stirred at 110° C. for 5 hours, LCMS indicated full conversion. The mixture was cooled to rt, diluted with DCM and water, the layers were separated, the water layer was extracted with DCM twice, the organic layers were combined, dried (anhydrous $Na_2SO_4$), filtered and concentrated, the residue was purified on silica gel column (eluted with 0 to 50% ethyl acetate in hexanes, UV at 221, 310 nm) to yield desired product tert-butyl 4-(2-bromo-6-methoxycarbonyl-3-pyridyl)piperazine-1-carboxylate (7.68 g, 74.1%) (Intermediate 107) as a white solid. 1H NMR (500 MHz, CHLOROFORM-d) 1.51 (9H, s), 3.14 (4H, br t), 3.60-3.71 (4H, m), 3.99 (3H, s), 7.32 (1H, d), 8.08 (1H, d); (m/z) (ES$^+$) [M+H]$^+$=402.

Intermediate 108: tert-butyl 4-[2-bromo-6-(methylcarbamoyl)-3-pyridyl]piperazine-1-carboxylate tert-Butyl 4-(2-bromo-6-methoxycarbonyl-3-pyridyl)piperazine-1-carboxylate (7.67 g, 19.16 mmol) (Intermediate 107) in methanamine (100 mL, 19.16 mmol) (33% in ethanol) in a sealed vessel was stirred at 60° C. for 4.5 h, LCMS indicated full conversion, the mixture was cooled to rt, concentrated, the residue was dissolved into DCM, washed with sat. NH$_4$Cl solution, dried (anhydrous Na$_2$SO$_4$), filtered and concentrated to yield tert-butyl 4-[2-bromo-6-(methylcarbamoyl)-3-pyridyl]piperazine-1-carboxylate (7.48 g, 98%) (Intermediate 108) as a white solid. 1H NMR (500 MHz, CHLOROFORM-d) 1.50 (9H, s), 3.02 (3H, d), 3.08 (4H, br t), 3.60-3.71 (4H, m), 7.36 (1H, d), 7.68 (1H, br d), 8.11 (1H, d); (m/z) (ES$^+$) [M+H]$^+$=401.

Intermediate 109: tert-butyl 4-[6-(methylcarbamoyl)-2-vinyl-3-pyridyl]piperazine-1-carboxylate A mixture of tert-butyl 4-[2-bromo-6-(methylcarbamoyl)-3-pyridyl]piperazine-1-carboxylate (1.344 g, 3.37 mmol) (Intermediate 108), tributyl(vinyl)stannane (1.174 g, 3.70 mmol) and Xphos Pd G2 (0.132 g, 0.17 mmol) in 1,4-dioxane (25 ml) was stirred at 100° C. under N$_2$ for 2.5 hr, LCMS indicated full conversion. The mixture was diluted with DCM, washed with sat. NH$_4$Cl, the organic layer was dried (anhydrous Na$_2$SO$_4$), filtered and concentrated, the residue was purified on silica gel column (eluted with 0 to 80% ethyl acetate in hexanes, UV at 226, 293 nm) to yield tert-butyl 4-[6-(methylcarbamoyl)-2-vinyl-3-pyridyl]piperazine-1-carboxylate (0.961 g, 82%) (Intermediate 109) as a white solid. 1H NMR (500 MHz, CHLOROFORM-d) 1.50 (9H, s), 2.90-3.01 (4H, m), 3.05 (3H, d), 3.55-3.68 (4H, m), 5.54 (1H, dd), 6.42 (1H, dd), 7.10 (1H, dd), 7.39 (1H, d), 7.98 (1H, br d), 8.07 (1H, d); m/z (ES$^+$) [M+H]$^+$=346.6, 348.5.

Intermediate 110: tert-butyl 4-[2-formyl-6-(methylcarbamoyl)-3-pyridyl]piperazine-1-carboxylate Osmium tetroxide in H$_2$O (0.0435 mL, 6.00 µmol) was added to a solution of tert-butyl 4-[6-(methylcarbamoyl)-2-vinyl-3-pyridyl]piperazine-1-carboxylate (960 mg, 2.77 mmol) (Intermediate 109), 2,6-lutidine (646 µl, 5.54 mmol) and sodium periodate (2371 mg, 11.08 mmol) in THF (25 mL)/water (5 mL)/tert-butanol (2650 µL, 27.71 mmol) and stirred at rt for overnight gave a yellow suspension. LCMS and TLC indicated full conversion. Reaction was diluted with water and extracted with ethyl acetate. After concentration the crude material was purified through silica column (eluted with 0 to 100% ethyl acetate in hexanes, UV at 226, 310 nm) to yield tert-butyl 4-[2-formyl-6-(methylcarbamoyl)-3-pyridyl]piperazine-1-carboxylate (0.732 g, 76%) (Intermediate 110) as a yellow solid. 1H NMR (500 MHz, CHLOROFORM-d) 1.50 (9H, s), 3.07 (3H, d), 3.15-3.30 (4H, m), 3.63-3.79 (4H, m), 7.48 (1H, d), 7.85 (1H, br d), 8.28 (1H, d), 10.10 (1H, s); (m/z) (ES$^+$) [M+H]$^+$=349.

Intermediate 111: tert-butyl 4-[2-(difluoromethyl)-6-(methylcarbamoyl)-3-pyridyl]piperazine-1-carboxylate tert-Butyl 4-[2-formyl-6-(methylcarbamoyl)-3-pyridyl]piperazine-1-carboxylate (730 mg, 2.10 mmol) (Intermediate 110) in CH$_2$Cl$_2$ (10 mL) was cooled to 0° C., DAST (692 µL, 5.24 mmol) in DCM (5 mL) was added to the mixture, the resulting mixture was then stirred at rt for 4 h, TLC and LCMS indicated full conversion. The reaction mixture was quenched with sat. aq NaHCO$_3$ solution dropwise, extracted with DCM, the organics were dried (anhydrous Na$_2$SO$_4$), filtered and concentrated, the residue was purified on silica gel column (eluted with 0 to 100% ethyl acetate in hexanes, UV at 254, 293 nm) to yield tert-butyl 4-[2-(difluoromethyl)-6-(methylcarbamoyl)-3-pyridyl]piperazine-1-carboxylate (0.666 g, 86%) (Intermediate 111) as a white solid. 1H NMR (500 MHz, CHLOROFORM-d) 1.50 (9H, s), 2.93-3.02 (4H, m), 3.05 (3H, d), 3.57-3.72 (4H, m), 6.99 (1H, t), 7.62 (1H, d), 7.92 (1H, br d), 8.27 (1H, d); (m/z) (ES$^+$) [M+H]$^+$=371.

Intermediate 60: 6-(difluoromethyl)-N-methyl-5-piperazin-1-yl-pyridine-2-carboxamide, 2HCl HCl 4M in Dioxane (7 mL, 28.00 mmol) was added to a flask charged with tert-butyl 4-[2-(difluoromethyl)-6-(methylcarbamoyl)-3-pyridyl]piperazine-1-carboxylate (665 mg, 1.80 mmol) (Intermediate 111) and a stir bar, the mixture was stirred at rt for 1 hr gave a yellow suspension. The solvent was removed, the residue was diluted with ether, the solid was collected by filtration, dried to yield 6-(difluoromethyl)-N-methyl-5-piperazin-1-yl-pyridine-2-carboxamide, 2HCl (0.617 g, 100%) (Intermediate 60) as an orange solid. (m/z) (ES$^+$) [M+H]$^+$=272.

Example 59: 6-(difluoromethyl)-5-[4-[(2-methoxy-5-methyl-3-oxo-4H-quinoxalin-6-yl)methyl]piperazin-1-yl]-N-methyl-pyridine-2-carboxamide To a suspension of 6-(difluoromethyl)-N-methyl-5-piperazin-1-yl-pyridine-2-carboxamide, 2HCl (87 mg, 0.25 mmol) (Intermediate 60) and 7-(bromomethyl)-3-methoxy-8-methyl-1H-quinoxalin-2-one (80 mg, 0.25 mmol) (Intermediate 104) in acetonitrile (6 mL) was added DIPEA (222 µL, 1.27 mmol), the resulting mixture was stirred at 70° C. for 2 h gave a clear solution, the mixture was cooled to rt gave a suspension, the solid was collected by filtration, washed with acetonitrile, water, dried to yield 6-(difluoromethyl)-5-[4-[(2-methoxy-5-methyl-3-oxo-4H-quinoxalin-6-yl)methyl]piperazin-1-yl]-N-methyl-pyridine-2-carboxamide (0.070 g, 58.3%) (Example 59) as a white solid. 1H NMR (500 MHz, DMSO-d6) 2.43 (3H, s), 2.59 (4H, br s), 2.83 (3H, br d), 2.98 (4H, br s), 3.60 (2H, s), 3.95 (3H, s), 6.92-7.29 (2H, m), 7.35 (1H, d), 7.85 (1H, br d), 8.08 (1H, d), 8.38 (1H, br d), 11.58 (1H, br s); ((m/z) (ES$^+$) [M+H]$^+$=473.

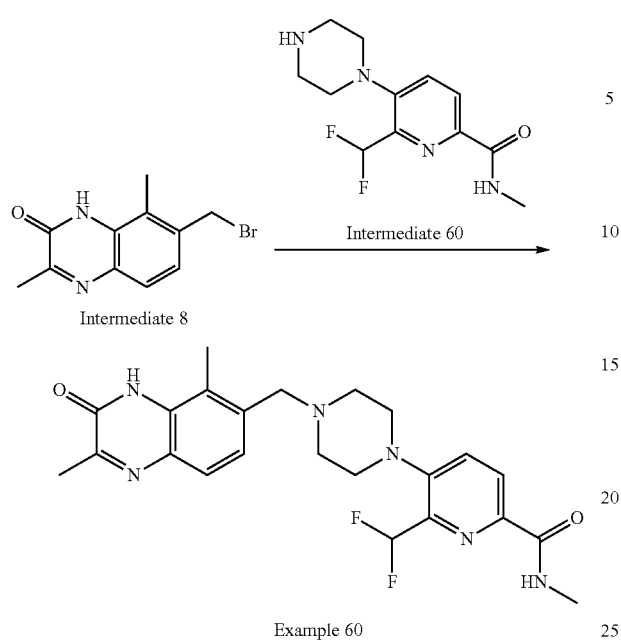

Example 60

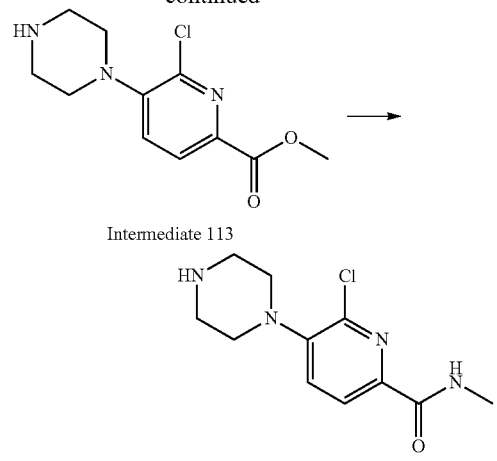

Example 60: 6-(difluoromethyl)-5-[4-[(2,5-dimethyl-3-oxo-4H-quinoxalin-6-yl)methyl]piperazin-1-yl]-N-methyl-pyridine-2-carboxamide A mixture of 7-(bromomethyl)-3,8-dimethyl-1H-quinoxalin-2-one (196 mg, 0.73 mmol) (Intermediate 8), 6-(difluoromethyl)-N-methyl-5-piperazin-1-yl-pyridine-2-carboxamide, 2HCl (252 mg, 0.73 mmol) (Intermediate 60) and Et₃N (0.614 mL, 4.41 mmol) in acetonitrile (25 mL) was stirred at 70° C. for 2 h gave a clear solution, LCMS indicated full conversion. The mixture was cooled to rt overnight. A solid crystallized from the mixture, the solid was collected by filtration, washed with acetonitrile, water, dried to yield part 1 of the product 141 mg, the filtrate was concentrated, purified on reverse phase gilson (eluted with 5 to 80% ACN/water/0.1% TFA) to yield a second portion of the product 92 mg as TFA salt. In total: 6-(difluoromethyl)-5-[4-[(2,5-dimethyl-3-oxo-4H-quinoxalin-6-yl)methyl]piperazin-1-yl]-N-methyl-pyridine-2-carboxamide (0.233 g, 64.0%) (Example 60) as an off white solid. 1H NMR (500 MHz, DMSO-d6) 2.40 (3H, s), 2.43 (3H, s), 2.60 (4H, br s), 2.83 (3H, d), 2.98 (4H, br d), 3.63 (2H, s), 6.95-7.22 (1H, m), 7.23-7.29 (1H, m), 7.51 (1H, d), 7.85 (1H, d), 8.08 (1H, d), 8.38 (1H, br d), 11.54 (1H, br s); (m/z) (ES⁺) [M+H]⁺=457.

Intermediate 113: methyl 6-chloro-5-(piperazin-1-yl)picolinate

Piperazine (1.0 g, 11.61 mmol) was added to methyl 6-chloro-5-fluoropicolinate (Intermediate 112, 1.0 g, 5.28 mmol) in MeCN (30 mL). The resulting mixture was stirred at 80° C. for 18 hours. The solvent was removed under reduced pressure. The crude product was purified by reverse phase chromatography, elution gradient 5 to 60% MeCN in water (0.1% NH₄HCO₃). Pure fractions were evaporated to dryness to afford methyl 6-chloro-5-(piperazin-1-yl)picolinate (Intermediate 113, 1.28 g, 95%) as a red oil. ¹H NMR (400 MHz, DMSO-d₆) δ 2.81-2.91 (4H, m), 3.04-3.08 (4H, m), 3.85 (3H, s), 7.61 (1H, d), 8.00 (1H, d) (NH proton is not shown); m/z (ES⁺) [M+H]⁺=256.

Intermediate 30: 6-chloro-N-methyl-5-(piperazin-1-yl)picolinamide

A 2 M solution of methylamine in THF (40 mL, 80.00 mmol) was added to methyl 6-chloro-5-(piperazin-1-yl)picolinate (Intermediate 113, 1.26 g, 4.93 mmol). The resulting mixture was stirred at 80° C. for 18 hours. The solvent was removed under reduced pressure. The crude product was purified by reverse phase chromatography, elution gradient 5 to 60% MeCN in water (0.1% NH₄HCO₃). Pure fractions were evaporated to dryness to afford 6-chloro-N-methyl-5-(piperazin-1-yl)picolinamide (Intermediate 30, 1.12 g, 89%) as a pale yellow oil. ¹H NMR (300 MHz, DMSO-d₆) δ 2.79 (3H, d), 2.85-2.89 (4H, m), 2.97-3.02 (4H, m), 7.63 (1H, d), 7.94 (1H, d), 8.45 (1H, q) (Piperazine-NH proton is not shown); m/z (ES⁺) [M+H]⁺=255.

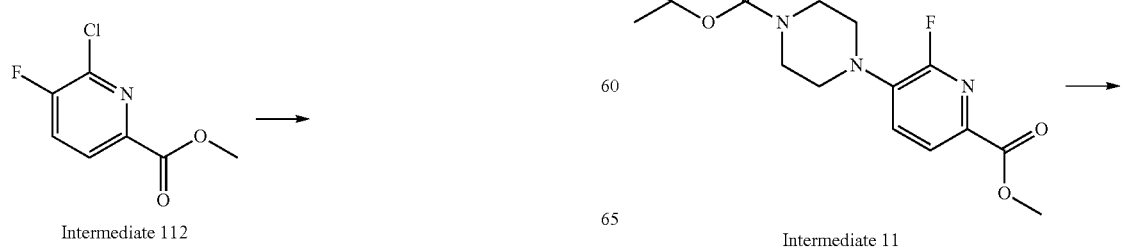

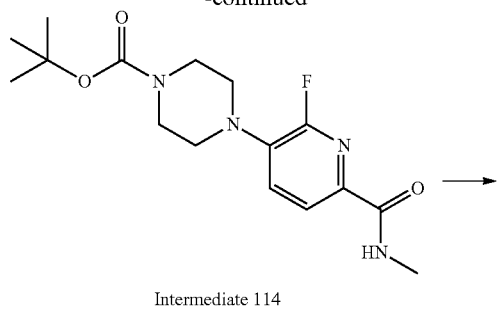

Intermediate 114

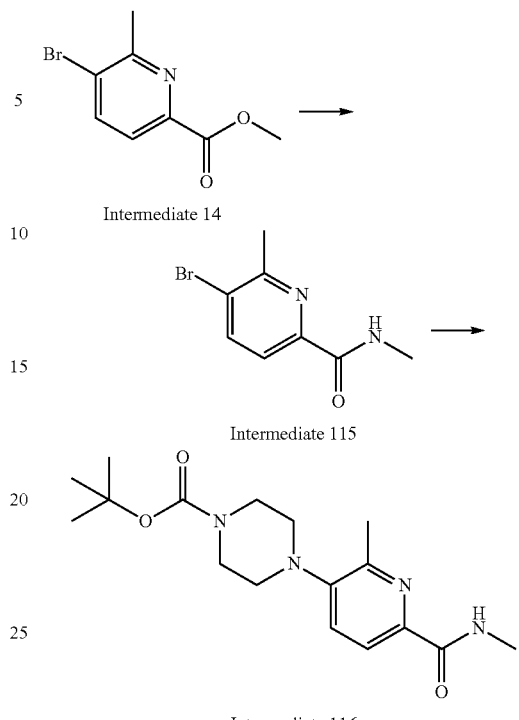

Intermediate 14

Intermediate 115

Intermediate 116

Intermediate 32

Intermediate 33

Intermediate 114: tert-butyl 4-[2-fluoro-6-(methyl-carbamoyl)-3-pyridyl]piperazine-1-carboxylate tert-butyl 4-(2-fluoro-6-methoxycarbonyl-3-pyridyl)piperazine-1-carboxylate (Intermediate 11, 12.49 g, 36.80 mmol) in methylamine (120 mL, 36.80 mmol, 33 wt % in ethanol) was stirred at rt for 24 hrs. (sealed tube). The solvent was removed under reduced pressure. The residue was dissolved into DCM and filtered through silica gel bed and washed with ethyl acetate. The filtrate was concentrated and dried under vacuum to afford tert-butyl 4-[2-fluoro-6-(methylcarbamoyl)-3-pyridyl]piperazine-1-carboxylate (Intermediate 114, 12.45 g, 100%) as a yellow solid. 1H NMR (500 MHz, DMSO-d6) 1.42 (9H, s), 2.77 (3H, d), 3.04-3.16 (4H, m), 3.43-3.56 (4H, m), 7.59 (1H, dd), 7.80-7.93 (1H, m), 8.41 (1H, q); m/z (ES$^+$) [M+H]$^+$=340.

Intermediate 32: 6-fluoro-N-methyl-5-piperazin-1-yl-pyridine-2-carboxamide

HCl (4M in dioxane, 100 ml, 400.00 mmol) was added to a solution of tert-butyl 4-[2-fluoro-6-(methylcarbamoyl)-3-pyridyl]piperazine-1-carboxylate (Intermediate 114, 12.5 g, 36.94 mmol) in 1,4-dioxane (50 mL) at 0° C. the reaction was stirred for 5 h during which the temperature was warmed to room temperature to give a yellow suspension. The suspension was diluted with ether, solid was filtered off and washed with ether. This solid was dried under vacuum to afford 6-fluoro-N-methyl-5-piperazin-1-yl-pyridine-2-carboxamide, 2HCl (Intermediate 32, 11.42 g, 99%) as a light-yellow solid. 1H NMR (500 MHz, DMSO-d6) δ ppm 2.8 (d, J=4.6 Hz, 3H) 3.3 (br s, 4H) 3.4 (br d, J=4.4 Hz, 4H) 7.6-7.7 (m, 1H) 7.9 (d, J=8.1 Hz, 1H) 8.4 (br d, J=4.4 Hz, 1H) 9.0-9.3 (m, 2H); m/z (ES$^+$) [M+H]$^+$=239

Intermediate 115: 5-bromo-N,6-dimethylpicolinamide

A 2 M solution of methylamine in THF (20 mL, 40.00 mmol) was added to methyl 5-bromo-6-methylpicolinate (Intermediate 14, 2.0 g, 8.69 mmol) and the resulting mixture was stirred at 80° C. for 18 hours. The solvent was removed under reduced pressure. The crude product was purified by reverse phase chromatography, elution gradient 5 to 80% MeOH in water (0.1% NH$_4$HCO$_3$). Pure fractions were evaporated to dryness to afford 5-bromo-N,6-dimethylpicolinamide (Intermediate 115, 1.5 g, 75%) as a pale yellow solid. $^1$H NMR (400 MHz, DMSO-d6) δ 2.65 (3H, s), 2.82 (3H, d), 7.75 (1H, d), 8.17 (1H, d), 8.57-8.76 (1H, m); m/z (ES$^+$) [M+H]$^+$=229

Intermediate 116: tert-butyl 4-(2-methyl-6-(methyl-carbamoyl)pyridin-3-yl)piperazine-1-carboxylate 5-bromo-N,6-dimethylpicolinamide (Intermediate 115, 1.0 g, 4.37 mmol) was added to tert-butyl piperazine-1-carboxylate (0.894 g, 4.80 mmol), BINAP (0.272 g, 0.44 mmol), Pd(OAc)$_2$ (0.098 g, 0.44 mmol) and Cs$_2$CO$_3$ (3.56 g, 10.91 mmol) in toluene (20 mL) under nitrogen. The resulting mixture was stirred at 80° C. for 16 hours. The solvent was removed under reduced pressure. The crude product was purified by reverse phase chromatography, elution gradient 5 to 30% MeOH in water (0.4% HCO₂H). Pure fractions were evaporated to dryness to afford tert-butyl 4-(2-methyl-6-(methylcarbamoyl)pyridin-3-yl)piperazine-1-carboxylate (Intermediate 116, 1.2 g, 82%) as a brown solid. $^1$H NMR (300 MHz, CD$_3$OD) δ 1.50 (9H, s), 2.58 (3H, s), 2.92-3.00 (7H, m), 3.62 (4H, m), 7.50 (1H, d), 7.88 (1H, d); m/z (ES$^+$) [M+H]$^+$=335.

Intermediate 33:
N,6-dimethyl-5-(piperazin-1-yl)picolinamide tert-butyl 4-(2-methyl-6-(methylcarbamoyl)pyridin-3-yl)piperazine-1-carboxylate (Intermediate 115, 1.18 g, 3.53 mmol) was added to a 4 M solution of HCl in the 1,4-dioxane (10 mL, 329.15 mmol). The resulting mixture was stirred at room temperature for 1 hour. The precipitate was collected by filtration, washed with petroleum ether (5 mL×2), Et$_2$O (5 mL×2), and dried under vacuum to afford N,6-dimethyl-5-(piperazin-1-yl)picolinamide (Intermediate 33, 0.77 g, 81%) as an yellow solid. $^1$H NMR (300 MHz, CD$_3$OD) δ 2.86 (3H, s), 3.02 (3H, s), 3.42-3.54 (8H, m), 8.29 (2H, d); m/z (ES$^+$) [M+H]$^+$=235.

layers were dried over anhydrous Na$_2$SO$_4$ and filtered. To this filtrate was added 3-(Diethylenetriamino)propyl-functionalized silica gel (12 g, 1.3 mmol/g loading) and the mixture was stirred at rt for 1 hr. The mixture was filtered, and the filtrate was concentrated to −100 mL. The crystalline yellow solid was filtered off, washed with ether and dried under vacuum to afford tert-butyl 4-(6-methoxycarbonyl-3-pyridyl)piperazine-1-carboxylate (Intermediate 117, 26.36 g, 82 mmol, 59.1%) as a yellow solid. 1H NMR (500 MHz, CHLOROFORM-d) 1.50 (9H, s), 3.31-3.42 (4H, m), 3.56-3.68 (4H, m), 3.98 (3H, s), 8.04 (1H, d), 8.37 (1H, d); m/z (ES$^+$) [M+H]$^+$=322.

Intermediate 118: tert-butyl 4-[6-(methylcarbamoyl)-3-pyridyl]piperazine-1-carboxylate Methylamine (100 mL, 1155.26 mmol, 40% in water) was added to a solution of tert-butyl 4-(6-methoxycarbonyl-3-pyridyl)piperazine-1-carboxylate (Intermediate 117, 36 g, 112.02 mmol) in MeOH (100 mL) and the reaction was stirred at room temperature for 4 hs to give a white suspension. The mixture was concentrated, the residue was parti-

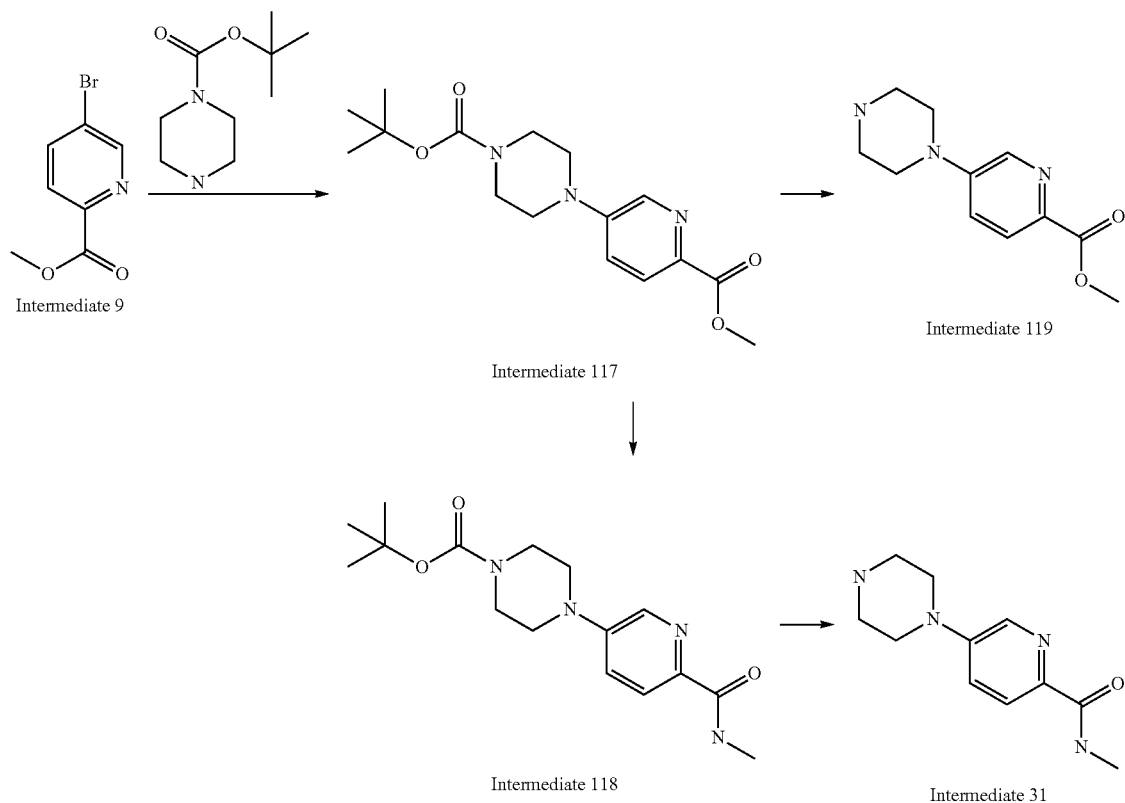

Intermediate 117: tert-butyl 4-(6-methoxycarbonyl-3-pyridyl)piperazine-1-carboxylate Ruphos Pd G3 (4.07 g, 4.86 mmol) was added to a degassed mixture of methyl 5-bromopyridine-2-carboxylate (Intermediate 9, 30 g, 138.87 mmol), tert-butyl piperazine-1-carboxylate (27.2 g, 145.81 mmol), Cs$_2$CO$_3$ (90 g, 277.73 mmol) in 1,4-dioxane (200 mL) and the mixture was stirred at 110° C. for 6 hrs under N$_2$ atmosphere. The mixture was then cooled to room temperature, diluted with water, extracted with ethyl acetate (150 ml×3). Combined organic tioned between sat. NH$_4$Cl solution and DCM, the layers were separated. The aqueous layer was extracted with DCM, the organic layers were combined, washed with brine, dried over Na$_2$SO$_4$, filtered and concentrated to give tert-butyl 4-[6-(methylcarbamoyl)-3-pyridyl]piperazine-1-carboxylate (Intermediate 118, 35.9 g, 100%) as a yellow solid. 1H NMR (500 MHz, CHLOROFORM-d) 1.49 (9H, s), 3.02 (3H, d), 3.26-3.35 (4H, m), 3.58-3.67 (4H, m), 7.23 (1H, dd), 7.81 (1H, br d), 8.07 (1H, d), 8.16 (1H, d); m/z (ES+) [M+H]+=321.

Intermediate 119: methyl 5-(piperazin-1-yl)picolinate

HCl 4M in Dioxane (20 ml, 576.01 mmol) was added to a mixture of tert-butyl 4-(6-(methoxycarbonyl)pyridin-3-yl) piperazine-1-carboxylate (Intermediate 117, 1.55 g, 4.82 mmol) in MeOH (2 mL) at 0° C., the reaction was stirred at r.t for 2 hr gave a suspension, LCMS indicated full conversion, the mixture was diluted with ether (~80 ml), the solid was collected by filtration, washed with ether, dried to yield methyl 5-(piperazin-1-yl)picolinate (intermediate 119) (1.384 g, 98%) as a yellow solid. 1H NMR (500 MHz, DMSO-d6) 3.21 (4H, br s), 3.66 (4H, br d), 3.83 (3H, s), 7.43-7.55 (1H, m), 7.95 (1H, br d), 8.43 (1H, br s), 9.49 (2H, br s); (m/z) (ES$^+$) [M+H]$^+$=223.0.

Intermediate 31: carboxylate N-methyl-5-piperazin-1-yl-pyridine-2-carboxamide HCl (4M in dioxane, 150 mL, 600.00 mmol) was added to a suspension of tert-butyl 4-[6-(methylcarbamoyl)-3-pyridyl]piperazine-1-carboxylate (Intermediate 118, 35.9 g, 112.05 mmol) in MeOH (50 mL) and the resulting orange suspension was stirred at rt for 4 hr. About 80 mL of solvent was removed under reduced pressure and the mixture was diluted with ether and hexanes (200 ml, 1/1). The solid was collected by filtration, washed with hexanes, dried and dried under vacuum to afford N-methyl-5-piperazin-1-yl-pyridine-2-carboxamide, 2HCl salt (Intermediate 31, 37.0 g, 100%) as a yellow solid. 1H NMR (500 MHz, DMSO-d6) 2.79 (3H, d), 3.22 (4H, br s), 3.53-3.67 (4H, m), 7.51 (1H, dd), 7.91 (1H, d), 8.33 (1H, d), 8.50 (1H, br s), 9.19-9.49 (2H, m); m/z (ES$^+$) [M+H]$^+$=221.

Example 61: Preparation of 6-fluoro-5-[4-[(5-fluoro-2-methyl-3-oxo-4H-quinoxalin-6-yl)methyl]piperazin-1-yl]-N-methyl-pyridine-2-carboxamide Crystalline Form B (anhydrous form)

Method 1

43 mg (0.10 mmol) of 6-fluoro-5-[4-[(5-fluoro-2-methyl-3-oxo-4H-quinoxalin-6-yl)methyl]piperazin-1-yl]-N-methyl-pyridine-2-carboxamide (from e.g. Example 20) was suspended in 1.0 ml of MeOH and 0.11 ml of 1 M methanesulfonic acid (MSA) aqueous solution was added to get a clear solution. To the solution, 0.11 ml of 1 N NaOH aqueous solution was added. White solid started to precipitate after completion of adding the NaOH solution. The slurry was stirred at the room temperature for 1 day. 36 mg of the white solid was filtered and dried in air. XRPD shows that the solid is pure 6-fluoro-5-[4-[(5-fluoro-2-methyl-3-oxo-4H-quinoxalin-6-yl)methyl]piperazin-1-yl]-N-methyl-pyridine-2-carboxamide Form B.

Method 2

Pyridine (93.5 g) was added to pure 6-fluoro-5-[4-[(5-fluoro-2-methyl-3-oxo-4H-quinoxalin-6-yl)methyl]piperazin-1-yl]-N-methyl-pyridine-2-carboxamide mesylate (4.67 kg, prepared via method 2 of Example 63) solution in water (47.9 kg) and ethanol (38.0 kg) at 75±5° C., followed by 6-fluoro-5-[4-[(5-fluoro-2-methyl-3-oxo-4H-quinoxalin-6-yl)methyl]piperazin-1-yl]-N-methyl-pyridine-2-carboxamide Form B seed (4.7 g) prepared according to method 1. The slurry was stirred at 75±5° C. for 40 min then pyridine (651 g) solution in 50:50 v:v water:ethanol (4.2 kg) was added gradually over 3 h 40 min. The slurry was stirred at 75±5° C. for 50 min then 4-methylmorpholine (900 g) solution in 50:50 v:v water:ethanol (4.1 kg) was added gradually over 3 h 50 min. The slurry was stirred at 75±5° C. for 1 h 10 min, cooled to 25±5° C. over 4 h 50 min, stirred at 25±5° C. for 15 h then filtered. The resulting solid was washed twice with 50:50 v:v water:ethanol (12.5 kg×2) and then dried under vacuum at between 25° C. and 50° C. for 1 day to give pure 6-fluoro-5-[4-[(5-fluoro-2-methyl-3-oxo-4H-quinoxalin-6-yl)methyl]piperazin-1-yl]-N-methyl-pyridine-2-carboxamide Form B (3.54 kg) in 93% yield.

Form B from method 1 was analyzed by XRPD and the results are tabulated below (Table 1) and shown in FIG. 1.

TABLE 1

| XRPD Peaks for Form B | |
|---|---|
| Angle (2θ ± 0.2°) | Intensity (%) |
| 18.2 | 100.0 |
| 9.6 | 86.7 |
| 9.1 | 80.7 |
| 18.7 | 55.8 |
| 12.7 | 24.1 |
| 8.5 | 23.9 |
| 10.0 | 15.6 |
| 20.1 | 14.8 |
| 21.7 | 13.9 |
| 23.2 | 12.3 |
| 12.4 | 12.2 |
| 16.1 | 9.6 |
| 14.3 | 9.2 |
| 6.2 | 8.9 |
| 15.6 | 7.7 |
| 27.4 | 6.9 |
| 26.4 | 6.6 |
| 29.7 | 6.2 |
| 27.1 | 6.0 |
| 25.0 | 5.0 |

Form B is characterized in providing at least one of the following 2θ values measured using CuKα radiation: 6.2, 14.3, and 15.6°.

Figure 2:
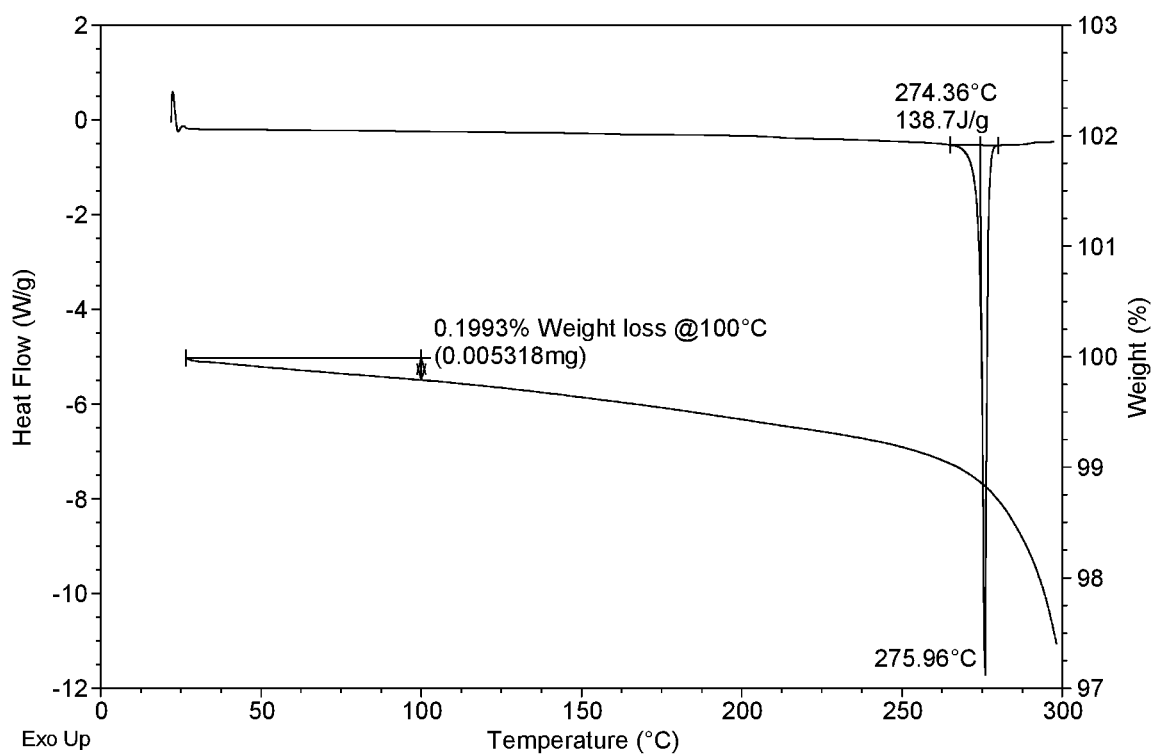
FIG. 2 shows a DSC trace of 6-fluoro-5-[4-[(5-fluoro-2-methyl-3-oxo-4H-quinoxalin-6-yl)methyl]piperazin-1-yl]-N-methyl-pyridine-2-carboxamide Form B

Form B (from method 1) was analyzed by thermal techniques. DSC analysis indicated that Form B has a melting point with an onset at 275° C. and a peak at 276° C. TGA indicated that Form B exhibits a mass loss of about 0.2% upon heating from about 25° C. to about 100° C. A representative DSC/TGA thermogram of Form B is shown in FIG. 2.

Example 62: Preparation of 6-fluoro-5-[4-[(5-fluoro-2-methyl-3-oxo-4H-quinoxalin-6-yl)methyl]piperazin-1-yl]-N-methyl-pyridine-2-carboxamide Crystalline Form D (anhydrous form)

5-6 mg of 6-fluoro-5-[4-[(5-fluoro-2-methyl-3-oxo-4H-quinoxalin-6-yl)methyl]piperazin-1-yl]-N-methyl-pyridine-2-carboxamide (Example 20) was dissolved in mixed solvents of MeOH/DCM/H$_2$O (0.50 ml/0.50 ml/0.20 ml), the clear solution was slowly evaporated in the ambient condition to obtain a white solid. XRPD shows that the resulting white solid is 6-fluoro-5-[4-[(5-fluoro-2-methyl-3-oxo-4H-quinoxalin-6-yl)methyl]piperazin-1-yl]-N-methyl-pyridine-2-carboxamide Form D.

Figure 3:
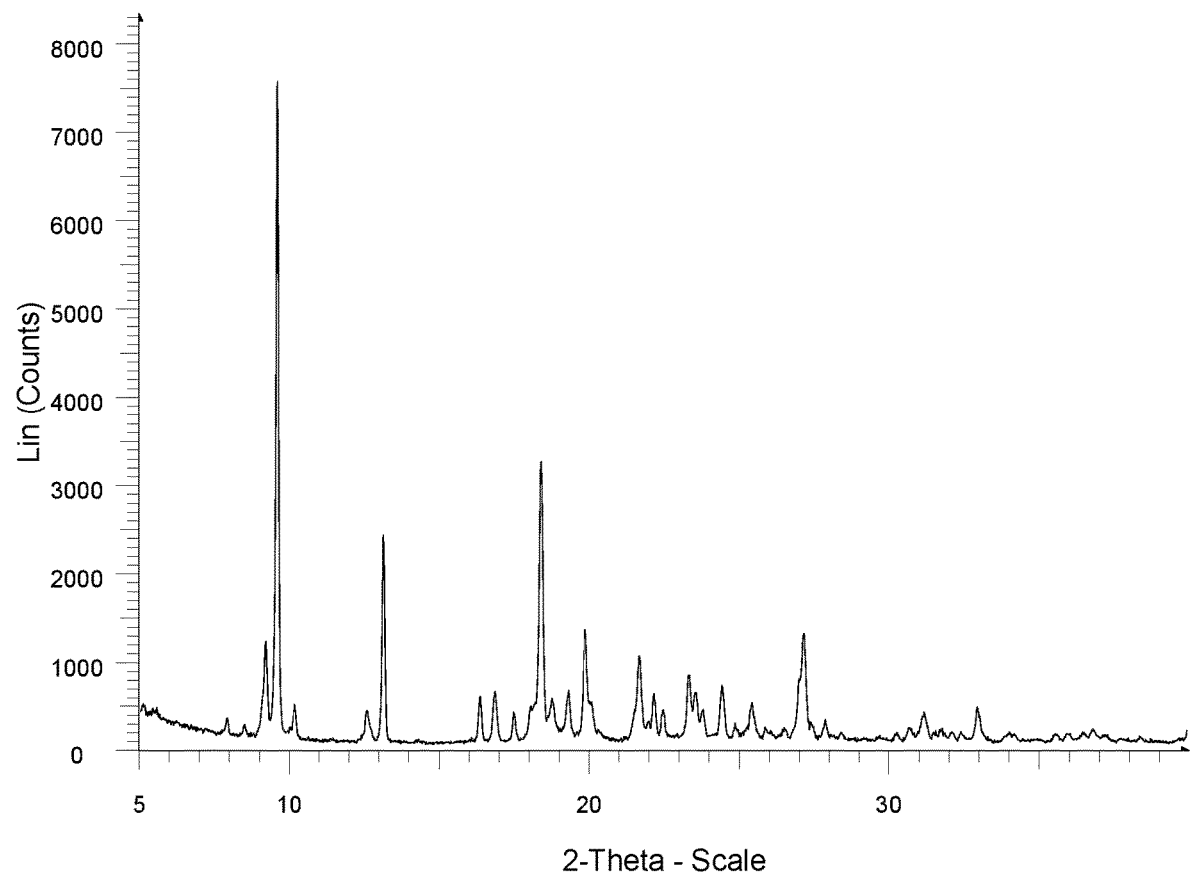
FIG. 3 shows an X-ray powder diffractogram of 6-fluoro-5-[4-[(5-fluoro-2-methyl-3-oxo-4H-quinoxalin-6-yl)methyl]piperazin-1-yl]-N-methyl-pyridine-2-carboxamide Form D

Form D was analyzed by XRPD and the results are tabulated below (Table 2) and shown in FIG. 3.

TABLE 2

XRPD Peaks for Form D

| Angle (2θ ± 0.2°) | Intensity (%) |
|---|---|
| 9.6 | 100.0 |
| 18.4 | 43.0 |
| 13.1 | 32.0 |
| 19.9 | 17.9 |
| 27.1 | 17.3 |
| 9.2 | 15.9 |
| 21.7 | 14.0 |
| 23.4 | 11.2 |
| 24.5 | 9.6 |
| 19.3 | 8.8 |
| 16.8 | 8.7 |
| 22.2 | 8.3 |
| 16.3 | 8.0 |
| 18.8 | 7.6 |
| 25.4 | 6.9 |
| 10.2 | 6.6 |
| 33.0 | 6.3 |
| 22.5 | 5.8 |
| 12.6 | 5.7 |
| 7.9 | 4.5 |

Form D is characterized in providing at least one of the following 2θ values measured using CuKα radiation: 7.9, 13.1 and 16.3°.

Figure 4:
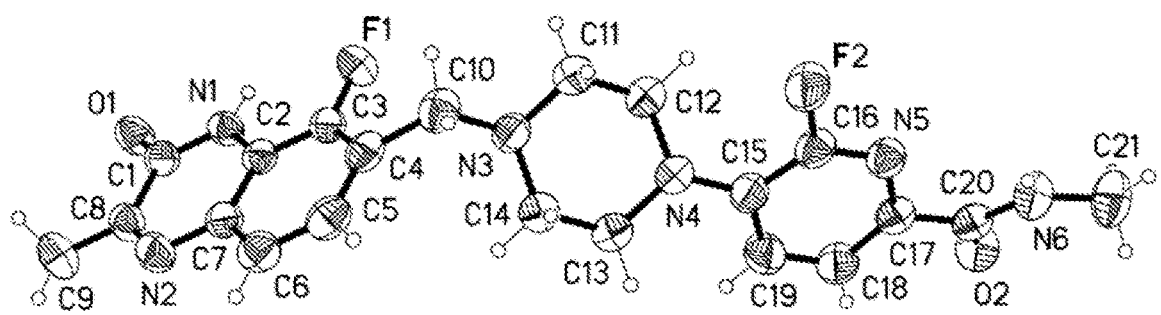
FIG. 4 shows a single crystal structure of 6-fluoro-5-[4-[(5-fluoro-2-methyl-3-oxo-4H-quinoxalin-6-yl)methyl]piperazin-1-yl]-N-methyl-pyridine-2-carboxamide Form D (ORTEP50)

Single crystals of Form D were obtained from evaporation of the DMF solution (or DMF/H$_2$O) of 6-fluoro-5-[4-[(5-fluoro-2-methyl-3-oxo-4H-quinoxalin-6-yl)methyl]piperazin-1-yl]-N-methyl-pyridine-2-carboxamide. Single crystal structure analysis confirmed that Form D is an anhydrous form. The molecular structure of 6-fluoro-5-[4-[(5-fluoro-2-methyl-3-oxo-4H-quinoxalin-6-yl)methyl]piperazin-1-yl]-N-methyl-pyridine-2-carboxamide Form D is shown in FIG. 4. Crystallographic data: Space group monoclinic P2$_1$/c, unit cell dimensions: a=17.4559(8) Å, b=5.0647(2) Å, c=22.564(1) Å, β=92.609(1°), V=1992.8(2) Å$^3$.

Example 63: Preparation of 6-fluoro-5-[4-[(5-fluoro-2-methyl-3-oxo-4H-quinoxalin-6-yl)methyl]piperazin-1-yl]-N-methyl-pyridine-2-carboxamide MSA Crystalline Salt Form C (anhydrous form)

Method 1

427 mg of 6-fluoro-5-[4-[(5-fluoro-2-methyl-3-oxo-4H-quinoxalin-6-yl)methyl]piperazin-1-yl]-N-methyl-pyridine-2-carboxamide (Example 20) was suspended in 8.0 ml of MeOH. To the suspension, 1.1 ml of 1.0 M aqueous MSA solution (1.1 mmol) was added, a clear solution was obtained. The resulting solution was filtered, and the solvents of the clear solution was removed. The resulting solid was suspended in 1.0 ml of EtOH and 2.0 ml of THF, to obtain a slurry. The slurry was stirred at the room temperature for 1 day. The solid was collected by filtration and air-dried. 452 mg of off-white solid was obtained. XRD shows that 6-fluoro-5-[4-[(5-fluoro-2-methyl-3-oxo-4H-quinoxalin-6-yl)methyl]piperazin-1-yl]-N-methyl-pyridine-2-carboxamide MSA salt Form C was obtained.

Method 2

Methanesulfonic acid (16.8 g) was added to a stirring suspension of 6-fluoro-5-[4-[(5-fluoro-2-methyl-3-oxo-4H-quinoxalin-6-yl)methyl]piperazin-1-yl]-N-methyl-pyridine-2-carboxamide (80.8 g, 92.8% w/w) in 4:1 v:v THF:ethanol (750 mL) at 25° C. The resulting suspension was stirred at 25° C. for 16 h and then filtered. The solid was washed with 4:1 v:v THF:ethanol (300 mL) and then dried at 35° C. under vacuum to give 6-fluoro-5-[4-[(5-fluoro-2-methyl-3-oxo-4H-quinoxalin-6-yl)methyl]piperazin-1-yl]-N-methyl-pyridine-2-carboxamide mesylate Form C (90.3 g) in 98% yield.

Figure 5:
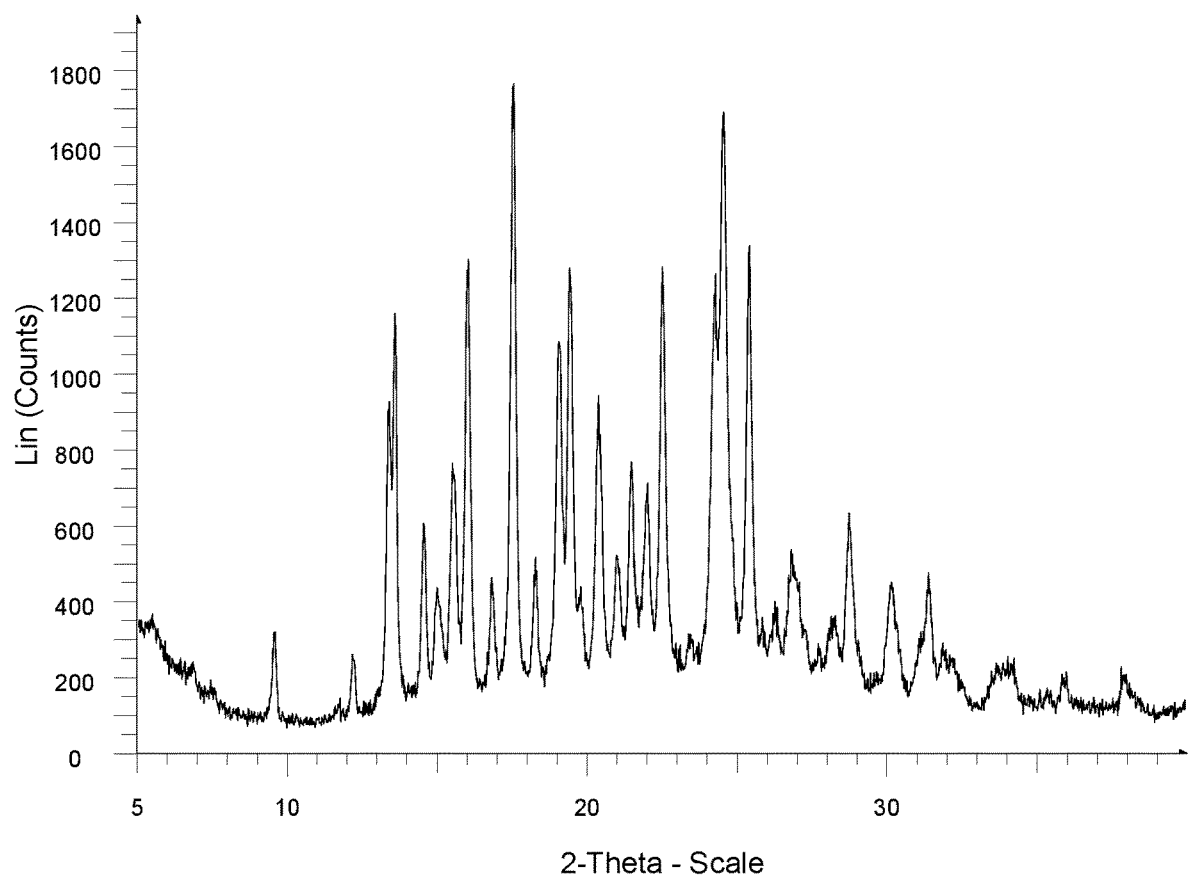
FIG. 5 shows an X-ray powder diffractogram of 6-fluoro-5-[4-[(5-fluoro-2-methyl-3-oxo-4H-quinoxalin-6-yl)methyl]piperazin-1-yl]-N-methyl-pyridine-2-carboxamide MSA salt Form C

MSA-Form C from method 1 was analyzed by XRPD and the results are tabulated below (Table 3) and shown in FIG. 5.

TABLE 3

XRPD Peaks for MSA-Form C

| Angle (2θ ± 0.2°) | Intensity (%) |
|---|---|
| 17.5 | 100.0 |
| 24.6 | 95.7 |
| 25.4 | 75.8 |
| 16.0 | 73.8 |
| 22.5 | 72.6 |
| 19.4 | 72.5 |
| 24.3 | 71.6 |
| 13.6 | 65.6 |
| 19.0 | 61.3 |
| 20.4 | 53.3 |
| 21.5 | 43.4 |
| 15.5 | 43.2 |
| 22.0 | 40.2 |
| 28.8 | 35.8 |
| 14.6 | 34.2 |
| 26.9 | 29.7 |
| 21.0 | 29.4 |
| 18.3 | 29.1 |
| 31.4 | 26.8 |
| 16.8 | 26.0 |

Figure 6:
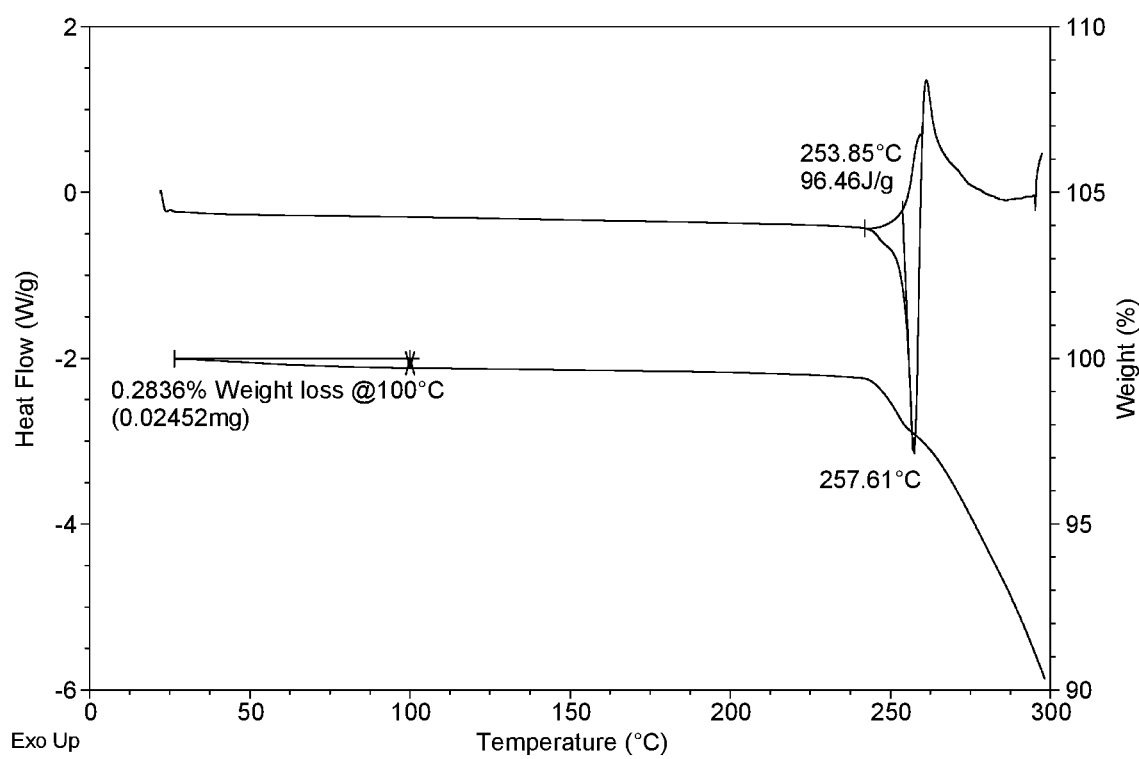
FIG. 6 shows a DSC trace of 6-fluoro-5-[4-[(5-fluoro-2-methyl-3-oxo-4H-quinoxalin-6-yl)methyl]piperazin-1-yl]-N-methyl-pyridine-2-carboxamide MSA salt Form C

MSA-Form C obtained from method 1 was analyzed by thermal techniques. DSC analysis indicated that MSA-Form C starts to melting and decomposition at the temperature with an onset at 254° C. and a peak at 258° C. TGA indicated that MSA-Form C exhibits a mass loss of about 0.3% upon heating from about 25° C. to about 100° C. A representative DSC/TGA thermogram of MSA-Form C is shown in FIG. 6.

Biological Assays

The following test procedures may be employed to determine the inhibitory properties of the compounds described herein.

PARP Fluorescence Anisotropy Binding Assays

Recombinant full length 6HIS tagged PARP1 protein was diluted to 6 nM with 50 mM Tris pH 8, 0.001% Triton X100, 10 mM MgCl$_2$, 150 mM NaCl and incubated for four hours with an equivalent volume of 2 nM fluorescent probe diluted with 50 mM Tris pH 8, 0.001% Triton X100, 10 mM MgCl$_2$, 150 mM NaCl. The final DMSO concentration of the probe was kept below 1% (v/v).

Recombinant full length PARP2 protein was diluted to 6 nM with 50 mM Tris pH 8, 0.001% Triton X100, 10 mM MgCl$_2$, 150 mM NaCl and incubated for four hours with an equivalent volume of 2 nM fluorescent probe diluted with 50 mM Tris pH 8, 0.001% Triton X100, 10 mM MgCl$_2$, 150 mM NaCl. The final DMSO concentration of the probe was kept below 1% (v/v).

Recombinant full length PARP3 protein was diluted to 100 nM with 50 mM Tris pH 8, 0.001% Triton X100, 10 mM MgCl$_2$, 150 mM NaCl and incubated for four hours with an equivalent volume of 6 nM fluorescent probe diluted with 50 mM Tris pH 8, 0.001% Triton X100, 10 mM MgCl$_2$, 150 mM NaCl. The final DMSO concentration of the probe was kept below 1% (v/v).

Recombinant PARP5a binding domain was diluted to 160 nM with 50 mM Tris pH 8, 0.001% Triton X100, 10 mM MgCl$_2$, 150 mM NaCl and incubated for four hours with an equivalent volume of 6 nM fluorescent probe diluted with 50 mM Tris pH 8, 0.001% Triton X100, 10 mM MgCl$_2$, 150 mM NaCl. The final DMSO concentration of the probe was kept below 1% (v/v).

Recombinant full length GST tagged PARP6 protein was diluted to 160 nM with 50 mM Tris pH 8, 0.001% Triton X100, 10 mM MgCl$_2$, 150 mM NaCl and incubated for four hours with an equivalent volume of 6 nM fluorescent probe diluted with 50 mM Tris pH 8, 0.001% Triton X100, 10 mM MgCl$_2$, 150 mM NaCl. The final DMSO concentration of the probe was kept below 1% (v/v).

Fluorescence anisotropy of the probe when bound to the proteins was measured using a BMG Pherastar FSX© in the presence of test compounds or solvent control and the effect on anisotropy determined. % inhibition values for different test compound concentrations were calculated and fitted to a four parameter logistic plot in order to determine the IC$_{50}$ value. Where necessary, the compound K$_i$ can be determined from the IC$_{50}$ value using a Munson Rodbard equation defined in *Anal Biochem.* 1980 Sep. 1; 107(1):220-39 and is based on the known K$_D$ of the probe binding to the relevant PARP protein PARP Proliferation Assay (7 Day Compound Dosing)

DLD1 and BRCA2 (−/−) DLD1 cells were harvested to a density of 5000 cells/ml and 2.5E4 cells/ml respectively in complete media, 40 µL/well seeded into 384-well plates (Greiner, Kremsmunster, Austria; 781090) using a Multidrop Combi then incubated at 37° C., 5% CO$_2$ overnight. Next day (Day 1) using a Multidrop Combi add sytoxgreen (5 ul, 2 uM) and saponin (10 ul, 0.25% stock) to a day 0 plate, seal the plate using a black adhesive lid and incubate for >3 h at rt. Cells were imaged using Cell Insight (Thermo Fisher) fitted with a 4× objective. Test compounds are added using an Echo 555 and placed in incubator maintained at 37° C., 5% CO$_2$ and incubated for 7 days. On Day 8 add sytox green (5 ul, 2 uM) and then saponin (10 ul, 0.25% stock) to plates, seal the plate using a black adhesive lid and incubate for >3 h at rt. Read all cells on the Cell Insight with 4× Objective. The rate of proliferation is determined in Genedata by assessing the total cell number output from the Cell Insight for Day 0 and Day 8 plates.

In Vitro Human Transporter Efflux

MDCKII cells expressing MDR1 and BCRP were seeded onto polyethylene membranes in 96-well Transwell insert systems at a density to form a confluent cell monolayer. Test and reference compounds were diluted with the transport buffer (HBSS HEPES pH7.4) to a concentration of 1 or 0.1 µM. The final percent volume of the organic solvent was less than 1%. Permeation of the test compounds from A to B direction and from B to A direction was determined over a 90-min incubation at 37° C. and 5% CO2 with a relative humidity of 95%. At the end of the incubation, samples from the apical and basolateral side were taken and then precipitated with cold acetonitrile containing internal standard. After centrifugation at 4000 rpm, the supernatant was diluted with 0.1% formic acid aqueous solution and quantified by LC-MS/MS. The integrity of the cell monolayers was confirmed by using the marker Lucifer yellow.

The permeability coefficient (1×10−6 cm/s) was calculated using the following equation $$Papp=(dCr/dt) \times Vr/(A \times C0)$$

(1) The efflux ratio was calculated using the following equation $$\text{Efflux ratio} = Papp(B \text{ to } A)/Papp(A \text{ to } B)$$

(2) where dCr/dt is the cumulative concentration of the compound in the receiver chamber as a function of time (in µM/s); Vr is the solution volume in the receiver chamber (0.1 ml on the apical side and 0.3 ml on the basolateral side); A is the surface area for the transport, that is, 0.11 cm2 for the area of the monolayer; and C0 is the initial concentration in the donor chamber (in µM).

Determination of Fraction Unbound in Plasma

The fraction unbound was determined using the RED Device.

Compounds were prepared as 10 mM solutions in DMSO. A 1 mM working stock was prepared by mixing up to 9 test compound (4 uL each) and 1 control (uL). If less than 9 test compounds were included then the addition volume of blank DMSO was added to make up volume to 40 uL.

Frozen plasma was thawed in a water bath at 37° C. Plasma was then centrifuged for 2 minutes at 4,000 rpm to remove clots and collect supernatant into a fresh tube. The pH of the plasma was checked and only used if within the range of pH 7 to pH 8. 3 µL of the working solution of each cassette was added to 597 µL of blank plasma and vortexed for 5 minutes at 1000 rpm. The final percent volume of organic solvent is 0.5% and the final concentration for test compound was 5 µM. Immediately transfer 50 µL of spiked plasma suspension to a 96-well plate to act as T=0 control sample. The samples are treated the same as the samples after incubation. The remaining plasma is kept at 37° C. prior to starting the dialysis.

Place inserts open end up into the wells of the base plate. Add 300 µL of spiked plasma sample into the sample chamber, indicated by the red ring. Add 500 µL of phosphate buffer (pH 7.4) to the buffer chamber. Cover the unit with gas permeable lid and incubate for 18 hours at 37° C. at 300 rpm with 5% CO2 on an orbital shaker in the CO2 incubator. At the end of incubation, remove lid and pipette 50 µL of post-dialysis samples from both buffer and plasma chambers into separated 96-well plate for analysis, respectively.

Samples were matrix matched by adding 50 µL of blank rat plasma to the buffer samples and an equal volume of PBS to the collected plasma samples and vortexed to mix. 400 µL of acetonitrile containing an appropriate internal standard (IS) was added to precipitate protein and release compound and mixed by vortexing the plate for 10 minutes followed by centrifugation for 30 minutes at 4,000 rpm. 250 µL of the supernatant was transferred to new 96-well plates and centrifuged again (4,000 rpm, 30 minutes). 100 µL of the supernatant was then transferred to new 96-well plates and mixed with 100 µL of distilled water to each sample by vortex for 5 minutes at 1,000 rpm. Samples were analysed by LC-MS/MS and drug concentrations were determined vs a calibration curve produced from spiked blank plasma with a typical range of 1-7500 nM.

The % unbound was determined as % Unbound=
(Conc. buffer chamber/Conc. plasma chamber)×
100%.

Fraction unbound=% unbound/100.

Determination of Fraction Unbound in Brain Slice

The principle for the method for the determination of volume unbound in brain slices has previously been published (Development of a High-Throughput Brain Slice Method for Studying Drug Distribution in the Central Nervous System; Friden et al; Drug Metabolism and Disposition, 2009, 37 (6) 1226-1233). In brief:

Compound stock solutions were prepared in DMSO at the concentration of 10 mM. A 1 mM working stock was prepared by mixing up to 9 test compound (4 uL each) and 1 control (4 uL). If less than 9 test compounds were included, then blank DMSO was added to make up volume to 40 uL. On the day of the experiment 4 ul was diluted in 40 mL ECF buffer to give a 100 nM solution of each test compounds which was then pre-warmed to 37° C. before the start of the incubation.

To prepare brain slices, rats weighing approximately 300 g were terminally anesthetised with isoflurane by inhalation, the brain carefully removed and immersed in ice-cold oxygenated ECF buffer. The rat brain was transferred to a dish containing ice-cold, 02 supplied ECF buffer and trimmed with razor before gluing to the tray of a microslicer with the brain placed with the back section surface down centrally on the tray. Ice cold ECF buffer was added to harden the glue and wet the brain. The tray was placed in the microslicer and using a suitable cutting speed, 100-400 µm were cut slices until the striatum area appeared. Four to six for each brain, 300 µm thick, coronal slices of striatum areas were cut and placed in ice cold 02 supplied buffer until incubation. Six slices were transferred to the incubation tray containing 40 mL pre warmed (37° C.) cassette mixture. The time from when the brain is removed until the slices are in the cocktail mixture was a maximum of 20 minutes. The incubation tray was covered with a gas permeable lid and placed in a water bath with O2 pumped into it at 37° C. and incubated at a shaking frequency of 45 rpm for 5 h.

Before incubation, 200 µL of the non-incubated cassette solution is saved as the T=0 sample. 200 µL was then mixed with 200 µL blank brain homogenate in ECF buffer (4 volumes (w/v). After incubation the pH in the cassette solution is measured and recorded, and the pH value must be above 7.3. 200 µL from the surface of the cassette solution was transferred in to a tube containing 200 µL blank brain homogenate in ECF buffer (4 volumes (w/v)). Each brain slice is dried on a filter paper and weighed in a 2 mL eppendorf tube. After addition of 9 volumes (w/v) of ECF buffer the slices are homogenized with a sonicator. The samples were precipitated and diluted as below.

50 µL aliquots from each sample and 3×50 µL from each cassette solution (mixed with blank homogenate) were transferred to 0.6 mL centrifuge tubes. The samples are precipitated with 200 µL ice cold acetonitrile containing internal standard and vortexed at 2,000 rpm for 3 minutes followed by centrifugation at 14000 rpm, for 15 minutes at 4° C. 100 µL of the supernatant was transferred to a new 96-well plate for analysis and 100 µL of distilled water to each sample and the plate shaken for 2 minutes at 1000 rpm for analysis by LC-MS/MS.

Then the mixed slice samples are further diluted in two steps, 10 and 100 times with double blank samples prepared with 150 µL of blank brain homogenate in ECF buffer (4 volumes (w/v)) are transferred to 1.5 mL centrifuge tubes containing 150 µL of ECF buffer, vortexed at 2,000 rpm for 2 minutes. The samples are precipitated with 1200 µL ice cold acetonitrile and vortexed at 2,000 rpm for 3 minutes followed by centrifugation at 14000 rpm, for 15 minutes at 4° C. Then transfer 100 µL of the supernatant to a new 96-well plate for analysis. Add 100 µL of distilled water to each sample to obtain the double blank samples.

The unbound volume brain ($V_{u,brain}$) was calculated as $V_u = (C_{slice} - V_0 * C_{ECF})/(1 - V_0) * C_{ECF}$ Where $C_{slice}$, $C_{ECF}$ and $V_0$ are amount of drug in the slice, the drug concentration in the ECF (representing the drug concentration in the brain ECF, i.e. the free concentration), and the water adhesion of the brain slice (0.0931), respectively.

The fraction unbound in brain $f_{u,brain} = 1/V_{u,brain}$

Determination of Kpuu in Rat

The ratio of total/unbound drug in plasma to total/unbound drug in brain (Kp/Kpuu) was determined as follows.

Compounds were formulated as a mixture at a concentration of 0.5 mM each in 1:1:1 tetraethyleneglycol:dimethylacetamide:water and administered to Han Wistar rats via intravenous infusion at 2 □mols/kg/h in a volume of 4 mL/kg. After 4 h the animals were sacrificed, and brain and blood samples collected. Plasma was prepared from blood and all samples were stored frozen at −20° C. until analysis. Following collection brain samples were homogenised in purified water at a ratio of 1:3 (w/v) and stored frozen at −20° C. until analysis.

Plasma and brain samples were analysed by protein precipitation followed by LC-MS/MS and concentrations determined against a calibration curve generated by spiking blank rat plasma or brain homogenate with drug across an appropriate concentration range. The brain concentration was corrected for the residual blood by subtracting 0.8% of the plasma concentration from the total brain concentration.

The Kp was then calculated as: Kp=((4*[brain homogenate])−(0.008*[plasma]))/[plasma]

The Kpuu was then calculated as: Kpuu=Kp*(fraction unbound in brain slice/fraction unbound in plasma)

TABLE 4

| Example Number | PARP1 IC50 (µM) | PARP2 IC50 (µM) | PARP3 IC50 (µM) | PARP5a IC50 (µM) | PARP6 IC50 (µM) | hERG IC50 (µM) | BRCA2 −/− DLD-1 prolif. 7 d IC50 (µM) | WT DLD-1 prolif. 7 d IC50 (µM) | MDCK-MDR1-BCRP Efflux Ratio | Rat Kpuu |
|---|---|---|---|---|---|---|---|---|---|---|
| 1 | 0.004 | >70 | >100 | >100 | >100 | >40 | 0.014 | 24 | 0.7 | 0.07 |
| 2 | 0.011 | 15 | | | | >40 | 0.734 | | | |
| 3 | 0.003 | >100 | >100 | >100 | >100 | >40 | 0.008 | 25 | 1.3 | |
| 4 | 0.005 | >83 | 78 | >100 | >100 | >40 | 0.081 | >14 | 0.8 | 0.13 |
| 5 | 0.005 | >63 | | | | | 2.89 | | | |
| 6 | 0.004 | >100 | | | | | | | | |
| 7 | 0.006 | 58 | | | | | 8.43 | >30 | | |
| 8 | 0.004 | >66 | >100 | >100 | >100 | >40 | 0.012 | >7.9 | | |
| 9 | 0.004 | >100 | >100 | >100 | >100 | >40 | 0.01 | >10 | 0.4 | |
| 10 | 0.013 | >100 | >100 | >100 | >100 | >40 | >30.0 | >30 | | |
| 11 | 0.003 | >100 | >100 | >100 | >100 | >40 | 0.009 | >30 | | |
| 12 | 0.015 | | 85 | >100 | >100 | >40 | 0.008 | | 4.2 | |
| 13 | 0.009 | >100 | 62 | >100 | >100 | >40 | 0.019 | 22 | 3.0 | |
| 14 | 0.013 | >83 | 52 | >100 | >100 | >40 | 0.015 | | 3.7 | |
| 15 | 0.012 | >100 | 43 | >100 | >100 | >38 | 0.014 | | 3.7 | |

TABLE 4-continued

| Example Number | PARP1 IC50 (μM) | PARP2 IC50 (μM) | PARP3 IC50 (μM) | PARP5a IC50 (μM) | PARP6 IC50 (μM) | hERG IC50 (μM) | BRCA2 -/- DLD-1 prolif. 7 d IC50 (μM) | WT DLD-1 prolif. 7 d IC50 (μM) | MDCK-MDR1-BCRP Efflux Ratio | Rat Kpuu |
|---|---|---|---|---|---|---|---|---|---|---|
| 16 | 0.01 | >100 | >100 | >29 | >100 | >40 | 3.62 | >30 | | |
| 17 | 0.006 | >100 | >100 | >100 | >100 | >40 | 1.05 | >10 | | |
| 18 | 0.005 | >100 | >100 | >100 | >100 | 14 | 4.33 | 21 | | |
| 19 | 0.013 | 40 | | | | >40 | 0.006 | | 2.4 | |
| 20 | <0.005 | >93 | >100 | >100 | >100 | >40 | 0.008 | >30 | 1.1 | 0.27 |
| 21 | 0.007 | >100 | 5.8 | >100 | >100 | >40 | 1.42 | | 1.6 | |
| 22 | 0.006 | 87 | | | | | | | | |
| 23 | 0.005 | >67 | >100 | >100 | >100 | >40 | 0.003 | >30 | 0.8 | 0.62 |
| 24 | 0.006 | >81 | >100 | >100 | >100 | >36 | 0.003 | >30 | 1.1 | |
| 25 | 0.005 | >100 | | | | | 0.297 | | | |
| 26 | 0.005 | 88 | | | | | | | | |
| 27 | 0.004 | >64 | >100 | >100 | >100 | >40 | 0.006 | 6.3 | 0.8 | 0.43 |
| 28 | 0.005 | >100 | >100 | >100 | >100 | >38 | 0.004 | | 0.8 | |
| 29 | 0.015 | >100 | >100 | >100 | >100 | >40 | 0.005 | >10 | 0.7 | 0.33 |
| 30 | 0.006 | >100 | >100 | >100 | >100 | >40 | 0.003 | >30 | 1.8 | |
| 31 | 0.007 | >100 | >100 | >100 | >100 | >40 | 0.007 | >30 | 1.6 | 0.19 |
| 32 | 0.007 | >100 | >100 | >100 | >100 | >40 | 1.08 | 23 | | |
| 33 | 0.167 | >100 | | | | | >30.0 | | | |
| 34 | 0.026 | >100 | | | | 29 | 8.44 | | | |
| 35 | 0.03 | >100 | | | | | 10.3 | >30 | | |
| 36 | 0.022 | >100 | | | | | 16.2 | | | |
| 37 | 0.026 | 57 | | | | | 0.01 | | 5.0 | |
| 38 | 0.012 | 21 | >100 | >100 | >100 | >40 | 0.547 | | | |
| 39 | 0.006 | >100 | >100 | >100 | >100 | >40 | 0.008 | | 1.9 | |
| 40 | 0.011 | >100 | >100 | 13 | >100 | >40 | 0.007 | | 2.0 | |
| 41 | 0.005 | >100 | >100 | >100 | >100 | >40 | 0.007 | | 2.4 | |
| 42 | 0.005 | >88 | | | | | 0.006 | | | |
| 43 | 0.005 | >100 | | | | | 0.01 | | | |
| 44 | 0.128 | >100 | | | | | >30.0 | | | |
| 45 | 0.006 | >100 | | | | | 0.006 | | 1.5 | |
| 46 | 0.01 | >100 | | | | | 0.013 | | | |
| 47 | 0.076 | >100 | >100 | >100 | >100 | >40 | 0.058 | | | |
| 48 | 0.039 | 26 | >100 | >100 | >100 | >40 | 0.018 | 27 | 8.8 | |
| 49 | 0.043 | 11 | >29 | >100 | >100 | >40 | 0.041 | | | |
| 50 | 0.060 | 35 | | | | >40 | 0.136 | | | |
| 51 | 0.006 | 1.2 | | | | | | | | |
| 52 | 0.085 | 3.8 | | | | | | | | |
| 53 | 0.026 | >100 | | | | | | | | |
| 54 | 0.111 | >100 | | | | | | | | |
| 55 | 0.005 | >100 | | | | | | | | |
| 56 | 0.008 | >100 | | | | | | | | |
| 57 | 0.011 | >100 | | | | | | | | |
| 58 | 0.008 | >100 | | | | | | | | |
| 59 | 0.006 | 2.1 | | | | | | | | |
| 60 | 0.023 | >100 | | | | | | | | |

The invention claimed is:

1. A compound of Formula I

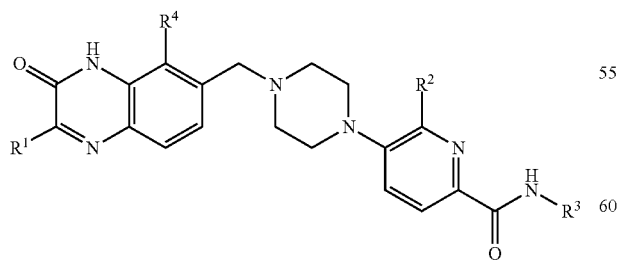

(I)

wherein:

$R^1$ is independently selected from H, $C_{1-4}$ alkyl, $C_{3-6}$ cycloalkyl, $C_{1-4}$ fluoroalkyl, and $C_{1-4}$ alkyloxy;

$R^2$ is independently selected from H, halo, $C_{1-4}$ alkyl, and $C_{1-4}$ fluoroalkyl; and $R^3$ is H or $C_{1-4}$ alkyl;

$R^4$ is halo or $C_{1-4}$ alkyl, or a pharmaceutically acceptable salt thereof.

2. The compound or a pharmaceutically acceptable salt thereof, of claim 1 wherein $R^1$ is selected from any one of methyl, ethyl, isopropyl, cyclopropyl, 1,1-difluoroethyl, 1-fluoroethyl, trifluoromethyl, difluoromethyl, and methoxy.

3. The compound or a pharmaceutically acceptable salt thereof, of claim 1 wherein $R^1$ is methyl or ethyl.

4. The compound or a pharmaceutically acceptable salt thereof, of claim 1 wherein $R^2$ is selected from any one of H, chloro, fluoro, methyl, and difluoromethyl.

5. The compound or a pharmaceutically acceptable salt thereof, of claim 1 wherein $R^2$ is selected from any one of chloro, fluoro and methyl.

6. The compound or a pharmaceutically acceptable salt thereof, of claim 1 wherein $R^4$ is selected from any one of chloro, fluoro, and methyl.

7. The compound or a pharmaceutically acceptable salt thereof, of claim 1 wherein $R^1$ is $C_{1-4}$ alkyl, $R^2$ is halo, $R^3$ is $C_{1-4}$ alkyl, $R^4$ is halo or $C_{1-4}$ alkyl.

8. The compound of claim 1 selected from:
5-[4-[(2,5-dimethyl-3-oxo-4H-quinoxalin-6-yl) methyl] piperazin-1-yl]-6-fluoro-N-methyl-pyridine-2-carboxamide,
5-[4-[(2,5-dimethyl-3-oxo-4H-quinoxalin-6-yl) methyl] piperazin-1-yl]-N-methyl-pyridine-2-carboxamide,
6-chloro-5-[4-[(2,5-dimethyl-3-oxo-4H-quinoxalin-6-yl) methyl]piperazin-1-yl]-N-methyl-pyridine-2-carboxamide,
5-[4-[(2,5-dimethyl-3-oxo-4H-quinoxalin-6-yl) methyl] piperazin-1-yl]-N,6-dimethyl-pyridine-2-carboxamide,
5-[4-[(2,5-dimethyl-3-oxo-4H-quinoxalin-6-yl) methyl] piperazin-1-yl]-6-fluoro-pyridine-2-carboxamide,
5-[4-[(5-fluoro-2-methyl-3-oxo-4H-quinoxalin-6-yl) methyl]piperazin-1-yl]-6-methyl-pyridine-2-carboxamide,
5-[4-[(2,5-dimethyl-3-oxo-4H-quinoxalin-6-yl) methyl] piperazin-1-yl]-6-methyl-pyridine-2-carboxamide,
6-chloro-5-[4-[(5-chloro-2-ethyl-3-oxo-4H-quinoxalin-6-yl) methyl]piperazin-1-yl]-N-methyl-pyridine-2-carboxamide,
5-[4-[(5-chloro-2-ethyl-3-oxo-4H-quinoxalin-6-yl) methyl]piperazin-1-yl]-6-fluoro-N-methyl-pyridine-2-carboxamide,
5-[4-[(5-chloro-2-ethyl-3-oxo-4H-quinoxalin-6-yl) methyl]piperazin-1-yl]-N-methyl-pyridine-2-carboxamide,
5-[4-[(5-chloro-2-ethyl-3-oxo-4H-quinoxalin-6-yl) methyl]piperazin-1-yl]-N,6-dimethyl-pyridine-2-carboxamide,
6-fluoro-5-[4-[[5-fluoro-2-[(1S and 1R)-1-fluoroethyl]-3-oxo-4H-quinoxalin-6-yl]methyl]piperazin-1-yl]-N-methyl-pyridine-2-carboxamide,
5-[4-[5-fluoro-2-[(1S and 1R)-1-fluoroethyl]-3-oxo-4H-quinoxalin-6-yl]methyl]piperazin-1-yl]-N,6-dimethyl-pyridine-2-carboxamide,
5-[4-[(5-chloro-2-methyl-3-oxo-4H-quinoxalin-6-yl) methyl]piperazin-1-yl]-N-methyl-pyridine-2-carboxamide,
5-[4-[(5-chloro-2-methyl-3-oxo-4H-quinoxalin-6-yl) methyl]piperazin-1-yl]-6-fluoro-N-methyl-pyridine-2-carboxamide,
5-[4-[(5-chloro-2-methyl-3-oxo-4H-quinoxalin-6-yl) methyl]piperazin-1-yl]-N,6-dimethyl-pyridine-2-carboxamide,
5-[4-[[2-(1,1-difluoroethyl)-5-fluoro-3-oxo-4H-quinoxalin-6-yl]methyl]piperazin-1-yl]-N,6-dimethyl-pyridine-2-carboxamide,
6-fluoro-5-[4-[(5-fluoro-2-methyl-3-oxo-4H-quinoxalin-6-yl) methyl]piperazin-1-yl]-N-methyl-pyridine-2-carboxamide,
6-(difluoromethyl)-5-[4-[(5-fluoro-2-methyl-3-oxo-4H-quinoxalin-6-yl) methyl]piperazin-1-yl]-N-methyl-pyridine-2-carboxamide,
6-fluoro-5-[4-[(5-fluoro-2-methyl-3-oxo-4H-quinoxalin-6-yl) methyl]piperazin-1-yl]pyridine-2-carboxamide,
5-[4-[(2-ethyl-5-fluoro-3-oxo-4H-quinoxalin-6-yl) methyl]piperazin-1-yl]-N,6-dimethyl-pyridine-2-carboxamide,
6-(difluoromethyl)-5-[4-[(2-ethyl-5-fluoro-3-oxo-4H-quinoxalin-6-yl) methyl]piperazin-1-yl]-N-methyl-pyridine-2-carboxamide,
5-[4-[(2-ethyl-5-fluoro-3-oxo-4H-quinoxalin-6-yl) methyl]piperazin-1-yl]pyridine-2-carboxamide,
5-[4-[(2-ethyl-5-fluoro-3-oxo-4H-quinoxalin-6-yl) methyl]piperazin-1-yl]-6-methyl-pyridine-2-carboxamide,
5-[4-[(2-ethyl-5-fluoro-3-oxo-4H-quinoxalin-6-yl) methyl]piperazin-1-yl]-6-fluoro-N-methyl-pyridine-2-carboxamide,
6-chloro-5-[4-[(2-ethyl-5-fluoro-3-oxo-4H-quinoxalin-6-yl) methyl]piperazin-1-yl]-N-methyl-pyridine-2-carboxamide,
5-[4-[(2-ethyl-5-fluoro-3-oxo-4H-quinoxalin-6-yl) methyl]piperazin-1-yl]-N-methyl-pyridine-2-carboxamide,
6-chloro-5-[4-[(5-fluoro-2-methyl-3-oxo-4H-quinoxalin-6-yl) methyl]piperazin-1-yl]-N-methyl-pyridine-2-carboxamide,
5-[4-[(5-fluoro-2-methyl-3-oxo-4H-quinoxalin-6-yl) methyl]piperazin-1-yl]-N,6-dimethyl-pyridine-2-carboxamide,
5-[4-[(5-fluoro-2-methyl-3-oxo-4H-quinoxalin-6-yl) methyl]piperazin-1-yl]-N-methyl-pyridine-2-carboxamide,
5-[4-[(5-fluoro-3-oxo-4H-quinoxalin-6-yl) methyl]piperazin-1-yl]-N-methyl-pyridine-2-carboxamide,
6-chloro-5-[4-[(5-fluoro-3-oxo-4H-quinoxalin-6-yl) methyl]piperazin-1-yl]-N-methyl-pyridine-2-carboxamide,
5-[4-[(5-fluoro-3-oxo-4H-quinoxalin-6-yl) methyl]piperazin-1-yl]-N,6-dimethyl-pyridine-2-carboxamide,
6-fluoro-5-[4-[(5-fluoro-3-oxo-4H-quinoxalin-6-yl) methyl]piperazin-1-yl]-N-methyl-pyridine-2-carboxamide,
5-[4-[[2-(difluoromethyl)-5-fluoro-3-oxo-4H-quinoxalin-6-yl]methyl]piperazin-1-yl]-N,6-dimethyl-pyridine-2-carboxamide,
5-[4-[(5-fluoro-2-methoxy-3-oxo-4H-quinoxalin-6-yl) methyl]piperazin-1-yl]-N-methyl-pyridine-2-carboxamide,
6-fluoro-5-[4-[(5-fluoro-2-methoxy-3-oxo-4H-quinoxalin-6-yl) methyl]piperazin-1-yl]-N-methyl-pyridine-2-carboxamide,
5-[4-[(5-fluoro-2-methoxy-3-oxo-4H-quinoxalin-6-yl) methyl]piperazin-1-yl]-N,6-dimethyl-pyridine-2-carboxamide,
6-chloro-5-[4-[(5-fluoro-2-methoxy-3-oxo-4H-quinoxalin-6-yl) methyl]piperazin-1-yl]-N-methyl-pyridine-2-carboxamide,
5-[4-[(2-ethyl-5-methyl-3-oxo-4H-quinoxalin-6-yl) methyl]piperazin-1-yl]-N,6-dimethyl-pyridine-2-carboxamide,
5-[4-[(2-ethyl-5-methyl-3-oxo-4H-quinoxalin-6-yl) methyl]piperazin-1-yl]-6-fluoro-N-methyl-pyridine-2-carboxamide,
5-[4-[(2-ethyl-5-methyl-3-oxo-4H-quinoxalin-6-yl) methyl]piperazin-1-yl]-N-methyl-pyridine-2-carboxamide,
N-ethyl-6-fluoro-5-[4-[(5-fluoro-2-methyl-3-oxo-4H-quinoxalin-6-yl) methyl]piperazin-1-yl]pyridine-2-carboxamide,
N-ethyl-5-[4-[(5-fluoro-2-methyl-3-oxo-4H-quinoxalin-6-yl) methyl]piperazin-1-yl]-6-methyl-pyridine-2-carboxamide,
5-[4-[5-fluoro-3-oxo-2-(trifluoromethyl)-4H-quinoxalin-6-yl]methyl]piperazin-1-yl]-N, 6-dimethyl-pyridine-2-carboxamide,
6-fluoro-5-[4-[[5-fluoro-3-oxo-2-(trifluoromethyl)-4H-quinoxalin-6-yl]methyl]piperazin-1-yl]-N-methyl-pyridine-2-carboxamide, 6-chloro-5-[4-[[5-fluoro-3-oxo-2-(trifluoromethyl)-4H-quinoxalin-6-yl]methyl]piperazin-1-yl]-N-methyl-pyridine-2-carboxamide, 5-[4-[[5-fluoro-3-oxo-2-(trifluoromethyl)-4H-quinoxalin-6-yl]methyl]piperazin-1-yl]-N-methyl-pyridine-2-carboxamide, 6-fluoro-5-[4-[(5-fluoro-2-isopropyl-3-oxo-4H-quinoxalin-6-yl) methyl]piperazin-1-yl]-N-methyl-pyridine-2-carboxamide, 5-[4-[(5-fluoro-2-isopropyl-3-oxo-4H-quinoxalin-6-yl) methyl]piperazin-1-yl]-N,6-dimethyl-pyridine-2-carboxamide, 5-[4-[(5-fluoro-2-isopropyl-3-oxo-4H-quinoxalin-6-yl) methyl]piperazin-1-yl]-N-methyl-pyridine-2-carboxamide, 5-[4-[(2-cyclopropyl-5-fluoro-3-oxo-4H-quinoxalin-6-yl) methyl]piperazin-1-yl]-6-fluoro-N-methyl-pyridine-2-carboxamide, 5-[4-[(2-cyclopropyl-5-fluoro-3-oxo-4H-quinoxalin-6-yl) methyl]piperazin-1-yl]-N,6-dimethyl-pyridine-2-carboxamide, 5-[4-[(2-cyclopropyl-5-fluoro-3-oxo-4H-quinoxalin-6-yl) methyl]piperazin-1-yl]-N-methyl-pyridine-2-carboxamide, 5-[4-[(2-methoxy-5-methyl-3-oxo-4H-quinoxalin-6-yl) methyl]piperazin-1-yl]-N,6-dimethyl-pyridine-2-carboxamide, 6-fluoro-5-[4-[(2-methoxy-5-methyl-3-oxo-4H-quinoxalin-6-yl) methyl]piperazin-1-yl]-N-methyl-pyridine-2-carboxamide, 6-(difluoromethyl)-5-[4-[(2-methoxy-5-methyl-3-oxo-4H-quinoxalin-6-yl) methyl]piperazin-1-yl]-N-methyl-pyridine-2-carboxamide, and 6-(difluoromethyl)-5-[4-[(2,5-dimethyl-3-oxo-4H-quinoxalin-6-yl) methyl]piperazin-1-yl]-N-methyl-pyridine-2-carboxamide, or a pharmaceutically acceptable salt thereof.

9. The compound or a pharmaceutically acceptable salt thereof, of claim 1 wherein $R^1$ is independently selected from H, $C_{1-4}$ alkyl, $C_{1-4}$ fluoroalkyl, and $C_{1-4}$ alkyloxy.

* * * * *